US006500437B1

(12) United States Patent
Reed et al.

(10) Patent No.: US 6,500,437 B1
(45) Date of Patent: Dec. 31, 2002

(54) LEISHMANIA ANTIGENS FOR USE IN THE THERAPY AND DIAGNOSIS OF LEISHMANIASIS

(75) Inventors: Steven G. Reed, Bellevue, WA (US); Antonio Campos-Neto, Bainbridge Island, WA (US); John R. Webb, Manotick (CA); Davin C. Dillon, Issaquah, WA (US); Yasir A. W. Skeiky, Seattle, WA (US); Ajay Bhatia, Seattle, WA (US)

(73) Assignee: Corixa Corporation, Seattle, WA (US)

( * ) Notice: Subject to any disclaimer, the term of this patent is extended or adjusted under 35 U.S.C. 154(b) by 0 days.

(21) Appl. No.: 09/551,974

(22) Filed: Apr. 14, 2000

Related U.S. Application Data

(63) Continuation-in-part of application No. 09/183,861, filed on Oct. 30, 1998, now Pat. No. 6,365,165, which is a continuation-in-part of application No. 09/022,765, filed on Feb. 12, 1998, now Pat. No. 6,375,955, which is a continuation-in-part of application No. 08/920,609, filed on Aug. 27, 1997, which is a continuation-in-part of application No. 08/798,841, filed on Feb. 12, 1997, which is a continuation-in-part of application No. 08/533,669, filed on Sep. 22, 1995, now Pat. No. 5,834,592.

(51) Int. Cl.[7] .................. A61K 39/008; A61K 39/00; A61K 38/00; A61K 39/002; A61K 45/00
(52) U.S. Cl. .................. 424/269.1; 424/265.1; 424/184.1; 424/85.2; 424/191.1; 424/192.1; 514/12; 514/44; 514/2; 530/300; 530/350; 435/69.7; 536/23.1; 536/23.4
(58) Field of Search .................. 424/191.1, 192.1, 424/184.1, 265.1, 269.1; 530/300, 350; 435/69.7; 536/23.1, 23.4; 514/122, 44

(56) References Cited

U.S. PATENT DOCUMENTS

| 4,870,006 A | 9/1989 | Dragon et al. |
| 5,411,865 A | 5/1995 | Reed |
| 5,719,263 A | 2/1998 | Reed |
| 5,834,592 A | 11/1998 | Reed et al. |
| 5,846,748 A | 12/1998 | Mandal et al. |
| 5,876,735 A | 3/1999 | Reed |
| 5,876,966 A | 3/1999 | Reed |
| 5,879,687 A | 3/1999 | Reed |
| 5,910,306 A | 6/1999 | Alving et al. |
| 5,912,166 A | 6/1999 | Reed et al. |
| 5,961,970 A | 10/1999 | Lowell et al. |
| 5,965,142 A | 10/1999 | Dillon et al. |
| 5,980,898 A | 11/1999 | Glenn et al. |
| 5,985,284 A | 11/1999 | Lowell |
| 6,013,268 A | 1/2000 | Reed |

FOREIGN PATENT DOCUMENTS

| WO | WO 95/29239 | 11/1995 |
| WO | WO 96/39524 | 12/1996 |
| WO | WO 97/11180 | 3/1997 |
| WO | WO 98/35045 | 8/1998 |

OTHER PUBLICATIONS

Bixler et al., *Synthetic Vaccines* vol. 1, CRC Press Inc., Boca Raton, Florida, 1987, Chapter 4, "B cell recognition of protein antigens–perspectives form the submolecular level," pp. 40–71.
Bowie et al., "Deciphering the message in protein sequences: Tolerance to amino acid substitution," *Science* 247:1306–1310, 1990.
Campos–Neto et al., "Cloning and expression of *Leishmania donovani* gene instructed by a peptide isolated from major hisotcompatability complex class II molecules of infected macrophages," *Journal of Experimental Medicine* 182(5):1423–1433, 1995.
Cornelissen et al., "Vaccines against protozoal diseases of veterinary importance," *FEMS Immunology and Medical Microbiology* 15(2–3):61–72, Sep. 1996.
Coulson et al., "Differential expression of Leishmania major beta–tubulin genes during the acquisition of promastigote infectivity," *Mol Biochem Parasitol* 82(2):227–236, Nov. 1996.
De Andrade et al., "Recombinant Leishmania Hs90 and Hsp70 are recognized by sera from visceral leishmaniasis patients but not Chagas' disease patients," *Journal of Clinical Microbiology* 30(2):330–335, 1992.
Dillon et al., "Characterization of a *Leishmania tropica* antigen that detects immune responses in desert storm viscerotropic leishmaniasis patients," *Proc. Natl. Acad. Sci USA* 92:7981–7985, 1995.
Fong and Lee, "Beta tubulin gene of the parasitic protozoan *Leishmania mexicana,*" *Mol Biochem Parasitol* 31(1):97–106, Oct. 1988.
Frommel et al., "Vaccine–induced immunity against cutaneous Leishmaniasis in BALB/c mice," *Infection and Immunity* 56(4):843–848, 1988.
GenBank Accession No. AC003679, "Leishmania major chromosome 1, complete sequence," Mar. 24, 1999.
GenBank Accession No. U73845, "Leishmania major protein antigen LmSTI1 mRNA," Dec. 3, 1996.
GenBank Accession No. X86551, "L. donovani mRNA for 23 kDa cell surface protein," Apr. 26, 1995.

(List continued on next page.)

*Primary Examiner*—Nita Minnifield
*Assistant Examiner*—Padma Baskar
(74) *Attorney, Agent, or Firm*—Seed Intellectual Property Law Group. PLLC

(57) ABSTRACT

Compositions and methods for preventing, treating and detecting leishmaniasis and stimulating immune responses in patients are disclosed. The compounds provided include polypeptides that contain at least an immunogenic portion of one or more Leishmania antigens, or a variant thereof. Vaccines and pharmaceutical compositions comprising such polypeptides, or polynucleotides encoding such polypeptides, are also provided and may be used, for example, for the prevention and therapy of leishmaniasis, as well as for the detection of Leishmania infection.

7 Claims, 33 Drawing Sheets

OTHER PUBLICATIONS

Houghten, "Relative importance of position and individual amino acid residues in peptide antigen–antibody interactions: Implications in the mechanism of antigenic drift and antigeni shift," *Vaccines 86:*21–25, 1986.

Mougneau et al., "Expression cloning of a protective Leishmania antigen," *Science 268:*563–566, 1995.

Nascimento et al., "Vaccination of humans against cutaneous leishmaniasis: cellular and humoral immune responses," *Infection and Immunity 58*(7):2198–2203, Jul. 1990.

Osland et al., "Isolation and characterization of recombinant antigens form *Leishmania aethiopica* that react with human antibodies," *Infection and Immunity 60*(4):1368–1374, Apr. 1992.

Pir2 Database Accession No. S54162, "*Leishmania donovani,*" Jul. 8, 1995.

Shapira and Pedraza, "Sequence analysis and transcriptional activation of heat shock protein 83 of *Leishmania mexicanca amazonensis,*" *Molecular and Biochemical Pathology 42*(2):247–255, 1990.

Skeiky et al., "A recombinant Leishmania antigen that stimulates human peripheral blood mononuclear cells to express a Th1–type cytokine profile and to produce interleukin 12," *Journal of Experimental Medicine 181*(4):1527–1537, 1995.

Sheiky et al., "Proliferative and cytokine responses of human PBMC to cloned *Leishmania braziliensis* heat shock and ribosomal antigens," *Journal of Immunology 158*(8 pt. 2):93A, Abstract #517, 1993.

Webb et al., "Human and murine immune responses to a novel Leishmania major recombinant protein encoded by members of a multicopy gene family," *Infection and Immunity 66*(7):3279–3289, Jul. 1998.

Yang et al., "Identification and characterization of host–protective T cell epitopes of a major surface glycoprotein (gp63) from Leishmania major," *Immunology 72*(1):3–9, Jan. 1991.

Afonso et al., The adjuvant effect of interleukin–12 in a vaccine against Leishmania major, *Science 263:*235–237, Jan. 14, 1994.

Bunn–Moreno et al., "Lectin(s) extracted from seeds of Artocarpus integrifolia (jackfruit): potent and selective stimulator(s) of distinct human T and B cell functions," *The Journal of Immunology 127*(2):427–429, Aug. 1981.

Burns et al., "Molecular characterization of a kinesin–related antigen of *Leishmania chagasi* that detects specific antibody in African and American visceral leishmaniasis," *Proc. Natl. Acad. Sci. USA 90:*775–779, Jan. 1993.

Champsi and McMahon–Pratt, "Membrane glycoprotein M–2 protects against *Leishmania amazonensis* infection," *Infection and Immunity 52*(12):3272–3279, Dec. 1988.

Chatelain et al., "IL–4 induces a Th2 response in Leishmania major–infected mice," *The Journal of Immunology 148*(4):1182–1187, Feb. 15, 1992.

Curry et al., "A sensitive immunochemical assay for biologically active MuIFN–$\gamma$," *Journal of Immunological Methods 104:*137–142, 1987.

Flinn et al., "Expression of a hydrophilic surface protein in infective stages of Leishmania major," *Molecular and Biochemical Parasitology 65:*259–270, 1994.

Mosmann and Fong, "Specific assay for cytokine production by T cells," *Journal of Immunological Methods 116:*151–158, 1989.

Pan et al., "Developmental life cycle of Leishmania—cultivation and characterization of cultured extracellular amastigotes," *The Journal of Eukaryotic Microbiology 40*(2):213–223, Mar.–Apr. 1993.

Reiner and Locksley, "The regulation of immunity to Leishmania major," *Annu. Rev. Immunol. 13:*151–177, 1995.

Rodrigues et al., "Selective inability of spleen antigen presenting cells from *Leishmania donovani* infected hamsters to mediate specific T cell proliferation to parasite antigens," *Parasite Immunology 14*(1):49–58, Jan. 1992.

Skeiky et al., "Antigens shared by Leishmania species and *Trypanosoma cruzi:* immunological comparison of the acidic ribosomal P0 proteins," *Infection and Immunity 62*(5):1643–1651, May 1994.

Skeiky et al., "Cloning and expression of *Trypanosoma cruzi* ribosomal protein P0 and epitope analysis of Anti–P0 autoantibodies in *Chagas'* disease patients," *J. Exp. Med. 176*(1):201–211, Jul. 1, 1992.

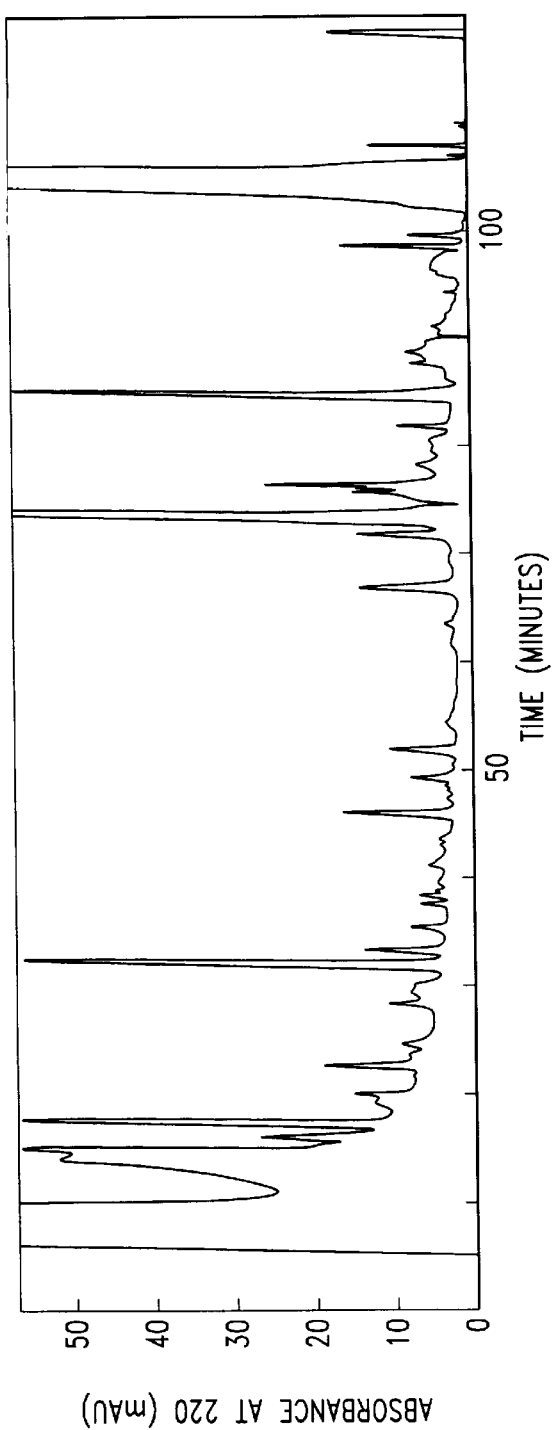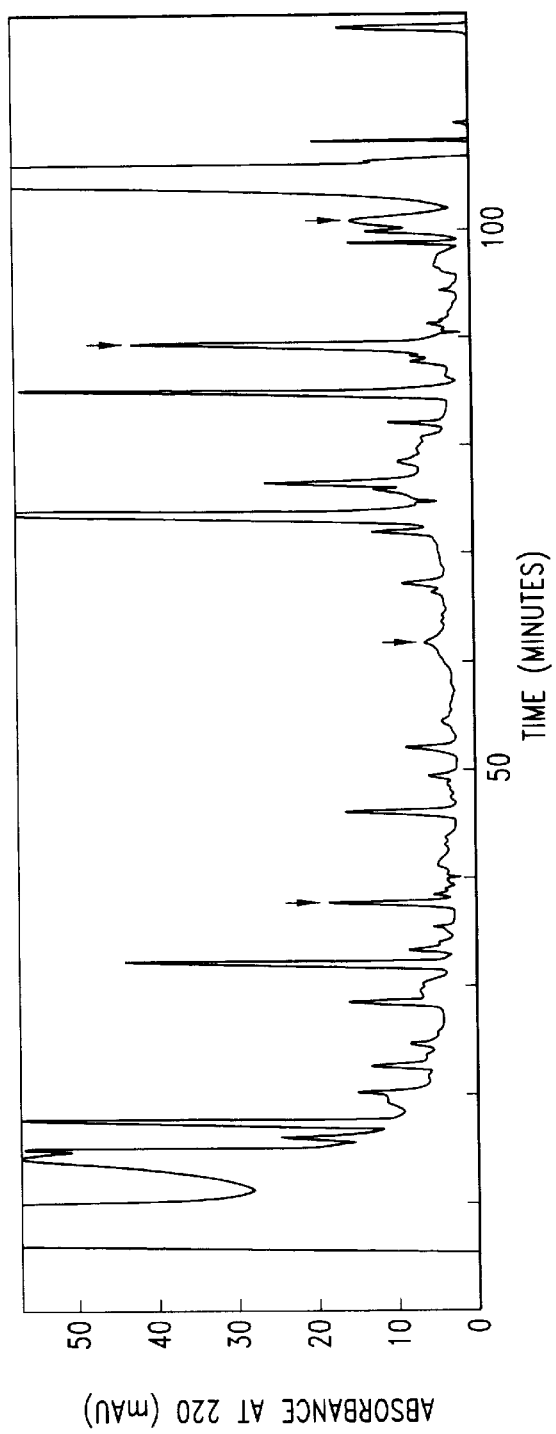
Fig. 2A
Fig. 2B

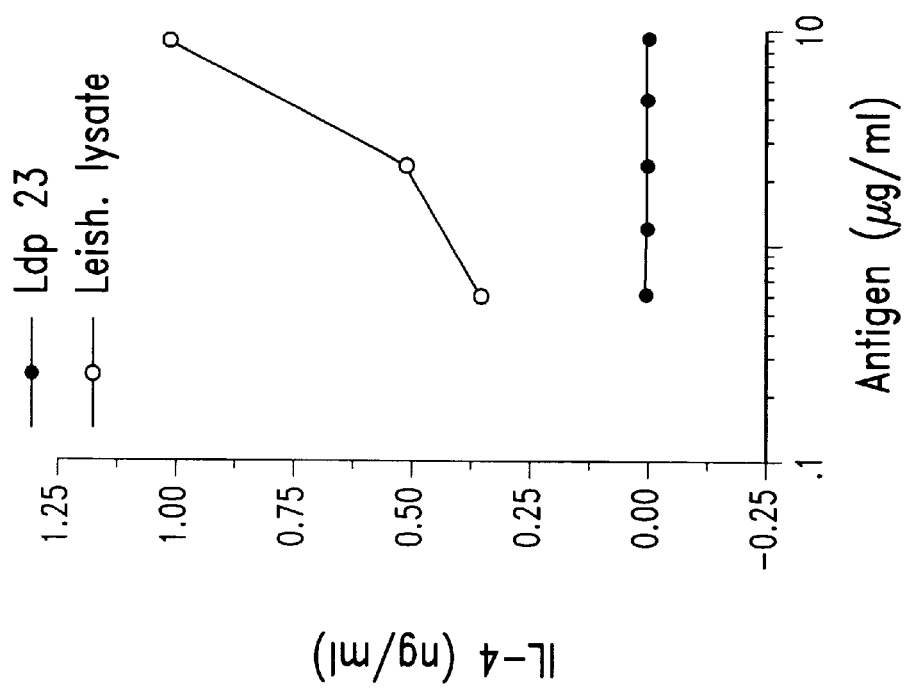
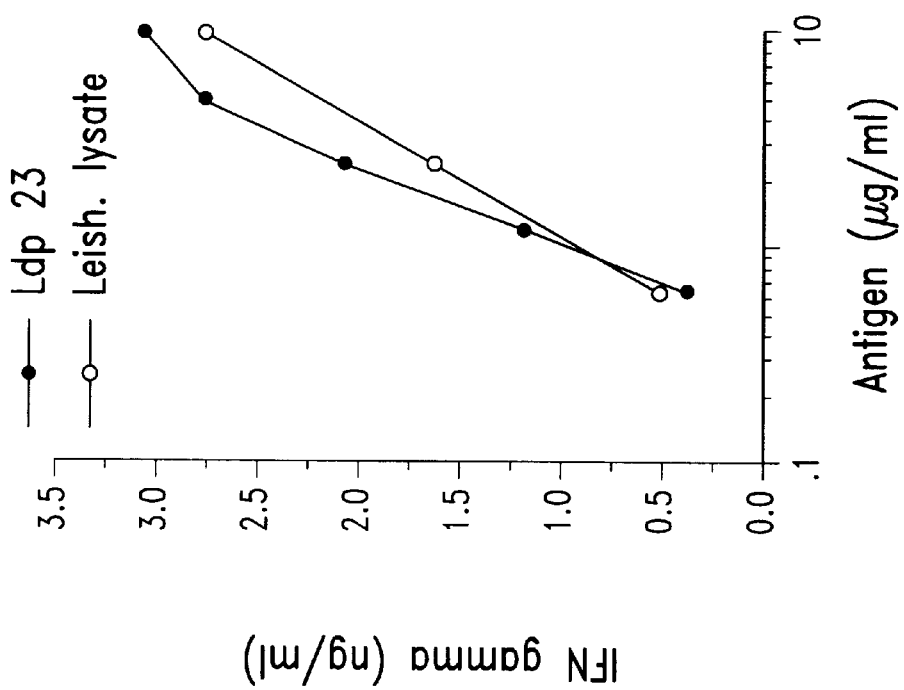
Fig. 8B
Fig. 8A

```
                                                 ----------------------------------------------------SLTDPAVLGEETHLRVRVVPDKANKTLTVEDNGIGMTK  85
                       MTETFAFQAEINQLMSLIINTFYSNKEIFLRDVISNASDACDKIRYQ.........DA.R.C......E..............  85
                       ............................................EL........NQ....D.S..I..............T......  85
MPEET░░░QPMEEEEV........A...................EL...S...L....E....SK.DSGKE.HINLI.N.QDRA..IV.T......  100

P                                                     P
ADLVNNLGTIARSGTKAFMEALEAGGDMSMIGQFGVGFYSAYLVADRVTVVSKNNSDEAY-WESSAGGTFTITSVQESDMKRGTSTTLHLKEDQQEYLEE  184
...............A.........................T......V.V..........AP.....LPARI........L....A  185
.E............................................D....T......V.PTPDC.L....RIV............  185
...I......K........Q..A.I............EK...IT.H.D..Q.A.......S..VRTDTGEP.G...KVI.......T.....  200

RRVKELIKKHSEFIGYDIELMVEKTAEKEVTDE----DEEEDESKKKSCGDEGEPKVEEVTEGG-ED-KKKKTKKVKEVKKT-YEVK---NKHKPLWTRD  274
..L.............T......----...---A..ADE.GE.........-E.-.......T.E-...Q---.........  272
..L.D..........AT......----..D.--AAATKNEEGE......KDDAE.GE.......TQE-FV..Q---.........  275
..I..IV....Q....P.T.F...ERD...S.DEAEEK.DKE.E..E.EEKESEDKPEI.DVGSDE..E..DGD..K.KKI.EK.ID.EEL..T..I...N  300

┌─Lbhsp83b
TKDVTKEEYAAFYKAISNDWEDTAATKHFSVEGQLEFRAIAFVPKRAPFDMFEPNKKRNNIKLYVRRVFIMDNCEDLCPDWLGFVKGVVDSEDLPLNISR  374
P............PP..........M.........L....................................................  372
P.........EPLS..............L..........S..................E..A..R............  375
PD.I.N...GE...SLT.....HL.V............LL...R.....L..NR..K............E.I.EY.N.IR............  400

ENLQQNKILKVIRKNIVKKCLELFEEIAENKEDYKQFYEQFGKNIKLGIHEDTANRKKLMELLRFYSTESGEEMTTLKDYVTRMKPEQKSIYYITGDSKK  474
...................M..V............................................V.........A..N......  472
............A...............K.....V.....S........H.S...D.........EG..C...V.....  475
.M...S........L......T.L.D..N..K....S.........SQ.....S....Y.TSA..D..VS....C....EN..H......ET.D  500

KLESSPFIEKARRCGLEVLFMTEPIDEYVMQQVKDFEDKKFACLTKEGVHFEESEEEKKQREEKKAACEKLCKTMKEVLGDKVEKVTVSERLLTSPCILV  574
.........Q.K.R.F......Y.......................E.T...................S.......  572
...T.....Q..R.F.......I..............T........E.T.Y.R...A..D.........V.....A.......  575
QVAN.A..V.RL.KH....IY.I......CV..L.E..G.TLVSV....LELP.D.....KQ....TKF.N....I..DI.EK.....V..N..V....C..  600

P
TSEFGWSAHMEQIMRNQALRDSSMAQYMVSKKTMEVNPDHPIIKELRRRVEADENDKAVKDLVFLLFDTSLLTSGFQLDDPTGYAERINRMIKLGLSLDE  674
........M...........M....L..K..........................E....-  671
............SA..M....I..A...V...K.........Y....A....T.....S.....H.........D  675
..TY..T.N..R..KA.....N.TMG..AA..HL.I....S..ET..QKA...K...S.....I..YE.A..S....S.E..QTH.N...Y.......GI..  700

EE--EEVA-EAPPAEAAPAEVTAGTSSMEQVD  703  Lbhsp83
..E--.E.V..AV..T............L..  701  Lahsp83
.D---NGNE..E..A.V...PV..........  704  Tchsp83
DDPTADDTSA.VTE.MP.L.GDDD..R..E..  734  Huhsp89
```

*Fig. 19*

```
GAATTCGGCACGAGGATCTGTACTTTATTGCTTCCAGCCTTTATTCACTCTTCGATTTCCTCTAACACCATGTCCTCCGAGCGCACCTTTATTGCCGTC  100
|5'-Adaptor|Spliced-leader|         5'-UT              |
                                                                          M  S  S  E  R  T  F  I  A  V
AAGCCGGACGGCGTGCAGCGCGGCCTCGTTGGCGAGATCATCGCCCGCTTCGAGCGCAAGGGCTACAAGCTCGTCGCCCTTGAAGATACTGCAGCCGACGA  200

K  P  D  G  V  Q  R  G  L  V  G  E  I  I  A  R  F  E  R  K  G  Y  K  L  V  A  L  K  I  L  Q  P  T
CGGAGCAGGCCCAGGGTCACTATAAGGACCTTTGCTCCAAGCCGTTTTTCCCGGCCCTTGTGAAGTACTTCTCCTCTGGCCCGATCGTGTGTATGGTGTG  300

T  E  Q  A  Q  G  H  Y  K  D  L  C  S  K  P  F  F  P  A  L  V  K  Y  F  S  S  G  P  I  V  C  M  V  W
GGAGGGTAAGAACGTGGTGAAGAGCGGCCGCGTGCTGCTCGGCGCGACGAACCCGGCCGACTCACAGCCCGGCACGATCCGTGGCGACTTTGCCGTGGAT  400

E  G  K  N  V  V  K  S  G  R  V  L  L  G  A  T  N  P  A  D  S  Q  P  G  T  I  R  G  D  F  A  V  D
GTGGGCCGCAACGTGTGCCACGGGTCCGACTCTGTGGAGAGCGCGGAGCGCGAGATCGCCTTTTGGTTCAAGGCGGATGAGATCGCGAGCTGGACGTCGC  500

V  G  R  N  V  C  H  G  S  D  S  V  E  S  A  E  R  E  I  A  F  W  F  K  A  D  E  I  A  S  W  T  S
ACTCCGTGTCCCAGATCTATGAGTAACGGTGATTGCGGACACGCTTTGAGGACGTAGCTGTACCCCCAATGAATTCTTCTCTGAAAACCACATCATAAGC  600
                                                                 |         3'-UT
 H  S  V  S  Q  I  Y  E
CTCTTAAGAGGTTATTTTTCTTGATCGATGCCCGGTGGTGACCAGCACCATTCCTTTATCGGATTCACTCACACTCCTAGCGAATCATGTAGTGCGGTGA  700
|                                 3'-UT                                                              |

GAGTGGGCTCTGGAGGAGACTGTTGTGTAGCCATGGCTTCAGGAGAGAAAACAAAATACAAGGAAAGGCAATATGTAACTATGGGGTTCCCTTTTTTACT  800
|                                 3'-UT                                                              |

ATGCAAAGTTTTTATAACTCCTGATCGGCAAAAACAACAACAACCGCCATACACCAAGAGCAAATGCTTTCTTCTGCGGACTGTGCTTCTGTTTTTTTTT  900
|                                 3'-UT                                                              |

ATGAAGGAGTGACTCGCGCGATGAAAAGTGTGTGCGTGGGAGATGTATTTCCTTTTTTTGTTCATAGTGGCGACAGCTCACTGTTGACGATGACAAAAAA  1000
|                                 3'-UT                                                              |

AAAAAAAAAAAAACTCGAG  1019
|Poly A tail/ Xhoi >
```

Fig. 21

SEQUENCE LISTING

<160> NUMBER OF SEQ ID NOS: 101

<210> SEQ ID NO 1
<211> LENGTH: 3134
<212> TYPE: DNA
<213> ORGANISM: Leishmania major -continued
<220> FEATURE:
<221> NAME/KEY: misc_feature
<222> LOCATION: (1)...(3134)
<223> OTHER INFORMATION: n = A,T,C or G

<400> SEQUENCE: 1

| | | | | | |
|---|---|---|---|---|---|
| caagtgtcga | aggacagtgt | tcnccgtgtg | agatcgccgg | ctgtgcgtgt | gaaggcggtg | 60 |
| ccatcggana | aacaacaccg | gtggannccgc | aggaaaccat | ctttctccgc | aggtctcttt | 120 |
| ttgttgtcga | ttgagagtgc | nccaaaccct | gctggtgccc | ttctcacata | tcatgttttt | 180 |
| cgttgtgcgc | tcgctttgcc | tttcctctcc | tttccctctc | ttccgtggtg | ccgtgtatac | 240 |
| ttctggcacc | cgctacgtca | cttcgctggt | ttgaacagaa | ccactgtgaa | cacccacggg | 300 |
| cgatcgcaca | catacacatc | cctcactcac | acacacagct | acatctatcc | tacataaagc | 360 |
| tgaaaaaaaa | gtctacgaac | aattttgttt | ttacagtgcg | ttgccgcaca | tttctccgta | 420 |
| atggacgcaa | ctgagctgaa | gaacaagggg | aacgaagagt | tctccgccgg | ccgctatgtg | 480 |
| gaggcggtga | actacttctc | aaaggcgatc | cagttggatg | agcagaacag | tgtcctctac | 540 |
| agcaaccgct | ccgcctgttt | tgcagccatg | cagaaataca | aggacgcgct | ggacgacgcc | 600 |
| gacaagtgca | tctcgatcaa | gccgaattgg | gccaagggct | acgtgcgccg | aggagcagct | 660 |
| ctccatggca | tgcgccgcta | cgacgatgcc | attgccgcgt | atgaaaaggg | gctcaaggtg | 720 |
| gaccct tcca | acagcggctg | cgcgcagggc | gtgaaggacg | tgcaggtagc | caaggcccgc | 780 |
| gaagcacgtg | accccatcgc | tcgcgtcttc | acccgggagg | cgttccgcaa | gatccaagag | 840 |
| aatcccaagc | tgtctctact | tatgctgcag | ccggactacg | tgaagatggt | agacaccgtc | 900 |
| atccgcgacc | cttcgcaggg | ccggctgtac | atggaagacc | agcgctttgc | cctgacgctc | 960 |
| atgtacctga | gcggaatgaa | gattcccaac | gatggtgatg | gcgaggagga | ggaacgtccg | 1020 |
| tctgcgaagg | cggcagagac | agcgaagcca | aagaggaga | agcctctcac | cgacaacgag | 1080 |
| aaggaggccc | tggcgctcaa | ggaggagggc | aacaagctgt | acctctcgaa | gaagtttgag | 1140 |
| gaggcgctga | ccaagtacca | agaggcgcag | gtgaaagacc | ccaacaacac | tttatacatt | 1200 |
| ctgaacgtgt | cggccgtgta | cttcgagcag | ggtgactacg | acaagtgcat | cgccgagtgc | 1260 |
| gagcacggta | tcgagcacgg | tcgcgagaac | cactgcgact | acacaatcat | tgcgaagctc | 1320 |
| atgacccgga | acgccttgtg | cctccagagg | cagaggaagt | acgaggctgc | tatcgacctt | 1380 |
| tacaagcgcg | cccttgtcga | gtggcgtaac | cctgacaccc | tcaagaagct | gacggagtgc | 1440 |
| gagaaggagc | accaaaaggc | ggtggaggaa | gcctacatcg | atcctgagat | cgcgaagcag | 1500 |
| aagaaagacg | aagtaaccca | gtacttcaag | gaggataagt | tccccgaggc | cgtggcagcg | 1560 |
| tacacggagg | ccatcaagcg | caaccctgcc | gagcacacct | cctacagcaa | tcgcgcggcc | 1620 |
| gcgtacatca | agcttggagc | cttcaacgac | gccctcaagg | acgcggagaa | gtgcattgag | 1680 |
| ctgaagcccg | actttgttaa | gggctacgcg | cgcaagggtc | atgcttactt | ttggaccaag | 1740 |
| cagtacaacc | gcgcgctgca | ggcgtacgat | gagggcctca | aggtggaccc | gagcaatgcg | 1800 |
| gactgcaagg | atgggcggta | tcgcacaatc | atgaagattc | aggagatggc | atctggccaa | 1860 |
| tccgcggatg | gcgacgaggc | ggcgcgccgg | gccatggacg | atcctgaaat | cgcggcaatc | 1920 |
| atgcaagata | gctacatgca | actagtgttg | aaggagatgc | agaacgatcc | cacgcgcatt | 1980 |
| caggagtaca | tgaaggactc | cgggatctca | tcgaagatca | acaagctgat | ttcagctggc | 2040 |
| atcattcgtt | ttggtcagta | gacttctacg | ctgcctcatc | ttttccgtgt | ctttgcgtcg | 2100 |
| gcgggtatcg | taaagcacaa | taaagcagcg | attcacatgc | acgagtaaag | tgctgcgcct | 2160 |

-continued

```
ctcaaacacg acgtcgaggc tgtggtgcag atgcgcgtcc tgcatgaagg tagtgaagag      2220
gaaagtaagg gatgttgttt gtgggccttc gtggctgcgc acacacctct tatctccttc      2280
gcttggtacc ttctcccttt ttcgtcttca ccccccttc tcttctcacg ctctccctgg       2340
cgcggtggtg caacgatttc gttttattta cgtctgtgta gctcctctat tcaacggtgc      2400
gatgacgcta acgaagctgg cctgtattcg gctaaggcga aggcaaaaga ctaggagggg      2460
ggggggaagg agacggcgtg accatcactg cgaagaaaca agccgaagaa aaggccccga      2520
acgcctgcat ttccgcgcgc cctcgcccgc cttccttcct tccttcgctc tctctctctc      2580
tctctctcgc tatcttctca acggagacat gaaaggcgtt tgttaggaaa agagggggg       2640 gggaagagtg ggacgacgcg ctgcgtcttt tgggcactgg tcacgtgcgt caccctcttt      2700
ttttatctct attggcactg tcttgtttct tttcccttc ctatcatacg cgtctcgcaa       2760
acgactccgc gctgagcagc catgtgctgc ggcgtggagg aagtacacag acatcacgga      2820
tgcatatgtg cgcgtccgtg tacgcgcttg tatgggcctt ctaacagcgc ctgtgtgtgt      2880
ttgtgtgtgt gtgtgtgtgt gtgtctgtgt atttcgagcg tctgtatgct attctattaa      2940
gcaccgaaga agagacacac acgacagcga aggagatggt gtcggctttt cggctaatca      3000
ctcccttcca tagcttctct gaaggaggct ctcttccaga ggaatagact gcagatgggg      3060
tccacgttta tctgaggagt caacggaaaa aaaaaaaaaa aaaaaaaaaa aaaaaaaaa       3120 aaaaaaaact cgag                                                        3134
```

<210> SEQ ID NO 2
<211> LENGTH: 546
<212> TYPE: PRT
<213> ORGANISM: Leishmania major

<400> SEQUENCE: 2

```
Met Asp Ala Thr Glu Leu Lys Asn Lys Gly Asn Glu Glu Phe Ser Ala
  1               5                  10                  15

Gly Arg Tyr Val Glu Ala Val Asn Tyr Phe Ser Lys Ala Ile Gln Leu
             20                  25                  30

Asp Glu Gln Asn Ser Val Leu Tyr Ser Asn Arg Ser Ala Cys Phe Ala
         35                  40                  45

Ala Met Gln Lys Tyr Lys Asp Ala Leu Asp Asp Ala Asp Lys Cys Ile
     50                  55                  60

Ser Ile Lys Pro Asn Trp Ala Lys Gly Tyr Val Arg Arg Gly Ala Ala
 65                  70                  75                  80

Leu His Gly Met Arg Arg Tyr Asp Asp Ala Ile Ala Ala Tyr Glu Lys
                 85                  90                  95

Gly Leu Lys Val Asp Pro Ser Asn Ser Gly Cys Ala Gln Gly Val Lys
            100                 105                 110

Asp Val Gln Val Ala Lys Ala Arg Glu Ala Arg Asp Pro Ile Ala Arg
        115                 120                 125

Val Phe Thr Pro Glu Ala Phe Arg Lys Ile Gln Glu Asn Pro Lys Leu
    130                 135                 140

Ser Leu Leu Met Leu Gln Pro Asp Tyr Val Lys Met Val Asp Thr Val
145                 150                 155                 160

Ile Arg Asp Pro Ser Gln Gly Arg Leu Tyr Met Glu Asp Gln Arg Phe
                165                 170                 175

Ala Leu Thr Leu Met Tyr Leu Ser Gly Met Lys Ile Pro Asn Asp Gly
            180                 185                 190

Asp Gly Glu Glu Glu Glu Arg Pro Ser Ala Lys Ala Ala Glu Thr Ala
```

|     |     |     |     | 195 |     |     |     |     | 200 |     |     |     |     | 205 |     |
|-----|-----|-----|-----|-----|-----|-----|-----|-----|-----|-----|-----|-----|-----|-----|-----|

Lys Pro Lys Glu Glu Lys Pro Leu Thr Asp Asn Glu Lys Glu Ala Leu
210                 215                 220

Ala Leu Lys Glu Glu Gly Asn Lys Leu Tyr Leu Ser Lys Lys Phe Glu
225                 230                 235                 240

Glu Ala Leu Thr Lys Tyr Gln Glu Ala Gln Val Lys Asp Pro Asn Asn
            245                 250                 255

Thr Leu Tyr Ile Leu Asn Val Ser Ala Val Tyr Phe Glu Gln Gly Asp
            260                 265                 270

Tyr Asp Lys Cys Ile Ala Glu Cys Glu His Gly Ile Glu His Gly Arg
        275                 280                 285

Glu Asn His Cys Asp Tyr Thr Ile Ile Ala Lys Leu Met Thr Arg Asn
    290                 295                 300

Ala Leu Cys Leu Gln Arg Gln Arg Lys Tyr Glu Ala Ala Ile Asp Leu
305                 310                 315                 320

Tyr Lys Arg Ala Leu Val Glu Trp Arg Asn Pro Asp Thr Leu Lys Lys
            325                 330                 335

Leu Thr Glu Cys Glu Lys Glu His Gln Lys Ala Val Glu Glu Ala Tyr
            340                 345                 350

Ile Asp Pro Glu Ile Ala Lys Gln Lys Lys Asp Glu Gly Asn Gln Tyr
        355                 360                 365

Phe Lys Glu Asp Lys Phe Pro Glu Ala Val Ala Ala Tyr Thr Glu Ala
370                 375                 380

Ile Lys Arg Asn Pro Ala Glu His Thr Ser Tyr Ser Asn Arg Ala Ala
385                 390                 395                 400

Ala Tyr Ile Lys Leu Gly Ala Phe Asn Asp Ala Leu Lys Asp Ala Glu
            405                 410                 415

Lys Cys Ile Glu Leu Lys Pro Asp Phe Val Lys Gly Tyr Ala Arg Lys
            420                 425                 430

Gly His Ala Tyr Phe Trp Thr Lys Gln Tyr Asn Arg Ala Leu Gln Ala
        435                 440                 445

Tyr Asp Glu Gly Leu Lys Val Asp Pro Ser Asn Ala Asp Cys Lys Asp
    450                 455                 460

Gly Arg Tyr Arg Thr Ile Met Lys Ile Gln Glu Met Ala Ser Gly Gln
465                 470                 475                 480

Ser Ala Asp Gly Asp Glu Ala Arg Arg Ala Met Asp Asp Pro Glu
            485                 490                 495

Ile Ala Ala Ile Met Gln Asp Ser Tyr Met Gln Leu Val Leu Lys Glu
            500                 505                 510

Met Gln Asn Asp Pro Thr Arg Ile Gln Glu Tyr Met Lys Asp Ser Gly
        515                 520                 525

Ile Ser Ser Lys Ile Asn Lys Leu Ile Ser Ala Gly Ile Ile Arg Phe
    530                 535                 540

Gly Gln
545

<210> SEQ ID NO 3
<211> LENGTH: 676
<212> TYPE: DNA
<213> ORGANISM: Leishmania donovani

<400> SEQUENCE: 3
aattcggcac gaggcattgt gcataatggt caagtcccac tacatctgcg cgggccgcct       60
ggtgcgcatc ctgcgtggcc cccgccagga ccgcgttggt gtgatcgtcg acattgtcga      120

-continued

| | |
|---|---|
| cgcgaaccgc gtgctggtgg agaacccgga ggacgcgaag atgtggcgcc acgtgcagaa | 180 |
| cctgaagaac gtggagccgc tgaagtactg cgtgagcgtc agccgcaact gcagcgcgaa | 240 |
| ggcgctgaag gatgcgctgg cctcgtcgaa ggcgctggaa agtacgcga agacgcgcac | 300 |
| tgctgcgcgc gtggaggcga agaaggcgtg cgccgcgtcg acggacttcg agcgctacca | 360 |
| gctgcgcgtt gcgcgccgtt ctcgcgcgca ctgggcgcgc aaggtgttcg acgagaagga | 420 |
| cgcgaagacg cccgtgtcgt ggcacaaggt tgcgctgaag aagatgcaga gaaggccgc | 480 |
| aaagatggac tcgaccgagg gcgctaagag gcgcatgcag aaggcgatcg ctgcccgcaa | 540 |
| ggcgaaaaag taaggccata ccctcacttc gcttgtttcg tgattttcg tgggagtcgg | 600 |
| tggccctacc agcggtcttt cattggctta tttctatccg gtctgaaaga ggtacaaaaa | 660 |
| aaaaaaaaaa aaaaaa | 676 |

<210> SEQ ID NO 4
<211> LENGTH: 175
<212> TYPE: PRT
<213> ORGANISM: Leishmania donovani

<400> SEQUENCE: 4

Met Val Lys Ser His Tyr Ile Cys Ala Gly Arg Leu Val Arg Ile Leu
1               5                   10                  15

Arg Gly Pro Arg Gln Asp Arg Val Gly Val Ile Val Asp Ile Val Asp
            20                  25                  30

Ala Asn Arg Val Leu Val Glu Asn Pro Glu Asp Ala Lys Met Trp Arg
        35                  40                  45

His Val Gln Asn Leu Lys Asn Val Glu Pro Leu Lys Tyr Cys Val Ser
    50                  55                  60

Val Ser Arg Asn Cys Ser Ala Lys Ala Leu Lys Asp Ala Leu Ala Ser
65                  70                  75                  80

Ser Lys Ala Leu Glu Lys Tyr Ala Lys Thr Arg Thr Ala Ala Arg Val
                85                  90                  95

Glu Ala Lys Lys Ala Cys Ala Ala Ser Thr Asp Phe Glu Arg Tyr Gln
            100                 105                 110

Leu Arg Val Ala Arg Arg Ser Arg Ala His Trp Ala Arg Lys Val Phe
        115                 120                 125

Asp Glu Lys Asp Ala Lys Thr Pro Val Ser Trp His Lys Val Ala Leu
    130                 135                 140

Lys Lys Met Gln Lys Lys Ala Ala Lys Met Asp Ser Thr Glu Gly Ala
145                 150                 155                 160

Lys Arg Arg Met Gln Lys Ala Ile Ala Ala Arg Lys Ala Lys Lys
                165                 170                 175

<210> SEQ ID NO 5
<211> LENGTH: 2040
<212> TYPE: DNA
<213> ORGANISM: Leishmania braziliensis

<400> SEQUENCE: 5

| | |
|---|---|
| cgcggtggcg gccgctctag aactagtgga tcccccgggc tgcaggaatt cggcacgaga | 60 |
| gagcctgacg gacccggcgg tgctgggcga ggagactcac ctgcgcgtcc gcgtggtgcc | 120 |
| ggacaaggcg aacaagacgc tgacggtgga ggataacggc atcggcatga ccaaggcgga | 180 |
| cctcgtgaac aatctgggca cgatcgcgcg ctccggcacg aaggctttca tggaggcact | 240 |
| ggaggccggc ggcgacatga gcatgatcgg ccagttcggt gtcggcttct actccgcgta | 300 |

-continued

```
ccttgtggcg gaccgcgtga cggtggtgtc gaagaacaac tcggacgagg cgtactggga    360
atcgtctgcg gggggcacgt tcaccatcac gagcgtgcag gagtcggaca tgaagcgcgg    420
cacgagtaca acgctgcacc taaaggagga ccagcaggag tacctggagg agcgccgggt    480
gaaggagctg atcaagaagc actccgagtt catcggctac gacatcgagc tgatggtgga    540
gaagacggcg gagaaggagg tgacggacga ggacgaggag gaggacgagt cgaagaagaa    600
gtcctgcggg gacgagggcg agccgaaggt ggaggaggtg acggagggcg gcgaggacaa    660
gaagaagaag acgaagaagg tgaaggaggt gaagaagacg tacgaggtca gaacaagca    720
caagccgctc tggacgcgcg cacgaagga cgtgacgaag gaggagtacg cggccttcta    780
caaggccatc tccaacgact gggaggacac ggcggcgacg aagcacttct cggtggaggg    840
ccagctggag ttccgcgcga tcgcgttcgt gccgaagcgc gcgccgttcg acatgttcga    900
gccgaacaag aagcgcaaca acatcaagct gtacgtgcgc cgcgtgttca tcatggacaa    960
ctgcgaggac ctgtgcccgg actggctcgg cttcgtgaag ggcgtcgtgg acagcgagga   1020
cctgccgctg aacatctcgc gcgagaacct gcagcagaac aagatcctga aggtgatccg   1080
caagaacatc gtgaagaagt gcctggagct gttcgaagag atagcggaga caaggagga   1140
ctacaagcag ttctacgagc agttcggcaa gaacatcaag ctgggcatcc acgaggacac   1200
ggcgaaccgc aagaagctga tggagttgct gcgcttctac agcaccgagt cgggggagga   1260
gatgacgaca ctgaaggact acgtgacgcg catgaagccg gagcagaagt cgatctacta   1320
catcactggc gacagcaaga agaagctgga gtcgtcgccg ttcatcgaga aggcgagacg   1380
ctgcgggctc gaggtgctgt tcatgacgga gccgatcgac gagtacgtga tgcagcaggt   1440
gaaggacttc gaggacaaga agttcgcgtg cctgacgaag gaaggcgtgc acttcgagga   1500
gtccgaggag gagaagaagc agcgcgagga gaagaaggcg gcgtgcgaga agctgtgcaa   1560
gacgatgaag gaggtgctgg gcgacaaggt ggagaaggtg accgtgtcgg agcgcctgtt   1620
gacgtcgccg tgcatcctgg tgacgtcgga gtttgggtgg tcggcgcaca tggaacagat   1680
catgcgcaac caggcgctgc gcgactccag catggcgcag tacatggtgt ccaagaagac   1740
gatggaggtg aacccgacc accccatcat caaggagctg cgccgccgcg tggaggcgga   1800
cgagaacgac aaggccgtga aggacctcgt cttcctgctc ttcgacacgt cgctgctcac   1860
gtccggcttc cagctggatg accccaccgg ctacgccgag cgcatcaacc gcatgatcaa   1920
gctcggcctg tcgctcgacg aggaggagga ggaggtcgcc gaggcgccgc cggccgaggc   1980
agccccgcg gaggtcaccg ccggcacctc cagcatggag caggtggact gagccggtaa   2040
```

<210> SEQ ID NO 6
<211> LENGTH: 656
<212> TYPE: PRT
<213> ORGANISM: Leshmania brailiensis

<400> SEQUENCE: 6

Ser Leu Thr Asp Pro Ala Val Leu Gly Glu Glu Thr His Leu Arg Val
 1               5                  10                  15

Arg Val Pro Asp Lys Ala Asn Lys Thr Leu Thr Val Glu Asp Asn
            20                  25                  30

Gly Ile Gly Met Thr Lys Ala Asp Leu Val Asn Asn Leu Gly Thr Ile
        35                  40                  45

Ala Arg Ser Gly Thr Lys Ala Phe Met Glu Ala Leu Glu Ala Gly Gly
    50                  55                  60

-continued

```
Asp Met Ser Met Ile Gly Gln Phe Gly Val Gly Phe Tyr Ser Ala Tyr
 65                  70                  75                  80

Leu Val Ala Asp Arg Val Thr Val Ser Lys Asn Asn Ser Asp Glu
             85                  90                  95

Ala Tyr Trp Glu Ser Ser Ala Gly Gly Thr Phe Thr Ile Thr Ser Val
            100                 105                 110

Gln Glu Ser Asp Met Lys Arg Gly Thr Ser Thr Thr Leu His Leu Lys
            115                 120                 125

Glu Asp Gln Gln Glu Tyr Leu Glu Arg Arg Val Lys Glu Leu Ile
        130                 135                 140

Lys Lys His Ser Glu Phe Ile Gly Tyr Asp Ile Glu Leu Met Val Glu
145                 150                 155                 160

Lys Thr Ala Glu Lys Glu Val Thr Asp Glu Asp Glu Glu Asp Glu
            165                 170                 175

Ser Lys Lys Lys Ser Cys Gly Asp Glu Gly Glu Pro Lys Val Glu Glu
            180                 185                 190

Val Thr Glu Gly Gly Glu Asp Lys Lys Lys Thr Lys Lys Val Lys
        195                 200                 205

Glu Val Lys Lys Thr Tyr Glu Val Lys Asn Lys His Lys Pro Leu Trp
        210                 215                 220

Thr Arg Asp Thr Lys Asp Val Thr Lys Glu Glu Tyr Ala Ala Phe Tyr
225                 230                 235                 240

Lys Ala Ile Ser Asn Asp Trp Glu Asp Thr Ala Ala Thr Lys His Phe
                245                 250                 255

Ser Val Glu Gly Gln Leu Glu Phe Arg Ala Ile Ala Phe Val Pro Lys
            260                 265                 270

Arg Ala Pro Phe Asp Met Phe Glu Pro Asn Lys Lys Arg Asn Asn Ile
            275                 280                 285

Lys Leu Tyr Val Arg Arg Val Phe Ile Met Asp Asn Cys Glu Asp Leu
        290                 295                 300

Cys Pro Asp Trp Leu Gly Phe Val Lys Gly Val Val Asp Ser Glu Asp
305                 310                 315                 320

Leu Pro Leu Asn Ile Ser Arg Glu Asn Leu Gln Gln Asn Lys Ile Leu
            325                 330                 335

Lys Val Ile Arg Lys Asn Ile Val Lys Lys Cys Leu Glu Leu Phe Glu
            340                 345                 350

Glu Ile Ala Glu Asn Lys Glu Asp Tyr Lys Gln Phe Tyr Glu Gln Phe
        355                 360                 365

Gly Lys Asn Ile Lys Leu Gly Ile His Glu Asp Thr Ala Asn Arg Lys
        370                 375                 380

Lys Leu Met Glu Leu Leu Arg Phe Tyr Ser Thr Glu Ser Gly Glu Glu
385                 390                 395                 400

Met Thr Thr Leu Lys Asp Tyr Val Thr Arg Met Lys Pro Glu Gln Lys
                405                 410                 415

Ser Ile Tyr Tyr Ile Thr Gly Asp Ser Lys Lys Leu Glu Ser Ser
            420                 425                 430

Pro Phe Ile Glu Lys Ala Arg Arg Cys Gly Leu Glu Val Leu Phe Met
        435                 440                 445

Thr Glu Pro Ile Asp Glu Tyr Val Met Gln Gln Val Lys Asp Phe Glu
        450                 455                 460

Asp Lys Lys Phe Ala Cys Leu Thr Lys Glu Gly Val His Phe Glu Glu
465                 470                 475                 480

Ser Glu Glu Glu Lys Lys Gln Arg Glu Glu Lys Lys Ala Ala Cys Glu
```

-continued

```
                485                 490                 495
Lys Leu Cys Lys Thr Met Lys Glu Val Leu Gly Asp Lys Val Glu Lys
                500                 505                 510
Val Thr Val Ser Glu Arg Leu Leu Thr Ser Pro Cys Ile Leu Val Thr
            515                 520                 525
Ser Glu Phe Gly Trp Ser Ala His Met Glu Gln Ile Met Arg Asn Gln
        530                 535                 540
Ala Leu Arg Asp Ser Ser Met Ala Gln Tyr Met Val Ser Lys Lys Thr
545                 550                 555                 560
Met Glu Val Asn Pro Asp His Pro Ile Ile Lys Glu Leu Arg Arg Arg
                565                 570                 575
Val Glu Ala Asp Glu Asn Asp Lys Ala Val Lys Asp Leu Val Phe Leu
            580                 585                 590
Leu Phe Asp Thr Ser Leu Leu Thr Ser Gly Phe Gln Leu Asp Asp Pro
        595                 600                 605
Thr Gly Tyr Ala Glu Arg Ile Asn Arg Met Ile Lys Leu Gly Leu Ser
    610                 615                 620
Leu Asp Glu Glu Glu Glu Val Ala Glu Ala Pro Pro Ala Glu Ala
625                 630                 635                 640
Ala Pro Ala Glu Val Thr Ala Gly Thr Ser Ser Met Glu Gln Val Asp
                645                 650                 655
```

<210> SEQ ID NO 7
<211> LENGTH: 1771
<212> TYPE: DNA
<213> ORGANISM: Leishmania tropica

<400> SEQUENCE: 7

| | | | | | |
|---|---|---|---|---|---|
| caggcccgcg | tccaggccct | cgaggaggca | gcgcgtctcc | gcgcggagct | ggaggcggcc | 60 |
| gaggaggcgg | cccgcctgga | tgtcatgcat | gcggccgagc | aggcccgtgt | ccaggccctc | 120 |
| gaggaggcag | cgcgtctccg | cgcggagctg | gaggaggccg | aggaggcggc | ccgcctggat | 180 |
| gtcatgcatg | cggccgagca | ggcccgcgtc | caggccctcg | aggaggcagc | gcgtctccgc | 240 |
| gcggagctgg | aggctgccga | ggaggcggcg | cgcctggagg | ccatgcacga | ggccgagcag | 300 |
| gcccgctccc | aggccctcga | ggaggcagcg | cgtctccgcg | cggagctgga | ggaagccgag | 360 |
| gaggcggccc | gcctggatgt | catgcatgcg | gccgagcagg | cccgcgtcca | ggccctcgag | 420 |
| gaggcagcgc | gtctccgcgc | ggagctggag | gaggccgagg | aggcggcccg | cctggaggcc | 480 |
| atgcacgagg | ccgagcaggc | ccgctcccag | gccctcgagg | aggcagcgcg | tctccgcgcg | 540 |
| gagctggagc | ggccgaggac | ggcggcccgc | ctggatgtca | tgcacgaggc | cgagcaggcc | 600 |
| cgtgtccagg | ccctcgagga | ggcggcgcgc | ctggatgtca | tgcacgaggc | cgagcaggcc | 660 |
| cgcgtccagg | ccctcgagga | ggcagcgcgt | ctccgcgcgg | agctggaggc | ggccgaggag | 720 |
| gcggcccgcc | tggatgtcat | gcacgaggcc | gagcaggccc | gcgtccaggc | cctcgaggag | 780 |
| gcagcgcgtc | tccgcgcgga | gctggaggcg | gccgaggagg | cggcccgcct | ggatgtcatg | 840 |
| cacgagggcg | agcaggcccg | tgtccaggcc | tcgaggagg | cggcccgcct | ggaggccatg | 900 |
| cacgaggccg | agcaggcccg | ctcccaggcc | tcgaggagg | cagcgcgtct | ctgcgcggag | 960 |
| ctggaggctg | aggaggagga | aaaagatgag | cggccggcga | cgtcgagcta | cagcgaggag | 1020 |
| tgcaaagggc | gactgctatc | gagggcgcgg | ccggatccgc | ggaggccgct | gccgcggccg | 1080 |
| ttcattggga | tgtcactgtt | ggaggatgtg | gagaagagta | ttctcattgt | ggacgggctc | 1140 |
| tacagggatg | ggccggcgta | ccagacgggc | atccgcctcg | gggatgtcct | cttgcgtatc | 1200 |

-continued

```
gcggggtttt acgtggattc aatagcgaag gcgaggcagg tggtcgatgc gcgttgccgc    1260
tgcggctgcg tcgttcccgt gacgctggcg acgaagatga accagcagta cagcgtggct    1320
ctgtatatca tgacggtgga tccgcagcac aacgacaagc cctttttttt tgatgtgcac    1380
atccaccacc gcatcgagag ctcgcacatg gggaagaagg cgcagtggat ggaagttctt    1440
gagagcccat ccgtatcttc ggctgccacc accctctcg tgccgctctt gcgtgagccg     1500
acgccgcgta ggggctcaga gctgcagtca agtgctcgtt ccgccttcgt tgccacgtct    1560
tacttctcga gcgcgcgcag gtcggtcagc tcagaaagtg agcgaccgcg cgggtcctct    1620
agcgtggcta tggcggagga ggcgatcgcg ctggcgccgc aagggtatac cccacccaac    1680
caagtgcgcg gccgtagttg acgtctctgt gtgagtgtgt gtcgctccgt ctccttcctt    1740
tttcgtcatg tgttttattc atttcttttt c                                   1771
```

<210> SEQ ID NO 8
<211> LENGTH: 566
<212> TYPE: PRT
<213> ORGANISM: Leishmania tropica

<400> SEQUENCE: 8

```
Gln Ala Arg Val Gln Ala Leu Glu Glu Ala Ala Arg Leu Arg Ala Glu
  1               5                  10                  15

Leu Glu Ala Ala Glu Glu Ala Ala Arg Leu Asp Val Met His Ala Ala
             20                  25                  30

Glu Gln Ala Arg Val Gln Ala Leu Glu Glu Ala Ala Arg Leu Arg Ala
         35                  40                  45

Glu Leu Glu Glu Ala Glu Glu Ala Ala Arg Leu Asp Val Met His Ala
     50                  55                  60

Ala Glu Gln Ala Arg Val Gln Ala Leu Glu Glu Ala Ala Arg Leu Arg
 65                  70                  75                  80

Ala Glu Leu Glu Ala Ala Glu Glu Ala Ala Arg Leu Glu Ala Met His
                 85                  90                  95

Glu Ala Glu Gln Ala Arg Ser Gln Ala Leu Glu Glu Ala Ala Arg Leu
            100                 105                 110

Arg Ala Glu Leu Glu Glu Ala Glu Glu Ala Ala Arg Leu Asp Val Met
        115                 120                 125

His Ala Ala Glu Gln Ala Arg Val Gln Ala Leu Glu Glu Ala Ala Arg
    130                 135                 140

Leu Arg Ala Glu Leu Glu Glu Ala Glu Glu Ala Ala Arg Leu Glu Ala
145                 150                 155                 160

Met His Glu Ala Glu Gln Ala Arg Ser Gln Ala Leu Glu Glu Ala Ala
                165                 170                 175

Arg Leu Arg Ala Glu Leu Glu Ala Ala Glu Glu Ala Ala Arg Leu Asp
            180                 185                 190

Val Met His Glu Ala Glu Gln Ala Arg Val Gln Ala Leu Glu Glu Ala
        195                 200                 205

Ala Arg Leu Asp Val Met His Glu Ala Glu Gln Ala Arg Val Gln Ala
    210                 215                 220

Leu Glu Glu Ala Ala Arg Leu Arg Ala Glu Leu Glu Ala Ala Glu Glu
225                 230                 235                 240

Ala Ala Arg Leu Asp Val Met His Glu Ala Glu Gln Ala Arg Val Gln
                245                 250                 255

Ala Leu Glu Glu Ala Ala Arg Leu Arg Ala Glu Leu Glu Ala Ala Glu
            260                 265                 270
```

```
Glu Ala Ala Arg Leu Asp Val Met His Glu Gly Glu Gln Ala Arg Val
                275                 280                 285

Gln Ala Leu Glu Glu Ala Ala Arg Leu Glu Ala Met His Glu Ala Glu
            290                 295                 300

Gln Ala Arg Ser Gln Ala Leu Glu Glu Ala Ala Arg Leu Cys Ala Glu
305                 310                 315                 320

Leu Glu Ala Glu Glu Glu Lys Asp Glu Arg Pro Ala Thr Ser Ser
                325                 330                 335

Tyr Ser Glu Glu Cys Lys Gly Arg Leu Leu Ser Arg Ala Arg Pro Asp
                340                 345                 350

Pro Arg Arg Pro Leu Pro Arg Pro Phe Ile Gly Met Ser Leu Leu Glu
                355                 360                 365

Asp Val Glu Lys Ser Ile Leu Ile Val Asp Gly Leu Tyr Arg Asp Gly
                370                 375                 380

Pro Ala Tyr Gln Thr Gly Ile Arg Leu Gly Asp Val Leu Leu Arg Ile
385                 390                 395                 400

Ala Gly Val Tyr Val Asp Ser Ile Ala Lys Ala Arg Gln Val Val Asp
                405                 410                 415

Ala Arg Cys Arg Cys Gly Cys Val Val Pro Val Thr Leu Ala Thr Lys
                420                 425                 430

Met Asn Gln Gln Tyr Ser Val Ala Leu Tyr Ile Met Thr Val Asp Pro
                435                 440                 445

Gln His Asn Asp Lys Pro Phe Phe Phe Asp Val His Ile His His Arg
                450                 455                 460

Ile Glu Ser Ser His Met Gly Lys Lys Ala Gln Trp Met Glu Val Leu
465                 470                 475                 480

Glu Ser Pro Ser Val Ser Ser Ala Ala Thr Thr Pro Leu Val Pro Leu
                485                 490                 495

Leu Arg Glu Pro Thr Pro Arg Arg Gly Ser Glu Leu Gln Ser Ser Ala
                500                 505                 510

Arg Ser Ala Phe Val Ala Thr Ser Tyr Phe Ser Ser Ala Arg Arg Ser
                515                 520                 525

Val Ser Ser Glu Ser Glu Arg Pro Arg Gly Ser Ser Ser Val Ala Met
                530                 535                 540

Ala Glu Glu Ala Ile Ala Leu Ala Pro Gln Gly Tyr Thr Pro Pro Asn
545                 550                 555                 560

Gln Val Arg Gly Arg Ser
                565

<210> SEQ ID NO 9
<211> LENGTH: 1618
<212> TYPE: DNA
<213> ORGANISM: Leishmania braziliensis

<400> SEQUENCE: 9
ccactctctc ggtcgtctgt ctcccacgcg cgcacgcagt tgatttccgc cttcttaaac    60
gctctctttt tttttatttt tcacctgacc aaccgcacca cgtcggcctc catcatgtcg   120
cagcaagacc gagttgcccc acaggaccag gactcgttcc tcgacgacca gcccggcgtc   180
cgcccgatcc cgtccttcga tgacatgccg ttgcaccaga accttctgcg cggcatctac   240
tcgtacggct tcgagaaacc gtccagcatc cagcagcgcg ccatcgcccc cttcacgcgc   300
ggcggcgaca tcatcgcgca ggcgcagtcc ggtaccggca gacgggcgc cttctccatc   360 ggcctgctgc agcgcctgga cttccgccac aacctgatcc agggcctcgt gctctccccg   420
```

```
acccgcgagc tggccctgca gacggcggag gtgatcagcc gcatcggcga gttcctgtcg      480
aacagcgcga agttctgtga gacctttgtg ggtggcacgc gcgtgcagga tgacctgcgc      540
aagctgcagg ctggcgtcgt cgtcgccgtg gggacgccgg gccgcgtgtc cgacgtgatc      600
aagcgcggcg cgctgcgcac cgagtccctg cgcgtgctgg tgctcgacga ggctgatgag      660
atgctgtctc agggcttcgc ggatcagatt tacgagatct tccgcttcct gccgaaggac      720
atccaggtcg cgctcttctc cgccacgatg ccggaggagg tgctggagct gacaaagaag      780
ttcatgcgcg accccgtacg cattctcgtg aagcgcgaga gcctgacgct ggagggcatc      840
aagcagttct tcatcgccgt cgaggaggag cacaagctgg acacgctgat ggacctgtac      900
gagaccgtgt ccatcgcgca gtccgtcatc ttcgccaaca cccgccgcaa ggtggactgg      960
atcgccgaga agctgaatca gagcaaccac accgtcagca gcatgcacgc cgagatgccc     1020
aagagcgacc gcgagcgcgt catgaacacc ttccgcagcg gcagctcccg cgtgctcgta     1080
acgaccgacc tcgtggcccg cggcatcgac gtgcaccacg tgaacatcgt catcaacttc     1140
gacctgccga cgaacaagga gaactacctg caccgcattg gccgcggcgg ccgctacggc     1200
gtaaagggtg ttgccatcaa cttcgtgacg gagaaagacg tggagctgct gcacgagatc     1260 gagggcact accacacgca gatcgatgag ctcccggtgg actttgccgc ctacctcggc     1320
gagtgagcgg gccctgccc ccttccctg ccccctctc gcgacgagag aacgcacatc      1380
gtaacacagc cacgcgaacg atagtaaggg cgtgcggcgg cgttccctc ctcctgccag     1440 cggcccccct ccgcagcgct tctcttttga gagggggca ggggaggcg ctgcgcctgg      1500 ctggatgtgt gcttgagctt gcattccgtc aagcaagtgc tttgttttaa ttatgcgcgc     1560
cgttttgttg ctcgtcccctt tcgttggtgt ttttcggcc gaaacggcgt ttaaagca       1618
```

<210> SEQ ID NO 10
<211> LENGTH: 403
<212> TYPE: PRT
<213> ORGANISM: Leishmania braziliensis

<400> SEQUENCE: 10

```
Met Ser Gln Gln Asp Arg Val Ala Pro Gln Asp Gln Asp Ser Phe Leu
  1               5                  10                  15

Asp Asp Gln Pro Gly Val Arg Pro Ile Pro Ser Phe Asp Asp Met Pro
                 20                  25                  30

Leu His Gln Asn Leu Leu Arg Gly Ile Tyr Ser Tyr Gly Phe Glu Lys
             35                  40                  45

Pro Ser Ser Ile Gln Gln Arg Ala Ile Ala Pro Phe Thr Arg Gly Gly
         50                  55                  60

Asp Ile Ile Ala Gln Ala Gln Ser Gly Thr Gly Lys Thr Gly Ala Phe
 65                  70                  75                  80

Ser Ile Gly Leu Leu Gln Arg Leu Asp Phe Arg His Asn Leu Ile Gln
                 85                  90                  95

Gly Leu Val Leu Ser Pro Thr Arg Glu Leu Ala Leu Gln Thr Ala Glu
            100                 105                 110

Val Ile Ser Arg Ile Gly Glu Phe Leu Ser Asn Ser Ala Lys Phe Cys
        115                 120                 125

Glu Thr Phe Val Gly Gly Thr Arg Val Gln Asp Asp Leu Arg Lys Leu
    130                 135                 140

Gln Ala Gly Val Val Val Ala Val Gly Thr Pro Gly Arg Val Ser Asp
145                 150                 155                 160
```

```
Val Ile Lys Arg Gly Ala Leu Arg Thr Glu Ser Leu Arg Val Leu Val
                165                 170                 175
Leu Asp Glu Ala Asp Glu Met Leu Ser Gln Gly Phe Ala Asp Gln Ile
            180                 185                 190
Tyr Glu Ile Phe Arg Phe Leu Pro Lys Asp Ile Gln Val Ala Leu Phe
        195                 200                 205
Ser Ala Thr Met Pro Glu Val Leu Glu Leu Thr Lys Lys Phe Met
    210                 215                 220
Arg Asp Pro Val Arg Ile Leu Val Lys Arg Glu Ser Leu Thr Leu Glu
225                 230                 235                 240
Gly Ile Lys Gln Phe Phe Ile Ala Val Glu Glu His Lys Leu Asp
                245                 250                 255
Thr Leu Met Asp Leu Tyr Glu Thr Val Ser Ile Ala Gln Ser Val Ile
            260                 265                 270
Phe Ala Asn Thr Arg Arg Lys Val Asp Trp Ile Ala Glu Lys Leu Asn
        275                 280                 285
Gln Ser Asn His Thr Val Ser Ser Met His Ala Glu Met Pro Lys Ser
    290                 295                 300
Asp Arg Glu Arg Val Met Asn Thr Phe Arg Ser Gly Ser Ser Arg Val
305                 310                 315                 320
Leu Val Thr Thr Asp Leu Val Ala Arg Gly Ile Asp Val His His Val
                325                 330                 335
Asn Ile Val Ile Asn Phe Asp Leu Pro Thr Asn Lys Glu Asn Tyr Leu
            340                 345                 350
His Arg Ile Gly Arg Gly Gly Arg Tyr Gly Val Lys Gly Val Ala Ile
        355                 360                 365
Asn Phe Val Thr Glu Lys Asp Val Glu Leu Leu His Glu Ile Glu Gly
    370                 375                 380
His Tyr His Thr Gln Ile Asp Glu Leu Pro Val Asp Phe Ala Ala Tyr
385                 390                 395                 400
Leu Gly Glu
```

<210> SEQ ID NO 11
<211> LENGTH: 12
<212> TYPE: PRT
<213> ORGANISM: Leishmania donovani
<220> FEATURE:
<221> NAME/KEY: VARIANT
<222> LOCATION: (1)...(5)
<223> OTHER INFORMATION: Xaa = any amino acid
<221> NAME/KEY: VARIANT
<222> LOCATION: (6)...(6)
<223> OTHER INFORMATION: Xaa = Leu or Lys
<221> NAME/KEY: VARIANT
<222> LOCATION: (7)...(12)
<223> OTHER INFORMATION: Xaa = any amino acid

<400> SEQUENCE: 11

```
Xaa Gln Xaa Pro Gln Xaa Val Phe Asp Glu Xaa Xaa
 1               5                   10
```

<210> SEQ ID NO 12
<211> LENGTH: 26
<212> TYPE: DNA
<213> ORGANISM: Artificial Sequence
<220> FEATURE:
<223> OTHER INFORMATION: Sense PCR pri mer
<221> NAME/KEY: modified_base
<222> LOCATION: (1)...(26)
<223> OTHER INFORMATION: I
<221> NAME/KEY: misc_feature

```
<222> LOCATION: (1)...(26)
<223> OTHER INFORMATION: n = A,T,C or G

<400> SEQUENCE: 12
ggaattcccc ncagctngtn ttcgac                                              26

<210> SEQ ID NO 13
<211> LENGTH: 5
<212> TYPE: PRT
<213> ORGANISM: Leishmania donovani

<400> SEQUENCE: 13

Lys Val Phe Asp Glu
 1               5

<210> SEQ ID NO 14
<211> LENGTH: 30
<212> TYPE: DNA
<213> ORGANISM: Artificial Sequence
<220> FEATURE:
<223> OTHER INFORMATION: PCR primer

<400> SEQUENCE: 14
ggatccatgg tcaagtccca ctacatctgc                                          30

<210> SEQ ID NO 15
<211> LENGTH: 33
<212> TYPE: DNA
<213> ORGANISM: Artificial Sequence
<220> FEATURE:
<223> OTHER INFORMATION: PCR primer

<400> SEQUENCE: 15
gaattcagac cggatagaaa taagccaatg aaa                                       33

<210> SEQ ID NO 16
<211> LENGTH: 701
<212> TYPE: PRT
<213> ORGANISM: Leishmania amozonensis

<400> SEQUENCE: 16
```

| Met | Thr | Glu | Thr | Phe | Ala | Phe | Gln | Ala | Glu | Ile | Asn | Gln | Leu | Met | Ser |
|---|---|---|---|---|---|---|---|---|---|---|---|---|---|---|---|
| 1 | | | | 5 | | | | | 10 | | | | | 15 | |

| Leu | lle | Ile | Asn | Thr | Phe | Tyr | Ser | Asn | Lys | Glu | Ile | Phe | Leu | Arg | Asp |
|---|---|---|---|---|---|---|---|---|---|---|---|---|---|---|---|
| | | 20 | | | | | 25 | | | | | 30 | | | |

| Val | Ile | Ser | Asn | Ala | Ser | Asp | Ala | Cys | Asp | Lys | Ile | Arg | Tyr | Gln | Ser |
|---|---|---|---|---|---|---|---|---|---|---|---|---|---|---|---|
| | | | 35 | | | | | 40 | | | | | 45 | | |

| Leu | Thr | Asp | Pro | Ala | Val | Leu | Gly | Asp | Ala | Thr | Arg | Leu | Cys | Val | Arg |
|---|---|---|---|---|---|---|---|---|---|---|---|---|---|---|---|
| | 50 | | | | | 55 | | | | | 60 | | | | |

| Val | Val | Pro | Asp | Lys | Glu | Asn | Lys | Thr | Leu | Thr | Val | Glu | Asp | Asn | Gly |
|---|---|---|---|---|---|---|---|---|---|---|---|---|---|---|---|
| 65 | | | | | 70 | | | | | 75 | | | | | 80 |

| Ile | Gly | Met | Thr | Lys | Ala | Asp | Leu | Val | Asn | Asn | Leu | Gly | Thr | Ile | Ala |
|---|---|---|---|---|---|---|---|---|---|---|---|---|---|---|---|
| | | | | 85 | | | | | 90 | | | | | 95 | |

| Arg | Ser | Gly | Thr | Lys | Ala | Phe | Met | Glu | Ala | Leu | Glu | Ala | Gly | Ala | Asp |
|---|---|---|---|---|---|---|---|---|---|---|---|---|---|---|---|
| | | | 100 | | | | | 105 | | | | | 110 | | |

| Met | Ser | Met | Ile | Gly | Gln | Phe | Gly | Val | Gly | Phe | Tyr | Ser | Ala | Tyr | Leu |
|---|---|---|---|---|---|---|---|---|---|---|---|---|---|---|---|
| | | 115 | | | | | 120 | | | | | 125 | | | |

| Val | Ala | Asp | Arg | Val | Thr | Val | Thr | Ser | Lys | Asn | Asn | Ser | Asp | Glu | Val |
|---|---|---|---|---|---|---|---|---|---|---|---|---|---|---|---|
| | 130 | | | | | 135 | | | | | 140 | | | | |

| Tyr | Val | Trp | Glu | Ser | Ser | Ala | Gly | Gly | Thr | Phe | Thr | Ile | Thr | Ser | Ala |
|---|---|---|---|---|---|---|---|---|---|---|---|---|---|---|---|
| 145 | | | | | 150 | | | | | 155 | | | | | 160 |

-continued

```
Pro Glu Ser Asp Met Lys Leu Pro Ala Arg Ile Thr Leu His Leu Lys
            165                 170                 175

Glu Asp Gln Leu Glu Tyr Leu Glu Ala Arg Arg Leu Lys Glu Leu Ile
        180                 185                 190

Lys Lys His Ser Glu Phe Ile Gly Tyr Asp Ile Glu Leu Met Val Glu
        195                 200                 205

Lys Thr Thr Glu Lys Glu Val Thr Asp Glu Asp Glu Glu Ala Lys
        210                 215                 220

Lys Ala Asp Glu Asp Gly Glu Glu Pro Lys Val Glu Glu Val Thr Glu
225                 230                 235                 240

Gly Glu Glu Asp Lys Lys Lys Thr Lys Lys Val Lys Glu Val Thr
                245                 250                 255

Lys Glu Tyr Glu Val Gln Asn Lys His Lys Pro Leu Trp Thr Arg Asp
            260                 265                 270

Pro Lys Asp Val Thr Lys Glu Glu Tyr Ala Ala Phe Tyr Lys Ala Ile
        275                 280                 285

Ser Asn Asp Trp Glu Asp Pro Pro Ala Thr Lys His Phe Ser Val Glu
        290                 295                 300

Gly Gln Leu Glu Phe Arg Ala Ile Met Phe Val Pro Lys Arg Ala Pro
305                 310                 315                 320

Phe Asp Met Leu Glu Pro Asn Lys Lys Arg Asn Asn Ile Lys Leu Tyr
                325                 330                 335

Val Arg Arg Val Phe Ile Met Asp Asn Cys Glu Asp Leu Cys Pro Asp
            340                 345                 350

Trp Leu Gly Phe Val Lys Gly Val Val Asp Ser Glu Asp Leu Pro Leu
        355                 360                 365

Asn Ile Ser Arg Glu Asn Leu Gln Gln Asn Lys Ile Leu Lys Val Ile
370                 375                 380

Arg Lys Asn Ile Val Lys Lys Cys Leu Glu Met Phe Glu Glu Val Ala
385                 390                 395                 400

Glu Asn Lys Glu Asp Tyr Lys Gln Phe Tyr Glu Gln Phe Gly Lys Asn
                405                 410                 415

Ile Lys Leu Gly Ile His Glu Asp Thr Ala Asn Arg Lys Lys Leu Met
            420                 425                 430

Glu Leu Leu Arg Phe Tyr Ser Thr Glu Ser Gly Glu Val Met Thr Thr
        435                 440                 445

Leu Lys Asp Tyr Val Thr Arg Met Lys Ala Glu Gln Asn Ser Ile Tyr
        450                 455                 460

Tyr Ile Thr Gly Asp Ser Lys Lys Lys Leu Glu Ser Ser Pro Phe Ile
465                 470                 475                 480

Glu Gln Ala Lys Arg Arg Gly Phe Glu Val Leu Phe Met Thr Glu Pro
                485                 490                 495

Tyr Asp Glu Tyr Val Met Gln Gln Val Lys Asp Phe Glu Asp Lys Lys
            500                 505                 510

Phe Ala Cys Leu Thr Lys Glu Gly Val His Phe Glu Glu Ser Glu Glu
        515                 520                 525

Glu Lys Lys Gln Arg Glu Glu Lys Ala Thr Cys Glu Lys Leu Cys
        530                 535                 540

Lys Thr Met Lys Glu Val Leu Gly Asp Lys Val Glu Lys Val Thr Val
545                 550                 555                 560

Ser Glu Arg Leu Ser Thr Ser Pro Cys Ile Leu Val Thr Ser Glu Phe
                565                 570                 575
```

-continued

```
Gly Trp Ser Ala His Met Glu Gln Met Met Arg Asn Gln Ala Leu Arg
            580                 585                 590

Asp Ser Ser Met Ala Gln Tyr Met Met Ser Lys Lys Thr Met Glu Leu
            595                 600                 605

Asn Pro Lys His Pro Ile Ile Lys Glu Leu Arg Arg Arg Val Glu Ala
            610                 615                 620

Asp Glu Asn Asp Lys Ala Val Lys Asp Leu Val Phe Leu Leu Phe Asp
625                 630                 635                 640

Thr Ser Leu Leu Thr Ser Gly Phe Gln Leu Glu Asp Pro Thr Tyr Ala
            645                 650                 655

Glu Arg Ile Asn Arg Met Ile Lys Leu Gly Leu Ser Leu Asp Glu Glu
            660                 665                 670

Glu Glu Glu Glu Ala Val Glu Ala Val Ala Glu Thr Ala Pro Ala
            675                 680                 685

Glu Val Thr Ala Gly Thr Ser Ser Met Glu Leu Val Asp
            690                 695                 700

<210> SEQ ID NO 17
<211> LENGTH: 704
<212> TYPE: PRT
<213> ORGANISM: T. Cruzi

<400> SEQUENCE: 17

Met Thr Glu Thr Phe Ala Phe Gln Ala Glu Ile Asn Gln Leu Met Ser
1               5                   10                  15

Leu Ile Ile Asn Thr Phe Tyr Ser Asn Lys Glu Ile Phe Leu Arg Glu
                20                  25                  30

Leu Ile Ser Asn Ala Ser Asp Ala Cys Asp Lys Ile Arg Tyr Gln Ser
            35                  40                  45

Leu Thr Asn Gln Ala Val Leu Gly Asp Glu Ser His Leu Arg Ile Arg
        50                  55                  60

Val Val Pro Asp Lys Ala Asn Lys Thr Leu Thr Val Glu Asp Thr Gly
65                  70                  75                  80

Ile Gly Met Thr Lys Ala Glu Leu Val Asn Asn Leu Gly Thr Ile Ala
                85                  90                  95

Arg Ser Gly Thr Lys Ala Phe Met Glu Ala Leu Glu Ala Gly Gly Asp
                100                 105                 110

Met Ser Met Ile Gly Gln Phe Gly Val Gly Phe Tyr Ser Ala Tyr Leu
            115                 120                 125

Val Ala Asp Arg Val Thr Val Val Ser Lys Asn Asn Asp Asp Glu Ala
    130                 135                 140

Tyr Thr Trp Glu Ser Ser Ala Gly Gly Thr Phe Thr Val Thr Pro Thr
145                 150                 155                 160

Pro Asp Cys Asp Leu Lys Arg Gly Thr Arg Ile Val Leu His Leu Lys
                165                 170                 175

Glu Asp Gln Gln Glu Tyr Leu Glu Glu Arg Arg Leu Lys Asp Leu Ile
                180                 185                 190

Lys Lys His Ser Glu Phe Ile Gly Tyr Asp Ile Glu Leu Met Val Glu
            195                 200                 205

Lys Ala Thr Glu Lys Glu Val Thr Asp Glu Asp Glu Asp Glu Ala Ala
    210                 215                 220

Ala Thr Lys Asn Glu Glu Gly Glu Glu Pro Lys Val Glu Glu Val Lys
225                 230                 235                 240

Asp Asp Ala Glu Glu Gly Glu Lys Lys Lys Thr Lys Lys Val Lys
                245                 250                 255
```

-continued

```
Glu Val Thr Gln Glu Phe Val Val Gln Asn Lys His Lys Pro Leu Trp
            260                 265                 270
Thr Arg Asp Pro Lys Asp Val Thr Lys Glu Glu Tyr Ala Ala Phe Tyr
            275                 280                 285
Lys Ala Ile Ser Asn Asp Trp Glu Glu Pro Leu Ser Thr Lys His Phe
            290                 295                 300
Ser Val Glu Gly Gln Leu Glu Phe Arg Ala Ile Leu Phe Val Pro Lys
305                 310                 315                 320
Arg Ala Pro Phe Asp Met Phe Glu Pro Ser Lys Lys Arg Asn Asn Ile
                325                 330                 335
Lys Leu Tyr Val Arg Arg Val Phe Ile Met Asp Asn Cys Glu Asp Leu
            340                 345                 350
Cys Pro Glu Trp Leu Ala Phe Val Arg Gly Val Val Asp Ser Glu Asp
            355                 360                 365
Leu Pro Leu Asn Ile Ser Arg Glu Asn Leu Gln Gln Asn Lys Ile Leu
            370                 375                 380
Lys Val Ile Arg Lys Asn Ile Val Lys Lys Ala Leu Glu Leu Phe Glu
385                 390                 395                 400
Glu Ile Ala Glu Asn Lys Glu Asp Tyr Lys Lys Phe Tyr Gln Phe
                405                 410                 415
Gly Lys Asn Val Lys Leu Gly Ile His Glu Asp Ser Ala Asn Arg Lys
                420                 425                 430
Lys Leu Met Glu Leu Leu Arg Phe His Ser Ser Glu Ser Gly Glu Asp
            435                 440                 445
Met Thr Thr Leu Lys Asp Tyr Val Thr Arg Met Lys Glu Gly Gln Lys
            450                 455                 460
Cys Ile Tyr Tyr Val Thr Gly Asp Ser Lys Lys Lys Leu Glu Thr Ser
465                 470                 475                 480
Pro Phe Ile Glu Gln Ala Arg Arg Arg Gly Phe Glu Val Leu Phe Met
                485                 490                 495
Thr Glu Pro Ile Asp Glu Tyr Val Met Gln Gln Val Lys Asp Phe Glu
            500                 505                 510
Asp Lys Lys Phe Ala Cys Leu Thr Lys Glu Gly Val His Phe Glu Glu
            515                 520                 525
Thr Glu Glu Glu Lys Lys Gln Arg Glu Glu Lys Thr Ala Tyr Glu
            530                 535                 540
Arg Leu Cys Lys Ala Met Lys Asp Val Leu Gly Asp Lys Val Glu Lys
545                 550                 555                 560
Val Val Val Ser Glu Arg Leu Ala Thr Ser Pro Cys Ile Leu Val Thr
                565                 570                 575
Ser Glu Phe Gly Trp Ser Ala His Met Glu Gln Ile Met Arg Asn Gln
            580                 585                 590
Ala Leu Arg Asp Ser Ser Met Ser Ala Tyr Met Met Ser Lys Lys Thr
            595                 600                 605
Met Glu Ile Asn Pro Ala His Pro Ile Val Lys Glu Leu Lys Arg Arg
            610                 615                 620
Val Glu Ala Asp Glu Asn Asp Lys Ala Val Lys Asp Leu Val Tyr Leu
625                 630                 635                 640
Leu Phe Asp Thr Ala Leu Leu Thr Ser Gly Phe Thr Leu Asp Asp Pro
                645                 650                 655
Thr Ser Tyr Ala Glu Arg Ile His Arg Met Ile Lys Leu Gly Leu Ser
                660                 665                 670
```

```
Leu Asp Asp Glu Asp Asn Gly Asn Glu Glu Ala Glu Pro Ala Ala Ala
            675                 680                 685

Val Pro Ala Glu Pro Val Ala Gly Thr Ser Ser Met Glu Gln Val Asp
        690                 695                 700

<210> SEQ ID NO 18
<211> LENGTH: 732
<212> TYPE: PRT
<213> ORGANISM: Homo sapien

<400> SEQUENCE: 18

Met Pro Glu Glu Thr Gln Thr Gln Asp Gln Pro Met Glu Glu Glu Glu
 1               5                  10                  15

Val Glu Thr Phe Ala Phe Gln Ala Glu Ile Ala Gln Leu Met Ser Leu
            20                  25                  30

Ile Ile Asn Thr Phe Tyr Ser Asn Lys Glu Ile Phe Leu Arg Glu Leu
        35                  40                  45

Ile Ser Asn Ser Ser Asp Ala Leu Asp Lys Ile Arg Tyr Glu Ser Leu
    50                  55                  60

Thr Asp Pro Ser Lys Leu Asp Ser Gly Lys Glu Leu His Ile Asn Leu
65                  70                  75                  80

Ile Pro Asn Lys Gln Asp Arg Ala Leu Thr Ile Val Asp Thr Gly Ile
                85                  90                  95

Gly Met Thr Lys Ala Asp Leu Ile Asn Asn Leu Gly Thr Ile Ala Lys
            100                 105                 110

Ser Gly Thr Lys Ala Phe Met Glu Ala Leu Gln Ala Gly Ala Asp Ile
        115                 120                 125

Ser Met Ile Gly Gln Phe Gly Val Gly Phe Tyr Ser Ala Tyr Leu Val
    130                 135                 140

Ala Glu Lys Val Thr Val Ile Thr Lys His Asn Asp Asp Glu Gln Tyr
145                 150                 155                 160

Ala Trp Glu Ser Ser Ala Gly Gly Ser Phe Thr Val Arg Thr Asp Thr
                165                 170                 175

Gly Glu Pro Met Gly Arg Gly Thr Lys Val Ile Leu His Leu Lys Glu
            180                 185                 190

Asp Gln Thr Glu Tyr Leu Glu Glu Arg Arg Ile Lys Glu Ile Val Lys
        195                 200                 205

Lys His Ser Gln Phe Ile Gly Tyr Pro Ile Thr Leu Phe Val Glu Lys
    210                 215                 220

Glu Arg Asp Lys Glu Val Ser Asp Asp Glu Ala Glu Glu Lys Glu Asp
225                 230                 235                 240

Lys Glu Glu Glu Lys Glu Lys Glu Glu Lys Glu Ser Glu Asp Lys Pro
                245                 250                 255

Glu Ile Glu Asp Val Gly Ser Asp Glu Glu Asp Glu Lys Lys Asp Gly
            260                 265                 270

Asp Lys Lys Lys Lys Lys Ile Lys Glu Lys Tyr Ile Asp Lys Glu
        275                 280                 285

Glu Leu Asn Lys Thr Lys Pro Ile Trp Thr Arg Asn Pro Asp Asp Ile
    290                 295                 300

Thr Asn Glu Glu Tyr Gly Glu Phe Tyr Lys Ser Leu Thr Asn Asp Trp
305                 310                 315                 320

Glu Asp His Leu Ala Val Lys His Phe Ser Val Glu Gly Gln Leu Glu
                325                 330                 335

Phe Arg Ala Leu Leu Phe Val Pro Arg Arg Ala Pro Phe Asp Leu Phe
            340                 345                 350
```

-continued

```
Glu Asn Arg Lys Lys Asn Asn Ile Lys Leu Tyr Val Arg Arg Val
            355                 360                 365

Phe Ile Met Asp Asn Cys Glu Glu Leu Ile Pro Glu Tyr Leu Asn Phe
    370                 375                 380

Ile Arg Gly Val Val Asp Ser Glu Asp Leu Pro Leu Asn Ile Ser Arg
385                 390                 395                 400

Glu Met Leu Gln Gln Ser Lys Ile Leu Lys Val Ile Arg Lys Asn Leu
                405                 410                 415

Val Lys Lys Cys Leu Glu Leu Phe Thr Glu Leu Ala Glu Asp Lys Glu
            420                 425                 430

Asn Tyr Lys Lys Phe Tyr Glu Gln Phe Ser Lys Asn Ile Lys Leu Gly
            435                 440                 445

Ile His Glu Asp Ser Gln Asn Arg Lys Lys Leu Ser Glu Leu Leu Arg
        450                 455                 460

Tyr Tyr Thr Ser Ala Ser Gly Asp Glu Met Val Ser Leu Lys Asp Tyr
465                 470                 475                 480

Cys Thr Arg Met Lys Glu Asn Gln Lys His Ile Tyr Tyr Ile Thr Gly
                485                 490                 495

Glu Thr Lys Asp Gln Val Ala Asn Ser Ala Phe Val Glu Arg Leu Arg
            500                 505                 510

Lys His Gly Leu Glu Val Ile Tyr Met Ile Glu Pro Ile Asp Glu Tyr
        515                 520                 525

Cys Val Gln Gln Leu Lys Glu Phe Glu Gly Lys Thr Leu Val Ser Val
            530                 535                 540

Thr Lys Glu Gly Leu Glu Leu Pro Glu Asp Glu Glu Lys Lys Lys
545                 550                 555                 560

Gln Glu Glu Lys Lys Thr Lys Phe Glu Asn Leu Cys Lys Ile Met Lys
                565                 570                 575

Asp Ile Leu Glu Lys Lys Val Glu Lys Val Val Ser Asn Arg Leu
            580                 585                 590

Val Thr Ser Pro Cys Cys Leu Val Thr Ser Thr Tyr Gly Trp Thr Ala
            595                 600                 605

Asn Met Glu Arg Ile Met Lys Ala Gln Ala Leu Arg Asp Asn Ser Thr
    610                 615                 620

Met Gly Tyr Met Ala Ala Lys Lys His Leu Glu Ile Asn Pro Asp His
625                 630                 635                 640

Ser Ile Ile Glu Thr Leu Arg Gln Lys Ala Glu Ala Asp Lys Asn Asp
                645                 650                 655

Lys Ser Val Lys Asp Leu Val Ile Leu Leu Tyr Glu Thr Ala Leu Leu
            660                 665                 670

Ser Ser Gly Phe Ser Leu Glu Asp Pro Gln Thr His Ala Asn Arg Ile
            675                 680                 685

Tyr Arg Met Ile Lys Leu Gly Leu Gly Ile Asp Glu Asp Pro Thr
        690                 695                 700

Ala Asp Asp Thr Ser Ala Ala Val Thr Glu Glu Met Pro Pro Leu Glu
705                 710                 715                 720

Gly Asp Asp Asp Thr Ser Arg Met Glu Glu Val Asp
                725                 730
```

<210> SEQ ID NO 19
<211> LENGTH: 1019
<212> TYPE: DNA
<213> ORGANISM: Leishmania major -continued

```
<400> SEQUENCE: 19
gaattcggca cgaggtttct gtactttatt gcttccagcc tttattcact cttcgatttc      60
ctctaacacc atgtcctccg agcgcacctt tattgccgtc aagccggacg gcgtgcagcg     120
cggcctcgtt ggcgagatca tcgcccgctt cgagcgcaag ggctacaagc tcgtcgcctt     180
gaagatactg cagccgacga cggagcaggc ccagggtcac tataaggacc tttgctccaa     240
gccgtttttc ccggcccttg tgaagtactt ctcctctggc ccgatcgtgt gtatggtgtg     300
ggagggtaag aacgtggtga agagcggccg cgtgctgctc ggcgcgacga acccggccga     360
ctcacagccc ggcacgatcc gtggcgactt tgccgtggat gtgggccgca acgtgtgcca     420
cgggtccgac tctgtggaga gcgcggagcg cgagatcgcc ttttggttca aggcggatga     480
gatcgcgagc tggacgtcgc actccgtgtc ccagatctat gagtaacggt gattgcggac     540
acgctttgag gacgtagctg taccccaat gaattcttct ctgaaaacca catcataagc     600
ctcttaagag gttatttttc ttgatcgatg cccggtggtg accagcacca ttcctttatc     660
ggattcactc acactcctag cgaatcatgt agtgcggtga gagtgggctc tggaggagac     720
tgttgtgtag ccatggcttc aggagagaaa acaaaataca aggaaaggca atatgtaact     780
atggggttcc ctttttttact atgcaaagtt tttataactc ctgatcggca aaaacaacaa     840
caaccgccat acaccaagag caaatgcttt cttctgcgga ctgtgcttct gttttttttt     900
atgaaggagt gactcgcgcg atgaaaagtg tgtgcgtggg agatgtattt ccttttttg      960
ttcatagtgg cgacagctca ctgttgacga tgacaaaaaa aaaaaaaaaa aaactcgag     1019

<210> SEQ ID NO 20
<211> LENGTH: 151
<212> TYPE: PRT
<213> ORGANISM: Leishmania major

<400> SEQUENCE: 20

Met Ser Ser Glu Arg Thr Phe Ile Ala Val Lys Pro Asp Gly Val Gln
  1               5                  10                  15

Arg Gly Leu Val Gly Glu Ile Ile Ala Arg Phe Glu Arg Lys Gly Tyr
             20                  25                  30

Lys Leu Val Ala Leu Lys Ile Leu Gln Pro Thr Thr Glu Gln Ala Gln
         35                  40                  45

Gly His Tyr Lys Asp Leu Cys Ser Lys Pro Phe Phe Pro Ala Leu Val
     50                  55                  60

Lys Tyr Phe Ser Ser Gly Pro Ile Val Cys Met Val Trp Glu Gly Lys
 65                  70                  75                  80

Asn Val Val Lys Ser Gly Arg Val Leu Leu Gly Ala Thr Asn Pro Ala
                 85                  90                  95

Asp Ser Gln Pro Gly Thr Ile Arg Gly Asp Phe Ala Val Asp Val Gly
            100                 105                 110

Arg Asn Val Cys His Gly Ser Asp Ser Val Glu Ser Ala Glu Arg Glu
        115                 120                 125

Ile Ala Phe Trp Phe Lys Ala Asp Glu Ile Ala Ser Trp Thr Ser His
    130                 135                 140

Ser Val Ser Gln Ile Tyr Glu
145                 150

<210> SEQ ID NO 21
<211> LENGTH: 1523
<212> TYPE: DNA
<213> ORGANISM: Leishmania major
```

<400> SEQUENCE: 21

```
gaattcggca cgagtgctgc ccgacatgac atgctcgctg accggacttc agtgcacaga      60
cccgaactgc aagacctgca caacttacgg tcagtgcaca gactgcaacg acggctacgg     120
tctcacctcc tccagcgttt gcgtgcgctg cagtgtagcg ggctgcaaga gctgccccgt     180
cgacgctaac gtctgcaaag tgtgtctcgg cggcagcgag ccgatcaaca atatgtgccc     240
ctgcaccgac cccaactgcg ccagctgccc cagcgacgct ggcacgtgca ctcagtgcgc     300
gaacggctac ggtctcgtgg acggcgcctg tgtgagatgc caggagccca actgcttcag     360
ctgcgacagc gacgcgaata agtgcacaca atgtgcgccg aactactacc tcaccccgct     420
cttgacctgc tccccggtgg cctgcaacat cgagcactgc atgcagtgcg acccacagac     480
gccgtcgcgc tgccaggagt gcgtgtcccc ctacgtggtt gacagctacg acggcctctg     540
caggctctcc gatgcctgct ccgtgcccaa ctgcaagaag tgcagaccg  gtacctccag     600
gctctgcgcc gagtgcgaca ccggctacag tctctccgcc gacgcgacga gctgcagcag     660
tccaaccacg cagccgtgcg aggtggagca ctgcaacaca tgtgtgaacg gcgatagcac     720
ccgctgtgcc tactgcaaca ccggctacta cgtctccgat ggcaagtgca aggccatgca     780
gggctgctac cgtgtcgaact gcgcgcagtg catgctgctt gacagcacca agtgctccac     840
gtgcgtgaaa gggtacctgc tcacgtcgtc ctacagttgc gtctcgcaga agtcatcaa     900
cagtgcggcc gcgccctact ctctgtgggt ggccgccgcc gtgctcctca cctcttttgc     960
catgcaccta gcatagtgcg cagcggcatg cgaacaaccc cactctcatt ctccaacatg    1020
tgcatacaca cacacacaga cagcggggca gcaccccctc cccacacaca cacacgcact    1080
tcccccttgt cttgttcttc tttcctcgtt cgcatttctt tctctcgtgc gctggcgccg    1140
gcctcctgca cgtcgctccc ctcccccctaa cctctattct ctctctctct ctctctcgcc    1200
ggcatcattg cttcttaccc ttttctgatc cttgctcgcg tgggcggaca ctgccacagt    1260
cccacagcgc agacacacgt gtttaaacgg cgcaggcatc cctccctatc acttcatttc    1320
tcctaaagcc actcaccaag tcgcacaccg ccctccccca tcggccgccc ttccgggcgc    1380
agctgtgcgg aatgggtgtg tgctcgacct cgttcctggc agctcactcg catgtgtaca    1440
gccactccaa ccacgaaagc tctcttctgc gcacataaaa aaaaaaaaa  aaaaaaact     1500
cgaggggggg cccggtaccc aaa                                             1523
```

<210> SEQ ID NO 22
<211> LENGTH: 320
<212> TYPE: PRT
<213> ORGANISM: Leishmania major

<400> SEQUENCE: 22

```
Val Leu Pro Asp Met Thr Cys Ser Leu Thr Gly Leu Gln Cys Thr Asp
  1               5                  10                  15

Pro Asn Cys Lys Thr Cys Thr Thr Tyr Gly Gln Cys Thr Asp Cys Asn
                 20                  25                  30

Asp Gly Tyr Gly Leu Thr Ser Ser Val Cys Val Arg Cys Ser Val
             35                  40                  45

Ala Gly Cys Lys Ser Cys Pro Val Asp Ala Asn Val Cys Lys Val Cys
         50                  55                  60

Leu Gly Gly Ser Glu Pro Ile Asn Asn Met Cys Pro Cys Thr Asp Pro
 65                  70                  75                  80

Asn Cys Ala Ser Cys Pro Ser Asp Ala Gly Thr Cys Thr Gln Cys Ala
```

|   | 85 | | | | 90 | | | | 95 | | | |
|---|---|---|---|---|---|---|---|---|---|---|---|---|

Asn Gly Tyr Gly Leu Val Asp Gly Ala Cys Val Arg Cys Gln Glu Pro
                100                 105                 110

Asn Cys Phe Ser Cys Asp Ser Asp Ala Asn Lys Cys Thr Gln Cys Ala
                115                 120                 125

Pro Asn Tyr Tyr Leu Thr Pro Leu Leu Thr Cys Ser Pro Val Ala Cys
                130                 135                 140

Asn Ile Glu His Cys Met Gln Cys Asp Pro Gln Thr Pro Ser Arg Cys
145                 150                 155                 160

Gln Glu Cys Val Ser Pro Tyr Val Val Asp Ser Tyr Asp Gly Leu Cys
                165                 170                 175

Arg Leu Ser Asp Ala Cys Ser Val Pro Asn Cys Lys Lys Cys Glu Thr
                180                 185                 190

Gly Thr Ser Arg Leu Cys Ala Glu Cys Asp Thr Gly Tyr Ser Leu Ser
                195                 200                 205

Ala Asp Ala Thr Ser Cys Ser Ser Pro Thr Thr Gln Pro Cys Glu Val
                210                 215                 220

Glu His Cys Asn Thr Cys Val Asn Gly Asp Ser Thr Arg Cys Ala Tyr
225                 230                 235                 240

Cys Asn Thr Gly Tyr Tyr Val Ser Asp Gly Lys Cys Lys Ala Met Gln
                245                 250                 255

Gly Cys Tyr Val Ser Asn Cys Ala Gln Cys Met Leu Leu Asp Ser Thr
                260                 265                 270

Lys Cys Ser Thr Cys Val Lys Gly Tyr Leu Leu Thr Ser Ser Tyr Ser
                275                 280                 285

Cys Val Ser Gln Lys Val Ile Asn Ser Ala Ala Ala Pro Tyr Ser Leu
                290                 295                 300

Trp Val Ala Ala Ala Val Leu Leu Thr Ser Phe Ala Met His Leu Ala
305                 310                 315                 320

<210> SEQ ID NO 23
<211> LENGTH: 797
<212> TYPE: DNA
<213> ORGANISM: Leishmania major

<400> SEQUENCE: 23

| | | |
|---|---|---|
| ctgtactta ttgccaccag ccagccatgt cctgcggtaa cgccaagatc aactctcccg | 60 |
| cgccgtcctt cgaggaggtg gcgctcatgc ccaacggcag cttcaagaag atcagcctct | 120 |
| cctcctacaa gggcaagtgg gtcgtgctct tcttctaccc gctcgacttt agcttcgtgt | 180 |
| gcccgacaga ggtcatcgcg ttctccgaca gcgtgagtcg cttcaacgag ctcaactgcg | 240 |
| aggtcctcgc gtgctcgata gacagcgagt acgcgcacct gcagtggacg ctgcaggacc | 300 |
| gcaagaaggg cggcctcggg accatggcga tcccaatgct agccgacaag accaagagca | 360 |
| tcgctcgttc ctacggcgtg ctggaggaga gccagggcgt ggcctaccgc ggtctcttca | 420 |
| tcatcgaccc ccatgcatg ctgcgtcaga tcaccgtcaa tgacatgccg gtgggccgca | 480 |
| gcgtggagga ggttctacgc ctgctggagg cttttcagtt cgtggagaag cacggcgagg | 540 |
| tgtgccccgc gaactggaag aagggcgccc ccacgatgaa gccggaaccg aatgcgtctg | 600 |
| tcgagggata cttcagcaag cagtaaacct gtgagcgtcg caggagtcag tgtgacctca | 660 |
| cccgcctctg ccagtgggtg cgagagggcg tgagggattg tgggaaggct gttggatatg | 720 |
| atgcagacag cgatgaatgc aactcccaca cactggccct cctcagccct ctccacacag | 780 |
| acacacgcac gcatgtg | 797 |

<210> SEQ ID NO 24
<211> LENGTH: 199
<212> TYPE: PRT
<213> ORGANISM: Leishmania major

<400> SEQUENCE: 24

```
Met Ser Cys Gly Asn Ala Lys Ile Asn Ser Pro Ala Pro Ser Phe Glu
  1               5                  10                  15

Glu Val Ala Leu Met Pro Asn Gly Ser Phe Lys Lys Ile Ser Leu Ser
             20                  25                  30

Ser Tyr Lys Gly Lys Trp Val Leu Phe Phe Tyr Pro Leu Asp Phe
         35                  40                  45

Ser Phe Val Cys Pro Thr Glu Val Ile Ala Phe Ser Asp Ser Val Ser
     50                  55                  60

Arg Phe Asn Glu Leu Asn Cys Glu Val Leu Ala Cys Ser Ile Asp Ser
 65                  70                  75                  80

Glu Tyr Ala His Leu Gln Trp Thr Leu Gln Asp Arg Lys Lys Gly Gly
                 85                  90                  95

Leu Gly Thr Met Ala Ile Pro Met Leu Ala Asp Lys Thr Lys Ser Ile
            100                 105                 110

Ala Arg Ser Tyr Gly Val Leu Glu Glu Ser Gln Gly Val Ala Tyr Arg
        115                 120                 125

Gly Leu Phe Ile Ile Asp Pro His Gly Met Leu Arg Gln Ile Thr Val
    130                 135                 140

Asn Asp Met Pro Val Gly Arg Ser Val Glu Glu Val Leu Arg Leu Leu
145                 150                 155                 160

Glu Ala Phe Gln Phe Val Glu Lys His Gly Glu Val Cys Pro Ala Asn
                165                 170                 175

Trp Lys Lys Gly Ala Pro Thr Met Lys Pro Glu Pro Asn Ala Ser Val
            180                 185                 190

Glu Gly Tyr Phe Ser Lys Gln
        195
```

<210> SEQ ID NO 25
<211> LENGTH: 637
<212> TYPE: DNA
<213> ORGANISM: Leishmania tropica

<400> SEQUENCE: 25

```
ttacatatgc atcaccacca ccaccacatg tcctgcggta acgccaagat caactctccc      60
gcgccgccct tcgaggagat ggcgctcatg cccaacggca gcttcaagaa gatcagcctc     120
tccgcctaca agggcaagtg ggtcgtgctc ttcttctacc cgctcgactt caccttcgtg     180
tgcccgacag agatcatcgc gttctccgac aacgtgagtc gcttcaacga gctcaactgc     240
gaggtcctcg cgtgctcgat ggacagcgag tacgcgcacc tgcagtggac gctgcaggac     300
cgcaagaagg gcggcctcgg ggccatggcg atcccaatgc tggccgacaa gactaagagc     360
atcgctcgtt cctacggcgt gctggaggag agccagggcg tggcctaccg cggtctcttc     420
atcatcgacc cccgtggcat ggtgcgtcag atcaccgtca acgacatgcc ggtgggccgc     480
aacgtggagg aggctctgcg cctgctggag gctttgcagt tcgtggagaa gcacggcgag     540
gtgtgccccg cgaactggaa gaagggcgcc ccacgatga agccggaacc gaaggcgtct     600
gtcgagggat acttcagcaa gcagtaagaa ttccatg                              637
```

<210> SEQ ID NO 26
<211> LENGTH: 206
<212> TYPE: PRT
<213> ORGANISM: Leishmania tropica

<400> SEQUENCE: 26

```
Met His His His His His Met Ser Cys Gly Asn Ala Lys Ile Asn
 1               5                  10                  15

Ser Pro Ala Pro Pro Phe Glu Glu Met Ala Leu Met Pro Asn Gly Ser
                20                  25                  30

Phe Lys Lys Ile Ser Leu Ser Ala Tyr Lys Gly Lys Trp Val Val Leu
            35                  40                  45

Phe Phe Tyr Pro Leu Asp Phe Thr Phe Val Cys Pro Thr Glu Ile Ile
    50                  55                  60

Ala Phe Ser Asp Asn Val Ser Arg Phe Asn Glu Leu Asn Cys Glu Val
65                  70                  75                  80

Leu Ala Cys Ser Met Asp Ser Glu Tyr Ala His Leu Gln Trp Thr Leu
                85                  90                  95

Gln Asp Arg Lys Lys Gly Gly Leu Gly Ala Met Ala Ile Pro Met Leu
            100                 105                 110

Ala Asp Lys Thr Lys Ser Ile Ala Arg Ser Tyr Gly Val Leu Glu Glu
        115                 120                 125

Ser Gln Gly Val Ala Tyr Arg Gly Leu Phe Ile Ile Asp Pro Arg Gly
    130                 135                 140

Met Val Arg Gln Ile Thr Val Asn Asp Met Pro Val Gly Arg Asn Val
145                 150                 155                 160

Glu Glu Ala Leu Arg Leu Leu Glu Ala Leu Gln Phe Val Glu Lys His
                165                 170                 175

Gly Glu Val Cys Pro Ala Asn Trp Lys Lys Gly Ala Pro Thr Met Lys
            180                 185                 190

Pro Glu Pro Lys Ala Ser Val Glu Gly Tyr Phe Ser Lys Gln
        195                 200                 205
```

<210> SEQ ID NO 27
<211> LENGTH: 51
<212> TYPE: DNA
<213> ORGANISM: Artificial Sequence
<220> FEATURE:
<223> OTHER INFORMATION: PCR primer

<400> SEQUENCE: 27
caattacata tgcatcacca tcaccatcac atgtcctgcg gtaacgccaa g          51

<210> SEQ ID NO 28
<211> LENGTH: 31
<212> TYPE: DNA
<213> ORGANISM: Artificial Sequence
<220> FEATURE:
<223> OTHER INFORMATION: PCR primer

<400> SEQUENCE: 28
catggaattc ttactgcttg ctgaagtatc c                                31

<210> SEQ ID NO 29
<211> LENGTH: 520
<212> TYPE: DNA
<213> ORGANISM: Leishmania major
<220> FEATURE:
<221> NAME/KEY: misc_feature
<222> LOCATION: (1)...(520)
<223> OTHER INFORMATION: n = A, T, C or G

<400> SEQUENCE: 29

```
ggcacgagcc cttgcctaca tttgctcgcc gatattcgcg gggagttctt caatttgcgt    60
cgcgtagaac tgctcaatgt cgcgcaacaa gcgcagctcg tcgtggcgca cgaaggtgat   120
ggccagtcca gtgcggccca tgcggccagt gcggccgatg cggtgaatgt actgctcacg   180
cgcgagcggc aaatcgtagc tgaggacgag cgagacgcgc tccacatcaa tgccacgcgc   240
ccacaggtcc gttgtaatga ncacgcggct gtgtccatta cggaatgccg cataatctcg   300
tcgcgctccg cctgggcat gtcgccgtgc atggcggaca cagcgaaatt ctcgcgcgtc   360
atcttcttgg caagctgctc cacctttttg cgggtgttgc anaaaaccac ngcgtgggcg   420
atcgttaagc tgtcgtacaa actccatcaa gaaatcgaat ttgtttttct cttcgtcnac   480
nganacaaan tactgtttaa cgctntccac ggtgatctca                          520
```

<210> SEQ ID NO 30
<211> LENGTH: 600
<212> TYPE: DNA
<213> ORGANISM: Leishmania major
<220> FEATURE:
<221> NAME/KEY: misc_feature
<222> LOCATION: (1)...(600)
<223> OTHER INFORMATION: n = A, T, C or G

<400> SEQUENCE: 30

```
ggcacaaggt tttcgggtta tcttcacgca tggtggagcg cagatgggtg aagtaaatac    60
gcggaccgaa ctgcttgatc atatcaacca gatcgttgtc agcacgcacg ccgtangaac   120
cggtgcacat ggtaaaaccg tntgccatgc tgtttacggt atcaaccatc cactgcatat   180
cttcaatggt ggaaacaatg cgcggcaggc cgaggatccg gcgcggctca tcatnnagnt   240
natnaaccan tcgcacgtct anttctgcac taaactacaa ntatcggtna catatnataa   300
ggccnatttt cggtccagga ntatgtnctn tcaaaatgcc ncgttannca ctcttaaatg   360
tctcangngn aaantngttc taagggtgt ccaaaanntn nttaccnttc cccncttact   420
tcaananctc ctcnaattcc cnggcccttn gacnannatt tnctattaaa anatanaann   480
ttcaaattna ttcccnacct nccntnncca aanntancna ataatcannc ccctntcann   540
anntcccanc ttaccctccn ntngnngggn nnnccnattn ccccaancc ncnctaaata    600
```

<210> SEQ ID NO 31
<211> LENGTH: 600
<212> TYPE: DNA
<213> ORGANISM: Leishmania major
<220> FEATURE:
<221> NAME/KEY: misc_feature
<222> LOCATION: (1)...(600)
<223> OTHER INFORMATION: n = A, T, C or G

<400> SEQUENCE: 31

```
ggcacgagcc tcagtggagc tcaatgaaga tattgcagta tcttactctg gatggcactc    60
aggtctccgg cacgctgccg ccccagtgga gcgcgatggc atcggtgcga attcttaacc   120
tgnagggtac tgaggtctct ggtacgctgc cgcctgagtg gatatcnatg ancaggctgc   180
aaactctgaa tctgcggcgc acgaaantat ccggcactct gccgcccgaa tgganttcta   240
tgaacagcct ggagtacttt cacctttatc ttactcaggt ctccggcacg ctgccgcccg   300
agtggagtgg gatgtcnaag gccgcatact tctggctgga atactgcgac ctgtccggca   360
ntctgccgcc cnagtggtcg tcnatgccaa agctgcgcgg tatctcactg ancggcaaca   420
```

```
aattcttgcg ngtgtntncc ngactcntgg gattcagaaa ggtggtcctt gttgttgggc    480
atcnaaggan caaaccccaa ngggcccncn aattgcttgg gcntgcttaa gganttgcac    540
naaccaacnc cnccaaaaac cccccccacc ncnaaannac nanccccac ttaannnccn     600
```

<210> SEQ ID NO 32
<211> LENGTH: 600
<212> TYPE: DNA
<213> ORGANISM: Leishmania major
<220> FEATURE:
<221> NAME/KEY: misc_feature
<222> LOCATION: (1)...(600)
<223> OTHER INFORMATION: n = A,T,C or G

<400> SEQUENCE: 32

```
ngcacgagaa gcgcaactgg cgcatcgcat ctgtgactat ctgcctgaac aggggcaatn    60
gtttgttggt aacagcctgg tggtacgtct gattgatncg cttncgcaan ttccggcagg    120
ttacccggtg tacancaacc gtggggccan cggtatcnac nggctgcttt cgaccgccgc    180
cggngttcan cgggcaancg gcaaaccgac gctggcgatt gtgggcgatc tctccgcact    240
ttacgatctc aacgcnctgg cgttattgcg tcaggtttct gcgccgctgg tattaattgt    300
ggtgaacaac aacggcnggg caaaattttc tcgctgttgc caacgccccc aaagcnagcg    360
tgaagcgttt ctatctgatg ccgcaaaacg tccattttga aacacgccgc cncccatgtt    420
tcganctgaa aatatcatcg tccgcaaaac tggcangaaa cttngaaaac cgcattttgc    480
cgacnccctg gcncacgccc aacccaccca ccggttgatt gaaaatggtg ggttaacgaa    540
nccnnatggg tgccccaaan cncnnccanc caaatttctg ggcccaggtt aaancccttt    600
```

<210> SEQ ID NO 33
<211> LENGTH: 600
<212> TYPE: DNA
<213> ORGANISM: Leishmania major
<220> FEATURE:
<221> NAME/KEY: misc_feature
<222> LOCATION: (1)...(600)
<223> OTHER INFORMATION: n = A,T,C or G

<400> SEQUENCE: 33

```
acgatgacca tgccccgaag gaggatggcc atgcgccgaa gaacgatgac catgccccga    60
aggaggatgg ccatgcgccg aagaacgatg accatgcccc gaaggaggat ggccatgcgc    120
cgaagaacga cggggatgtg cagaanaaga gcgaagatgg agacaacgtg ggagagggag    180
gcaagggcaa tgaggatggt aacgatgatc agccgaagga gcacgctgcc ggcaactagt    240
gggctgcgtc cgggcttgtg tgcgganccgt gctctgcacc ccgccgctcg tgcatcctcg    300
catgtggact gcgtgtgtct ctcccgcttt gtctctctcc cccacacagt ggctgatgcc    360
tgcacggggt tgctgtggct gcacctcctg accactgcca gctttcttgg cttgcctccc    420
ctctgcgcct ccgctcgtgc cgctcgtgcc gaattcgata tcaagcttat cgataccgtc    480
nacctcgaag gggggcccgg ttacccattc gccctatant gagtcntatt acaattcctg    540
gcgtcgtttt acacgtcgtg actgggaaaa accctggcgt tccccactta tcgccttgca    600
```

<210> SEQ ID NO 34
<211> LENGTH: 516
<212> TYPE: DNA
<213> ORGANISM: Leishmania major

<400> SEQUENCE: 34

```
agctgcagca gcgcctagac accgccacgc agcagcgcgc cgagctggag gcacgggtgg    60
cacggctggc cgcggaccgc gacgaggcgc gccagcagct ggccgcgaac gccgaggagc   120
tgcagcagcg cctagacacc gccacgcagc agcgcgccga gctggaggca cgggtggcac   180
ggctggccgc ggacggcgac gaggcccgcc agcagctggc cgcgaacgcc gaggagctgc   240
agcagcgcct agacaccgcc acgcagcagc gcgccgagct ggaggcacag gtggcacggc   300
tggccgcgaa cgccgaggag ctgcagcagc gcctagacac cgccacgcag cagcgcgccg   360
agctggaggc acgggtggca cggctggccg cggaccgcga cgaggcgcgc cagcagctgg   420
ccgcgaacgc cgaggagctg cagcagcgcc tagacaccgc cacgcagcag cgcgccgagc   480
tggargcaca ggtggcacgg ctggccgcga amgccg                             516
```

<210> SEQ ID NO 35
<211> LENGTH: 822
<212> TYPE: DNA
<213> ORGANISM: Leishmania major
<220> FEATURE:
<221> NAME/KEY: misc_feature
<222> LOCATION: (1)...(822)
<223> OTHER INFORMATION: n = A,T,C or G

<400> SEQUENCE: 35

```
ggcacganag atcttcgtga agacgctgac cggcaanacg atcgcgctgg aggtggagcc    60
gagcgacacg atcgagaacg tgaaggccaa gatccaggac aaggagggca tcccgccgga   120
ccagcagcgc ctgatcttcg ccggcaagca gctggaggan ggccgcacgc tctcggacta   180
caacatccag aaggagtcca cgctgcacct ggtgctgcgc ctgcgcggcg gcatgcanat   240
cttcgtgaaa acgctnaccg gcaanacaat cgcgctggaa gtggagccga acgaccnatc   300
gaaaacgtga aggccnanat ccangacaag gaaggcntcc cgccggagca gcacgcctga   360
tcttccnccg gcaaccactt gangaagggc ncacgctctc ngactacnac atccanaaag   420
gattccnccc tgcaccttgt tgcttgcncc ttgctcgggg ggcatgccna atcttccttn   480
aaaacctcaa ccggcaanaa caatcccccn cngaagttgg aacccaacca ncccattcna   540
aaactttaaa ggccnnnatt ccngaacaan gaagggcttc ccccccggac cnncaancnc   600
cctgattntt ccccccggnnn ncantttgga angaagggcc ccnccctccn ccgaattncn   660
acntcccnaa anggattccc ccctncccct tgnttttgc gccnnnnnnc ggcnncntnc    720
cnaaattccg nccnaaggnc cccantanan cnactttccc nttccccccc nnnnttttgc   780
ntaaantttt tncccccnna aanntcccnt ttncnanttn an                      822
```

<210> SEQ ID NO 36
<211> LENGTH: 146
<212> TYPE: PRT
<213> ORGANISM: Leishmania major
<220> FEATURE:
<221> NAME/KEY: VARIANT
<222> LOCATION: (1)...(146)
<223> OTHER INFORMATION: Xaa = Any Amino Acid

<400> SEQUENCE: 36

```
Gly Thr Ser Pro Cys Leu His Leu Leu Ala Asp Ile Arg Gly Glu Phe
 1               5                  10                  15

Phe Asn Leu Arg Arg Val Glu Leu Leu Asn Val Ala Gln Gln Ala Gln
            20                  25                  30

Leu Val Val Ala His Glu Gly Asp Gly Gln Ser Ser Ala Ala His Ala
        35                  40                  45

Ala Ser Ala Ala Asp Ala Val Asn Val Leu Leu Thr Arg Glu Arg Gln
```

```
                    50                  55                  60
Ile Val Ala Glu Asp Glu Arg Asp Ala Leu His Ile Asn Ala Thr Arg
 65                  70                  75                  80

Pro Gln Val Arg Cys Asn Xaa His Ala Ala Val Ser Ile Thr Glu Cys
                 85                  90                  95

Arg Ile Ile Ser Ser Arg Ser Ala Trp Gly Met Ser Pro Cys Met Ala
                100                 105                 110

Asp Thr Ala Lys Phe Ser Arg Val Ile Phe Leu Ala Ser Cys Ser Thr
                115                 120                 125

Phe Leu Arg Val Leu Xaa Lys Thr Thr Ala Trp Ala Ile Val Lys Leu
                130                 135                 140

Ser Tyr
145

<210> SEQ ID NO 37
<211> LENGTH: 77
<212> TYPE: PRT
<213> ORGANISM: Leishmania major
<220> FEATURE:
<221> NAME/KEY: VARIANT
<222> LOCATION: (1)...(77)
<223> OTHER INFORMATION: Xaa = Any Amino Acid

<400> SEQUENCE: 37

Ala Gln Gly Phe Arg Val Ile Phe Thr His Gly Gly Ala Gln Met Gly
  1               5                  10                  15

Glu Val Asn Thr Arg Thr Glu Leu Leu Asp His Ile Asn Gln Ile Val
                 20                  25                  30

Val Ser Thr His Ala Val Xaa Thr Gly Ala His Gly Lys Thr Val Cys
                 35                  40                  45

His Ala Val Tyr Gly Ile Asn His Pro Leu His Ile Phe Asn Gly Gly
             50                  55                  60

Asn Asn Ala Arg Gln Ala Glu Asp Pro Ala Arg Leu Ile
 65                  70                  75

<210> SEQ ID NO 38
<211> LENGTH: 68
<212> TYPE: PRT
<213> ORGANISM: Leishmania major
<220> FEATURE:
<221> NAME/KEY: VARIANT
<222> LOCATION: (1)...(68)
<223> OTHER INFORMATION: Xaa = Any Amino Acid

<400> SEQUENCE: 38

His Glu Pro Gln Trp Ser Ser Met Lys Ile Leu Gln Tyr Leu Thr Leu
  1               5                  10                  15

Asp Gly Thr Gln Val Ser Gly Thr Leu Pro Pro Gln Trp Ser Ala Met
                 20                  25                  30

Ala Ser Val Arg Ile Leu Asn Leu Xaa Gly Thr Glu Val Ser Gly Thr
                 35                  40                  45

Leu Pro Pro Glu Trp Ile Ser Met Xaa Arg Leu Gln Thr Leu Asn Leu
             50                  55                  60

Arg Arg Thr Lys
 65

<210> SEQ ID NO 39
<211> LENGTH: 65
<212> TYPE: PRT
<213> ORGANISM: Leishmania major
```

```
<220> FEATURE:
<221> NAME/KEY: VARIANT
<222> LOCATION: (1)...(65)
<223> OTHER INFORMATION: Xaa = Any Amino Acid

<400> SEQUENCE: 39
```

Ala Arg Glu Ala Gln Leu Ala His Arg Ile Cys Asp Tyr Leu Pro Glu
 1               5                  10                  15

Gln Gly Gln Xaa Phe Val Gly Asn Ser Leu Val Val Arg Leu Ile Asp
            20                  25                  30

Xaa Leu Xaa Gln Xaa Pro Ala Gly Tyr Pro Val Tyr Xaa Asn Arg Gly
        35                  40                  45

Ala Xaa Gly Ile Xaa Xaa Leu Leu Ser Thr Ala Ala Gly Val Xaa Arg
    50                  55                  60

Ala
65

```
<210> SEQ ID NO 40
<211> LENGTH: 78
<212> TYPE: PRT
<213> ORGANISM: Leishmania major
<220> FEATURE:
<221> NAME/KEY: VARIANT
<222> LOCATION: (1)...(78)
<223> OTHER INFORMATION: Xaa = Any Amino Acid

<400> SEQUENCE: 40
```

Asp Asp His Ala Pro Lys Glu Asp Gly His Ala Pro Lys Asn Asp Asp
 1               5                  10                  15

His Ala Pro Lys Glu Asp Gly His Ala Pro Lys Asn Asp Asp His Ala
            20                  25                  30

Pro Lys Glu Asp Gly His Ala Pro Lys Asn Asp Gly Asp Val Gln Xaa
        35                  40                  45

Lys Ser Glu Asp Gly Asp Asn Val Gly Glu Gly Gly Lys Gly Asn Glu
    50                  55                  60

Asp Gly Asn Asp Asp Gln Pro Lys Glu His Ala Ala Gly Asn
65                  70                  75

```
<210> SEQ ID NO 41
<211> LENGTH: 169
<212> TYPE: PRT
<213> ORGANISM: Leishmania major

<400> SEQUENCE: 41
```

Leu Gln Gln Arg Leu Asp Thr Ala Thr Gln Gln Arg Ala Glu Leu Glu
 1               5                  10                  15

Ala Arg Val Ala Arg Leu Ala Ala Asp Arg Asp Glu Ala Arg Gln Gln
            20                  25                  30

Leu Ala Ala Asn Ala Glu Glu Leu Gln Gln Arg Leu Asp Thr Ala Thr
        35                  40                  45

Gln Gln Arg Ala Glu Leu Glu Ala Arg Val Ala Arg Leu Ala Ala Asp
    50                  55                  60

Gly Asp Glu Ala Arg Gln Gln Leu Ala Ala Asn Ala Glu Glu Leu Gln
65                  70                  75                  80

Gln Arg Leu Asp Thr Ala Thr Gln Gln Arg Ala Glu Leu Glu Ala Gln
                85                  90                  95

Val Ala Arg Leu Ala Ala Asn Ala Glu Glu Leu Gln Gln Arg Leu Asp
                100                 105                 110

Thr Ala Thr Gln Gln Arg Ala Glu Leu Glu Ala Arg Val Ala Arg Leu

```
                115                 120                 125
Ala Ala Asp Arg Asp Glu Ala Arg Gln Gln Leu Ala Ala Asn Ala Glu
        130                 135                 140

Glu Leu Gln Gln Arg Leu Asp Thr Ala Thr Gln Gln Arg Ala Glu Leu
145                 150                 155                 160

Glu Ala Gln Val Ala Arg Leu Ala Ala
                165

<210> SEQ ID NO 42
<211> LENGTH: 98
<212> TYPE: PRT
<213> ORGANISM: Leishmania major
<220> FEATURE:
<221> NAME/KEY: VARIANT
<222> LOCATION: (1)...(98)
<223> OTHER INFORMATION: Xaa = Any Amino Acid

<400> SEQUENCE: 42

Ala Arg Xaa Ile Phe Val Lys Thr Leu Thr Gly Xaa Thr Ile Ala Leu
1               5                   10                  15

Glu Val Glu Pro Ser Asp Thr Ile Glu Asn Val Lys Ala Lys Ile Gln
            20                  25                  30

Asp Lys Glu Gly Ile Pro Pro Asp Gln Gln Arg Leu Ile Phe Ala Gly
        35                  40                  45

Lys Gln Leu Glu Xaa Gly Arg Thr Leu Ser Asp Tyr Asn Ile Gln Lys
50                  55                  60

Glu Ser Thr Leu His Leu Val Leu Arg Leu Arg Gly Gly Met Xaa Ile
65                  70                  75                  80

Phe Val Lys Thr Leu Thr Gly Xaa Thr Ile Ala Leu Glu Val Glu Pro
                85                  90                  95

Asn Asp

<210> SEQ ID NO 43
<211> LENGTH: 39
<212> TYPE: PRT
<213> ORGANISM: Leishmania major

<400> SEQUENCE: 43

Leu Gln Gln Arg Leu Asp Thr Ala Thr Gln Gln Arg Ala Glu Leu Glu
1               5                   10                  15

Ala Arg Val Ala Arg Leu Ala Ala Asp Arg Asp Glu Ala Arg Gln Gln
            20                  25                  30

Leu Ala Ala Asn Ala Glu Glu
        35

<210> SEQ ID NO 44
<211> LENGTH: 600
<212> TYPE: DNA
<213> ORGANISM: Leishmania chagasi
<220> FEATURE:
<221> NAME/KEY: misc_feature
<222> LOCATION: (1)...(600)
<223> OTHER INFORMATION: n = A,T,C or G

<400> SEQUENCE: 44
cggccgcctc agcgaggagg agatcgagcg catggtgcgc gaggctgccg agttcgagga      60
tgaggaccgc aaggtgcgcg aacgtgtcga agcgaagaac tcgctagaga gcatcgcgta    120
ctcgcttcgc aaccagatca acgacaagga caagcttggt gacaagctcg ccgcggacga    180
caagaaggcg atcgaggagg ctgtgaagga tgccctcgac tttgtccacg agaaccccaa    240
```

```
tgcagaccgt gaggagttcg aggctgctcg cacgaagctg cagagtgtga cgaaccccat    300
cattcaaaag gtgtaccagg gcgccgccgg ctctggtgca aaagaggcgg acgcgatgga    360
tgacttgtta gtcggccgcg tgaaaagaaa aacagggaaa gcgggaacat nccacaannaa   420 ccnaagaaga aaggggtng cgacaccgct cgaacaccga cggcncacat ncntcatggg     480
catgctcagc tttcctctcc ccaacaaacc agaaggtttt ctccaaacnc cgtctcngcn    540
cccaaaatac ggaaangtta ancgaaaaan ccccttccac caattgnngt tcttttgttt    600
```

<210> SEQ ID NO 45
<211> LENGTH: 1748
<212> TYPE: DNA
<213> ORGANISM: Leishmania chagasi

<400> SEQUENCE: 45

```
ctagtggatc ccccgggctg caggaattca cggaatacgt acctcctccc ccttcttggt     60
agaagaacaa caacaacgtt caagacgacg ccgcgccttc ttgtaccgca tttgcttctg    120
agcacgttca atccgtgcct tgcaaacatg gaggcgtaca agaagctgga acgatctttt   180
acgaaggtct accgcctgga ccacttcctc ggtctgggca actgggacat gaacacaaac   240 atgccccca agggcgagga atcacgcggt gaggcgatgg cgatgctctc ggagctccgc   300
tttggcttca tcacggcacc ggaggtgaaa agcctgattg agagtgccac caagggcagc   360
gaggagctga atgcggtgca gcgcgctaac ttgcgggaga tgaggcgtgc gtggaagagc   420
gccaccgcct tgccggctga gtttgtgggc cgcaagatgc gcctcacgac acacgcgcac   480
agcgtgtggc gcgacagccg caaagcaaat gacttcgcca agttcctacc ggtgctcagg   540
gacctggtgg cgctcgcccg tgaggagggc tcatacctcg ccgccggcac ctccctctcc   600
ccgtatgagg cgctcatgaa cgagtacgag ccaggaatca cgacacaaaa gctggatgag   660
gtgtacgcaa atgtaaagtc gtggctgccg cagctgctaa aggacattgt gcagaagcag   720
tccggcgagt cggtgattgc gttctcgcat aagttcccgc aggacaagca ggaagcactg   780
tgcaaggaat tcatgaagat ctggcacttc gacaccgatg ccggtcgcct cgacgtcagc   840 ccccacccgtt tcacgggaat gacgaaggag gactgccgac tcacaacaaa ctacatcgaa   900
gacacgtttg ttcagagctt gtatggcgtc atccacgaga gtgggcatgg caagtacgag   960
cagaactgtg gcccacgcga gcacatcacg cagccggtgt gcaacgcccg ctctcttggc  1020
ctgcatgaga gccagagcct ctttgcggag tttcagatcg ccacgcgac gcccttcatc  1080 gactacctca caactcgcct tcctgagttc ttcgaggcgc agccagcgtt ctcgcaggac  1140
aacatgcgca agtcgctgca gcaggtgaag ccgggctaca ttcgcgtcga tgccgatgag  1200
gtgtgctacc ctctgcacgt gatcctgcgc tacgagatcg agcgcgactt gatggagggc  1260
aaaatggagg tggaagacgt gccgcgcgcg tggaacgcaa agatgcagga gtacttgggt  1320
ctctcaacgg agggccgtga cgacgttggg tgcctgcagg acgtgcattg gtccatggtg  1380
cgctcggcta ctctccgacg tactcgctcg gcgccatgta tgcggcgcag atcatggcga  1440
gcatccgaaa ggagctggga gacgacaagg tggatgagtg cctgcgcacc ggtgagctcg  1500
gccccctcct ggaaaagcag caggagaaga tctgggatca tgggtgcctg tacgagacgg  1560
acgacctcat gacgcgtgcg acgggcgaga cgctgaaccc cgagtacctg cgccgccacc  1620
tggaggcgcg ctacataaac gcctgagtcg cgagcggttg acacacgcgc tcgctagcac  1680
atgacgcgtc tttattattc tttgttgtgc attcggaatt ccgcggaatt cgatatcaag  1740
```

```
cttatcga                                                            1748

<210> SEQ ID NO 46
<211> LENGTH: 560
<212> TYPE: DNA
<213> ORGANISM: Leishmania chagasi
<220> FEATURE:
<221> NAME/KEY: misc_feature
<222> LOCATION: (1)...(560)
<223> OTHER INFORMATION: n = A,T,C or G

<400> SEQUENCE: 46
cggaaggagg atggccatac acagaaaaat gacggcgatg gccctaagga ggacggccgt      60
acacagaaaa acgacgacgg tggccctaag gaggacggcc atacacagaa aaatgacggc     120
gatggcccta aggaggacgg ccgtacacag aaaaataacg gcgatggccc tnaggaggac     180
ggccatacac agaaaaatga cggcgatgcc cctnaggagg acggccgtac acanaaaaat     240
gacggcnatg gccctnagga ggacggccgt acacagaaaa atgacngcca tggcccttag     300
gangacgccg tacacagaaa aatgacgcna tggccctnag gaggacggc catacccana      360 aaaattgacg gcnatngccc ttaggangac ggccgtnccc anaaanantg acngcggtng     420
cccttaagga agatgaaaat ctgccaccaa aacnattggg aatgcncagg aaaanaacna     480
anatngaccc cacgtggggg atgganctta cngcnattaa nattgttacc attatcnacc     540
naaggacnng ttgccgncaa                                                 560

<210> SEQ ID NO 47
<211> LENGTH: 600
<212> TYPE: DNA
<213> ORGANISM: Leishmania chagasi
<220> FEATURE:
<221> NAME/KEY: misc_feature
<222> LOCATION: (1)...(600)
<223> OTHER INFORMATION: n = A,T,C or G

<400> SEQUENCE: 47
cgtccgagaa acccgtacat gtatgctgct ggtagaaggc gcagagctgg tccctctgat      60
gcacaagcat gaggtcgtac attgcctggt tcgtcatttt ccagagcaca acgagcagcg     120
tcatcataca gcatccaata gccgccagag tgaatgcgat gcgcacacca agtcgaaagt     180
ggtcgaccag tagggaatg tgaccctggc tggcgtgcaa catgatcgcc acgccagcgg      240
tgggccacac cacaacagag gcgacgaaag agaacatgaa cttgctcacg aagctnacaa     300
taagggcgtc gctngtgatg ctaagaacca cgccnaggta gacggcgaag ancaaactaa     360
acacaagcgt gacgatcccg aaaagaagga tctctgcgga attttcgtga gataganaat     420
gcccgtactg gaaaaanaag ccggcaggcg cgcgataacg ctgcaacttg ccgctcctcg     480
cgggcgcgtt ttcgctcctt ctccgacttg atggcgcngt cngncttgac aaaacggtta     540
agctcctcat gccccagccg attccagct cacggtccac ttccggccat gcccacggac      600

<210> SEQ ID NO 48
<211> LENGTH: 1053
<212> TYPE: DNA
<213> ORGANISM: Leishmania chagasi
<220> FEATURE:
<221> NAME/KEY: misc_feature
<222> LOCATION: (1)...(1053)
<223> OTHER INFORMATION: n = A,T,C or G

<400> SEQUENCE: 48
gggaaaaaag tggagctcca ccgcggtggc ggccgctcta gaactagtgg atcccccggg      60
```

```
ctgcaggaat tccgcggaat tccgcggaat tccgcggaat tccgtccgac gcggcacccg    120
cacaggggtc gacagtgacg caacctcctc caccactgcg gcctacgacg gcgccggctc    180
cgcgccagtg atggttgacg ccaatgtgag ccaccctccg tacgcgggc atgaccaagt     240 gtacatgcac gtcggcaagc ccatcgtggg caacaccctc gacggataca acgggtgcgt    300
gttcgcctac gggcanacgg gcagcggcaa aaccttcacg atgctcggnt acgcgccgag    360
cacgancgac atccgcgctc gcaaaggtc cgtcccctgc ggggccagca gcatggagaa     420
cagcactcct cttgacagcg ctgtggagcc gtttgagagc gatgacggcg acgacgtggt    480
ggacaagacg gggctggatc cgaacgagct gcaaggcatc atcccgcgcg cgtgcacgga    540
cctgttcgat ggtctccgtg cgaagcgcgc caaggactcc gacttcacgt accgcgtgga    600
ggtgtcttac tacgagatct acaacgagaa ggtgttcgat ctcatccggc cgcagcgcaa    660
cacggacctg aggatacgta actcgcccaa ctccggtcca tttatcgaag gcctgacgtg    720
gaagatggtg tccaaggagg aagacgtcgc ccgcgtgatt cgcaagggca tgcaggagcg    780
ccacacggct gcgaccaagt tcaacgaccg cagcagccgc agccacgcca tcctcacctt    840
caacattgtg cagctgtcga tggacgactc cgacaacgcg ttccagatgc gcagcaagct    900
gaacctggtg gaccttgctg gtcggagcg cactggtgcg gccggagccg agggcaatga    960
gttccacgac ggtgtgaaga tcaaccactc gctgacggtg ctggggcgcg tgatcgaccg    1020
tctggcggac ctctcgcaga acaagggagg ggg                                1053
```

<210> SEQ ID NO 49
<211> LENGTH: 136
<212> TYPE: PRT
<213> ORGANISM: Leishmania chagasi

<400> SEQUENCE: 49

```
Gly Arg Leu Ser Glu Glu Glu Ile Glu Arg Met Val Arg Glu Ala Ala
  1               5                  10                  15

Glu Phe Glu Asp Glu Arg Lys Val Arg Glu Arg Val Glu Ala Lys
                 20                  25                  30

Asn Ser Leu Glu Ser Ile Ala Tyr Ser Leu Arg Asn Gln Ile Asn Asp
             35                  40                  45

Lys Asp Lys Leu Gly Asp Lys Leu Ala Ala Asp Lys Lys Ala Ile
         50                  55                  60

Glu Glu Ala Val Lys Asp Ala Leu Asp Phe Val His Glu Asn Pro Asn
 65                  70                  75                  80

Ala Asp Arg Glu Glu Phe Glu Ala Ala Arg Thr Lys Leu Gln Ser Val
                 85                  90                  95

Thr Asn Pro Ile Ile Gln Lys Val Tyr Gln Gly Ala Ala Gly Ser Gly
            100                 105                 110

Ala Glu Glu Ala Asp Ala Met Asp Asp Leu Leu Val Gly Arg Val Lys
            115                 120                 125

Arg Lys Thr Gly Lys Ala Gly Thr
            130                 135
```

<210> SEQ ID NO 50
<211> LENGTH: 510
<212> TYPE: PRT
<213> ORGANISM: Leishmania chagasi

<400> SEQUENCE: 50

Tyr Leu Leu Pro Leu Leu Gly Arg Arg Thr Thr Thr Thr Phe Lys Thr

-continued

```
  1               5                   10                  15
Thr Pro Arg Leu Leu Val Pro His Leu Leu Ser Thr Phe Asn Pro
                20                  25              30
Cys Leu Ala Asn Met Glu Ala Tyr Lys Leu Glu Thr Ile Phe Thr
            35                  40              45
Lys Val Tyr Arg Leu Asp His Phe Leu Gly Leu Gly Asn Trp Asp Met
    50                  55              60
Asn Thr Asn Met Pro Pro Lys Gly Glu Glu Ser Arg Gly Glu Ala Met
65                  70              75                  80
Ala Met Leu Ser Glu Leu Arg Phe Gly Phe Ile Thr Ala Pro Glu Val
                85                  90              95
Lys Ser Leu Ile Glu Ser Ala Thr Lys Gly Ser Glu Glu Leu Asn Ala
                100                 105             110
Val Gln Arg Ala Asn Leu Arg Glu Met Arg Arg Ala Trp Lys Ser Ala
            115                 120             125
Thr Ala Leu Pro Ala Glu Phe Val Gly Arg Lys Met Arg Leu Thr Thr
    130                 135             140
His Ala His Ser Val Trp Arg Asp Ser Arg Lys Ala Asn Asp Phe Ala
145                 150             155                 160
Lys Phe Leu Pro Val Leu Arg Asp Leu Val Ala Leu Ala Arg Glu Glu
                165                 170             175
Gly Ser Tyr Leu Ala Ala Gly Thr Ser Leu Ser Pro Tyr Glu Ala Leu
                180                 185             190
Met Asn Glu Tyr Glu Pro Gly Ile Thr Thr Gln Lys Leu Asp Glu Val
            195                 200             205
Tyr Ala Asn Val Lys Ser Trp Leu Pro Gln Leu Leu Lys Asp Ile Val
    210                 215             220
Gln Lys Gln Ser Gly Glu Ser Val Ile Ala Phe Ser His Lys Phe Pro
225                 230             235                 240
Gln Asp Lys Gln Glu Ala Leu Cys Lys Glu Phe Met Lys Ile Trp His
            245                 250             255
Phe Asp Thr Asp Ala Gly Arg Leu Asp Val Ser Pro His Pro Phe Thr
            260                 265             270
Gly Met Thr Lys Glu Asp Cys Arg Leu Thr Thr Asn Tyr Ile Glu Asp
            275                 280             285
Thr Phe Val Gln Ser Leu Tyr Gly Val Ile His Glu Ser Gly His Gly
    290                 295             300
Lys Tyr Glu Gln Asn Cys Gly Pro Arg Glu His Ile Thr Gln Pro Val
305                 310             315                 320
Cys Asn Ala Arg Ser Leu Gly Leu His Glu Ser Gln Ser Leu Phe Ala
            325                 330             335
Glu Phe Gln Ile Gly His Ala Thr Pro Phe Ile Asp Tyr Leu Thr Thr
            340                 345             350
Arg Leu Pro Glu Phe Phe Glu Ala Gln Pro Ala Phe Ser Gln Asp Asn
            355                 360             365
Met Arg Lys Ser Leu Gln Gln Val Lys Pro Gly Tyr Ile Arg Val Asp
    370                 375             380
Ala Asp Glu Val Cys Tyr Pro Leu His Val Ile Leu Arg Tyr Glu Ile
385                 390             395                 400
Glu Arg Asp Leu Met Glu Gly Lys Met Glu Val Glu Asp Val Pro Arg
                405                 410             415
Ala Trp Asn Ala Lys Met Gln Glu Tyr Leu Gly Leu Ser Thr Glu Gly
            420                 425             430
```

-continued

```
Arg Asp Asp Val Gly Cys Leu Gln Asp Val His Trp Ser Met Val Arg
            435                 440                 445

Ser Ala Thr Leu Arg Arg Thr Arg Ser Ala Pro Cys Met Arg Arg
    450                 455                 460

Ser Trp Arg Ala Ser Glu Arg Ser Trp Glu Thr Thr Arg Trp Met Ser
465                 470                 475                 480

Ala Cys Ala Pro Val Ser Ser Ala Pro Ser Trp Lys Ser Ser Arg Arg
                485                 490                 495

Arg Ser Gly Ile Met Gly Ala Cys Thr Arg Arg Thr Thr Ser
            500                 505                 510

<210> SEQ ID NO 51
<211> LENGTH: 107
<212> TYPE: PRT
<213> ORGANISM: Leishmania chagasi
<220> FEATURE:
<221> NAME/KEY: VARIANT
<222> LOCATION: (1)...(107)
<223> OTHER INFORMATION: Xaa = Any Amino Acid

<400> SEQUENCE: 51

Gly Arg Arg Met Ala Ile His Arg Lys Met Thr Ala Met Ala Leu Arg
1               5                  10                  15

Arg Thr Ala Val His Arg Lys Thr Thr Thr Val Ala Leu Arg Arg Thr
            20                  25                  30

Ala Ile His Arg Lys Met Thr Ala Met Ala Leu Arg Arg Thr Ala Val
        35                  40                  45

His Arg Lys Ile Thr Ala Met Ala Leu Arg Arg Thr Ala Ile His Arg
    50                  55                  60

Lys Met Thr Ala Met Pro Leu Arg Arg Thr Ala Val His Xaa Lys Met
65                  70                  75                  80

Thr Ala Met Ala Leu Arg Arg Thr Ala Val His Arg Lys Met Thr Ala
                85                  90                  95

Met Ala Leu Arg Xaa Thr Pro Tyr Thr Glu Lys
            100                 105

<210> SEQ ID NO 52
<211> LENGTH: 63
<212> TYPE: PRT
<213> ORGANISM: Leishmania chagasi

<400> SEQUENCE: 52

Val Arg Glu Thr Arg Thr Cys Met Leu Leu Val Glu Gly Ala Glu Leu
1               5                  10                  15

Val Pro Leu Met His Lys His Glu Val Val His Cys Leu Val Arg His
            20                  25                  30

Phe Pro Glu His Asn Glu Gln Arg His His Thr Ala Ser Asn Ser Arg
        35                  40                  45

Gln Ser Glu Cys Asp Ala His Thr Lys Ser Lys Val Val Asp Gln
    50                  55                  60

<210> SEQ ID NO 53
<211> LENGTH: 324
<212> TYPE: PRT
<213> ORGANISM: Leishmania chagasi
<220> FEATURE:
<221> NAME/KEY: VARIANT
<222> LOCATION: (1)...(324)
<223> OTHER INFORMATION: Xaa = Any Amino Acid
```

<400> SEQUENCE: 53

| | | | | | | | | | | | | | | |
|---|---|---|---|---|---|---|---|---|---|---|---|---|---|---|
|Phe|Arg|Gly|Ile|Pro|Arg|Asn|Ser|Val|Arg|Gly|Thr|Arg|Thr|Gly|
|1| | | |5| | | |10| | | |15| | |
|Val|Asp|Ser|Asp|Ala|Thr|Ser|Ser|Thr|Thr|Ala|Ala|Tyr|Asp|Gly|Ala|
| | | |20| | | | |25| | | | |30| | |
|Gly|Ser|Ala|Pro|Val|Met|Val|Asp|Ala|Asn|Val|Ser|His|Pro|Pro|Tyr|
| | | |35| | | | |40| | | | |45| | |
|Ala|Gly|His|Asp|Gln|Val|Tyr|Met|His|Val|Gly|Lys|Pro|Ile|Val|Gly|
| |50| | | | |55| | | | |60| | | | |
|Asn|Thr|Leu|Asp|Gly|Tyr|Asn|Gly|Cys|Val|Phe|Ala|Tyr|Gly|Xaa|Thr|
|65| | | | |70| | | | |75| | | | |80|
|Gly|Ser|Gly|Lys|Thr|Phe|Thr|Met|Leu|Gly|Tyr|Ala|Pro|Ser|Thr|Xaa|
| | | | |85| | | | |90| | | | |95| |
|Asp|Ile|Arg|Ala|Arg|Lys|Gly|Ser|Val|Pro|Cys|Gly|Ala|Ser|Ser|Met|
| | | | |100| | | | |105| | | | |110| |
|Glu|Asn|Ser|Thr|Pro|Leu|Asp|Ser|Ala|Val|Glu|Pro|Phe|Glu|Ser|Asp|
| | | | |115| | | | |120| | | | |125| |
|Asp|Gly|Asp|Val|Val|Asp|Lys|Thr|Gly|Leu|Asp|Pro|Asn|Glu|Leu|
| | |130| | | | |135| | | | |140| | |
|Gln|Gly|Ile|Ile|Pro|Arg|Ala|Cys|Thr|Asp|Leu|Phe|Asp|Gly|Leu|Arg|
|145| | | | |150| | | | |155| | | | |160|
|Ala|Lys|Arg|Ala|Lys|Asp|Ser|Asp|Phe|Thr|Tyr|Arg|Val|Glu|Val|Ser|
| | | | |165| | | | |170| | | | |175| |
|Tyr|Tyr|Glu|Ile|Tyr|Asn|Glu|Lys|Val|Phe|Asp|Leu|Ile|Arg|Pro|Gln|
| | | | |180| | | | |185| | | | |190| |
|Arg|Asn|Thr|Asp|Leu|Arg|Ile|Arg|Asn|Ser|Pro|Asn|Ser|Gly|Pro|Phe|
| | | | |195| | | | |200| | | | |205| |
|Ile|Glu|Gly|Leu|Thr|Trp|Lys|Met|Val|Ser|Lys|Glu|Glu|Asp|Val|Ala|
|210| | | | |215| | | | |220| | | | | |
|Arg|Val|Ile|Arg|Lys|Gly|Met|Gln|Glu|Arg|His|Thr|Ala|Ala|Thr|Lys|
|225| | | | |230| | | | |235| | | | |240|
|Phe|Asn|Asp|Arg|Ser|Ser|Arg|Ser|His|Ala|Ile|Leu|Thr|Phe|Asn|Ile|
| | | | |245| | | | |250| | | | |255| |
|Val|Gln|Leu|Ser|Met|Asp|Asp|Ser|Asp|Asn|Ala|Phe|Gln|Met|Arg|Ser|
| | | | |260| | | | |265| | | | |270| |
|Lys|Leu|Asn|Leu|Val|Asp|Leu|Ala|Gly|Ser|Glu|Arg|Thr|Gly|Ala|Ala|
| | | | |275| | | | |280| | | | |285| |
|Gly|Ala|Glu|Gly|Asn|Glu|Phe|His|Asp|Gly|Val|Lys|Ile|Asn|His|Ser|
| |290| | | | |295| | | | |300| | | | |
|Leu|Thr|Val|Leu|Gly|Arg|Val|Ile|Asp|Arg|Leu|Ala|Asp|Leu|Ser|Gln|
|305| | | | |310| | | | |315| | | | |320|
|Asn|Lys|Gly|Gly|

<210> SEQ ID NO 54
<211> LENGTH: 1585
<212> TYPE: DNA
<213> ORGANISM: Leishmania major
<220> FEATURE:
<221> NAME/KEY: misc_feature
<222> LOCATION: (1)...(1585)
<223> OTHER INFORMATION: n = A,T,C or G

<400> SEQUENCE: 54
aaagctggag ctccaccgcg gtggcggccg ctctagaact agtggatccc ccgggctgca    60
ggaattcggc acgagtgctg cccgacatga catgctcgct gaccggactt cagtgcacag   120

-continued

```
acccgaactg caagacctgc acaacttacg gtcagtgcac agactgcaac gacggctacg    180
gtctcacctc ctccagcgtt tgcgtgcgct gcagtgtagc gggctgcaag agctgccccg    240
tcgacgctaa cgtctgcaaa gtgtgtctcg gcggcagcga gccgatcaac aatatgtgcc    300
cctgcaccga ccccaactgc gccagctgcc ccagcgacgc tggcacgtgc actcagtgcg    360
cgaacggcta cggtctcgtg gacggcgcct gtgtgagatg ccaggagccc aactgcttca    420
gctgcgacag cgacgcgaat aagtgcacac aatgtgcgcc gaactactac ctcaccccgc    480
tcttgacctg ctccccggtg gcctgcaaca tcgagcactg catgcagtgc gacccacaga    540
cgccgtcgcg ctgccaggag tgcgtgtccc cctacgtggt tgacagctac gacggcctct    600
gcaggctctc cgatgcctgc tccgtgccca actgcaagaa gtgcgagacc ggtacctcca    660
ggctctgcgc cgagtgcgac accggctaca gtctctccgc cgacgcgacg agctgcagca    720
gtccaaccac gcagccgtgc gaggtggagc actgcaacac atgtgtgaac ggcgatagca    780
cccgctgtgc ctactgcaac accggctact acgtctccga tggcaagtgc aaggccatgc    840
agggctgcta cgtgtcgaac tgcgcgcagt gcatgctgct tgcagcacc aagtgctcca    900
cgtgcgtgaa agggtacctg ctcacgtcgt cctacagttg cgtctcgcag aaagtcatca    960
acagtgcggc cgcgccctac tctctgtggg tggccgccgc cgtgctcctc acctcttttg   1020
ccatgcacct agcatagtgc gcagcggcat gcgaacaacc ccactctcat tctccaacat   1080
gtgcatacac acacacacag acagcggggc agcacccccct ccccacacac acacacgcac   1140
ttccccccttg tcttgttctt ctttcctcgn ttcgcatttc tttctctcgt gcgctggcgc   1200
cggcctcctg cacgtcgctc ccctcccccct aacctctatt ctctctctct ctctctctcg   1260
ccggcatcat tgcttcttac ccttttctga tccttgctcg cgtgggcgga cactgccaca   1320
gtcccacagc gcagacacac gtgtttaaac ggcgcaggca tccctcccta tcacttcatt   1380
tctcctaaag ccactcacca agtcgcacac cgccctcccc catcggccgc ccttccgggc   1440
gcagctgtgc ggaatgggtg tgtgctcgac ctcgttcctg gcagctcact cgcatgtgta   1500
cagccactcc aaccacgaaa gctctcttct gcgcacataa aaaaaaaaa aaaaaaaaa    1560
ctcgaggggg ggcccggtac ccaaa                                         1585
```

<210> SEQ ID NO 55
<211> LENGTH: 320
<212> TYPE: PRT
<213> ORGANISM: Leishmania major

<400> SEQUENCE: 55

```
Val Leu Pro Asp Met Thr Cys Ser Leu Thr Gly Leu Gln Cys Thr Asp
  1               5                  10                  15

Pro Asn Cys Lys Thr Cys Thr Thr Tyr Gly Gln Cys Thr Asp Cys Asn
             20                  25                  30

Asp Gly Tyr Gly Leu Thr Ser Ser Val Cys Val Arg Cys Ser Val
         35                  40                  45

Ala Gly Cys Lys Ser Cys Pro Val Asp Ala Asn Val Cys Lys Val Cys
     50                  55                  60

Leu Gly Ser Glu Pro Ile Asn Asn Met Cys Pro Cys Thr Asp Pro
 65                  70                  75                  80

Asn Cys Ala Ser Cys Pro Ser Asp Ala Gly Thr Cys Thr Gln Cys Ala
             85                  90                  95

Asn Gly Tyr Gly Leu Val Asp Gly Ala Cys Val Arg Cys Gln Glu Pro
            100                 105                 110
```

```
Asn Cys Phe Ser Cys Asp Ser Asp Ala Asn Lys Cys Thr Gln Cys Ala
            115                 120                 125

Pro Asn Tyr Tyr Leu Thr Pro Leu Leu Thr Cys Ser Pro Val Ala Cys
    130                 135                 140

Asn Ile Glu His Cys Met Gln Cys Asp Pro Gln Thr Pro Ser Arg Cys
145                 150                 155                 160

Gln Glu Cys Val Ser Pro Tyr Val Val Asp Ser Tyr Asp Gly Leu Cys
                165                 170                 175

Arg Leu Ser Asp Ala Cys Ser Val Pro Asn Cys Lys Lys Cys Glu Thr
            180                 185                 190

Gly Thr Ser Arg Leu Cys Ala Glu Cys Asp Thr Gly Tyr Ser Leu Ser
        195                 200                 205

Ala Asp Ala Thr Ser Cys Ser Ser Pro Thr Thr Gln Pro Cys Glu Val
    210                 215                 220

Glu His Cys Asn Thr Cys Val Asn Gly Asp Ser Thr Arg Cys Ala Tyr
225                 230                 235                 240

Cys Asn Thr Gly Tyr Tyr Val Ser Asp Gly Lys Cys Lys Ala Met Gln
                245                 250                 255

Gly Cys Tyr Val Ser Asn Cys Ala Gln Cys Met Leu Leu Asp Ser Thr
            260                 265                 270

Lys Cys Ser Thr Cys Val Lys Gly Tyr Leu Leu Thr Ser Ser Tyr Ser
        275                 280                 285

Cys Val Ser Gln Lys Val Ile Asn Ser Ala Ala Pro Tyr Ser Leu
    290                 295                 300

Trp Val Ala Ala Val Leu Leu Thr Ser Phe Ala Met His Leu Ala
305                 310                 315                 320

<210> SEQ ID NO 56
<211> LENGTH: 14
<212> TYPE: PRT
<213> ORGANISM: Leishmania major

<400> SEQUENCE: 56

Pro Lys Glu Asp Gly His Ala Pro Lys Asn Asp Asp His Ala
1               5                   10

<210> SEQ ID NO 57
<211> LENGTH: 7
<212> TYPE: PRT
<213> ORGANISM: Leishmania major

<400> SEQUENCE: 57

Pro Lys Glu Asp Gly His Ala
1               5

<210> SEQ ID NO 58
<211> LENGTH: 7
<212> TYPE: PRT
<213> ORGANISM: Leishmania major

<400> SEQUENCE: 58

Pro Lys Asn Asp Asp His Ala
1               5

<210> SEQ ID NO 59
<211> LENGTH: 264
<212> TYPE: DNA
<213> ORGANISM: Leishmania chagasi
```

<400> SEQUENCE: 59

| atgcaccatc | atcaccatca | catgggaagc | tcctgcacga | aggactccgc | aaaggagccc | 60 |
| cagaagcgtg | ctgataacat | cgatacgacc | actcgaagcg | atgagaagga | cggcatccat | 120 |
| gtccaggaga | gcgccggtcc | tgtgcaggag | aacttcgggg | atgcgcagga | agaacgaa   | 180 |
| gatggacaca | acgtggggga | tggagctaac | gacaatgagg | atggtaacga | tgatcagccg | 240 |
| aaggagcagg | ttgccggcaa | ctag       |            |            |            | 264 |

<210> SEQ ID NO 60
<211> LENGTH: 744
<212> TYPE: DNA
<213> ORGANISM: Leishmania chagasi

<400> SEQUENCE: 60

| atgggagcct | actgcacgaa | ggactccgca | aaggagcccc | agaagcgtgc | tgataacatc | 60 |
| cataaaacca | ctgaggccaa | tcacagaggc | gccgccggtg | tgcccccgaa | gcacgccggc | 120 |
| ggtgcgatga | acgactctgc | cccgaaggag | gatggccata | cagaaaaaa  | tgacggcgat | 180 |
| ggccctaagg | aggacggccg | tacacagaaa | aacgacgacg | gtggccctaa | ggaggacggc | 240 |
| catacacaga | aaaatgacgg | cgatggccct | aaggaggacg | gccgtacaca | gaaaaataac | 300 |
| ggcgatggcc | ctaaggagga | cggccataca | cagaaaaatg | acggcgatgc | cctaaggag  | 360 |
| gacggccgta | cacagaaaaa | tgacggcgat | ggccctaagg | aggacggccg | tacacagaaa | 420 |
| aatgacggcg | atgccctaa  | ggaggacggc | cgtacacaga | aaatgacgg  | cgatggcccct | 480 |
| aaggaggacg | gccgtacaca | gaaaaatgac | ggcgatggcc | ctaaggagga | cggccataca | 540 |
| cagaaaaatg | acggcgatgg | ccctaaggag | gacggccgta | cacagaaaaa | tgacggcggt | 600 |
| ggccctaagg | aggatgagaa | tctgcagcaa | acgatggga  | atgcgcagga | agaacgaa   | 660 |
| gatggacaca | acgtggggga | tggagctaac | ggcaatgagg | atggtaacga | tgatcagccg | 720 |
| aaggagcagg | ttgccggcaa | ctag       |            |            |            | 744 |

<210> SEQ ID NO 61
<211> LENGTH: 80
<212> TYPE: PRT
<213> ORGANISM: Leishmania chagasi

<400> SEQUENCE: 61

Met Gly Ser Ser Cys Thr Lys Asp Ser Ala Lys Glu Pro Gln Lys Arg
 1               5                  10                  15

Ala Asp Asn Ile Asp Thr Thr Thr Arg Ser Asp Glu Lys Asp Gly Ile
            20                  25                  30

His Val Gln Glu Ser Ala Gly Pro Val Gln Glu Asn Phe Gly Asp Ala
        35                  40                  45

Gln Glu Lys Asn Glu Asp Gly His Asn Val Gly Asp Gly Ala Asn Asp
    50                  55                  60

Asn Glu Asp Gly Asn Asp Asp Gln Pro Lys Glu Gln Val Ala Gly Asn
65                  70                  75                  80

<210> SEQ ID NO 62
<211> LENGTH: 247
<212> TYPE: PRT
<213> ORGANISM: Leishmania chagasi

<400> SEQUENCE: 62

Met Gly Ala Tyr Cys Thr Lys Asp Ser Ala Lys Glu Pro Gln Lys Arg
 1               5                  10                  15

```
Ala Asp Asn Ile His Lys Thr Thr Glu Ala Asn His Arg Gly Ala Ala
            20                  25                  30

Gly Val Pro Pro Lys His Ala Gly Ala Met Asn Asp Ser Ala Pro
        35                  40                  45

Lys Glu Asp Gly His Thr Gln Lys Asn Asp Gly Asp Gly Pro Lys Glu
 50                  55                  60

Asp Gly Arg Thr Gln Lys Asn Asp Asp Gly Gly Pro Lys Glu Asp Gly
 65                  70                  75                  80

His Thr Gln Lys Asn Asp Gly Asp Gly Pro Lys Glu Asp Gly Arg Thr
                85                  90                  95

Gln Lys Asn Asn Gly Asp Gly Pro Lys Glu Asp Gly His Thr Gln Lys
            100                 105                 110

Asn Asp Gly Asp Ala Pro Lys Glu Asp Gly Arg Thr Gln Lys Asn Asp
            115                 120                 125

Gly Asp Gly Pro Lys Glu Asp Gly Arg Thr Gln Lys Asn Asp Gly Asp
        130                 135                 140

Gly Pro Lys Glu Asp Gly Arg Thr Gln Lys Asn Asp Gly Asp Gly Pro
145                 150                 155                 160

Lys Glu Asp Gly Arg Thr Gln Lys Asn Asp Gly Asp Gly Pro Lys Glu
                165                 170                 175

Asp Gly His Thr Gln Lys Asn Asp Gly Asp Gly Pro Lys Glu Asp Gly
            180                 185                 190

Arg Thr Gln Lys Asn Asp Gly Gly Pro Lys Glu Asp Glu Asn Leu
            195                 200                 205

Gln Gln Asn Asp Gly Asn Ala Gln Glu Lys Asn Glu Asp Gly His Asn
        210                 215                 220

Val Gly Asp Gly Ala Asn Gly Asn Glu Asp Gly Asn Asp Asp Gln Pro
225                 230                 235                 240

Lys Glu Gln Val Ala Gly Asn
                245
```

```
<210> SEQ ID NO 63
<211> LENGTH: 14
<212> TYPE: PRT
<213> ORGANISM: Leishmania chagasi
<220> FEATURE:
<221> NAME/KEY: VARIANT
<222> LOCATION: (6)...(6)
<223> OTHER INFORMATION: Xaa = His or Arg
<221> NAME/KEY: VARIANT
<222> LOCATION: (12)...(12)
<223> OTHER INFORMATION: Xaa = Gly or Asp
<221> NAME/KEY: VARIANT
<222> LOCATION: (13)...(13)
<223> OTHER INFORMATION: Xaa = Asp or Gly

<400> SEQUENCE: 63

Pro Lys Glu Asp Gly Xaa Thr Gln Lys Asn Asp Xaa Xaa Gly
 1               5                  10

<210> SEQ ID NO 64
<211> LENGTH: 7
<212> TYPE: PRT
<213> ORGANISM: Leishmania chagasi
<220> FEATURE:
<221> NAME/KEY: VARIANT
<222> LOCATION: (6)...(6)
<223> OTHER INFORMATION: Xaa = His or Arg

<400> SEQUENCE: 64
```

```
Pro Lys Glu Asp Gly Xaa Thr
 1               5

<210> SEQ ID NO 65
<211> LENGTH: 7
<212> TYPE: PRT
<213> ORGANISM: Leishmania chagasi
<220> FEATURE:
<221> NAME/KEY: VARIANT
<222> LOCATION: (5)...(5)
<223> OTHER INFORMATION: Xaa = Gly or Asp
<221> NAME/KEY: VARIANT
<222> LOCATION: (6)...(6)
<223> OTHER INFORMATION: Xaa = Asp or Gly

<400> SEQUENCE: 65

Gln Lys Asn Asp Xaa Xaa Gly
 1               5

<210> SEQ ID NO 66
<211> LENGTH: 17
<212> TYPE: PRT
<213> ORGANISM: Artificial Sequence
<220> FEATURE:
<223> OTHER INFORMATION: Synthetic peptide to asses diagnostic potential
      of repeat in Lc Gene B

<400> SEQUENCE: 66

Gly Cys Gly Pro Lys Glu Asp Gly Arg Thr Gln Lys Asn Asp Gly Asp
 1               5                  10                  15

Gly

<210> SEQ ID NO 67
<211> LENGTH: 31
<212> TYPE: PRT
<213> ORGANISM: Artificial Sequence
<220> FEATURE:
<223> OTHER INFORMATION: Synthetic peptide to asses diagnostic potential
      of repeat in Lc Gene B

<400> SEQUENCE: 67

Gly Cys Gly Pro Lys Glu Asp Gly Arg Thr Gln Lys Asn Asp Gly Asp
 1               5                  10                  15

Gly Pro Lys Glu Asp Gly Arg Thr Gln Lys Asn Asp Gly Asp Gly
            20                  25                  30

<210> SEQ ID NO 68
<211> LENGTH: 45
<212> TYPE: PRT
<213> ORGANISM: Artificial Sequence
<220> FEATURE:
<223> OTHER INFORMATION: Synthetic peptide to asses diagnostic potential
      of repeat in Lc Gene B

<400> SEQUENCE: 68

Gly Cys Gly Pro Lys Glu Asp Gly Arg Thr Gln Lys Asn Asp Gly Asp
 1               5                  10                  15

Gly Pro Lys Glu Asp Gly Arg Thr Gln Lys Asn Asp Gly Asp Gly Pro
            20                  25                  30

Lys Glu Asp Gly Arg Thr Gln Lys Asn Asp Gly Asp Gly
                35                  40                  45

<210> SEQ ID NO 69
<211> LENGTH: 17
<212> TYPE: PRT
<213> ORGANISM: Artificial Sequence
```

-continued

<220> FEATURE:
<223> OTHER INFORMATION: Synthetic peptide to asses diagnostic potential
      of repeat in Lc Gene B

<400> SEQUENCE: 69

Gly Cys Gly Pro Lys Glu Asp Gly His Thr Gln Lys Asn Asp Gly Asp
1               5                   10                  15

Gly

<210> SEQ ID NO 70
<211> LENGTH: 31
<212> TYPE: PRT
<213> ORGANISM: Artificial Sequence
<220> FEATURE:
<223> OTHER INFORMATION: Synthetic peptide to asses diagnostic potential
      of repeat in Lc Gene B

<400> SEQUENCE: 70

Gly Cys Gly Pro Lys Glu Asp Gly His Thr Gln Lys Asn Asp Gly Asp
1               5                   10                  15

Gly Pro Lys Glu Asp Gly His Thr Gln Lys Asn Asp Gly Asp Gly
            20                  25                  30

<210> SEQ ID NO 71
<211> LENGTH: 45
<212> TYPE: PRT
<213> ORGANISM: Gly Cys Gly Pro Lys Glu Asp Gly His Thr Gln
<220> FEATURE:
<223> OTHER INFORMATION: Synthetic peptide to asses diagnostic potential
      of repeat in Lc Gene B

<400> SEQUENCE: 71

Gly Cys Gly Pro Lys Glu Asp Gly His Thr Gln Lys Asn Asp Gly Asp
1               5                   10                  15

Gly Pro Lys Glu Asp Gly His Thr Gln Lys Asn Asp Gly Asp Gly Pro
            20                  25                  30

Lys Glu Asp Gly His Thr Gln Lys Asn Asp Gly Asp Gly
            35                  40                  45

<210> SEQ ID NO 72
<211> LENGTH: 664
<212> TYPE: DNA
<213> ORGANISM: Leishmania major
<220> FEATURE:
<221> NAME/KEY: misc_feature
<222> LOCATION: (1)...(664)
<223> OTHER INFORMATION: n = A,T,C or G

<400> SEQUENCE: 72
gctgcaggaa ttcggcacga gattgcttcc cagcccacct tcgctatcca gccactctcg      60
ctcttctaca tctcccaccc cctcacaccg ccatggcttc ttcccgcaag gcttccaacc     120
cgcacaagtc gcaccgcaag ccgaagcgct cgtggaacgt gtacgtgggc cgctcgctga     180
aggcgatcaa cgcccagatg tcgatgtcgc accgcacgat gaagatcgtg aactcgtacg     240
tgaacgacgt gatggagcgc atctgcactg aggccgcgtc gattgttcgc gcgaacaaga     300
agcgcacgtt gggtgcgcgc gaggtgcaga cggcggtgcg cattgtgctg ccggcggagc     360
tcgcgaagca tgccatggct gagggcacga aggccgtgtc gagcgcgtcc cgctaaagcg     420
gcttgccgga tgccgtgtga gtaggagggt ggcttgccgc aaacgctgac ctcggcgatt     480
gcggcgtggc gctccccttc tcctccttgt ccggcggtgt gtgtcatgca tttgcgtgac     540
tcctccctct tatagatgca agcttttttt ttctcttgac gttttatttt ctcctccccc     600
tcccttaacg tgaagtgtat atganagcgt actggacatg ananaaaaaa aaaanaaact    660
cgag    664

<210> SEQ ID NO 73
<211> LENGTH: 1432
<212> TYPE: DNA
<213> ORGANISM: Leishmania major
<220> FEATURE:
<221> NAME/KEY: misc_feature
<222> LOCATION: (1)...(1432)
<223> OTHER INFORMATION: n = A,T,C or G

<400> SEQUENCE: 73
gatgaagaag aggaggacac caccatcaac aactccgacg tggtggtgcg ctacaagaag    60
gccgcaacgt ggtgcaatga acgttgcgc gtgcttatcg atgccacaaa acctggcgcc    120 aaggtgtgccg acctgtgccg cctcggtgat gacaccatca ccgccnaggt caagacaatg    180
ttcaaaggca cggaaaaagg catcgctttc ccgacctgca tctcggtcaa caactgcgta    240
tgccacaaca gccctggcgt gtcggacgag acgacgcagc aagagatcgc gatgggtgac    300
gtcgtgcact acgacctggg catccacgtg gacggctact gcgccgtcgt cgcgcacacc    360
attcaggtga cagaggacaa tgagcttggc aaggacgaga aggcggcgcg cgtcattaca    420
gcggcgtaca acatcctgaa cacggcgctg cgccagatgc gtcccggtac gaccatctac    480
caggtgacag acgtagttga gaaggctgcg gagcactaca aggtgactcc ggtagacggc    540
gtcctctcgc atatgatgaa gcgctacatc atagacngat accgctgtat cccgcagcgc    600
agggtcgcgg agcacatggt gcacgactac gatctcgaga agcgcaggt gtggacgcta    660 gacattgtca tgacctccgg caagggcaag ctgaaggagc gcgatgcgcg gccgtgcgtg    720
ttcaaggtgg ctctggactc caactactct gtgaaaatgg aaagcgcgaa ggaggttcag    780
aaggaaatcg actccnagta tgccaccttc ccctttgcca tccgcaacct ggaggccaag    840
aaggcccgcc tcggtctcaa cgagatggcg aagcacggtg ctgtcatccc gtaccctatt    900
ctcttcgaaa aggaaggcga ggtcgtcgcc catttcaaga ttacggtgct catcagcaac    960
aagaagattg agccgattac cggcctgaag ccgcagaagg ccccggcgct cgagccatac    1020
acggacgaga tgctgcttgc gacgaacaag ctcttcgctg tcgctagaga agaaggcggc    1080
gaagtagacg gccgtggcat ccgtgacgct gtactgcgag ctttcgtagg cgtacgcctc    1140
ttgtgaggcg tacacgtgtg ctgtttgcgg acgaggaggc acccattctg ttcccccttct    1200 tcgctaatct tcgcgtttcc tctgacgctg gcttctytgc cggagtgtgg tgaggcgcgt    1260
gggggagaaa cggcccacty gcatgcctgt gcatacgcga gcacggtagg gagcgcggtg    1320
tgtgtgtgtg tgggggggcg tgttacgagt acaaagagg ctcgatcttt gcgatctttt    1380
ctttctgtaa acaggaacat aagtaaccaa aaaaaaaaaa aaaaaactcg ag    1432

<210> SEQ ID NO 74
<211> LENGTH: 873
<212> TYPE: DNA
<213> ORGANISM: Leishmania major
<220> FEATURE:
<221> NAME/KEY: misc_feature
<222> LOCATION: (1)...(873)
<223> OTHER INFORMATION: n = A,T,C or G

<400> SEQUENCE: 74
ctttattgtc atcactgtaa agcactgttt tttctttcac ttttcttga gtgttttctt    60

-continued

| | |
|---|---|
| ctattcacca tgagcattat caaggaggac gacgccgtgg gctgctacat gacggtgacc | 120 |
| ctcgtggacg acaccaaggt ggagggtacc atcttcacct acaattccaa ggagggcatc | 180 |
| atagtactcc tgtccctccg cgacgatcag acgaacatga agctaatccg cactccgtac | 240 |
| atcaaagact tcagcctttc acacgctgag gagggagcgc acctgccccc ggcactggac | 300 |
| tccttcaacg agcttccgtc catgcacgcc ggccgcgaca agtccatctt caagcacgcc | 360 |
| agcacgcagc tcaagaacgc cgaggcgaac cgcgaaaagc acttcaactc tgtcacgacc | 420 |
| gacacaccga ttgccacact tgatgcgtac ctcaagctcc tgcggctata ccccttaatt | 480 |
| gagtggaaca gcgacgaggg tgtcatccag gtctcggaca ccgtcattgt cgtaggagac | 540 |
| cccgactggc ggacgcccaa ggcaatgctg gtggacggcg ccctgagaa ggacagaccg | 600 |
| cttgtagatc gcctgcaggt tgcgctcggm aacggcaaga agtgattcag tgtgtagcgg | 660 |
| acagaacatc gtgtgcttgt gtgtctgttt gangtttgtt tgttttctct ttgtggtact | 720 |
| gcgtacgacg gcgccttctc ccggtggtgg gtgagtccat aagcagttga gttctyggtt | 780 |
| gtagnaavgc ctyacygccg accatatggg agagggcgaa caaatntttg atagaagttg | 840 |
| aaaatcccaa agtyaaaaga aaaaaaaaan aaa | 873 |

<210> SEQ ID NO 75
<211> LENGTH: 1238
<212> TYPE: DNA
<213> ORGANISM: Leishmania major
<220> FEATURE:
<221> NAME/KEY: misc_feature
<222> LOCATION: (1)...(1238)
<223> OTHER INFORMATION: n = A,T,C or G

<400> SEQUENCE: 75

| | |
|---|---|
| tttctgtact ttattgaaca tcagtagaac acgttcttcc cgcaaagatg gccaagaagc | 60 |
| acctcaagcg cttgtatgcg cccaaggact ggatgctgag caagctgacc ggcgtgttcg | 120 |
| cgccgcgtcc gcgtccgggt ccgcacaagc tgcgcgagtg cctgccgctc tggtgatca | 180 |
| tccgcaaccg gctgaagtac gcgctgaacg cgcgcgaggg tgagatgatc ctgcgccagg | 240 |
| gtctggtgca cgtggacaac cacccgcgcc gcgacggcaa gtatcccgcc ggtttcatgg | 300 |
| acgtggtcga gatcccgaag acgggcgacc gcttccgcct gatgtacgac gtcaagggcc | 360 |
| gcttcgcgtt ggtgaacctg tccgaggcgg aggcgcagat caagctgatg aaggttgtga | 420 |
| acctgtacac ggccaccggc cgcgtgccgg tcgctgtgac gcacgacggc caccgcatcc | 480 |
| gctacccgga cccgcacacc tccattggtg acaccatcgt gtacaacgtc aaggagaaga | 540 |
| agtgcgtgga cctgatcaag aaccgccagg gcaaggccgt gatcgtgacc ggtggcgcca | 600 |
| accgcggccg catcggcgag atcgtgaagg tggagtgcca ccccggtgcg ttcaacattg | 660 |
| cgcacctgaa ggacgcgtcc ggcgccgagt tcgccacccg cgccgcgaac atcttcgtga | 720 |
| tcggcaagga cctgaacaac ctgcaggtaa cggtgccgaa gcagcagggc ctgcgcatga | 780 |
| acgtgatcca gggcgcgag gagcgcctga tcgcggcgga ggcccgcaag aacgcgccgg | 840 |
| ctcgtggtgc ccgcagggcc cgcaagtgag gaggcgatta cacgcatgcg tgtttgtggc | 900 |
| tctgaagcga cttggcgggt cggctgtgag ggtttgagag gaggtgtgtg atgcgtgtga | 960 |
| agtccttctc cgttctcagc tctctctgtg ctgtagctgt gcctttcccc agatcgcttt | 1020 |
| accgcatttg catacatctg tgtagtcgca tgtgcgtgtt tctgtctctc ggtgggtctc | 1080 |
| cctctccctc cctttctgcc tctctctttg agtgggtgtg catgcgtcgc gcgcgacggg | 1140 |
| ctccgcttna gtgattctct cgtgtttttan ggctgttttt tttctyagtt nagcgttttty | 1200 |

<210> SEQ ID NO 76
<211> LENGTH: 712
<212> TYPE: DNA
<213> ORGANISM: Leishmania major
<220> FEATURE:
<221> NAME/KEY: misc_feature
<222> LOCATION: (1)...(712)
<223> OTHER INFORMATION: n = A,T,C or G

<400> SEQUENCE: 76

```
ctgacggagt tccagacgaa ccttgtgccg tacccgcgca tccacttcgt gctgacaagc      60
tacgctccgg tggtgtctgc cgagaaggcg taccacgagc agctntccgt cgcggacatc     120
acgaactcgg tntttgagcc tgctggcatg ctnacaaagt gcgatcctcg ccacggcaag     180
tacatgtcgt gctgcctcat gtaccgcggt gatgtcgtgc cgaaggatgt caacgccgcg     240
attgcgacga tcaagacgaa gcgcacaatt cagttcgtgg actggtgccc gaccggcttc     300
aagtgcggca tcaactacca gccgccgacc gttgtgcccg cggtgacct cgcgaaggtg      360
cagcgcgccg tgtgcatgat gccaactcg accgcgatcg ctgaggtgtt tgcccgcatc     420
gaccacaagt tcgacctgat gtacagcaag cgcgcgtttg tgcactggta cgtgggtgag     480
ggcatggagg agggcgagtt ctccgaggcg cgcgaggatc tcgctgcgct ggagaaggac     540
tacgaggagg ttggcgccga gtccgccgac gacatgggcg aggaggacgt cgaggagtac     600
taaggtagac tcgtgccgcg cgctgatgat gtaggtgcac gcgtgcgtgt gctgcagcgg     660
agccgccgcc accgcgactg tgtgtgtgtg cgcgcgtgac gaccggctcg ag            712
```

<210> SEQ ID NO 77
<211> LENGTH: 1086
<212> TYPE: DNA
<213> ORGANISM: Leishmania major
<220> FEATURE:
<221> NAME/KEY: misc_feature
<222> LOCATION: (1)...(1086)
<223> OTHER INFORMATION: n = A,T,C or G

<400> SEQUENCE: 77

```
caagaagtgg atcaagcagg agacgaacgc cgatggcgag cgcgtgcgcc gcgcgttctg      60
ccagttctgc ctagacccca tctaccagat cttcgacgct gtgatgaacg agaagaagga     120
caaggtggac aagatgctca agtcgctgca cgtgacgctn acggctgagg agcgcgagca     180
ggtgccgaan aagcttctga agacggtgat gatgaattc ctgccggctg ctgagacgct      240
gctacagatg atcgtggcgc acctgccgtc gcccaagaag gcgcaggcgt accgtgcgga     300
gatgctgtac tctggcgagg cgtcgccgga ggacaagtac ttcatgggta tcaagaactg     360
cgaccccgct gcgccgctca tgctgtacat cagcaagatg gtgccgacgg ccgaccgcgg     420
ccgcttcttc gcctttggcc gcatcttctc cggtaaggtg cgcagcggcc agaaggtgcg     480
catcatgggt aacaactacg tctacggcaa gaagcaggac ctgtacgagg acaagcctgt     540
gcagcgctcc gtgctgatga tgggccgcta ccaggaggcc gtggaggaca tgccgtgcgg     600
taacgtggtg ggccttgtgg gcgtggacaa gtacatcgtg aagtccgcga cgatcacgga     660
cgatggcgag agcccgcacc cgctgcgcga catgaagtac tctgtgtcgc ccgtcgtgcg     720
tgtgccgtg gaggcgaaga accgtccga cctgccgaag cttgtggagg cctgaagcg        780
ccttgccaag tccgacccgc tggtggtgtg cagcattgag gagtctggcg agcacattgt     840
```

```
tgccggcgct ggcgagcttc accttgagat ttgcctgaag gatctccagg aggacttcat      900
gaacggcgcg ccgctnaaga tctccgagcc ggtggtgtcg ttccgcgaga cggtgacgga      960
tgtgtcgtcg cagcagtgcc tgtcgaagtc tgcgaacaag cacaaccgtc tcttctgccg     1020
cggtgcgccg ctnacagagg anctggcgct ggcgatngan gaaggcaccg ctggtcccga     1080 ngcgga                                                                1086
```

<210> SEQ ID NO 78
<211> LENGTH: 447
<212> TYPE: DNA
<213> ORGANISM: Leishmania major
<220> FEATURE:
<221> NAME/KEY: misc_feature
<222> LOCATION: (1)...(447)
<223> OTHER INFORMATION: n = A,T,C or G

<400> SEQUENCE: 78

```
cgcatcaacg tctacttcga tnagtcgacg ggaggccgct acgtgccgcg cgccgtgctg       60
atggacctcg agcccggcac tatggactcc gttcgcgccg gcccgtacgg ccagctgttc      120
cgcccggaca acttcatctt tggtcagtcc ggcgctggca caactgggc caagggccac       180 tacactgagg gcgcggagct gatcgactcc gtgcttgatg tgtgccgcaa ggaggcggag      240
agctgcgact gcctgcaggg cttccagctg tctcactccc tcggcggcgg cacgggctcc      300
ggcatgggca cgctgctcat ttccaanctg cgcgangagt accggaccg gatcatgatg       360 accttctccg tcatcccgtc ccccgcgtg tcggataccg ttgtggancc gtacaacacg       420
accctctctg tgcaccagct cgtggaa                                          447
```

<210> SEQ ID NO 79
<211> LENGTH: 375
<212> TYPE: DNA
<213> ORGANISM: Leishmania major
<220> FEATURE:
<221> NAME/KEY: misc_feature
<222> LOCATION: (1)...(375)
<223> OTHER INFORMATION: n = A,T,C or G

<400> SEQUENCE: 79

```
gtaacccgct ggtgtacgca tatgtagaca cagacgggca gcacgagacg acgttcctcg       60
cgatccctgt ggtgcttggc atgaatggaa tcgagaagcg cctgccgatt ggtccgctgc      120
actcgacgga ggaaacgctg ctgaaggcg cactgccggt gatcaagaag aatatcgtga       180
agggcagcga gttcgcgcgc tcacacctgt agcacctcag cttttttttt ttgcgttaaa      240
cgggcgtggg aagcacctcg atacttcgct tcgcgctgac ggacccgcac gacatcgttc      300
gtcatccccc tccccctctt cggccctata cgcatgaagg agtggaatta tgcaacagca      360
tgttnatatc aagtg                                                       375
```

<210> SEQ ID NO 80
<211> LENGTH: 107
<212> TYPE: PRT
<213> ORGANISM: Leishmania major

<400> SEQUENCE: 80

```
Met Ala Ser Ser Arg Lys Ala Ser Asn Pro His Lys Ser His Arg Lys
  1               5                  10                  15

Pro Lys Arg Ser Trp Asn Val Tyr Val Gly Arg Ser Leu Lys Ala Ile
             20                  25                  30

Asn Ala Gln Met Ser Met Ser His Arg Thr Met Lys Ile Val Asn Ser
```

-continued

```
                    35                  40                  45
Tyr Val Asn Asp Val Met Glu Arg Ile Cys Thr Glu Ala Ala Ser Ile
 50                  55                  60

Val Arg Ala Asn Lys Lys Arg Thr Leu Gly Ala Arg Glu Val Gln Thr
 65                  70                  75                  80

Ala Val Arg Ile Val Leu Pro Ala Glu Leu Ala Lys His Ala Met Ala
                     85                  90                  95

Glu Gly Thr Lys Ala Val Ser Ser Ala Ser Arg
                    100                 105

<210> SEQ ID NO 81
<211> LENGTH: 381
<212> TYPE: PRT
<213> ORGANISM: Leishmania major
<220> FEATURE:
<221> NAME/KEY: VARIANT
<222> LOCATION: (1)...(381)
<223> OTHER INFORMATION: Xaa = Any Amino Acid

<400> SEQUENCE: 81

Asp Glu Glu Glu Glu Asp Thr Thr Ile Asn Asn Ser Asp Val Val Val
  1               5                  10                  15

Arg Tyr Lys Lys Ala Ala Thr Trp Cys Asn Glu Thr Leu Arg Val Leu
                 20                  25                  30

Ile Asp Ala Thr Lys Pro Gly Ala Lys Val Cys Asp Leu Cys Arg Leu
             35                  40                  45

Gly Asp Asp Thr Ile Thr Ala Xaa Val Lys Thr Met Phe Lys Gly Thr
 50                  55                  60

Glu Lys Gly Ile Ala Phe Pro Thr Cys Ile Ser Val Asn Asn Cys Val
 65                  70                  75                  80

Cys His Asn Ser Pro Gly Val Ser Asp Glu Thr Thr Gln Gln Glu Ile
                 85                  90                  95

Ala Met Gly Asp Val Val His Tyr Asp Leu Gly Ile His Val Asp Gly
                100                 105                 110

Tyr Cys Ala Val Val Ala His Thr Ile Gln Val Thr Glu Asp Asn Glu
            115                 120                 125

Leu Gly Lys Asp Glu Lys Ala Ala Arg Val Ile Thr Ala Ala Tyr Asn
130                 135                 140

Ile Leu Asn Thr Ala Leu Arg Gln Met Arg Pro Gly Thr Thr Ile Tyr
145                 150                 155                 160

Gln Val Thr Asp Val Val Glu Lys Ala Ala Glu His Tyr Lys Val Thr
                165                 170                 175

Pro Val Asp Gly Val Leu Ser His Met Met Lys Arg Tyr Ile Ile Asp
                180                 185                 190

Xaa Tyr Arg Cys Ile Pro Gln Arg Arg Val Ala Glu His Met Val His
            195                 200                 205

Asp Tyr Asp Leu Glu Lys Ala Gln Val Trp Thr Leu Asp Ile Val Met
210                 215                 220

Thr Ser Gly Lys Gly Lys Leu Lys Glu Arg Asp Ala Arg Pro Cys Val
225                 230                 235                 240

Phe Lys Val Ala Leu Asp Ser Asn Tyr Ser Val Lys Met Glu Ser Ala
                245                 250                 255

Lys Glu Val Gln Lys Glu Ile Asp Ser Xaa Tyr Ala Thr Phe Pro Phe
                260                 265                 270

Ala Ile Arg Asn Leu Glu Ala Lys Ala Arg Leu Gly Leu Asn Glu
            275                 280                 285
```

-continued

```
Met Ala Lys His Gly Ala Val Ile Pro Tyr Pro Ile Leu Phe Glu Lys
    290                 295                 300

Glu Gly Glu Val Val Ala His Phe Lys Ile Thr Val Leu Ile Ser Asn
305                 310                 315                 320

Lys Lys Ile Glu Pro Ile Thr Gly Leu Lys Pro Gln Lys Ala Pro Ala
                325                 330                 335

Leu Glu Pro Tyr Thr Asp Glu Met Leu Leu Ala Thr Asn Lys Leu Phe
            340                 345                 350

Ala Val Ala Arg Glu Gly Gly Glu Val Asp Gly Arg Gly Ile Arg
            355                 360                 365

Asp Ala Val Leu Arg Ala Phe Val Gly Val Arg Leu Leu
        370                 375                 380

<210> SEQ ID NO 82
<211> LENGTH: 191
<212> TYPE: PRT
<213> ORGANISM: Leishmania major

<400> SEQUENCE: 82

Met Ser Ile Ile Lys Glu Asp Asp Ala Val Gly Cys Tyr Met Thr Val
1               5                   10                  15

Thr Leu Val Asp Asp Thr Lys Val Glu Gly Thr Ile Phe Thr Tyr Asn
            20                  25                  30

Ser Lys Glu Gly Ile Ile Val Leu Leu Ser Leu Arg Asp Asp Gln Thr
        35                  40                  45

Asn Met Lys Leu Ile Arg Thr Pro Tyr Ile Lys Asp Phe Ser Leu Ser
    50                  55                  60

His Ala Glu Glu Gly Ala His Leu Pro Pro Ala Leu Asp Ser Phe Asn
65                  70                  75                  80

Glu Leu Pro Ser Met His Ala Gly Arg Asp Lys Ser Ile Phe Lys His
                85                  90                  95

Ala Ser Thr Gln Leu Lys Asn Ala Glu Ala Asn Arg Glu Lys His Phe
            100                 105                 110

Asn Ser Val Thr Thr Asp Thr Pro Ile Ala Thr Leu Asp Ala Tyr Leu
        115                 120                 125

Lys Leu Leu Arg Leu Tyr Pro Leu Ile Glu Trp Asn Ser Asp Glu Gly
    130                 135                 140

Val Ile Gln Val Ser Asp Thr Val Ile Val Gly Asp Pro Asp Trp
145                 150                 155                 160

Arg Thr Pro Lys Ala Met Leu Val Asp Gly Ala Pro Glu Lys Asp Arg
                165                 170                 175

Pro Leu Val Asp Arg Leu Gln Val Ala Leu Gly Asn Gly Lys Lys
            180                 185                 190

<210> SEQ ID NO 83
<211> LENGTH: 273
<212> TYPE: PRT
<213> ORGANISM: Leishmania major

<400> SEQUENCE: 83

Met Ala Lys Lys His Leu Lys Arg Leu Tyr Ala Pro Lys Asp Trp Met
1               5                   10                  15

Leu Ser Lys Leu Thr Gly Val Phe Ala Pro Arg Pro Arg Gly Pro
            20                  25                  30

His Lys Leu Arg Glu Cys Leu Pro Leu Val Ile Arg Asn Arg
        35                  40                  45
```

-continued

```
Leu Lys Tyr Ala Leu Asn Ala Arg Glu Gly Glu Met Ile Leu Arg Gln
     50                  55                  60
Gly Leu Val His Val Asp Asn His Pro Arg Arg Asp Gly Lys Tyr Pro
 65                  70                  75                  80
Ala Gly Phe Met Asp Val Val Glu Ile Pro Lys Thr Gly Asp Arg Phe
                 85                  90                  95
Arg Leu Met Tyr Asp Val Lys Gly Arg Phe Ala Leu Val Asn Leu Ser
            100                 105                 110
Glu Ala Glu Ala Gln Ile Lys Leu Met Lys Val Val Asn Leu Tyr Thr
        115                 120                 125
Ala Thr Gly Arg Val Pro Val Ala Val Thr His Asp Gly His Arg Ile
    130                 135                 140
Arg Tyr Pro Asp Pro His Thr Ser Ile Gly Asp Thr Ile Val Tyr Asn
145                 150                 155                 160
Val Lys Glu Lys Lys Cys Val Asp Leu Ile Lys Asn Arg Gln Gly Lys
                165                 170                 175
Ala Val Ile Val Thr Gly Gly Ala Asn Arg Gly Arg Ile Gly Glu Ile
            180                 185                 190
Val Lys Val Glu Cys His Pro Gly Ala Phe Asn Ile Ala His Leu Lys
        195                 200                 205
Asp Ala Ser Gly Ala Glu Phe Ala Thr Arg Ala Ala Asn Ile Phe Val
    210                 215                 220
Ile Gly Lys Asp Leu Asn Asn Leu Gln Val Thr Val Pro Lys Gln Gln
225                 230                 235                 240
Gly Leu Arg Met Asn Val Ile Gln Glu Arg Glu Glu Arg Leu Ile Ala
                245                 250                 255
Ala Glu Ala Arg Lys Asn Ala Pro Ala Arg Gly Ala Arg Arg Ala Arg
            260                 265                 270
Lys

<210> SEQ ID NO 84
<211> LENGTH: 200
<212> TYPE: PRT
<213> ORGANISM: Leishmania major

<400> SEQUENCE: 84

Leu Thr Glu Phe Gln Thr Asn Leu Val Pro Tyr Pro Arg Ile His Phe
  1               5                  10                  15
Val Leu Thr Ser Tyr Ala Pro Val Val Ser Ala Glu Lys Ala Tyr His
                 20                  25                  30
Glu Gln Leu Ser Val Ala Asp Ile Thr Asn Ser Val Phe Glu Pro Ala
            35                  40                  45
Gly Met Leu Thr Lys Cys Asp Pro Arg His Gly Lys Tyr Met Ser Cys
     50                  55                  60
Cys Leu Met Tyr Arg Gly Asp Val Val Pro Lys Asp Val Asn Ala Ala
 65                  70                  75                  80
Ile Ala Thr Ile Lys Thr Lys Arg Thr Ile Gln Phe Val Asp Trp Cys
                 85                  90                  95
Pro Thr Gly Phe Lys Cys Gly Ile Asn Tyr Gln Pro Pro Thr Val Val
            100                 105                 110
Pro Gly Gly Asp Leu Ala Lys Val Gln Arg Ala Val Cys Met Ile Ala
        115                 120                 125
Asn Ser Thr Ala Ile Ala Glu Val Phe Ala Arg Ile Asp His Lys Phe
    130                 135                 140
```

```
Asp Leu Met Tyr Ser Lys Arg Ala Phe Val His Trp Tyr Val Gly Glu
145                 150                 155                 160

Gly Met Glu Glu Gly Glu Phe Ser Glu Ala Arg Glu Asp Leu Ala Ala
            165                 170                 175

Leu Glu Lys Asp Tyr Glu Glu Val Gly Ala Glu Ser Ala Asp Asp Met
        180                 185                 190

Gly Glu Glu Asp Val Glu Glu Tyr
        195                 200

<210> SEQ ID NO 85
<211> LENGTH: 361
<212> TYPE: PRT
<213> ORGANISM: Leishmania major
<220> FEATURE:
<221> NAME/KEY: VARIANT
<222> LOCATION: (1)...(361)
<223> OTHER INFORMATION: Xaa = Any Amino Acid

<400> SEQUENCE: 85

Lys Lys Trp Ile Lys Gln Glu Thr Asn Ala Asp Gly Glu Arg Val Arg
1               5                   10                  15

Arg Ala Phe Cys Gln Phe Cys Leu Asp Pro Ile Tyr Gln Ile Phe Asp
            20                  25                  30

Ala Val Met Asn Glu Lys Lys Asp Lys Val Asp Lys Met Leu Lys Ser
        35                  40                  45

Leu His Val Thr Leu Thr Ala Glu Glu Arg Glu Gln Val Pro Xaa Lys
    50                  55                  60

Leu Leu Lys Thr Val Met Met Xaa Phe Leu Pro Ala Ala Glu Thr Leu
65                  70                  75                  80

Leu Gln Met Ile Val Ala His Leu Pro Ser Pro Lys Lys Ala Gln Ala
                85                  90                  95

Tyr Arg Ala Glu Met Leu Tyr Ser Gly Glu Ala Ser Pro Glu Asp Lys
            100                 105                 110

Tyr Phe Met Gly Ile Lys Asn Cys Asp Pro Ala Ala Pro Leu Met Leu
        115                 120                 125

Tyr Ile Ser Lys Met Val Pro Thr Ala Asp Arg Gly Arg Phe Phe Ala
    130                 135                 140

Phe Gly Arg Ile Phe Ser Gly Lys Val Arg Ser Gly Gln Lys Val Arg
145                 150                 155                 160

Ile Met Gly Asn Asn Tyr Val Tyr Gly Lys Lys Gln Asp Leu Tyr Glu
                165                 170                 175

Asp Lys Pro Val Gln Arg Ser Val Leu Met Met Gly Arg Tyr Gln Glu
            180                 185                 190

Ala Val Glu Asp Met Pro Cys Gly Asn Val Val Gly Leu Val Gly Val
        195                 200                 205

Asp Lys Tyr Ile Val Lys Ser Ala Thr Ile Thr Asp Asp Gly Glu Ser
    210                 215                 220

Pro His Pro Leu Arg Asp Met Lys Tyr Ser Val Ser Pro Val Val Arg
225                 230                 235                 240

Val Ala Val Glu Ala Lys Asn Pro Ser Asp Leu Pro Lys Leu Val Glu
                245                 250                 255

Gly Leu Lys Arg Leu Ala Lys Ser Asp Pro Leu Val Val Cys Ser Ile
            260                 265                 270

Glu Glu Ser Gly Glu His Ile Val Ala Gly Ala Gly Glu Leu His Leu
        275                 280                 285
```

-continued

```
Glu Ile Cys Leu Lys Asp Leu Gln Asp Phe Met Asn Gly Ala Pro
        290                 295                 300
Leu Lys Ile Ser Glu Pro Val Ser Phe Arg Glu Thr Val Thr Asp
305                 310                 315                 320
Val Ser Ser Gln Gln Cys Leu Ser Lys Ser Ala Asn Lys His Asn Arg
                    325                 330                 335
Leu Phe Cys Arg Gly Ala Pro Leu Thr Glu Xaa Leu Ala Leu Ala Xaa
                340                 345                 350
Xaa Glu Gly Thr Ala Gly Pro Xaa Ala
            355                 360

<210> SEQ ID NO 86
<211> LENGTH: 149
<212> TYPE: PRT
<213> ORGANISM: Leishmania major
<220> FEATURE:
<221> NAME/KEY: VARIANT
<222> LOCATION: (1)...(149)
<223> OTHER INFORMATION: Xaa = Any Amino Acid

<400> SEQUENCE: 86

Arg Ile Asn Val Tyr Phe Asp Xaa Ser Thr Gly Gly Arg Tyr Val Pro
1               5                   10                  15
Arg Ala Val Leu Met Asp Leu Glu Pro Gly Thr Met Asp Ser Val Arg
                20                  25                  30
Ala Gly Pro Tyr Gly Gln Leu Phe Arg Pro Asp Asn Phe Ile Phe Gly
            35                  40                  45
Gln Ser Gly Ala Gly Asn Asn Trp Ala Lys Gly His Tyr Thr Glu Gly
    50                  55                  60
Ala Glu Leu Ile Asp Ser Val Leu Asp Val Cys Arg Lys Glu Ala Glu
65                  70                  75                  80
Ser Cys Asp Cys Leu Gln Gly Phe Gln Leu Ser His Ser Leu Gly Gly
                85                  90                  95
Gly Thr Gly Ser Gly Met Gly Thr Leu Leu Ile Ser Xaa Leu Arg Xaa
            100                 105                 110
Glu Tyr Pro Asp Arg Ile Met Met Thr Phe Ser Val Ile Pro Ser Pro
        115                 120                 125
Arg Val Ser Asp Thr Val Val Xaa Pro Tyr Asn Thr Thr Leu Ser Val
    130                 135                 140
His Gln Leu Val Glu
145

<210> SEQ ID NO 87
<211> LENGTH: 69
<212> TYPE: PRT
<213> ORGANISM: Leishmania major

<400> SEQUENCE: 87

Asn Pro Leu Val Tyr Ala Tyr Val Asp Thr Asp Gly Gln His Glu Thr
1               5                   10                  15
Thr Phe Leu Ala Ile Pro Val Val Leu Gly Met Asn Gly Ile Glu Lys
                20                  25                  30
Arg Leu Pro Ile Gly Pro Leu His Ser Thr Glu Glu Thr Leu Leu Lys
            35                  40                  45
Ala Ala Leu Pro Val Ile Lys Lys Asn Ile Val Lys Gly Ser Glu Phe
    50                  55                  60
Ala Arg Ser His Leu
65
```

<210> SEQ ID NO 88
<211> LENGTH: 54
<212> TYPE: DNA
<213> ORGANISM: Artificial Sequence
<220> FEATURE:
<223> OTHER INFORMATION: PCR primer

<400> SEQUENCE: 88
agtattcata tgcaccacca ccaccaccac atgtcctgcg gtaacgccaa gatc    54

<210> SEQ ID NO 89
<211> LENGTH: 33
<212> TYPE: DNA
<213> ORGANISM: Artificial Sequence
<220> FEATURE:
<223> OTHER INFORMATION: PCR primer

<400> SEQUENCE: 89
ctcacaggat ccctgcttgc tgaagtatcc ttc    33

<210> SEQ ID NO 90
<211> LENGTH: 36
<212> TYPE: DNA
<213> ORGANISM: Artificial Sequence
<220> FEATURE:
<223> OTHER INFORMATION: PCR primer

<400> SEQUENCE: 90
catttcggat ccatggacgc aactgagctg aagaac    36

<210> SEQ ID NO 91
<211> LENGTH: 33
<212> TYPE: DNA
<213> ORGANISM: Artificial Sequence
<220> FEATURE:
<223> OTHER INFORMATION: PCR primer

<400> SEQUENCE: 91
cgtagagaat tcctgaccaa aacgaatgat gcc    33

<210> SEQ ID NO 92
<211> LENGTH: 33
<212> TYPE: DNA
<213> ORGANISM: Artificial Sequence
<220> FEATURE:
<223> OTHER INFORMATION: PCR primer

<400> SEQUENCE: 92
caccacgaat tcatggcgca gaatgataag atc    33

<210> SEQ ID NO 93
<211> LENGTH: 34
<212> TYPE: DNA
<213> ORGANISM: Artificial Sequence
<220> FEATURE:
<223> OTHER INFORMATION: PCR primer

<400> SEQUENCE: 93
actgacctcg aggaattctt agtcgcgcat gaac    34

<210> SEQ ID NO 94
<211> LENGTH: 3012
<212> TYPE: DNA
<213> ORGANISM: Artificial Sequence
<220> FEATURE:

<223> OTHER INFORMATION: DNA sequence encoding fusion (poly-protein) constructs comprising multiple Leishmania antigens

<400> SEQUENCE: 94

| | |
|---|---|
| catatgcacc accaccacca ccacatgtcc tgcggtaacg ccaagatcaa ctctcccgcg | 60 |
| ccgtccttcg aggaggtggc gctcatgccc aacggcagct tcaagaagat cagcctctcc | 120 |
| tcctacaagg gcaagtgggt cgtgctcttc ttctacccgc tcgacttcac cttcgtgtgc | 180 |
| ccgacagagg tcatcgcgtt ctccgacagc gtgagtcgct tcaacgagct caactgcgag | 240 |
| gtcctcgcgt gctcgataga cagcgagtac gcgcacctgc agtggacgct gcaggaccgc | 300 |
| aagaagggcg gcctcgggac catggcgatc ccaatgctag ccgacaagac caagagcatc | 360 |
| gctcgttcct acgcgtgct ggaggagagc cagggcgtgg cctaccgcgg tctcttcatc | 420 |
| atcgaccccc atggcatgct gcgtcagatc accgtcaatg acatgccggt gggccgcagc | 480 |
| gtggaggagg ttctacgcct gctggaggct tttcagttcg tggagaagca cggcgaggtg | 540 |
| tgccccgcga actggaagaa gggcgccccc acgatgaagc cggaaccgaa tgcgtctgtc | 600 |
| gagggatact tcagcaagca gggatccatg acgcaactg agctgaagaa caaggggaac | 660 |
| gaagagttct ccgccggccg ctatgtggag gcggtgaact acttctcaaa ggcgatccag | 720 |
| ttggatgagc agaacagtgt cctctacagc aaccgctccg cctgttttgc agccatgcag | 780 |
| aaatacaagg acgcgctgga cgacgccgac aagtgcatct cgatcaagcc gaattgggcc | 840 |
| aagggctacg tgcgccgagg agcagctctc catggcatgc ccgctacga cgatgccatt | 900 |
| gccgcgtatg aaaagggggct caaggtggac ccttccaaca gcggctgcgc gcagggcgtg | 960 |
| aaggacgtgc aggtagccaa ggcccgcgaa gcacgtgacc ccatcgctcg cgtcttcacc | 1020 |
| ccggaggcgt tccgcaagat ccaagagaat cccaagctgt ctctacttat gctgcagccg | 1080 |
| gactacgtga agatggtaga caccgtcatc cgcgacccct cgcagggccg gctgtacatg | 1140 |
| gaagaccagc gctttgccct gacgctcatg tacctgagcg gaatgaagat tcccaacgat | 1200 |
| ggtgatggcg aggaggagga acgtccgtct gcgaaggcgg cagagacagc gaagccaaaa | 1260 |
| gaggagaagc ctctcaccga caacgagaag gaggccctgg cgctcaagga ggagggcaac | 1320 |
| aagctgtacc tctcgaagaa gttttgaggag gcgctgacca agtaccaaga ggcgcaggtg | 1380 |
| aaagacccca caacactttt atacattctg aacgtgtcgg ccgtgtactt cgagcagggt | 1440 |
| gactacgaca agtgcatcgc cgagtgcgag cacggtatcg agcacggtcg cgagaaccac | 1500 |
| tgcgactaca caatcattgc gaagctcatg acccggaacg ccttgtgcct ccagaggcag | 1560 |
| aggaagtacg aggctgctat cgaccttac aagcgcgccc ttgtcgagtg cgtaacccct | 1620 |
| gacaccctca gaagctgac ggagtgcgag aaggagcacc aaaaggcggt ggaggaagcc | 1680 |
| tacatcgatc ctgagatcgc gaagcagaag aaagacgaag gtaaccagta cttcaaggag | 1740 |
| gataagttcc ccgaggccgt ggcagcgtac acggaggcca tcaagcgcaa ccctgccgag | 1800 |
| cacacctcct acagcaatcg cgcggccgcg tacatcaagc ttggagcctt caacgacgcc | 1860 |
| ctcaaggacg cggagaagtg cattgagctg aagcccgact tgttaaggg ctacgcgcgc | 1920 |
| aagggtcatg cttactttg gaccaagcag tacaaccgcg cgctgcaggc gtacaatgag | 1980 |
| ggcctcaagg tggacccgag caatgcggac tgcaaggatg gcggtatcg cacaatcatg | 2040 |
| aagattcagg agatggcatc tggccaatcc gcggatggcg acgaggcggc gcgccgggcc | 2100 |
| atggacgatc ctgaaatcgc ggcaatcatg caagatagct acatgcaact agtgttgaag | 2160 |
| gagatgcaga acgatcccac gcgcattcag gagtacatga aggactccgg gatctcatcg | 2220 |

-continued

```
aagatcaaca agctgatttc agctggcatc attcgttttg gtcaggaatt catggcgcag    2280
aatgataaga tcgcccccca ggaccaggac tccttcctcg atgaccagcc cggcgttcgc    2340
ccgatcccgt ccttcgacga catgccgctg caccagaacc tgctgcgtgg catctactcg    2400
tacgggttcg agaagccgtc cagcatccag cagcgcgcga tagccccctt cacgcgcggc    2460
ggcgacatca tcgcgcaggc ccagtccggt accggcaaga cgggtgcctt ctccatcggt    2520
ctgctgcagc gcctggactt ccgccacaac ctgatccagg gcctcgtgct ctcccccact    2580
cgcgagctgg ccctgcagac ggcggaggtg atcagccgca tcggtgagtt cctgtcgaac    2640
agctccaagt tctgcgagac ctttgtcggc ggcacgcgcg tgcaggatga cctgcgcaag    2700
ctgcaggccg gcgtcatcgt tgccgtgggc acgccgggcc gcgtgtccga cgtgatcaag    2760
cgtggcgcgc tgcgcacaga gtcgctgcgc gtgctggtgc tcgacgaggc tgatgagatg    2820
ctgtctcagg gcttcgcgga ccagatttac gagatcttcc gcttcctgcc gaaggacatc    2880
caggtcgcgc tcttctccgc cacgatgccg gaggaggtac tggagctgac gaagaagttc    2940
atgcgcgact aagaattcct cgagcagatc cggctgctaa caaagcccga aggaagctg    3000 aatggctgct gc                                                        3012
```

<210> SEQ ID NO 95
<211> LENGTH: 982
<212> TYPE: PRT
<213> ORGANISM: Artificial Sequence
<220> FEATURE:
<223> OTHER INFORMATION: Fusion (poly-protein) constructs comprising multiple Leishmania antigens

<400> SEQUENCE: 95

```
Met His His His His His His Met Ser Cys Gly Asn Ala Lys Ile Asn
                 5                  10                  15

Ser Pro Ala Pro Ser Phe Glu Glu Val Ala Leu Met Pro Asn Gly Ser
            20                  25                  30

Phe Lys Lys Ile Ser Leu Ser Ser Tyr Lys Gly Lys Trp Val Val Leu
        35                  40                  45

Phe Phe Tyr Pro Leu Asp Phe Thr Phe Val Cys Pro Thr Glu Val Ile
    50                  55                  60

Ala Phe Ser Asp Ser Val Ser Arg Phe Asn Glu Leu Asn Cys Glu Val
65                  70                  75                  80

Leu Ala Cys Ser Ile Asp Ser Glu Tyr Ala His Leu Gln Trp Thr Leu
                85                  90                  95

Gln Asp Arg Lys Lys Gly Gly Leu Gly Thr Met Ala Ile Pro Met Leu
            100                 105                 110

Ala Asp Lys Thr Lys Ser Ile Ala Arg Ser Tyr Gly Val Leu Glu Glu
        115                 120                 125

Ser Gln Gly Val Ala Tyr Arg Gly Leu Phe Ile Ile Asp Pro His Gly
    130                 135                 140

Met Leu Arg Gln Ile Thr Val Asn Asp Met Pro Val Gly Arg Ser Val
145                 150                 155                 160

Glu Glu Val Leu Arg Leu Leu Glu Ala Phe Gln Phe Val Lys His
                165                 170                 175

Gly Glu Val Cys Pro Ala Asn Trp Lys Lys Gly Ala Pro Thr Met Lys
            180                 185                 190

Pro Glu Pro Asn Ala Ser Val Glu Gly Tyr Phe Ser Lys Gln Gly Ser
        195                 200                 205

Met Asp Ala Thr Glu Leu Lys Asn Lys Gly Asn Glu Glu Phe Ser Ala
```

```
            210                 215                 220
Gly Arg Tyr Val Glu Ala Val Asn Tyr Phe Ser Lys Ala Ile Gln Leu
225                 230                 235                 240

Asp Glu Gln Asn Ser Val Leu Tyr Ser Asn Arg Ser Ala Cys Phe Ala
                245                 250                 255

Ala Met Gln Lys Tyr Lys Asp Ala Leu Asp Asp Ala Asp Lys Cys Ile
                260                 265                 270

Ser Ile Lys Pro Asn Trp Ala Lys Gly Tyr Val Arg Arg Gly Ala Ala
                275                 280                 285

Leu His Gly Met Arg Arg Tyr Asp Asp Ala Ile Ala Ala Tyr Glu Lys
                290                 295                 300

Gly Leu Lys Val Asp Pro Ser Asn Ser Gly Cys Ala Gln Gly Val Lys
305                 310                 315                 320

Asp Val Gln Val Ala Lys Ala Arg Glu Ala Arg Asp Pro Ile Ala Arg
                325                 330                 335

Val Phe Thr Pro Glu Ala Phe Arg Lys Ile Gln Glu Asn Pro Lys Leu
                340                 345                 350

Ser Leu Leu Met Leu Gln Pro Asp Tyr Val Lys Met Val Asp Thr Val
                355                 360                 365

Ile Arg Asp Pro Ser Gln Gly Arg Leu Tyr Met Glu Asp Gln Arg Phe
370                 375                 380

Ala Leu Thr Leu Met Tyr Leu Ser Gly Met Lys Ile Pro Asn Asp Gly
385                 390                 395                 400

Asp Gly Glu Glu Glu Arg Pro Ser Ala Lys Ala Ala Glu Thr Ala
                405                 410                 415

Lys Pro Lys Glu Glu Lys Pro Leu Thr Asp Asn Glu Lys Glu Ala Leu
                420                 425                 430

Ala Leu Lys Glu Glu Gly Asn Lys Leu Tyr Leu Ser Lys Lys Phe Glu
                435                 440                 445

Glu Ala Leu Thr Lys Tyr Gln Glu Ala Gln Val Lys Asp Pro Asn Asn
                450                 455                 460

Thr Leu Tyr Ile Leu Asn Val Ser Ala Val Tyr Phe Glu Gln Gly Asp
465                 470                 475                 480

Tyr Asp Lys Cys Ile Ala Glu Cys Glu His Gly Ile Glu His Gly Arg
                485                 490                 495

Glu Asn His Cys Asp Tyr Thr Ile Ile Ala Lys Leu Met Thr Arg Asn
                500                 505                 510

Ala Leu Cys Leu Gln Arg Gln Arg Lys Tyr Glu Ala Ala Ile Asp Leu
                515                 520                 525

Tyr Lys Arg Ala Leu Val Glu Trp Arg Asn Pro Asp Thr Leu Lys Lys
530                 535                 540

Leu Thr Glu Cys Glu Lys Glu His Gln Lys Ala Val Glu Glu Ala Tyr
545                 550                 555                 560

Ile Asp Pro Glu Ile Ala Lys Gln Lys Asp Glu Gly Asn Gln Tyr
                565                 570                 575

Phe Lys Glu Asp Lys Phe Pro Glu Ala Val Ala Ala Tyr Thr Glu Ala
                580                 585                 590

Ile Lys Arg Asn Pro Ala Glu His Thr Ser Tyr Ser Asn Arg Ala Ala
                595                 600                 605

Ala Tyr Ile Lys Leu Gly Ala Phe Asn Asp Ala Leu Lys Asp Ala Glu
                610                 615                 620

Lys Cys Ile Glu Leu Lys Pro Asp Phe Val Lys Gly Tyr Ala Arg Lys
625                 630                 635                 640
```

```
Gly His Ala Tyr Phe Trp Thr Lys Gln Tyr Asn Arg Ala Leu Gln Ala
                645                 650                 655

Tyr Asn Glu Gly Leu Lys Val Asp Pro Ser Asn Ala Asp Cys Lys Asp
            660                 665                 670

Gly Arg Tyr Arg Thr Ile Met Lys Ile Gln Glu Met Ala Ser Gly Gln
        675                 680                 685

Ser Ala Asp Gly Asp Glu Ala Ala Arg Arg Ala Met Asp Asp Pro Glu
690                 695                 700

Ile Ala Ala Ile Met Gln Asp Ser Tyr Met Gln Leu Val Leu Lys Glu
705                 710                 715                 720

Met Gln Asn Asp Pro Thr Arg Ile Gln Glu Tyr Met Lys Asp Ser Gly
                725                 730                 735

Ile Ser Ser Lys Ile Asn Lys Leu Ile Ser Ala Gly Ile Ile Arg Phe
            740                 745                 750

Gly Gln Glu Phe Met Ala Gln Asn Asp Lys Ile Ala Pro Gln Asp Gln
        755                 760                 765

Asp Ser Phe Leu Asp Asp Gln Pro Gly Val Arg Pro Ile Pro Ser Phe
770                 775                 780

Asp Asp Met Pro Leu His Gln Asn Leu Leu Arg Gly Ile Tyr Ser Tyr
785                 790                 795                 800

Gly Phe Glu Lys Pro Ser Ser Ile Gln Gln Arg Ala Ile Ala Pro Phe
                805                 810                 815

Thr Arg Gly Gly Asp Ile Ile Ala Gln Ala Gln Ser Gly Thr Gly Lys
            820                 825                 830

Thr Gly Ala Phe Ser Ile Gly Leu Leu Gln Arg Leu Asp Phe Arg His
        835                 840                 845

Asn Leu Ile Gln Gly Leu Val Leu Ser Pro Thr Arg Glu Leu Ala Leu
850                 855                 860

Gln Thr Ala Glu Val Ile Ser Arg Ile Gly Glu Phe Leu Ser Asn Ser
865                 870                 875                 880

Ser Lys Phe Cys Glu Thr Phe Val Gly Gly Thr Arg Val Gln Asp Asp
                885                 890                 895

Leu Arg Lys Leu Gln Ala Gly Val Ile Val Ala Val Gly Thr Pro Gly
            900                 905                 910

Arg Val Ser Asp Val Ile Lys Arg Gly Ala Leu Arg Thr Glu Ser Leu
        915                 920                 925

Arg Val Leu Val Leu Asp Glu Ala Asp Glu Met Leu Ser Gln Gly Phe
930                 935                 940

Ala Asp Gln Ile Tyr Glu Ile Phe Arg Phe Leu Pro Lys Asp Ile Gln
945                 950                 955                 960

Val Ala Leu Phe Ser Ala Thr Met Pro Glu Glu Val Leu Glu Leu Thr
                965                 970                 975

Lys Lys Phe Met Arg Asp
            980

<210> SEQ ID NO 96
<211> LENGTH: 1641
<212> TYPE: PRT
<213> ORGANISM: Artificial Sequence
<220> FEATURE:
<223> OTHER INFORMATION: Fusion (poly-protein) constructs comprising
      multiple Leishmania antigens

<400> SEQUENCE: 96

Met His His His His His Met Ser Cys Gly Asn Ala Lys Ile Asn
```

```
                  5                   10                   15
Ser Pro Ala Pro Ser Phe Glu Glu Val Ala Leu Met Pro Asn Gly Ser
                20                  25                  30

Phe Lys Lys Ile Ser Leu Ser Ser Tyr Lys Gly Lys Trp Val Val Leu
                35                  40                  45

Phe Phe Tyr Pro Leu Asp Phe Thr Phe Val Cys Pro Thr Glu Val Ile
                50                  55                  60

Ala Phe Ser Asp Ser Val Ser Arg Phe Asn Glu Leu Asn Cys Glu Val
 65                  70                  75                  80

Leu Ala Cys Ser Ile Asp Ser Glu Tyr Ala His Leu Gln Trp Thr Leu
                85                  90                  95

Gln Asp Arg Lys Lys Gly Gly Leu Gly Thr Met Ala Ile Pro Met Leu
               100                 105                 110

Ala Asp Lys Thr Lys Ser Ile Ala Arg Ser Tyr Gly Val Leu Glu Glu
               115                 120                 125

Ser Gln Gly Val Ala Tyr Arg Gly Leu Phe Ile Ile Asp Pro His Gly
               130                 135                 140

Met Leu Arg Gln Ile Thr Val Asn Asp Met Pro Val Gly Arg Ser Val
145                 150                 155                 160

Glu Glu Val Leu Arg Leu Leu Glu Ala Phe Gln Phe Val Glu Lys His
               165                 170                 175

Gly Glu Val Cys Pro Ala Asn Trp Lys Lys Gly Ala Pro Thr Met Lys
               180                 185                 190

Pro Glu Pro Asn Ala Ser Val Glu Gly Tyr Phe Ser Lys Gln Gly Ser
               195                 200                 205

Met Asp Ala Thr Glu Leu Lys Asn Lys Gly Asn Glu Glu Phe Ser Ala
               210                 215                 220

Gly Arg Tyr Val Glu Ala Val Asn Tyr Phe Ser Lys Ala Ile Gln Leu
225                 230                 235                 240

Asp Glu Gln Asn Ser Val Leu Tyr Ser Asn Arg Ser Ala Cys Phe Ala
               245                 250                 255

Ala Met Gln Lys Tyr Lys Asp Ala Leu Asp Asp Ala Asp Lys Cys Ile
               260                 265                 270

Ser Ile Lys Pro Asn Trp Ala Lys Gly Tyr Val Arg Arg Gly Ala Ala
               275                 280                 285

Leu His Gly Met Arg Arg Tyr Asp Asp Ala Ile Ala Ala Tyr Glu Lys
               290                 295                 300

Gly Leu Lys Val Asp Pro Ser Asn Ser Gly Cys Ala Gln Gly Val Lys
305                 310                 315                 320

Asp Val Gln Val Ala Lys Ala Arg Glu Ala Arg Asp Pro Ile Ala Arg
               325                 330                 335

Val Phe Thr Pro Glu Ala Phe Arg Lys Ile Gln Glu Asn Pro Lys Leu
               340                 345                 350

Ser Leu Leu Met Leu Gln Pro Asp Tyr Val Lys Met Val Asp Thr Val
               355                 360                 365

Ile Arg Asp Pro Ser Gln Gly Arg Leu Tyr Met Glu Asp Gln Arg Phe
               370                 375                 380

Ala Leu Thr Leu Met Tyr Leu Ser Gly Met Lys Ile Pro Asn Asp Gly
385                 390                 395                 400

Asp Gly Glu Glu Glu Glu Arg Pro Ser Ala Lys Ala Ala Glu Thr Ala
               405                 410                 415

Lys Pro Lys Glu Glu Lys Pro Leu Thr Asp Asn Glu Lys Glu Ala Leu
               420                 425                 430
```

```
Ala Leu Lys Glu Glu Gly Asn Lys Leu Tyr Leu Ser Lys Lys Phe Glu
            435                 440                 445

Glu Ala Leu Thr Lys Tyr Gln Glu Ala Gln Val Lys Asp Pro Asn Asn
        450                 455                 460

Thr Leu Tyr Ile Leu Asn Val Ser Ala Val Tyr Phe Glu Gln Gly Asp
465                 470                 475                 480

Tyr Asp Lys Cys Ile Ala Glu Cys Glu His Gly Ile Glu His Gly Arg
                485                 490                 495

Glu Asn His Cys Asp Tyr Thr Ile Ile Ala Lys Leu Met Thr Arg Asn
                500                 505                 510

Ala Leu Cys Leu Gln Arg Gln Arg Lys Tyr Glu Ala Ala Ile Asp Leu
            515                 520                 525

Tyr Lys Arg Ala Leu Val Glu Trp Arg Asn Pro Asp Thr Leu Lys Lys
        530                 535                 540

Leu Thr Glu Cys Glu Lys Glu His Gln Lys Ala Val Glu Glu Ala Tyr
545                 550                 555                 560

Ile Asp Pro Glu Ile Ala Lys Gln Lys Lys Asp Glu Gly Asn Gln Tyr
                565                 570                 575

Phe Lys Glu Asp Lys Phe Pro Glu Ala Val Ala Ala Tyr Thr Glu Ala
            580                 585                 590

Ile Lys Arg Asn Pro Ala Glu His Thr Ser Tyr Ser Asn Arg Ala Ala
        595                 600                 605

Ala Tyr Ile Lys Leu Gly Ala Phe Asn Asp Ala Leu Lys Asp Ala Glu
610                 615                 620

Lys Cys Ile Glu Leu Lys Pro Asp Phe Val Lys Gly Tyr Ala Arg Lys
625                 630                 635                 640

Gly His Ala Tyr Phe Trp Thr Lys Gln Tyr Asn Arg Ala Leu Gln Ala
                645                 650                 655

Tyr Asn Glu Gly Leu Lys Val Asp Pro Ser Asn Ala Asp Cys Lys Asp
            660                 665                 670

Gly Arg Tyr Arg Thr Ile Met Lys Ile Gln Glu Met Ala Ser Gly Gln
        675                 680                 685

Ser Ala Asp Gly Asp Glu Ala Ala Arg Arg Ala Met Asp Asp Pro Glu
690                 695                 700

Ile Ala Ala Ile Met Gln Asp Ser Tyr Met Gln Leu Val Leu Lys Glu
705                 710                 715                 720

Met Gln Asn Asp Pro Thr Arg Ile Gln Glu Tyr Met Lys Asp Ser Gly
                725                 730                 735

Ile Ser Ser Lys Ile Asn Lys Leu Ile Ser Ala Gly Ile Ile Arg Phe
            740                 745                 750

Gly Gln Glu Phe Ser Leu Thr Asp Pro Ala Val Leu Gly Glu Glu Thr
        755                 760                 765

His Leu Arg Val Arg Val Pro Asp Lys Ala Asn Lys Thr Leu Thr
770                 775                 780

Val Glu Asp Asn Gly Ile Gly Met Thr Lys Ala Asp Leu Val Asn Asn
785                 790                 795                 800

Leu Gly Thr Ile Ala Arg Ser Gly Thr Lys Ala Phe Met Glu Ala Leu
                805                 810                 815

Glu Ala Gly Gly Asp Met Ser Met Ile Gly Gln Phe Gly Val Gly Phe
            820                 825                 830

Tyr Ser Ala Tyr Leu Val Ala Asp Arg Val Thr Val Val Ser Lys Asn
        835                 840                 845
```

-continued

```
Asn Ser Asp Glu Ala Tyr Val Trp Glu Ser Ser Ala Gly Gly Thr Phe
850                 855                 860

Thr Ile Thr Ser Val Pro Glu Ser Asp Met Lys Arg Gly Thr Arg Ile
865                 870                 875                 880

Thr Leu His Leu Lys Glu Asp Gln Gln Glu Tyr Leu Glu Arg Arg
                885                 890                 895

Val Lys Glu Leu Ile Lys Lys His Ser Glu Phe Ile Gly Tyr Asp Ile
                900                 905                 910

Glu Leu Met Val Glu Lys Thr Ala Glu Lys Val Thr Asp Glu Asp
                915                 920                 925

Glu Glu Glu Asp Glu Ser Lys Lys Ser Cys Gly Asp Glu Gly Glu
        930                 935                 940

Pro Lys Val Glu Glu Val Thr Glu Gly Gly Glu Asp Lys Lys Lys
945                 950                 955                 960

Thr Lys Lys Val Lys Glu Val Thr Lys Thr Tyr Glu Val Gln Asn Lys
                965                 970                 975

His Lys Pro Leu Trp Thr Arg Asp Pro Lys Asp Val Thr Lys Glu Glu
                980                 985                 990

Tyr Ala Ala Phe Tyr Lys Ala Ile Ser Asn Asp Trp Glu Asp Pro Ala
                995                 1000                1005

Ala Thr Lys His Phe Ser Val Glu Gly Gln Leu Glu Phe Arg Ala Ile
        1010                1015                1020

Ala Phe Val Pro Lys Arg Ala Pro Phe Asp Met Phe Glu Pro Asn Lys
1025                1030                1035                1040

Lys Arg Asn Asn Ile Lys Leu Tyr Val Arg Arg Val Phe Ile Met Asp
                1045                1050                1055

Asn Cys Glu Asp Leu Cys Pro Asp Trp Leu Gly Phe Val Lys Gly Val
                1060                1065                1070

Val Asp Ser Glu Asp Leu Pro Leu Asn Ile Ser Arg Glu Asn Leu Gln
                1075                1080                1085

Gln Asn Lys Ile Leu Lys Val Ile Arg Lys Asn Ile Val Lys Lys Cys
        1090                1095                1100

Leu Glu Leu Phe Glu Glu Ile Ala Glu Asn Lys Glu Asp Tyr Lys Gln
1105                1110                1115                1120

Phe Tyr Glu Gln Phe Gly Lys Asn Ile Lys Leu Gly Ile His Glu Asp
                1125                1130                1135

Thr Ala Asn Arg Lys Lys Leu Met Glu Leu Leu Arg Phe Tyr Ser Thr
        1140                1145                1150

Glu Ser Gly Glu Glu Met Thr Thr Leu Lys Asp Tyr Val Thr Arg Met
                1155                1160                1165

Lys Pro Glu Gln Lys Ser Ile Tyr Tyr Ile Thr Gly Asp Ser Lys Lys
        1170                1175                1180

Lys Leu Glu Ser Ser Pro Phe Ile Glu Lys Ala Arg Arg Cys Gly Leu
1185                1190                1195                1200

Glu Val Leu Phe Met Thr Glu Pro Ile Asp Glu Tyr Val Met Gln Gln
                1205                1210                1215

Val Lys Asp Phe Glu Asp Lys Lys Phe Ala Cys Leu Thr Lys Glu Gly
                1220                1225                1230

Val His Phe Glu Glu Ser Glu Glu Lys Lys Gln Arg Glu Glu Lys
        1235                1240                1245

Lys Ala Ala Cys Glu Lys Leu Cys Lys Thr Met Lys Glu Val Leu Gly
        1250                1255                1260

Asp Lys Val Glu Lys Val Thr Val Ser Glu Arg Leu Ser Thr Ser Pro
```

```
                1265                1270                1275                1280
Cys Ile Leu Val Thr Ser Glu Phe Gly Trp Ser Ala His Met Glu Gln
                    1285                1290                1295

Ile Met Arg Asn Gln Ala Leu Arg Asp Ser Ser Met Ala Gln Tyr Met
            1300                1305                1310

Val Ser Lys Lys Thr Met Glu Val Asn Pro Asp His Pro Ile Ile Lys
        1315                1320                1325

Glu Leu Arg Arg Arg Val Glu Ala Asp Glu Asn Asp Lys Ala Val Lys
    1330                1335                1340

Asp Leu Val Phe Leu Leu Phe Asp Thr Ser Leu Leu Thr Ser Gly Phe
1345                1350                1355                1360

Gln Leu Asp Asp Pro Thr Gly Tyr Ala Glu Arg Ile Asn Arg Met Ile
                1365                1370                1375

Lys Leu Gly Leu Ser Leu Asp Glu Glu Glu Glu Val Ala Glu Ala
            1380                1385                1390

Pro Pro Ala Glu Ala Ala Pro Ala Glu Val Thr Ala Gly Thr Ser Ser
        1395                1400                1405

Met Glu Gln Val Asp Asp Ile Met Ala Gln Asn Asp Lys Ile Ala Pro
    1410                1415                1420

Gln Asp Gln Asp Ser Phe Leu Asp Asp Gln Pro Gly Val Arg Pro Ile
1425                1430                1435                1440

Pro Ser Phe Asp Asp Met Pro Leu His Gln Asn Leu Leu Arg Gly Ile
                1445                1450                1455

Tyr Ser Tyr Gly Phe Glu Lys Pro Ser Ser Ile Gln Gln Arg Ala Ile
            1460                1465                1470

Ala Pro Phe Thr Arg Gly Gly Asp Ile Ile Ala Gln Ala Gln Ser Gly
        1475                1480                1485

Thr Gly Lys Thr Gly Ala Phe Ser Ile Gly Leu Leu Gln Arg Leu Asp
    1490                1495                1500

Phe Arg His Asn Leu Ile Gln Gly Leu Val Leu Ser Pro Thr Arg Glu
1505                1510                1515                1520

Leu Ala Leu Gln Thr Ala Glu Val Ile Ser Arg Ile Gly Glu Phe Leu
                1525                1530                1535

Ser Asn Ser Ser Lys Phe Cys Glu Thr Phe Val Gly Gly Thr Arg Val
            1540                1545                1550

Gln Asp Asp Leu Arg Lys Leu Gln Ala Gly Val Ile Ala Val Gly
        1555                1560                1565

Thr Pro Gly Arg Val Ser Asp Val Ile Lys Arg Gly Ala Leu Arg Thr
    1570                1575                1580

Glu Ser Leu Arg Val Leu Val Leu Asp Glu Ala Asp Glu Met Leu Ser
1585                1590                1595                1600

Gln Gly Phe Ala Asp Gln Ile Tyr Glu Ile Phe Arg Phe Leu Pro Lys
                1605                1610                1615

Asp Ile Gln Val Ala Leu Phe Ser Ala Thr Met Pro Glu Glu Val Leu
            1620                1625                1630

Glu Leu Thr Lys Lys Phe Met Arg Asp
        1635                1640

<210> SEQ ID NO 97
<211> LENGTH: 1427
<212> TYPE: PRT
<213> ORGANISM: Artificial Sequence
<220> FEATURE:
<223> OTHER INFORMATION: Fusion (poly-protein) constructs comprising
      multiple Leishmania antigens
```

-continued

```
<400> SEQUENCE: 97

Met His His His His His Met Ser Cys Gly Asn Ala Lys Ile Asn
                 5                  10                  15

Ser Pro Ala Pro Ser Phe Glu Glu Val Ala Leu Met Pro Asn Gly Ser
             20                  25                  30

Phe Lys Lys Ile Ser Leu Ser Ser Tyr Lys Gly Lys Trp Val Val Leu
         35                  40                  45

Phe Phe Tyr Pro Leu Asp Phe Thr Phe Val Cys Pro Thr Glu Val Ile
     50                  55                  60

Ala Phe Ser Asp Ser Val Ser Arg Phe Asn Glu Leu Asn Cys Glu Val
 65                  70                  75                  80

Leu Ala Cys Ser Ile Asp Ser Glu Tyr Ala His Leu Gln Trp Thr Leu
                 85                  90                  95

Gln Asp Arg Lys Lys Gly Gly Leu Gly Thr Met Ala Ile Pro Met Leu
            100                 105                 110

Ala Asp Lys Thr Lys Ser Ile Ala Arg Ser Tyr Gly Val Leu Glu Glu
        115                 120                 125

Ser Gln Gly Val Ala Tyr Arg Gly Leu Phe Ile Ile Asp Pro His Gly
    130                 135                 140

Met Leu Arg Gln Ile Thr Val Asn Asp Met Pro Val Gly Arg Ser Val
145                 150                 155                 160

Glu Glu Val Leu Arg Leu Leu Glu Ala Phe Gln Phe Val Glu Lys His
                165                 170                 175

Gly Glu Val Cys Pro Ala Asn Trp Lys Lys Gly Ala Pro Thr Met Lys
            180                 185                 190

Pro Glu Pro Asn Ala Ser Val Glu Gly Tyr Phe Ser Lys Gln Gly Ser
        195                 200                 205

Met Asp Ala Thr Glu Leu Lys Asn Lys Gly Asn Glu Glu Phe Ser Ala
    210                 215                 220

Gly Arg Tyr Val Glu Ala Val Asn Tyr Phe Ser Lys Ala Ile Gln Leu
225                 230                 235                 240

Asp Glu Gln Asn Ser Val Leu Tyr Ser Asn Arg Ser Ala Cys Phe Ala
                245                 250                 255

Ala Met Gln Lys Tyr Lys Asp Ala Leu Asp Asp Ala Asp Lys Cys Ile
            260                 265                 270

Ser Ile Lys Pro Asn Trp Ala Lys Gly Tyr Val Arg Arg Gly Ala Ala
        275                 280                 285

Leu His Gly Met Arg Arg Tyr Asp Asp Ala Ile Ala Ala Tyr Glu Lys
    290                 295                 300

Gly Leu Lys Val Asp Pro Ser Asn Ser Gly Cys Ala Gln Gly Val Lys
305                 310                 315                 320

Asp Val Gln Val Ala Lys Ala Arg Glu Ala Arg Asp Pro Ile Ala Arg
                325                 330                 335

Val Phe Thr Pro Glu Ala Phe Arg Lys Ile Gln Glu Asn Pro Lys Leu
            340                 345                 350

Ser Leu Leu Met Leu Gln Pro Asp Tyr Val Lys Met Val Asp Thr Val
        355                 360                 365

Ile Arg Asp Pro Ser Gln Gly Arg Leu Tyr Met Glu Asp Gln Arg Phe
    370                 375                 380

Ala Leu Thr Leu Met Tyr Leu Ser Gly Met Lys Ile Pro Asn Asp Gly
385                 390                 395                 400

Asp Gly Glu Glu Glu Glu Arg Pro Ser Ala Lys Ala Ala Glu Thr Ala
```

-continued

```
                405                 410                 415
Lys Pro Lys Glu Glu Lys Pro Leu Thr Asp Asn Glu Lys Glu Ala Leu
            420                 425                 430
Ala Leu Lys Glu Glu Gly Asn Lys Leu Tyr Leu Ser Lys Lys Phe Glu
            435                 440                 445
Glu Ala Leu Thr Lys Tyr Gln Glu Ala Gln Val Lys Asp Pro Asn Asn
            450                 455                 460
Thr Leu Tyr Ile Leu Asn Val Ser Ala Val Tyr Phe Glu Gln Gly Asp
465                 470                 475                 480
Tyr Asp Lys Cys Ile Ala Glu Cys Glu His Gly Ile Glu His Gly Arg
                485                 490                 495
Glu Asn His Cys Asp Tyr Thr Ile Ile Ala Lys Leu Met Thr Arg Asn
                500                 505                 510
Ala Leu Cys Leu Gln Arg Gln Arg Lys Tyr Glu Ala Ala Ile Asp Leu
            515                 520                 525
Tyr Lys Arg Ala Leu Val Glu Trp Arg Asn Pro Asp Thr Leu Lys Lys
530                 535                 540
Leu Thr Glu Cys Glu Lys Glu His Gln Lys Ala Val Glu Glu Ala Tyr
545                 550                 555                 560
Ile Asp Pro Glu Ile Ala Lys Gln Lys Lys Asp Glu Gly Asn Gln Tyr
                565                 570                 575
Phe Lys Glu Asp Lys Phe Pro Glu Ala Val Ala Ala Tyr Thr Glu Ala
            580                 585                 590
Ile Lys Arg Asn Pro Ala Glu His Thr Ser Tyr Ser Asn Arg Ala Ala
            595                 600                 605
Ala Tyr Ile Lys Leu Gly Ala Phe Asn Asp Ala Leu Lys Asp Ala Glu
610                 615                 620
Lys Cys Ile Glu Leu Lys Pro Asp Phe Val Lys Gly Tyr Ala Arg Lys
625                 630                 635                 640
Gly His Ala Tyr Phe Trp Thr Lys Gln Tyr Asn Arg Ala Leu Gln Ala
                645                 650                 655
Tyr Asn Glu Gly Leu Lys Val Asp Pro Ser Asn Ala Asp Cys Lys Asp
            660                 665                 670
Gly Arg Tyr Arg Thr Ile Met Lys Ile Gln Glu Met Ala Ser Gly Gln
            675                 680                 685
Ser Ala Asp Gly Asp Glu Ala Arg Arg Ala Met Asp Asp Pro Glu
690                 695                 700
Ile Ala Ala Ile Met Gln Asp Ser Tyr Met Gln Leu Val Leu Lys Glu
705                 710                 715                 720
Met Gln Asn Asp Pro Thr Arg Ile Gln Glu Tyr Met Lys Asp Ser Gly
                725                 730                 735
Ile Ser Ser Lys Ile Asn Lys Leu Ile Ser Ala Gly Ile Ile Arg Phe
                740                 745                 750
Gly Gln Glu Phe Ser Leu Thr Asp Pro Ala Val Leu Gly Glu Glu Thr
            755                 760                 765
His Leu Arg Val Arg Val Pro Asp Lys Ala Asn Lys Thr Leu Thr
            770                 775                 780
Val Glu Asp Asn Gly Ile Gly Met Thr Lys Ala Asp Leu Val Asn Asn
785                 790                 795                 800
Leu Gly Thr Ile Ala Arg Ser Gly Thr Lys Ala Phe Met Glu Ala Leu
                805                 810                 815
Glu Ala Gly Gly Asp Met Ser Met Ile Gly Gln Phe Gly Val Gly Phe
                820                 825                 830
```

-continued

```
Tyr Ser Ala Tyr Leu Val Ala Asp Arg Val Thr Val Ser Lys Asn
        835                 840                 845
Asn Ser Asp Glu Ala Tyr Val Trp Glu Ser Ser Ala Gly Gly Thr Phe
850                 855                 860
Thr Ile Thr Ser Val Pro Glu Ser Asp Met Lys Arg Gly Thr Arg Ile
865                 870                 875                 880
Thr Leu His Leu Lys Glu Asp Gln Gln Glu Tyr Leu Glu Arg Arg
                885                 890                 895
Val Lys Glu Leu Ile Lys Lys His Ser Glu Phe Ile Gly Tyr Asp Ile
            900                 905                 910
Glu Leu Met Val Glu Lys Thr Ala Glu Lys Glu Val Thr Asp Glu Asp
            915                 920                 925
Glu Glu Glu Asp Glu Ser Lys Lys Ser Cys Gly Asp Glu Gly Glu
930                 935                 940
Pro Lys Val Glu Val Thr Glu Gly Gly Glu Asp Lys Lys Lys Lys
945                 950                 955                 960
Thr Lys Lys Val Lys Glu Val Thr Lys Thr Tyr Glu Val Gln Asn Lys
                965                 970                 975
His Lys Pro Leu Trp Thr Arg Asp Pro Lys Asp Val Thr Lys Glu Glu
            980                 985                 990
Tyr Ala Ala Phe Tyr Lys Ala Ile Ser Asn Asp Trp Glu Asp Pro Ala
            995                 1000                1005
Ala Thr Lys His Phe Ser Val Glu Gly Gln Leu Glu Phe Arg Ala Ile
        1010                1015                1020
Ala Phe Val Pro Lys Arg Ala Pro Phe Asp Met Phe Glu Pro Asn Lys
1025                1030                1035                1040
Lys Arg Asn Asn Ile Lys Leu Tyr Val Arg Arg Val Phe Ile Met Asp
                1045                1050                1055
Asn Cys Glu Asp Leu Cys Pro Asp Trp Leu Gly Phe Val Lys Gly Val
            1060                1065                1070
Val Asp Ser Glu Asp Leu Pro Leu Asn Ile Ser Arg Glu Asn Leu Gln
            1075                1080                1085
Gln Asn Lys Ile Leu Lys Val Ile Arg Lys Asn Ile Val Lys Lys Cys
        1090                1095                1100
Leu Glu Leu Phe Glu Glu Ile Ala Glu Asn Lys Glu Asp Tyr Lys Gln
1105                1110                1115                1120
Phe Tyr Glu Gln Phe Gly Lys Asn Ile Lys Leu Gly Ile His Glu Asp
                1125                1130                1135
Thr Ala Asn Arg Lys Lys Leu Met Glu Leu Leu Arg Phe Tyr Ser Thr
            1140                1145                1150
Glu Ser Gly Glu Glu Met Thr Thr Leu Lys Asp Tyr Val Thr Arg Met
            1155                1160                1165
Lys Pro Glu Gln Lys Ser Ile Tyr Tyr Ile Thr Gly Asp Ser Lys Lys
        1170                1175                1180
Lys Leu Glu Ser Ser Pro Phe Ile Glu Lys Ala Arg Arg Cys Gly Leu
1185                1190                1195                1200
Glu Val Leu Phe Met Thr Glu Pro Ile Asp Glu Tyr Val Met Gln Gln
                1205                1210                1215
Val Lys Asp Phe Glu Asp Lys Lys Phe Ala Cys Leu Thr Lys Glu Gly
            1220                1225                1230
Val His Phe Glu Glu Ser Glu Glu Glu Lys Lys Gln Arg Glu Glu Lys
            1235                1240                1245
```

```
Lys Ala Ala Cys Glu Lys Leu Cys Lys Thr Met Lys Glu Val Leu Gly
    1250                1255                1260

Asp Lys Val Glu Lys Val Thr Val Ser Glu Arg Leu Ser Thr Ser Pro
1265                1270                1275                1280

Cys Ile Leu Val Thr Ser Glu Phe Gly Trp Ser Ala His Met Glu Gln
                1285                1290                1295

Ile Met Arg Asn Gln Ala Leu Arg Asp Ser Ser Met Ala Gln Tyr Met
            1300                1305                1310

Val Ser Lys Lys Thr Met Glu Val Asn Pro Asp His Pro Ile Ile Lys
        1315                1320                1325

Glu Leu Arg Arg Arg Val Glu Ala Asp Glu Asn Asp Lys Ala Val Lys
    1330                1335                1340

Asp Leu Val Phe Leu Leu Phe Asp Thr Ser Leu Leu Thr Ser Gly Phe
1345                1350                1355                1360

Gln Leu Asp Asp Pro Thr Gly Tyr Ala Glu Arg Ile Asn Arg Met Ile
                1365                1370                1375

Lys Leu Gly Leu Ser Leu Asp Glu Glu Glu Glu Val Ala Glu Ala
            1380                1385                1390

Pro Pro Ala Glu Ala Ala Pro Ala Glu Val Thr Ala Gly Thr Ser Ser
        1395                1400                1405

Met Glu Gln Val Asp Asp Ile His His Thr Gly Gly Arg Ser Ser Arg
    1410                1415                1420

Ser Gly Cys
1425

<210> SEQ ID NO 98
<211> LENGTH: 4929
<212> TYPE: DNA
<213> ORGANISM: Artificial Sequence
<220> FEATURE:
<223> OTHER INFORMATION: DNA sequence encoding fusion (poly-protein)
      constructs comprising multiple Leishmania antigens

<400> SEQUENCE: 98
catatgcacc accaccacca ccacatgtcc tgcggtaacg ccaagatcaa ctctcccgcg      60
ccgtccttcg aggaggtggc gctcatgccc aacggcagct tcaagaagat cagcctctcc     120
tcctacaagg gcaagtgggt cgtgctcttc ttctacccgc tcgacttcac cttcgtgtgc     180
ccgacagagg tcatcgcgtt ctccgacagc gtgagtcgct caacgagct caactgcgag     240 gtcctcgcgt gctcgataga cagcgagtac gcgcacctgc agtggacgct gcaggaccgc     300
aagaagggcg gcctcgggac catggcgatc ccaatgctag ccgacaagac caagagcatc     360
gctcgttcct acggcgtgct ggaggagagc cagggcgtgg cctaccgcgg tctcttcatc     420
atcgaccccc atggcatgct gcgtcagatc accgtcaatg acatgccggt gggccgcagc     480
gtggaggagg ttctacgcct gctggaggct tttcagttcg tggagaagca cggcgaggtg     540
tgccccgcga actggaagaa gggcgccccc acgatgaagc cggaaccgaa tgcgtctgtc     600
gagggatact tcagcaagca gggatccatg acgcaactg agctgaagaa caaggggaac     660
gaagagttct ccgccggccg ctatgtggag gcggtgaact acttctcaaa ggcgatccag     720
ttggatgagc agaacagtgt cctctacagc aaccgctccg cctgttttgc agccatgcag     780
aaatacaagg acgcgctgga cgacgccgac aagtgcatct cgatcaagcc gaattgggcc     840
aagggctacg tgcgccgagg agcagctctc catggcatgc gccgctacga cgatgccatt     900
gccgcgtatg aaaagggggct caaggtggac ccttccaaca gcggctgcgc gcaggggcgtg    960
```

-continued

```
aaggacgtgc aggtagccaa ggcccgcgaa gcacgtgacc ccatcgctcg cgtcttcacc    1020
ccggaggcgt tccgcaagat ccaagagaat cccaagctgt ctctacttat gctgcagccg    1080
gactacgtga agatggtaga caccgtcatc cgcgacccct tcgcagggcg gctgtacatg    1140
gaagaccagc gctttgccct gacgctcatg tacctgagcg gaatgaagat tcccaacgat    1200
ggtgatggcg aggaggagga acgtccgtct gcgaaggcgg cagagacagc gaagccaaaa    1260
gaggagaagc ctctcaccga caacgagaag gaggccctgg cgctcaagga ggagggcaac    1320
aagctgtacc tctcgaagaa gtttgaggag gcgctgacca agtaccaaga ggcgcaggtg    1380
aaagacccca caacactttt atacattctg aacgtgtcgg ccgtgtactt cgagcagggt    1440
gactacgaca agtgcatcgc cgagtgcgag cacggtatcg agcacggtcg cgagaaccac    1500
tgcgactaca caatcattgc gaagctcatg acccggaacg ccttgtgcct ccagaggcag    1560
aggaagtacg aggctgctat cgaccttttac aagcgcgccc ttgtcgagtg gcgtaacccct    1620 gcacccctca agaagctgac ggagtgcgag aaggagcacc aaaaggcggt ggaggaagcc    1680
tacatcgatc ctgagatcgc gaagcagaag aaagacgaag gtaaccagta cttcaaggag    1740
gataagttcc ccgaggccgt ggcagcgtac acggaggcca tcaagcgcaa ccctgccgag    1800
cacacctcct acagcaatcg cgcggccgcg tacatcaagc ttggagcctt caacgacgcc    1860
ctcaaggacg cggagaagtg cattgagctg aagcccgact ttgttaaggg ctacgcgcgc    1920
aagggtcatg cttacttttg gaccaagcag tacaaccgcg cgctgcaggc gtacaatgag    1980
ggcctcaagg tggacccgag caatgcggac tgcaaggatg ggcggtatcg cacaatcatg    2040
aagattcagg agatggcatc tggccaatcc gcggatggcg acgaggcggc gcgccgggcc    2100
atggacgatc ctgaaatcgc ggcaatcatg caagatagc acatgcaact agtgttgaag    2160
gagatgcaga acgatcccac gcgcattcag gagtacatga aggactccgg gatctcatcg    2220
aagatcaaca agctgatttc agctggcatc attcgttttg gtcaggaatt cagcctgacg    2280
gacccggcgg tgctgggcga ggagactcac ctgcgcgtcc gcgtggtgcc ggacaaggcg    2340
aacaagacgc tgacggtgga ggataacggc atcggcatga ccaaggcgga cctcgtgaac    2400
aatctgggca cgatcgcgcg ctccggcacg aaggcgttca tggaggcact ggaggccggc    2460
ggcgacatga gcatgatcgg ccagttcggt gtcggcttct actccgcgta ccttgtggcg    2520
gaccgcgtga cggtggtgtc gaagaacaac tcggacgagg cgtacgtatg ggagtcgtcc    2580
gcgggcggca cgttcaccat cacgagcgtg ccggagtcgg acatgaagcg cggcacgcgc    2640
atcacgctgc acctaaagga ggaccagcag gagtacctgg aggagcgccg ggtgaaggag    2700
ctgatcaaga agcactccga gttcatcggc tacgacatcg agctgatggt ggagaagacg    2760
gcggagaagg aggtgacgga cgaggacgag gaggaggacg agtcgaagaa gaagtcctgc    2820
ggggacgagg gcgagccgaa ggtggaggag gtgacggagg gcggcgagga caagaagaag    2880
aagacgaaga aggtgaagga ggtgacgaag acgtacgagg tccagaacaa gcacaagccg    2940
ctctggacgc gcgaccccgaa ggacgtgacg aaggaggagt acgcggcctt ctacaaggcc    3000
atctccaacg actgggagga cccggcggcg acgaagcact tctcggtgga gggccagctg    3060
gagttccgcg cgatcgcgtt cgtgccgaag cgcgcgcccgt tcgacatgtt cgagccgaac    3120
aagaagcgca acaacatcaa gctgtacgtg cgccgcgtgt tcatcatgga caactgcgag    3180
gacctgtgcc cggactggct cggcttcgtg aagggcgtcg tggacagcga ggacctgccg    3240
ctgaacatct cgcgcgagaa cctgcagcag aacaagatcc tgaaggtgat ccgcaagaac    3300
atcgtgaaga agtgcctgga gctgttcgaa gagatagcgg agaacaagga ggactacaag    3360
```

| | |
|---|---|
| cagttctacg agcagttcgg caagaacatc aagctgggca tccacgagga cacggcgaac | 3420 |
| cgcaagaagc tgatggagtt gctgcgcttc tacagcaccg agtcggggga ggagatgacg | 3480 |
| acactgaagg actacgtgac gcgcatgaag ccggagcaga agtcgatcta ctacatcact | 3540 |
| ggcgacagca agaagaagct ggagtcgtcg ccgttcatcg agaaggcgag acgctgcggg | 3600 |
| ctcgaggtgc tgttcatgac ggagccgatc gacgagtacg tgatgcagca ggtgaaggac | 3660 |
| ttcgaggaca agaagttcgc gtgcctgacg aaggaaggcg tgcacttcga ggagtccgag | 3720 |
| gaggagaaga agcagcgcga ggagaagaag gcggcgtgcg agaagctgtg caagacgatg | 3780 |
| aaggaggtgc tgggcgacaa ggtggagaag gtgaccgtgt cggagcgcct gtcgacgtcg | 3840 |
| ccgtgcatcc tggtgacgtc ggagtttggg tggtcggcgc acatggaaca gatcatgcgc | 3900 |
| aaccaggcgc tgcgcgactc cagcatggcg cagtacatgg tgtccaagaa gacgatggag | 3960 |
| gtgaaccccg accaccccat catcaaggag ctgcgccgcc gcgtggaggc ggacgagaac | 4020 |
| gacaaggccg tgaaggacct cgtcttcctg ctcttcgaca cgtcgctgct cacgtccggc | 4080 |
| ttccagctgg atgaccccac cggctacgcc gagcgcatca accgcatgat caagctcggc | 4140 |
| ctgtcgctcg acgaggagga ggaggaggtc gccgaggcgc cgccggccga ggcagccccc | 4200 |
| gcggaggtca ccgccggcac ctccagcatg gagcaggtgg acgatatcat ggcgcagaat | 4260 |
| gataagatcg cccccccagga ccaggactcc ttcctcgatg accagcccgg cgttcgcccg | 4320 |
| atcccgtcct cgacgacat gccgctgcac cagaacctgc tgcgtggcat ctactcgtac | 4380 |
| gggttcgaga gccgtccag catccagcag cgcgcgatag cccccttcac gcgcggcggc | 4440 |
| gacatcatcg cgcaggccca gtccggtacc ggcaagacgg gtgccttctc catcggtctg | 4500 |
| ctgcagcgcc tggacttccg ccacaacctg atccagggcc tcgtgctctc ccccactcgc | 4560 |
| gagctggccc tgcagacggc ggaggtgatc agccgcatcg gtgagttcct gtcgaacagc | 4620 |
| tccaagttct gcgagacctt tgtcggcggc acgcgcgtgc aggatgacct gcgcaagctg | 4680 |
| caggccggcg tcatcgttgc cgtgggcacg ccgggccgcg tgtccgacgt gatcaagcgt | 4740 |
| ggcgcgctgc gcacagagtc gctgcgcgtg ctggtgctcg acgaggctga tgagatgctg | 4800 |
| tctcagggct tcgcggacca gatttacgag atcttccgct tcctgccgaa ggacatccag | 4860 |
| gtcgcgctct tctccgccac gatgccggag gaggtactgg agctgacgaa gaagttcatg | 4920 |
| cgcgactaa | 4929 |

<210> SEQ ID NO 99
<211> LENGTH: 4233
<212> TYPE: DNA
<213> ORGANISM: Artificial Sequence
<220> FEATURE:
<223> OTHER INFORMATION: DNA sequence encoding fusion (poly-protein)
      constructs comprising multiple Leishmania antigens

<400> SEQUENCE: 99

| | |
|---|---|
| ccagtgtggt ggatgtcctg cggtaacgcc aagatcaact ctcccgcgcc gtccttcgag | 60 |
| gaggtggcgc tcatgcccaa cggcagcttc aagaagatca gcctctcctc ctacaagggc | 120 |
| aagtgggtcg tgctcttctt ctacccgctc gacttcacct tcgtgtgccc gacagaggtc | 180 |
| atcgcgttct ccgacagcgt gagtcgcttc aacgagctca actgcgaggt cctcgcgtgc | 240 |
| tcgatagaca gcgagtacgc gcacctgcag tggacgctgc aggaccgcaa gaagggcggc | 300 |
| ctcgggacca tggcgatccc aatgctagcc gacaagacca agagcatcgc tcgttcctac | 360 |
| ggcgtgctgg aggagagcca gggcgtggcc taccgcggtc tcttcatcat cgaccccat | 420 |

```
ggcatgctgc gtcagatcac cgtcaatgac atgccggtgg gccgcagcgt ggaggaggtt      480
ctacgcctgc tggaggcttt tcagttcgtg gagaagcacg gcgaggtgtg ccccgcgaac      540
tggaagaagg gcgccccac  gatgaagccg gaaccgaatg cgtctgtcga gggatacttc      600
agcaagcagg gatccatgga cgcaactgag ctgaagaaca aggggaacga agagttctcc      660
gccggccgct atgtggaggc ggtgaactac ttctcaaagg cgatccagtt ggatgagcag      720
aacagtgtcc tctacagcaa ccgctccgcc tgttttgcag ccatgcagaa atacaaggac      780
gcgctggacg acgccgacaa gtgcatctcg atcaagccga attgggccaa gggctacgtg      840
cgccgaggag cagctctcca tggcatgcgc cgctacgacg atgccattgc cgcgtatgaa      900
aaggggctca aggtggaccc ttccaacagc ggctgcgcgc agggcgtgaa ggacgtgcag      960
gtagccaagg cccgcgaagc acgtgacccc atcgctcgcg tcttcacccc ggaggcgttc     1020
cgcaagatcc aagagaatcc caagctgtct ctacttatgc tgcagccgga ctacgtgaag     1080
atggtagaca ccgtcatccg cgaccttcg  cagggccggc tgtacatgga agaccagcgc     1140
tttgccctga cgctcatgta cctgagcgga atgaagattc ccaacgatgg tgatggcgag     1200
gaggaggaac gtccgtctgc gaaggcggca gagacagcga agccaaaaga ggagaagcct     1260
ctcaccgaca cgagaagga  ggccctggcg ctcaaggagg agggcaacaa gctgtacctc     1320
tcgaagaagt ttgaggaggc gctgaccaag taccaagagg cgcaggtgaa agaccccaac     1380
aacactttat acattctgaa cgtgtcggcc gtgtacttcg agcagggtga ctacgacaag     1440
tgcatcgccg agtgcgagca cggtatcgag cacggtcgcg agaaccactg cgactacaca     1500
atcattgcga agctcatgac ccggaacgcc ttgtgcctcc agaggcagag gaagtacgag     1560
gctgctatcg acctttacaa gcgcgccctt gtcgagtggc gtaaccctga caccctcaag     1620
aagctgacgg agtgcgagaa ggagcaccaa aaggcggtgg aggaagccta catcgatcct     1680
gagatcgcga agcagaagaa agacgaaggt aaccagtact tcaaggagga taagttcccc     1740
gaggccgtgg cagcgtacac ggaggccatc aagcgcaacc ctgccgagca cacctcctac     1800
agcaatcgcg cggccgcgta catcaagctt ggagccttca acgacgccct caaggacgcg     1860
gagaagtgca ttgagctgaa gcccgacttt gttaagggct acgcgcgcaa gggtcatgct     1920
tactttggga ccaagcagta caaccgcgcg ctgcaggcgt acaatgaggg cctcaaggtg     1980
gacccgagca atgcggactg caaggatggg cggtatcgca caatcatgaa gattcaggag     2040
atggcatctg gccaatccgc ggatggcgac gaggcggcgc gccgggccat ggacgatcct     2100
gaaatcgcgg caatcatgca agatagctac atgcaactag tgttgaagga gatgcagaac     2160
gatcccacgc gcattcagga gtacatgaag gactccggga tctcatcgaa gatcaacaag     2220
ctgatttcag ctggcatcat tcgttttggt caggaattca gcctgacgga cccggcggtg     2280
ctgggcgagg agactcacct gcgcgtccgc gtggtgccgg acaaggcgaa caagacgctg     2340
acggtggagg ataacggcat cggcatgacc aaggcggacc tcgtgaacaa tctgggcacg     2400
atcgcgcgct ccgcacgaa  ggcgttcatg gaggcactgg aggccggcgg cgacatgagc     2460
atgatcggcc agttcggtgt cggcttctac tccgcgtacc ttgtggcgga ccgcgtgacg     2520
gtggtgtcga gaacaactc  ggacgaggcg tacgtatggg agtcgtccgc gggcggcacg     2580
ttcaccatca cgagcgtgcc ggagtcggac atgaagcgcg gcacgcgcat cacgctgcac     2640
ctaaaggagg accagcagga gtacctggag gagcgccggg tgaaggagct gatcaagaag     2700
cactccgagt tcatcggcta cgacatcgag ctgatggtgg agaagacggc ggagaaggag     2760
```

```
gtgacggacg aggacgagga ggaggacgag tcgaagaaga agtcctgcgg ggacgagggc    2820
gagccgaagg tggaggaggt gacggagggc ggcgaggaca agaagaagaa gacgaagaag    2880
gtgaaggagg tgacgaagac gtacgaggtc cagaacaagc acaagccgct ctggacgcgc    2940
gacccgaagg acgtgacgaa ggaggagtac gcggccttct acaaggccat ctccaacgac    3000
tgggaggacc cggcggcgac gaagcacttc tcggtggagg gccagctgga gttccgcgcg    3060
atcgcgttcg tgccgaagcg cgcgccgttc gacatgttcg agccgaacaa gaagcgcaac    3120
aacatcaagc tgtacgtgcg ccgcgtgttc atcatggaca ctgcgaggga cctgtgcccg    3180
gactggctcg gcttcgtgaa gggcgtcgtg gacagcgagg acctgccgct gaacatctcg    3240
cgcgagaacc tgcagcagaa caagatcctg aaggtgatcc gcaagaacat cgtgaagaag    3300
tgcctggagc tgttcgaaga gatagcggag aacaaggagg actacaagca gttctacgag    3360
cagttcggca agaacatcaa gctgggcatc cacgaggaca cggcgaaccg caagaagctg    3420
atggagttgc tgcgcttcta cagcaccgag tcgggggagg agatgacgac actgaaggac    3480
tacgtgacgc gcatgaagcc ggagcagaag tcgatctact acatcactgg cgacagcaag    3540
aagaagctgg agtcgtcgcc gttcatcgag aaggcgagag gctgcgggct cgaggtgctg    3600
ttcatgacgg agccgatcga cgagtacgtg atgcagcagg tgaaggactt cgaggacaag    3660
aagttcgcgt gcctgacgaa ggaaggcgtg cacttcgagg agtccgagga ggagaagaag    3720
cagcgcgagg agaagaaggc ggcgtgcgag aagctgtgca agacgatgaa ggaggtgctg    3780
ggcgacaagg tggagaaggt gaccgtgtcg gagcgcctgt cgacgtcgcc gtgcatcctg    3840
gtgacgtcgg agtttgggtg gtcggcgcac atggaacaga tcatgcgcaa ccaggcgctg    3900
cgcgactcca gcatggcgca gtacatggtg tccaagaaga cgatggaggt gaaccccgac    3960
caccccatca tcaaggagct gcgccgccgc gtggaggcgg acgagaacga caaggccgtg    4020
aaggacctcg tcttcctgct cttcgacacg tcgctgctca cgtccggctt ccagctggat    4080
gacccccacg gctacgccga gcgcatcaac cgcatgatca agctcggcct gtcgctcgac    4140
gaggaggagg aggaggtcgc cgaggcgccg ccggccgagg cagcccccgc ggaggtcacc    4200
gccggcacct ccagcatgga gcaggtggac taa                                4233
```

<210> SEQ ID NO 100
<211> LENGTH: 4917
<212> TYPE: DNA
<213> ORGANISM: Artificial Sequence
<220> FEATURE:
<223> OTHER INFORMATION: DNA sequence encoding fusion (poly-protein)
      constructs comprising multiple Leishmania antigens

<400> SEQUENCE: 100

```
ccagtgtggt ggatgtcctg cggtaacgcc aagatcaact ctcccgcgcc gtccttcgag      60
gaggtggcgc tcatgcccaa cggcagcttc aagaagatca gcctctcctc ctacaagggc     120
aagtgggtcg tgctcttctt ctacccgctc gacttcacct tcgtgtgccc gacagaggtc     180
atcgcgttct ccgacagcgt gagtcgcttc aacgagctca actgcgaggt cctcgcgtgc     240
tcgatagaca gcgagtacgc gcacctgcag tggacgctgc aggaccgcaa gaagggcggc     300
ctcgggacca tggcgatccc aatgctagcc gacaagacca agagcatcgc tcgttcctac     360
ggcgtgctgg aggagagcca gggcgtggcc taccgcggtc tcttcatcat cgaccccat      420 ggcatgctgc gtcagatcac cgtcaatgac atgccggtgg ccgcagcgt ggaggaggtt      480 ctacgcctgc tggaggcttt tcagttcgtg gagaagcacg gcgaggtgtg ccccgcgaac     540
```

-continued

| | | | |
|---|---|---|---|
| tggaagaagg gcgccccac gatgaagccg gaaccgaatg cgtctgtcga gggatacttc | 600 |
| agcaagcagg gatccatgga cgcaactgag ctgaagaaca aggggaacga agagttctcc | 660 |
| gccggccgct atgtggaggc ggtgaactac ttctcaaagg cgatccagtt ggatgagcag | 720 |
| aacagtgtcc tctacagcaa ccgctccgcc tgttttgcag ccatgcagaa atacaaggac | 780 |
| gcgctggacg acgccgacaa gtgcatctcg atcaagccga attgggccaa gggctacgtg | 840 |
| cgccgaggag cagctctcca tggcatgcgc cgctacgacg atgccattgc cgcgtatgaa | 900 |
| aagggggctca aggtggaccc ttccaacagc ggctgcgcgc agggcgtgaa ggacgtgcag | 960 |
| gtagccaagg cccgcgaagc acgtgacccc atcgctcgcg tcttcacccc ggaggcgttc | 1020 |
| cgcaagatcc aagagaatcc caagctgtct ctacttatgc tgcagccgga ctacgtgaag | 1080 |
| atggtagaca ccgtcatccg cgacccttcg cagggccggc tgtacatgga agaccagcgc | 1140 |
| tttgccctga cgctcatgta cctgagcgga atgaagattc ccaacgatgg tgatggcgag | 1200 |
| gaggaggaac gtccgtctgc gaaggcggca gagacagcga agccaaaaga ggagaagcct | 1260 |
| ctcaccgaca acgagaagga ggccctggcg ctcaaggagg agggcaacaa gctgtacctc | 1320 |
| tcgaagaagt ttgaggaggc gctgaccaag taccaagagg cgcaggtgaa agaccccaac | 1380 |
| aacactttat acattctgaa cgtgtcggcc gtgtacttcg agcagggtga ctacgacaag | 1440 |
| tgcatcgccg agtgcgagca cggtatcgag cacggtcgcg agaaccactg cgactacaca | 1500 |
| atcattgcga agctcatgac ccggaacgcc ttgtgcctcc agaggcagag gaagtacgag | 1560 |
| gctgctatcg acctttacaa gcgcgccctt gtcgagtggc gtaaccctga caccctcaag | 1620 |
| aagctgacgg agtgcgagaa ggagcaccaa aaggcggtgg aggaagccta catcgatcct | 1680 |
| gagatcgcga agcagaagaa agacgaaggt aaccagtact tcaaggagga taagttcccc | 1740 |
| gaggccgtgg cagcgtacac ggaggccatc aagcgcaacc ctgccgagca cacctcctac | 1800 |
| agcaatcgcg cggccgcgta catcaagctt ggagccttca cgacgccct caaggacgcg | 1860 |
| gagaagtgca ttgagctgaa gcccgacttt gttaagggct acgcgcgcaa gggtcatgct | 1920 |
| tactttgga ccaagcagta caccgcgcg ctgcaggcgt acaatgaggg cctcaaggtg | 1980 |
| gacccgagca atgcggactg caaggatggg cggtatcgca caatcatgaa gattcaggag | 2040 |
| atggcatctg gccaatccgc ggatggcgac gaggcggcgc gccgggccat ggacgatcct | 2100 |
| gaaatcgcgg caatcatgca agatagctac atgcaactag tgttgaagga gatgcagaac | 2160 |
| gatcccacgc gcattcagga gtacatgaag gactccggga tctcatcgaa gatcaacaag | 2220 |
| ctgatttcag ctggcatcat tcgttttggt caggaattca gcctgacgga cccggcggtg | 2280 |
| ctgggcgagg agactcacct gcgcgtccgc gtggtgccgg acaaggcgaa caagacgctg | 2340 |
| acggtggagg ataacggcat cggcatgacc aaggcggacc tcgtgaacaa tctgggcacg | 2400 |
| atcgcgcgct ccggcacgaa ggcgttcatg gaggcactgg aggccggcgg cgacatgagc | 2460 |
| atgatcggcc agttcggtgt cggcttctac tccgcgtacc ttgtggcgga ccgcgtgacg | 2520 |
| gtggtgtcga gaacaactc ggacgaggcg tacgtatggg agtcgtccgc gggcggcacg | 2580 |
| ttcaccatca cgagcgtgcc ggagtcggac atgaagcgcg gcacgcgcat cacgctgcac | 2640 |
| ctaaaggagg accagcagga gtacctggag gagcgccggg tgaaggagct gatcaagaag | 2700 |
| cactccgagt tcatcggcta cgacatcgag ctgatggtgg agaagacggc ggagaaggag | 2760 |
| gtgacggacg aggacgagga ggaggacgag tcgaagaaga gtcctgcgg ggacgagggc | 2820 |
| gagccgaagg tggaggaggt gacggagggc ggcgaggaca agaagaagaa gacgaagaag | 2880 |
| gtgaaggagg tgacgaagac gtacgaggtc cagaacaagc acaagccgct ctggacgcgc | 2940 |

-continued

```
gacccgaagg acgtgacgaa ggaggagtac gcggccttct acaaggccat ctccaacgac    3000
tgggaggacc cggcggcgac gaagcacttc tcggtggagg ccagctgga gttccgcgcg    3060 atcgcgttcg tgccgaagcg cgcgccgttc gacatgttcg agccgaacaa gaagcgcaac    3120
aacatcaagc tgtacgtgcg ccgcgtgttc atcatggaca actgcgagga cctgtgcccg    3180
gactggctcg gcttcgtgaa gggcgtcgtg gacagcgagg acctgccgct gaacatctcg    3240
cgcgagaacc tgcagcagaa caagatcctg aaggtgatcc gcaagaacat cgtgaagaag    3300
tgcctggagc tgttcgaaga gatagcggag aacaaggagg actacaagca gttctacgag    3360
cagttcggca agaacatcaa gctgggcatc cacgaggaca cggcgaaccg caagaagctg    3420
atggagttgc tgcgcttcta cagcaccgag tcggggaggg agatgacgac actgaaggac    3480
tacgtgacgc gcatgaagcc ggagcagaag tcgatctact acatcactgg cgacagcaag    3540
aagaagctgg agtcgtcgcc gttcatcgag aaggcgagac gctgcgggct cgaggtgctg    3600
ttcatgacgg agccgatcga cgagtacgtg atgcagcagg tgaaggactt cgaggacaag    3660
aagttcgcgt gcctgacgaa ggaaggcgtg cacttcgagg agtccgagga ggagaagaag    3720
cagcgcgagg agaagaaggc ggcgtgcgag aagctgtgca agacgatgaa ggaggtgctg    3780
ggcgacaagg tggagaaggt gaccgtgtcg gagcgcctgt cgacgtcgcc gtgcatcctg    3840
gtgacgtcgg agtttgggtg gtcggcgcac atggaacaga tcatgcgcaa ccaggcgctg    3900
cgcgactcca gcatggcgca gtacatggtg tccaagaaga cgatggaggt gaaccccgac    3960 cacccccatca tcaaggagct gcgccgccgc gtggaggcgg acgagaacga caaggccgtg    4020
aaggacctcg tcttcctgct cttcgacacg tcgctgctca cgtccggctt ccagctggat    4080
gaccccaccg gctacgccga gcgcatcaac cgcatgatca agctcggcct gtcgctcgac    4140
gaggaggagg aggaggtcgc cgaggcgccc ccggccgagg cagcccccgc ggaggtcacc    4200
gccggcacct ccagcatgga gcaggtggac gatatcatgg cgcagaatga taagatcgcc    4260
ccccaggacc aggactcctt cctcgatgac cagcccggcg ttcgcccgat cccgtccttc    4320
gacgacatgc cgctgcacca gaacctgctg cgtggcatct actcgtacgg gttcgagaag    4380
ccgtccagca tccagcagcg cgcgatagcc cccttcacgc gcggcggcga catcatcgcg    4440
caggcccagt ccggtaccgg caagacgggt gccttctcca tcggtctgct gcagcgcctg    4500
gacttccgcc acaacctgat ccagggcctc gtgctctccc ccactcgcga gctggccctg    4560
cagacggcgg aggtgatcag ccgcatcggt gagttcctgt cgaacagctc caagttctgc    4620
gagacctttg tcggcggcac gcgcgtgcag gatgacctgc gcaagctgca ggccggcgtc    4680
atcgttgccg tgggcacgcc gggccgcgtg tccgacgtga tcaagcgtgg cgcgctgcgc    4740
acagagtcgc tgcgcgtgct ggtgctcgac gaggctgatg agatgctgtc tcagggcttc    4800
gcggaccaga tttacgagat cttccgcttc ctgccgaagg acatccaggt cgcgctcttc    4860
tccgccacga tgccggagga ggtactggag ctgacgaaga agttcatgcg cgactaa       4917
```

<210> SEQ ID NO 101
<211> LENGTH: 2735
<212> TYPE: DNA
<213> ORGANISM: Artificial Sequence
<220> FEATURE:
<223> OTHER INFORMATION: DNA sequence encoding fusion (poly-protein) constructs comprising multiple Leishmania antigens

<400> SEQUENCE: 101

```
catatgcacc accaccacca ccacatgtcc tgcggtaacg ccaagatcaa ctctcccgcg      60
```

-continued

```
ccgtccttcg aggaggtggc gctcatgccc aacggcagct tcaagaagat cagcctctcc    120
tcctacaagg gcaagtgggt cgtgctcttc ttctacccgc tcgacttcac cttcgtgtgc    180
ccgacagagg tcatcgcgtt ctccgacagc gtgagtcgct tcaacgagct caactgcgag    240
gtcctcgcgt gctcgataga cagcgagtac gcgcacctgc agtggacgct gcaggaccgc    300
aagaagggcg gcctcgggac catggcgatc ccaatgctag ccgacaagac caagagcatc    360
gctcgttcct acggcgtgct ggaggagagc cagggcgtgg cctaccgcgg tctcttcatc    420
atcgacccca tggcatgct gcgtcagatc accgtcaatg acatgccggt gggccgcagc    480
gtggaggagg ttctacgcct gctggaggct tttcagttcg tggagaagca cggcgaggtg    540
tgccccgcga actggaagaa gggcgccccc acgatgaagc cggaaccgaa tgcgtctgtc    600
gagggatact tcagcaagca gggatccatg gacgcaactg agctgaagaa caaggggaac    660
gaagagttct ccgccggccg ctatgtggag gcggtgaact acttctcaaa ggcgatccag    720
ttggatgagc agaacagtgt cctctacagc aaccgctccg cctgttttgc agccatgcag    780
aaatacaagg acgcgctgga cgacgccgac aagtgcatct cgatcaagcc gaattgggcc    840
aagggctacg tgcgccgagg agcagctctc catggcatgc gccgctacga cgatgccatt    900
gccgcgtatg aaaaggggct caaggtggac ccttccaaca gcggctgcgc gcagggcgtg    960
aaggacgtgc aggtagccaa ggcccgcgaa gcacgtgacc ccatcgctcg cgtcttcacc   1020
ccggaggcgt tccgcaagat ccaagagaat cccaagctgt ctctacttat gctgcagccg   1080
gactacgtga agatggtaga caccgtcatc cgcgaccctt cgcagggccg gctgtacatg   1140
gaagaccagc gctttgccct gacgctcatg tacctgagcg gaatgaagat tcccaacgat   1200
ggtgatggcg aggaggagga acgtccgtct gcgaaggcgg cagagacagc gaagccaaaa   1260
gaggagaagc ctctcaccga caacgagaag gaggccctgg cgctcaagga ggagggcaac   1320
aagctgtacc tctcgaagaa gtttgaggag gcgctgacca agtaccaaga ggcgcaggtg   1380
aaagacccca caacactttt atacattctg aacgtgtcgg ccgtgtactt cgagcagggt   1440
gactacgaca agtgcatcgc cgagtgcgag cacggtatcg agcacggtcg cgagaaccac   1500
tgcgactaca caatcattgc gaagctcatg acccggaacg ccttgtgcct ccagaggcag   1560
aggaagtacg aggctgctat cgacctttac aagcgcgccc ttgtcgagtg gcgtaaccct   1620
gacaccctca gaagctgac ggagtgcgag aaggagcacc aaaaggcggt ggaggaagcc   1680
tacatcgatc ctgagatcgc gaagcagaag aaagacgaag gtaaccagta cttcaaggag   1740
gataagttcc ccgaggccgt ggcagcgtac acggaggcca tcaagcgcaa ccctgccgag   1800
cacacctcct acagcaatcg cgcggccgcg tacatcaagc ttggagcctt caacgacgcc   1860
ctcaaggacg cggagaagtg cattgagctg aagcccgact tgttaaggg ctacgcgcgc   1920 aagggtcatg cttacttttg gaccaagcag tacaaccgcg cgctgcaggc gtacaatgag   1980
ggcctcaagg tggacccgag caatgcggac tgcaaggatg gcggtatcg cacaatcatg   2040 aagattcagg agatggcatc tggccaatcc gcggatggcg acgaggcggc gcgccgggcc   2100
atggacgatc ctgaaatcgc ggcaatcatg caagatagct acatgcaact agtgttgaag   2160
gagatgcaga acgatccac gcgcattcag gagtacatga aggactccgg gatctcatcg   2220
aagatcaaca agctgatttc agctggcatc attcgttttg gtcaggaatt ctgcagatat   2280
ccatcacact ggcggccgct cgagcagatc cggctgctaa caaagcccga aggaagctg   2340 agttggctgc tgccaccgct gagcaataac tagcataacc ccttggggcc tctaaacggg   2400
```

-continued

```
tcttgagggg ttttttgctg aaaggaggaa ctatatccgg ataattcttg aagacgaaag    2460
ggcctcgtga tacgcctatt tttataggtt aatgtcatga taataatggt ttcttagacg    2520
tcaggtggca cttttcgggg aaatgtgcgc ggaaccccta tttggttatt tttctaaata    2580
cattcaaata tgtatccgct catgagacaa taacccytga taaatgcttc aataatattg    2640
aaaaaaggaa gaatatgaag tatttcaaca tttcccgggt ccccttatt ccctttttt     2700 gccgccattt tgcctttctg tttttggttc accca                               2735
```

LEISHMANIA ANTIGENS FOR USE IN THE THERAPY AND DIAGNOSIS OF LEISHMANIASIS

REFERENCE TO RELATED APPLICATIONS

This application is a continuation-in-part of U.S. patent application Ser. No. 09/183,861, filed Oct. 30, 1998, U.S. Pat. No. 6,365,165 which is a continuation in part of U.S. patent application Ser. No. 09/022,765, filed Feb. 12, 1998, U.S. Pat. No. 6,375,955 which is a continuation-in-part of U.S. patent application Ser. No. 08/920,609, filed Aug. 27, 1997, which is a continuation-in-part of U.S. patent application Ser. No. 08/798,841, filed Feb. 12, 1997, which is a continuation-in-part of U.S. patent application Ser. No. 08/533,669, filed Sep. 22, 1995, now U.S. Pat. No. 5,834,592.

TECHNICAL FIELD

The present invention relates generally to compositions and methods for preventing, treating and detecting leishmaniasis, and for stimulating immune responses in patients. The invention is more particularly related to polypeptides comprising an immunogenic portion of a Leishmania antigen or a variant thereof, and to vaccines and pharmaceutical compositions comprising one or more such polypeptides. The vaccines and pharmaceutical compositions may be used, for example, for the prevention and therapy of leishmaniasis, as well as for the detection of Leishmania infection.

BACKGROUND OF THE INVENTION

Leishmania organisms are intracellular protozoan parasites of macrophages that cause a wide range of clinical diseases in humans and domestic animals, primarily dogs. In some infections, the parasite may lie dormant for many years. In other cases, the host may develop one of a variety of forms of leishmaniasis. For example, the disease may be asymptomatic or may be manifested as subclinical visceral leishmaniasis, which is characterized by mild symptoms of malaise, diarrhea and intermittent hepatomegaly. Patients with subclinical or asymptomatic disease usually have low antibody titers, making Patients with subclinical or asymptomatic disease usually have low antibody titers, making the disease difficult to detect with standard techniques. Alternatively, leishmaniasis may be manifested as a cutaneous disease, which is a severe medical problem but is generally self-limiting, or as a highly destructive mucosal disease, which is not self-limiting. Finally, and most seriously, the disease may be manifested as an acute visceral infection involving the spleen, liver and lymph nodes, which, untreated, is generally a fatal disease. Symptoms of acute visceral leishmaniasis include hepatosplenomegaly, fever, leukopenia, anemia and hypergammaglobulinemia.

Leishmaniasis is a serious problem in much of the world, including Brazil, China, East Africa, India and areas of the Middle East. The disease is also endemic in the Mediterranean region, including southern France, Italy, Greece, Spain, Portugal and North Africa. The number of cases of leishmaniasis has increased dramatically in the last 20 years, and millions of cases of this disease now exist worldwide. About 2 million new cases are diagnosed each year, 25% of which are visceral leishmaniasis. There are, however, no vaccines or effective treatments currently available.

Accurate diagnosis of leishmaniasis is frequently difficult to achieve. There are 20 species of Leishmania that infect humans, including *L. donovani, L. chagasi, L. infantum, L. major, L. amazonensis, L. braziliensis, L. panamensis, L. mexicana, L. tropica,* and *L. guyanensis,* and there are no distinctive signs or symptoms that unambiguously indicate the presence of Leishmania infection. Parasite detection methods have been used, but such methods are neither sensitive nor clinically practical. Current skin tests typically use whole or lysed parasites. Such tests are generally insensitive, irreproducible and prone to cross-reaction with a variety of other diseases. In addition, the preparations employed in such tests are often unstable. Thus, there is a need for improved methods for the detection of Leishmania infection.

Current experimental vaccines consisting of whole organisms have not proven effective in humans. Accordingly, there remains a need in the art for vaccines to prevent leishmaniasis in humans and dogs, and for improved therapeutic compositions for the treatment of leishmaniasis.

SUMMARY OF THE INVENTION

Briefly stated, the present invention provides compositions and methods for preventing, treating and detecting leishmaniasis, as well as for stimulating immune responses in patients. In one aspect, polypeptides are provided which comprise at least an immunogenic portion of a Leishmania antigen, or a variant of such an antigen that differs only in conservative substitutions and/or modifications. In specific embodiments of the invention, the Leishmania antigen comprises an amino acid sequence selected from the group consisting of SEQ ID NO: 2, 4, 20, 22, 24, 26, 36–38, 41, 50–53 and 82. DNA sequences encoding the above polypeptides, recombinant expression vectors comprising these DNA sequences and host cells transformed or transfected with such expression vectors are also provided.

In further aspects, the present invention provides fusion proteins comprising Leishmania antigens, together with polynucleotides encoding such fusion proteins. In certain specific embodiments, such fusion proteins comprise an amino acid sequence selected from the group consisting of SEQ ID NO: 95, 96 and 97.

In related aspects, the present invention provides pharmaceutical compositions which comprise one or more of the polypeptides and/or fusion proteins described herein, or a polynucleotide encoding such polypeptides and fusion proteins, and a physiologically acceptable carrier. Vaccines which comprise one or more such polypeptides, fusion proteins or polynucleotides, together with an immunostimulant are also provided. In specific embodiments of these aspects, the Leishmania antigen has an amino acid sequence selected from the group consisting of SEQ ID NO: 2, 4, 20, 22, 24, 26, 36–38, 41, 50–53 and 82.

In still further related embodiments, the pharmaceutical compositions and vaccines comprise at least two different polypeptides, each polypeptide comprising an immunogenic portion of a Leishmania antigen having an amino acid sequence selected from the group consisting of sequences recited in SEQ ID NO: 2, 4, 6, 8, 10, 20, 22, 24, 26, 36–38, 41, 50–53, 82, and variants thereof that differ only in conservative substitutions and/or modifications. In other embodiments, the inventive pharmaceutical compositions comprise one or more of the inventive polypeptides in combination with a known Leishmania antigen.

In yet other related embodiments, the pharmaceutical compositions and vaccines comprise soluble Leishmania antigens.

In another aspect, the present invention provides methods for inducing protective immunity against leishmaniasis in a patient, comprising administering to a patient a pharmaceutical composition or vaccine as described above.

In further aspects, methods and diagnostic kits are provided for detecting Leishmania infection in a patient. The methods comprise: (a) contacting dermal cells of a patient with a pharmaceutical composition as described above; and (b) detecting an immune response on the patient's skin, therefrom detecting Leishmania infection in the patient. The diagnostic kits comprise: (a) a pharmaceutical composition as described above; and (b) an apparatus sufficient to contact the pharmaceutical composition with the dermal cells of a patient.

In further aspects, the present invention provides methods for stimulating a cellular and/or humoral immune response in a patient, comprising administering to a patient a pharmaceutical composition or vaccine as described above.

In a related aspect, methods are provided for treating a patient afflicted with a disease responsive to IL-12 stimulation, comprising administering to a patient a pharmaceutical composition or vaccine as described above.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIG. 2 illustrates representative HPLC profiles of peptides isolated from MHC class II molecules of P388D1 macrophages. Panel A shows peptides isolated from uninfected macrophages and panel B shows peptides isolated from L. donovani infected macrophages. The arrows in panel B indicate peptide peaks present only in the infected macrophage preparation.

T-cells ($10^5$/well) were purified from lymph nodes of BALB/c mice immunized in the foot pad with L. donovani promastigotes in CFA and were cultured with various concentrations of the purified recombinant Ldp23 in the presence of $2\times10^5$ Mitomycin C-treated normal BALB/c spleen mononuclear cells. Proliferation of T-cells was measured at 27 hours of culture. Values are expressed as cpm and represent the mean of [$^3H$]TdR incorporation of triplicate cultures.

FIG. 8 illustrates Ldp23-induced cytokine production by lymph node cells of BALB/c mice. Cultures were incubated with varying amounts of Ldp23 or Leishmania lysate, presented as μg/mL, and were assayed by ELISA for the production of interferon-γ (panel A) or interleukin-4 (panel B), both of which are shown as ng/mL.

Figure 9A:
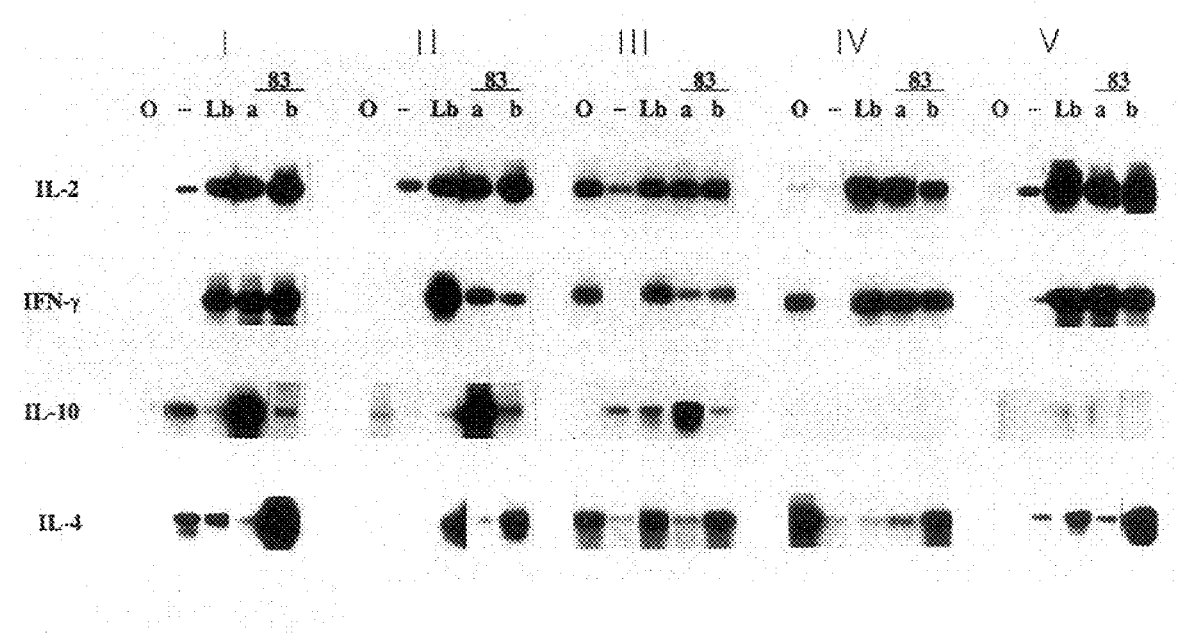
Figure 9B:
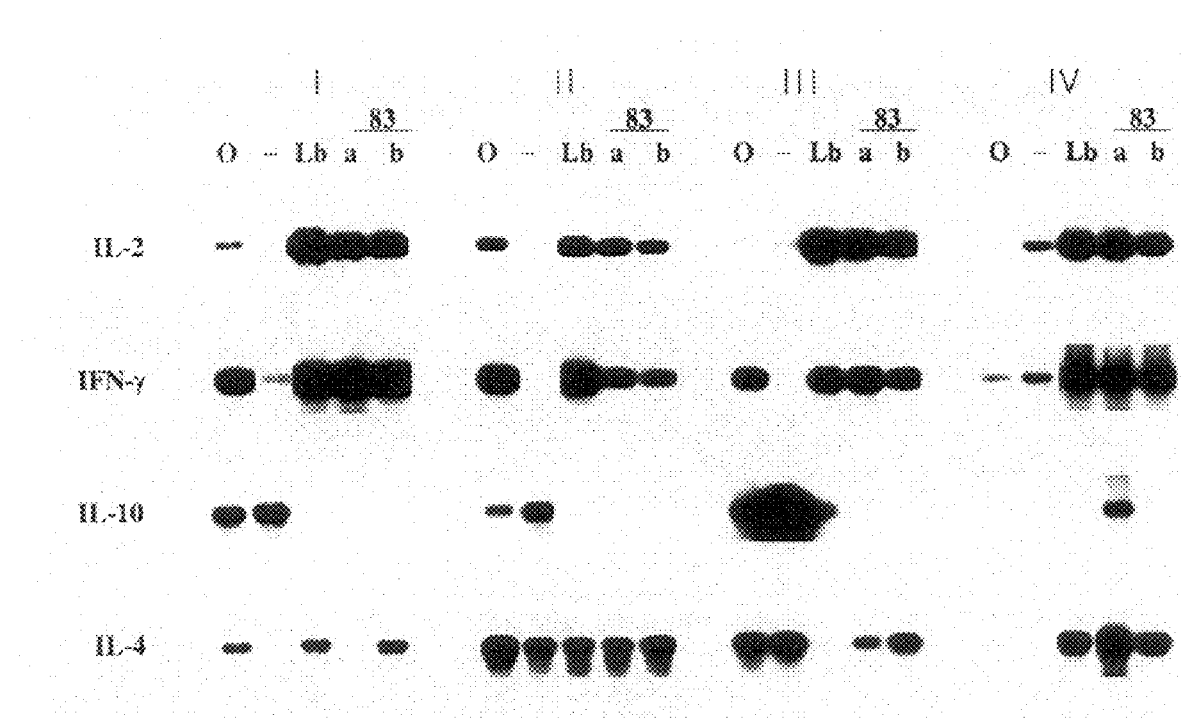

FIG. 9 shows the PCR amplification of cytokine mRNAs isolated from mucosal leishmaniasis (Panel A) and cutaneous leishmaniasis (panel B) patient PBMC before and after stimulation with representative polypeptides of the present invention. Lanes O and—indicate the level of PCR products at the initiation of culture and after 72 hours of culture, respectively, in the absence of added polypeptide; lanes Lb, 83a and 83b indicate the level of PCR products following culturing of PBMC with L. braziliensis lysate, and the Leishmania antigens Lbhsp83a and Lbhsp83b, respectively.

FIG. 10 presents a comparison of the levels of interferon-γ (panel A) and TNF-α (panel B) in the supernatants of 72 hour PBMC cultures from Leishmania-infected and control individuals in response to stimulation with parasite lysate or the indicated polypeptides.

Figure 11:
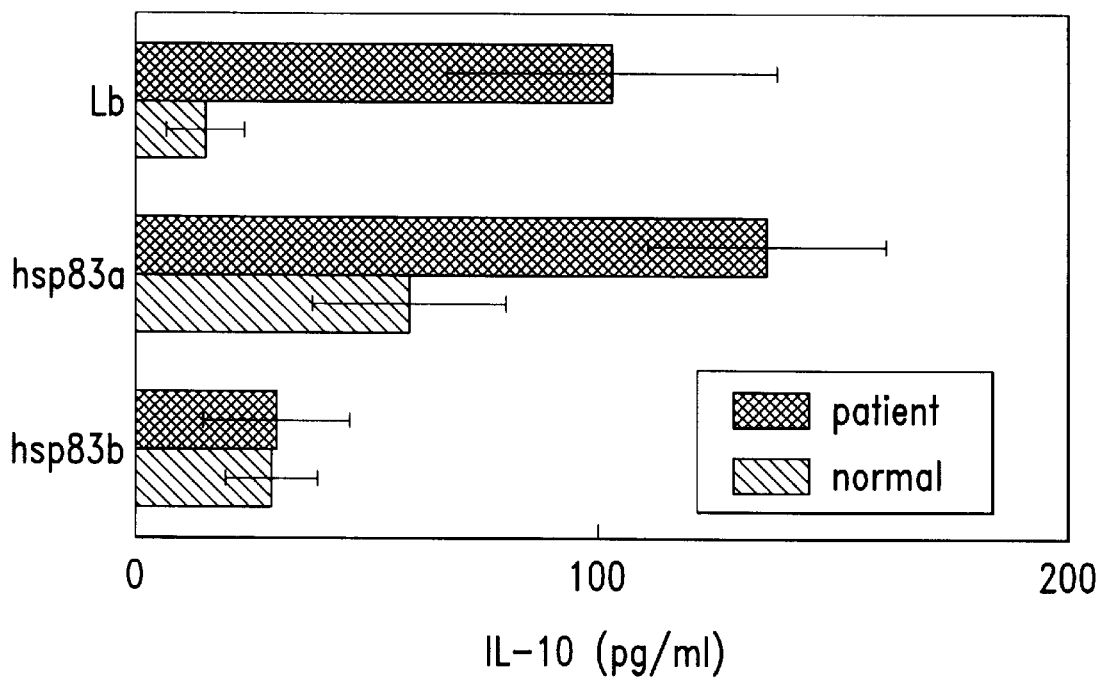

FIG. 11 illustrates the levels of IL-10p40 (in pg/mL) in the supernatant of PBMC cultures from L. braziliensis-infected individuals and uninfected controls 72 hours following stimulation with parasite promastigote lysate (Lb), Lbhsp83a or Lbhsp83b.

Figure 12:
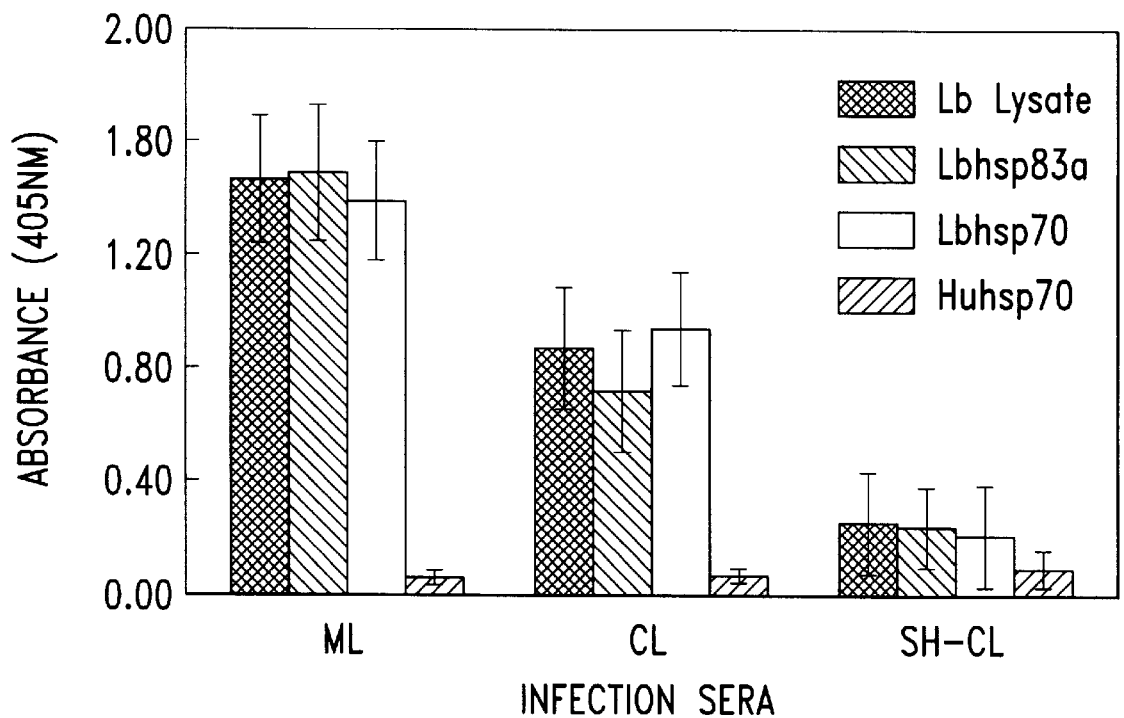

FIG. 12 presents the reactivities of sera from L. braziliensis infected-patients with representative polypeptides of the present invention in a standard ELISA. Values are expressed as absorbance at 405 nm.

Figure 13A:
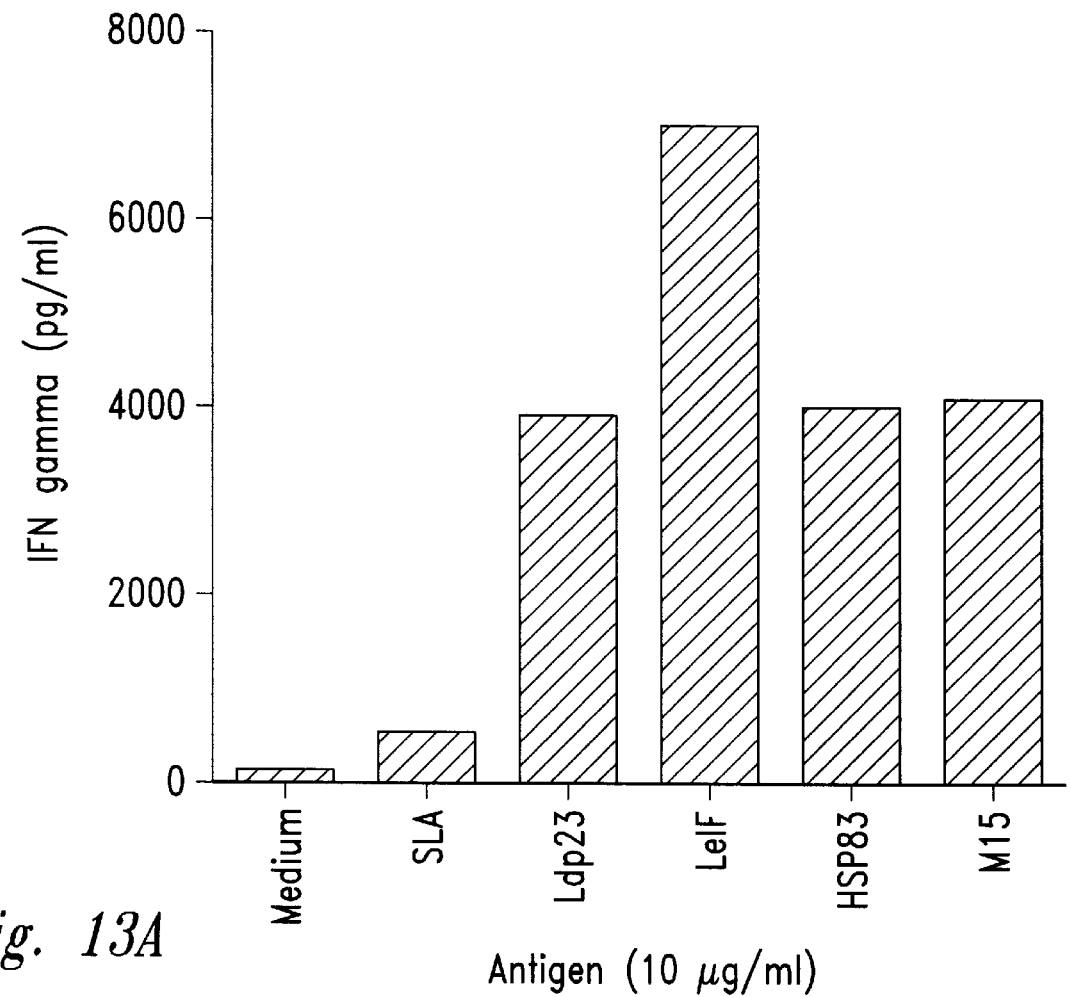
Figure 13B:
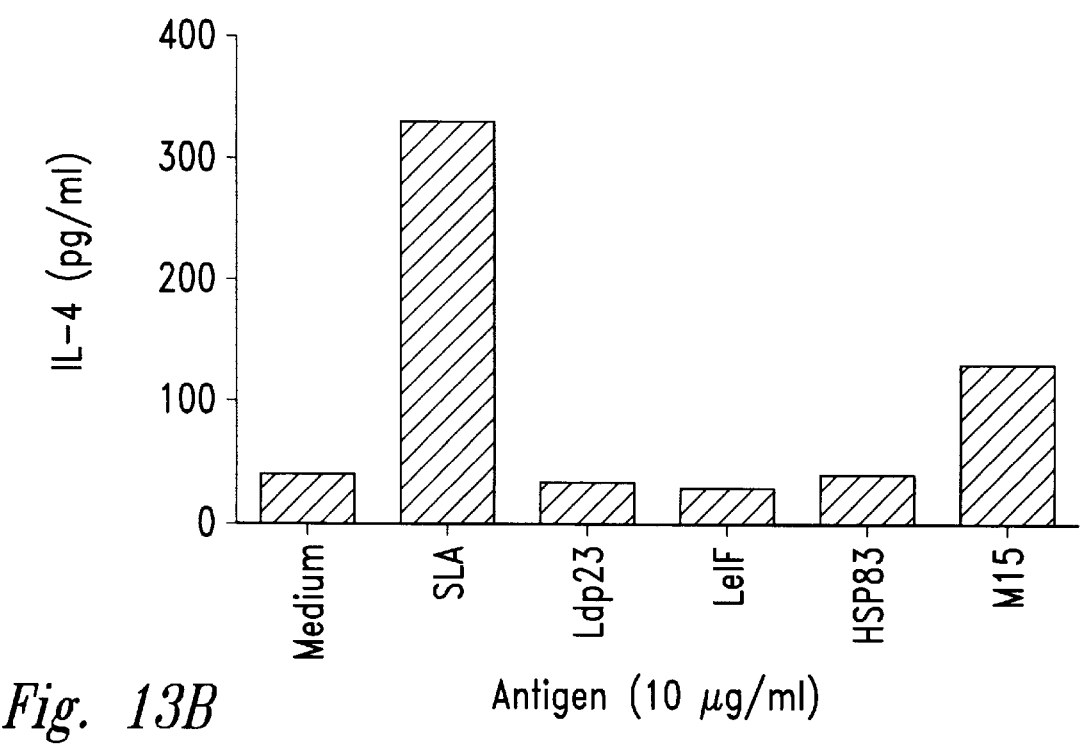

FIGS. 13A and 13B illustrate the level of secreted IL-4 and IFN-γ (in pg/mL) stimulated in mouse lymph node cultures by the addition of representative polypeptides of the present invention.

Figure 14:
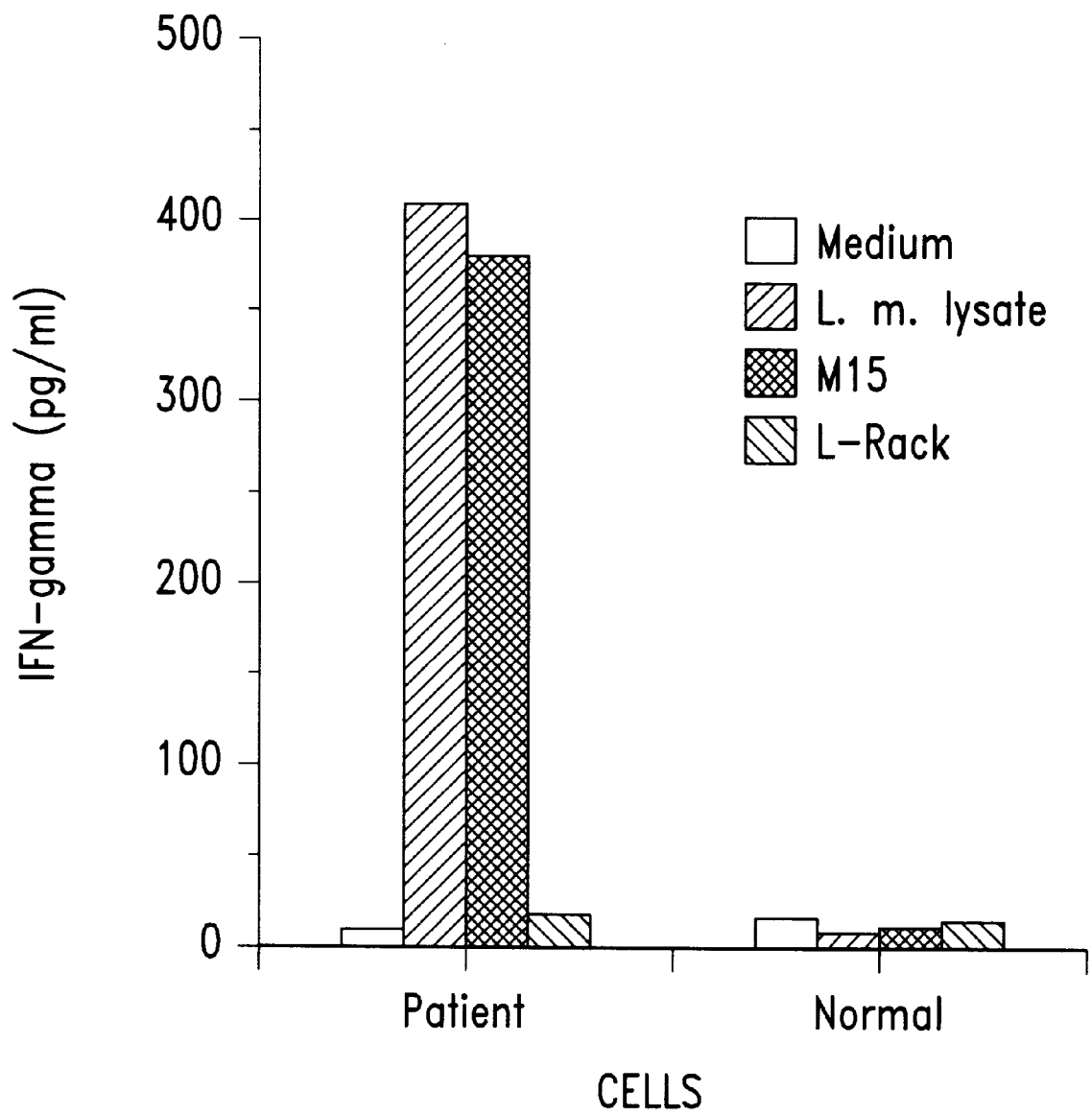

FIG. 14 shows the level of IFN-γ (in pg/mL) secreted by Leishmania-infected and uninfected human PBMC stimulated by the Leishmania antigen M15, as compared to the levels stimulated by L. major lysate and L-Rack, an antigen that does not appear to be recognized by Leishmania-infected humans.

Figure 15:
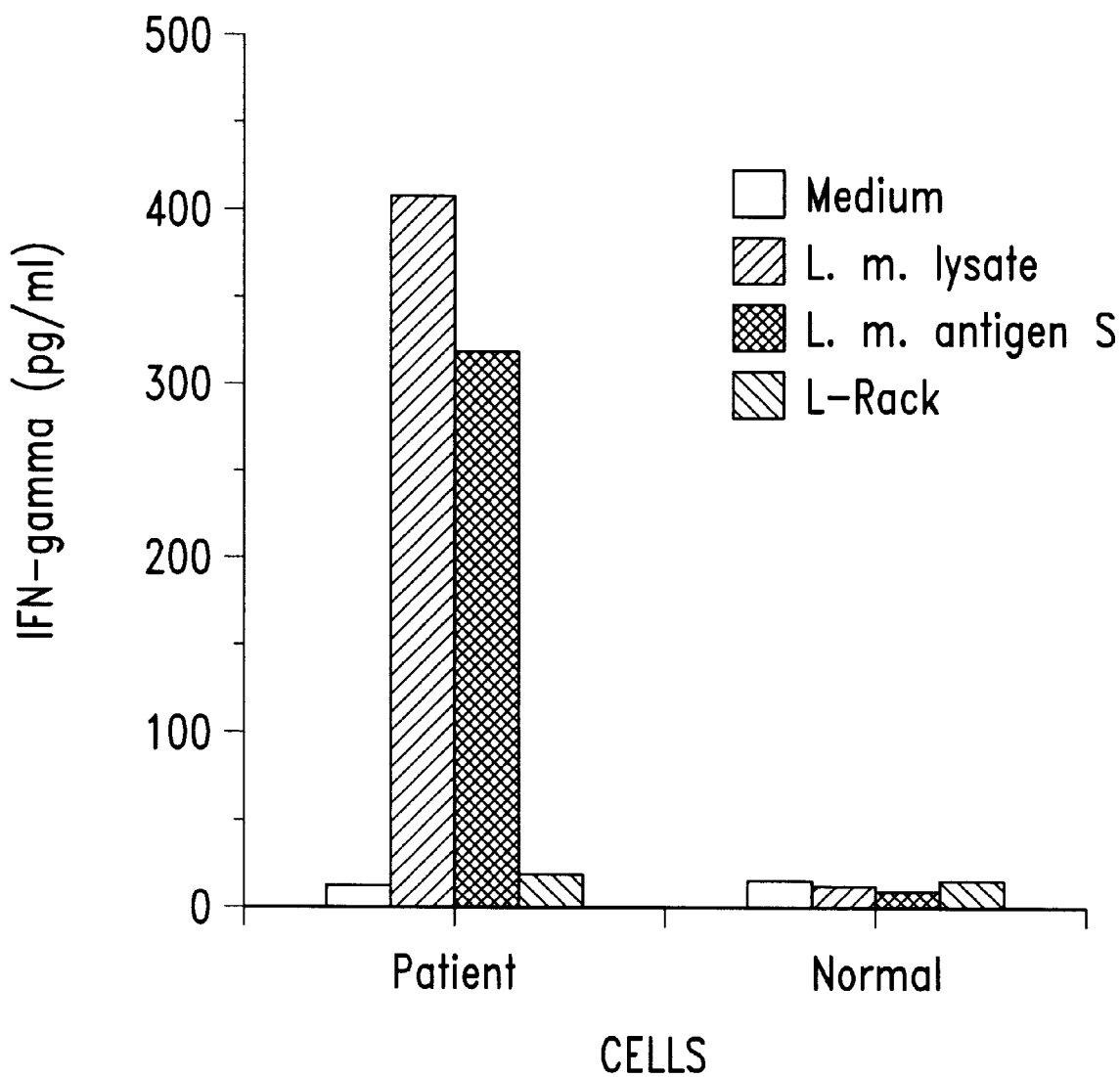

FIG. 15 shows the level of IFN-γ (in pg/mL) secreted by infected and uninfected human PBMC stimulated by soluble Leishmania antigens (S antigens), as compared to the levels stimulated by L. major lysate and L-Rack.

Figure 16:
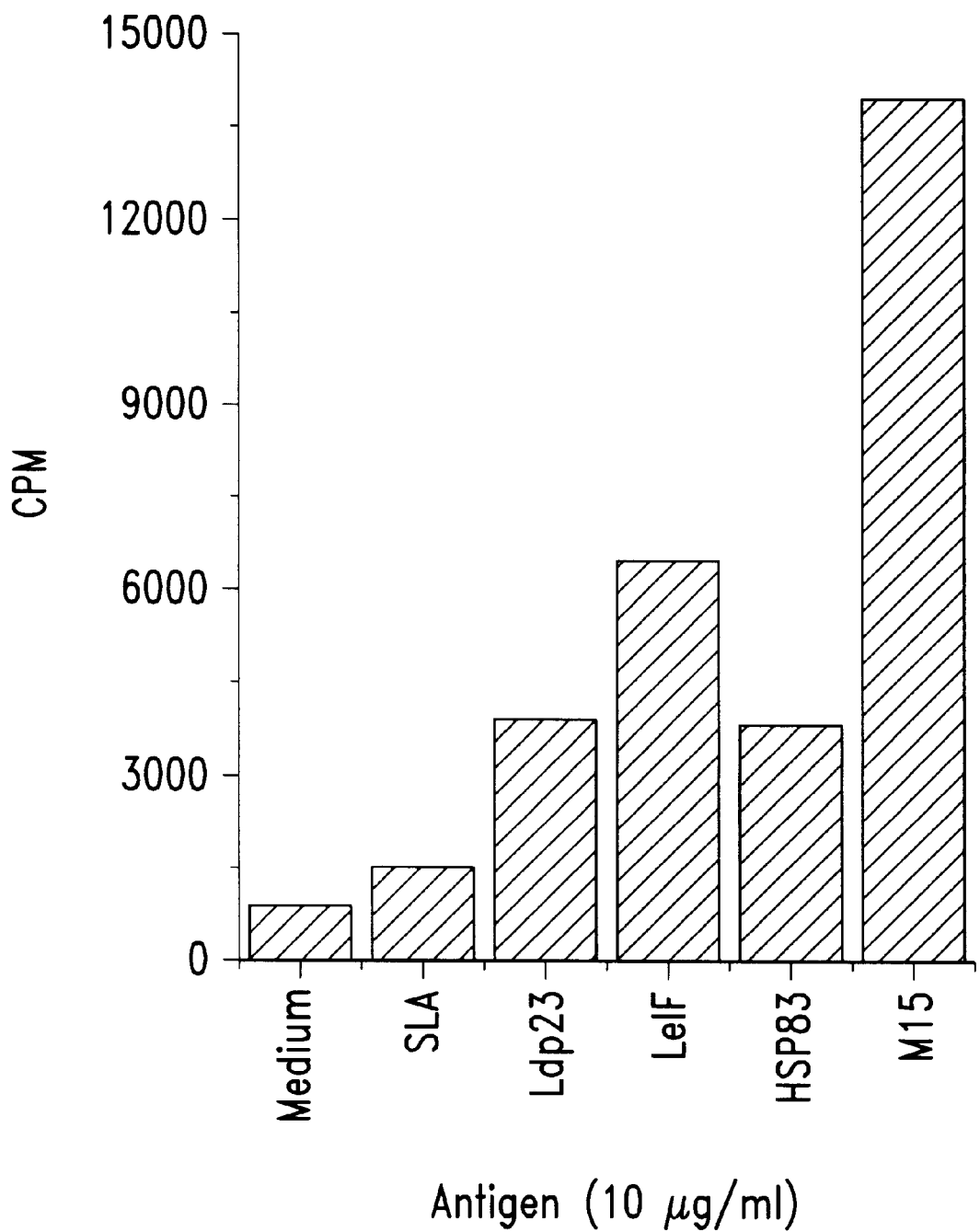

FIG. 16 illustrates the proliferation of murine lymph node cultures stimulated by the addition of representative polypeptides of the present invention. Values are expressed as cpm.

Figure 17:
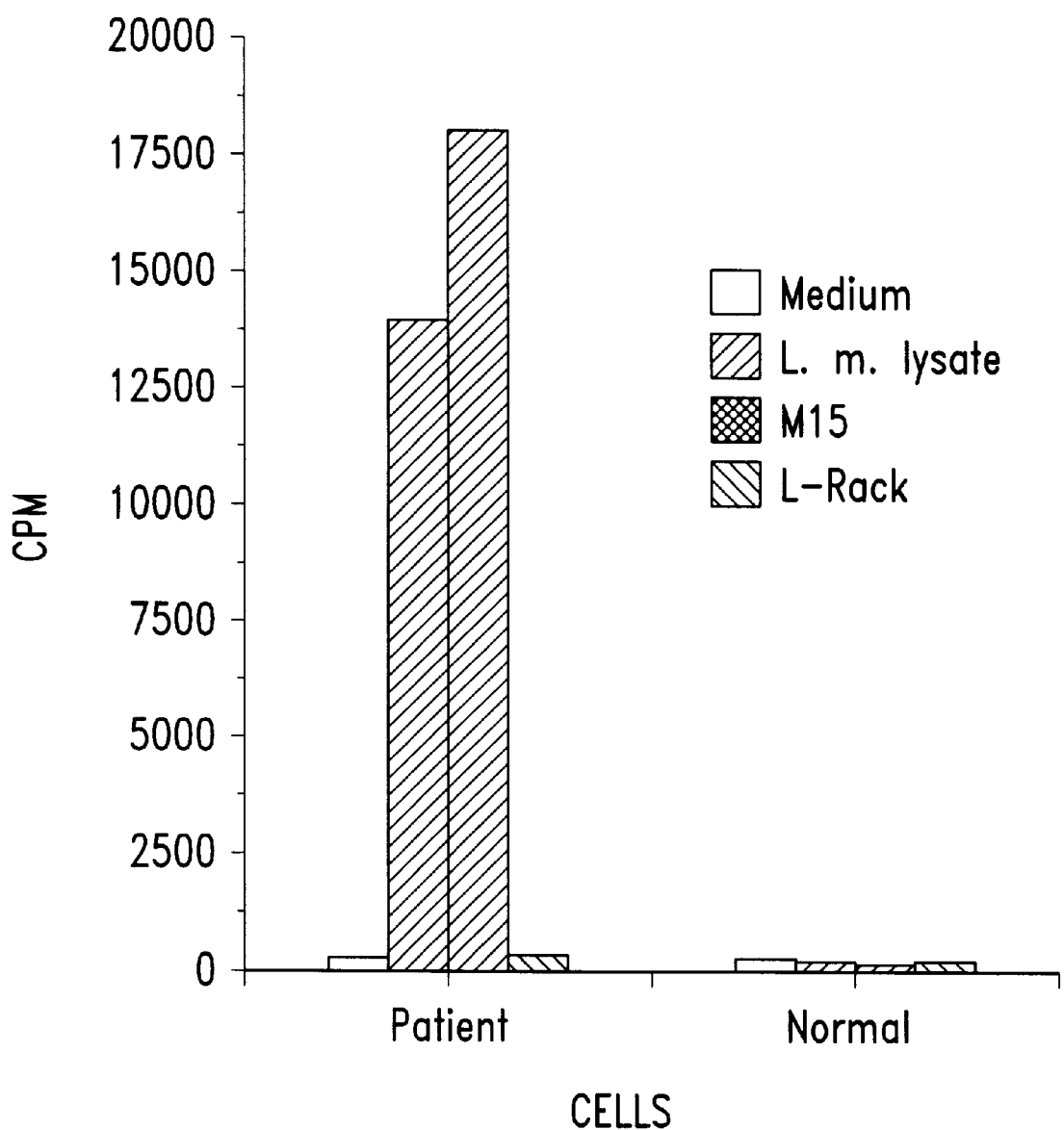

FIG. 17 shows the proliferation of human PBMC, prepared from Leishmania-immune and uninfected individuals, stimulated by M15 as compared to the proliferation stimulated by L. major lysate and L-Rack. Values are expressed as cpm.

Figure 18:
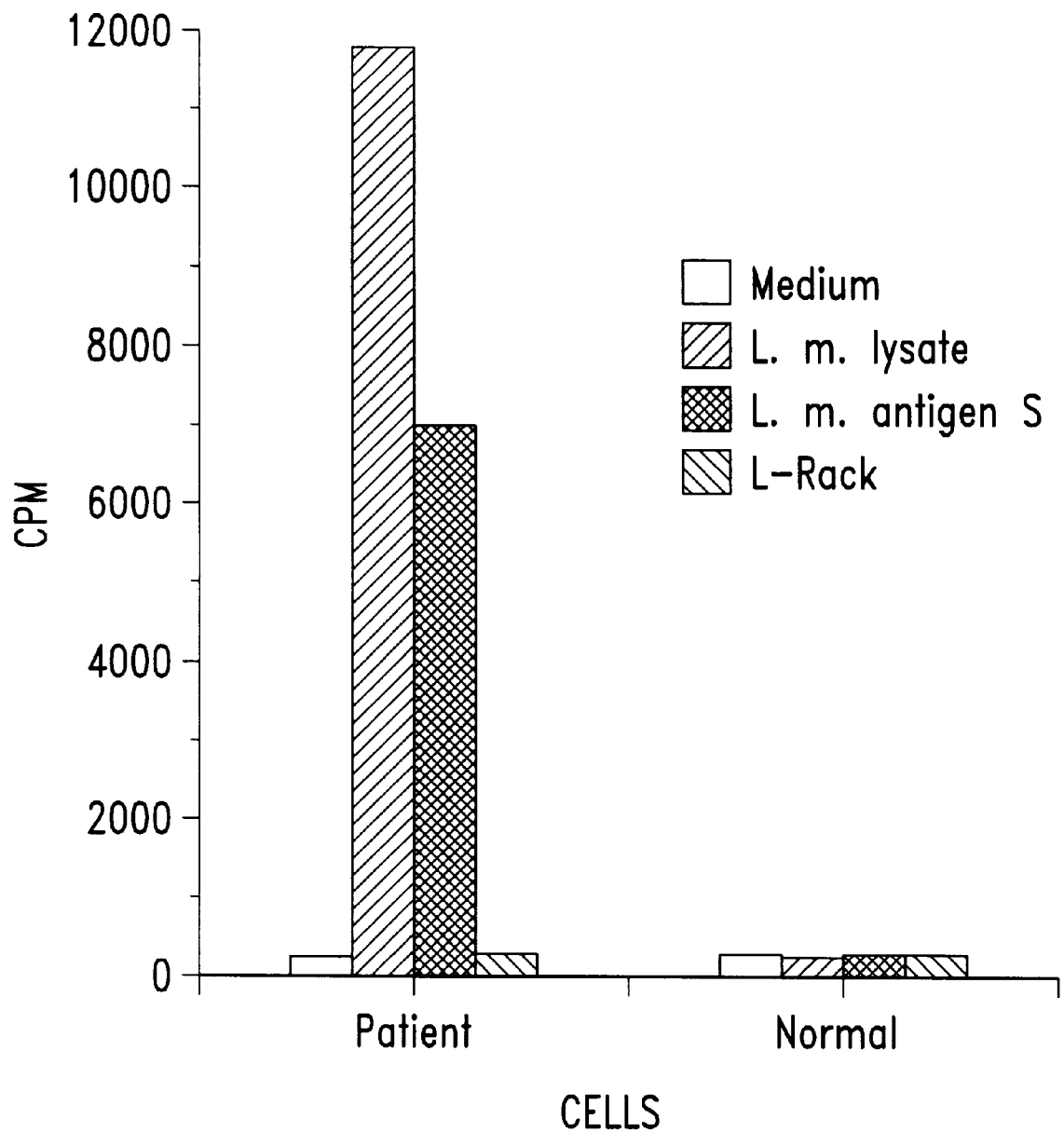

FIG. 18 illustrates the proliferation of human PBMC, prepared from Leishmania-infected and uninfected individuals, stimulated by soluble Leishmania antigens as compared to the proliferation stimulated by culture medium, L. major lysate and L-Rack. Values are expressed as cpm.

FIG. 19 presents a comparison of a Lbhsp83 sequence (SEQ ID NO:6) with homologous sequences from L. amazonensis (Lahsp83) (SEQ ID NO:16), T. cruzi (Tchsp83) (SEQ ID NO:17) and humans (Huhsp89) (SEQ ID NO:18).

Figure 20:
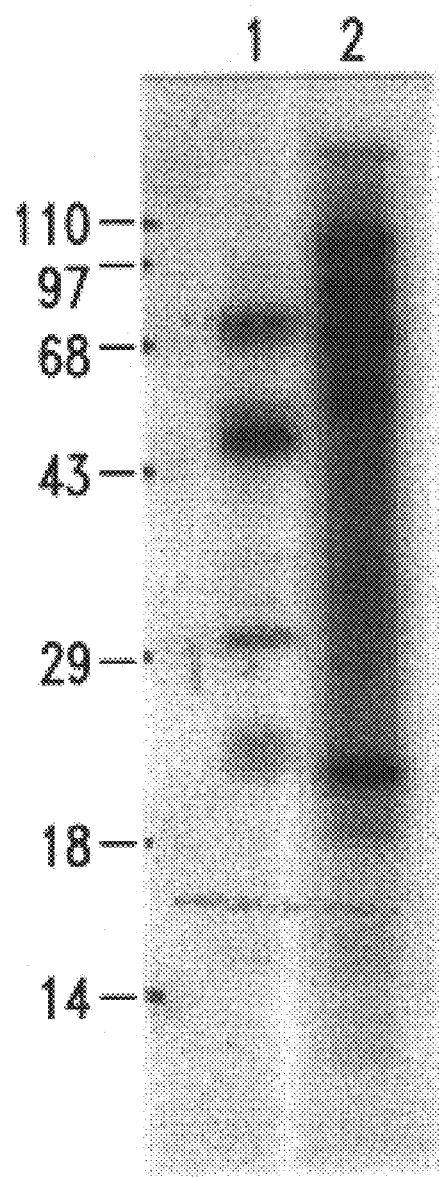

FIG. 20 illustrates the reactivity of rabbit sera raised against soluble Leishmania antigens with Leishmania promastigote lysate (lane 1) and soluble Leishmania antigens (lane 2).

FIG. 21 shows the cDNA and predicted amino acid sequence for the Leishmania antigen Lmsp1a.

Figure 22:
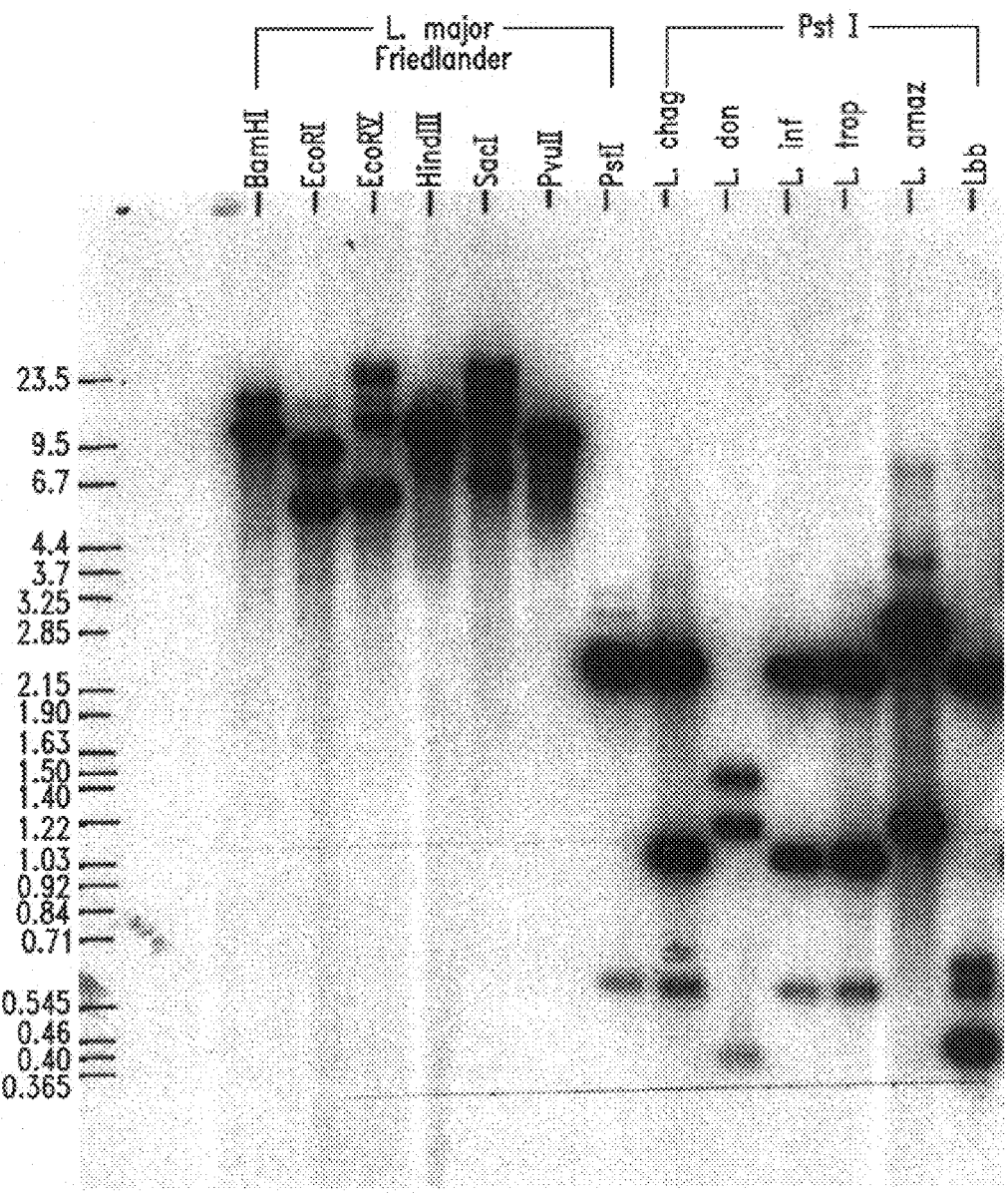

FIG. 22 shows a Southern blot of genomic DNA from L. major digested with a panel of restriction enzymes (lanes 1 to 7) and six other Leishmania species digested with PstI (lanes 8 to 13) probed with the full-length cDNA insert of Lmsp1a.

Figure 23:
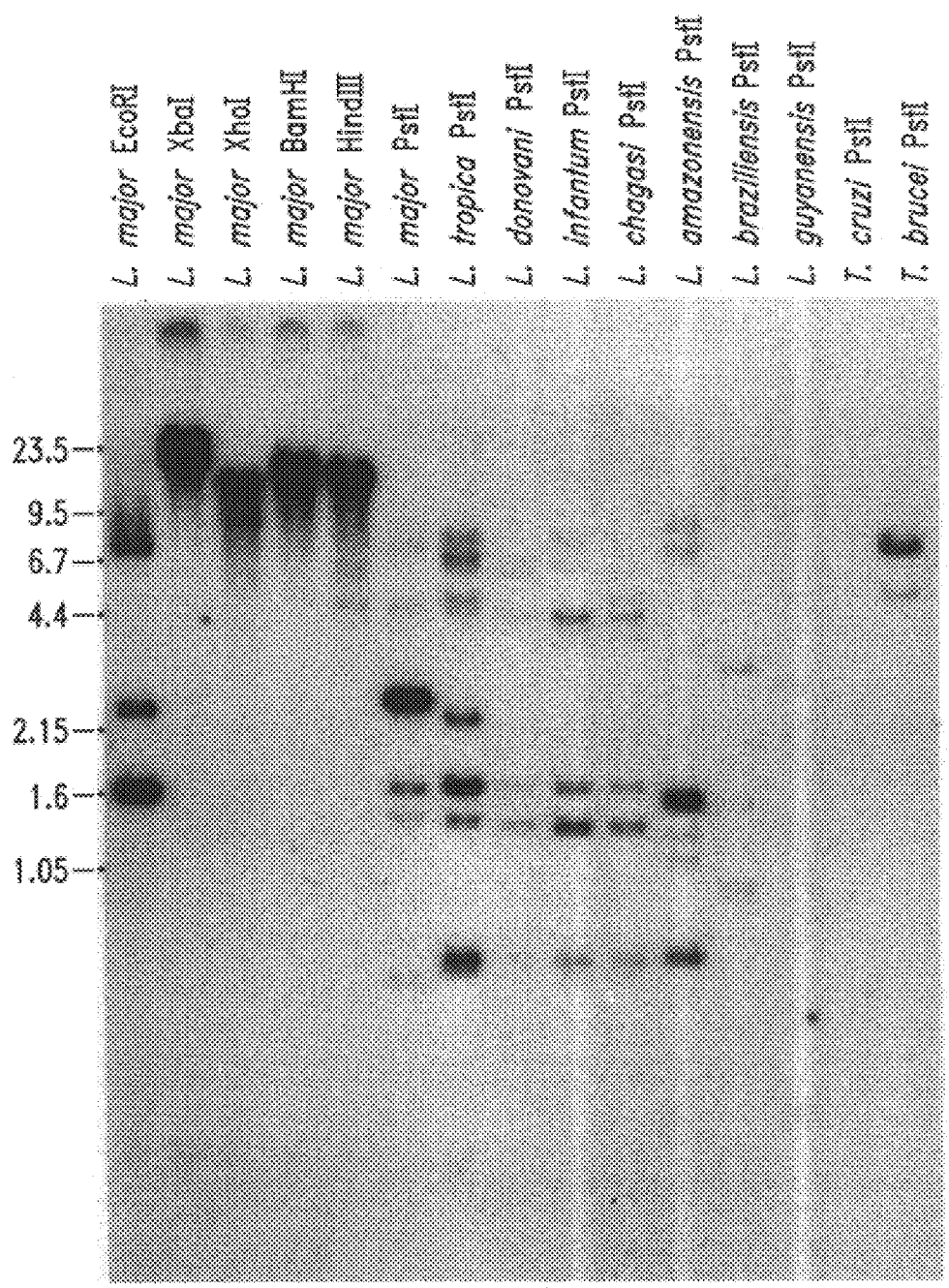

FIG. 23 shows a Southern blot of genomic DNA from L. major digested with a panel of restriction enzymes, six other Leishmania species digested with PstI and the infectious pathogens T. cruzi and T. brucei, probed with the full-length cDNA insert of the Leishmania antigen MAPS-1A.

Figure 24:
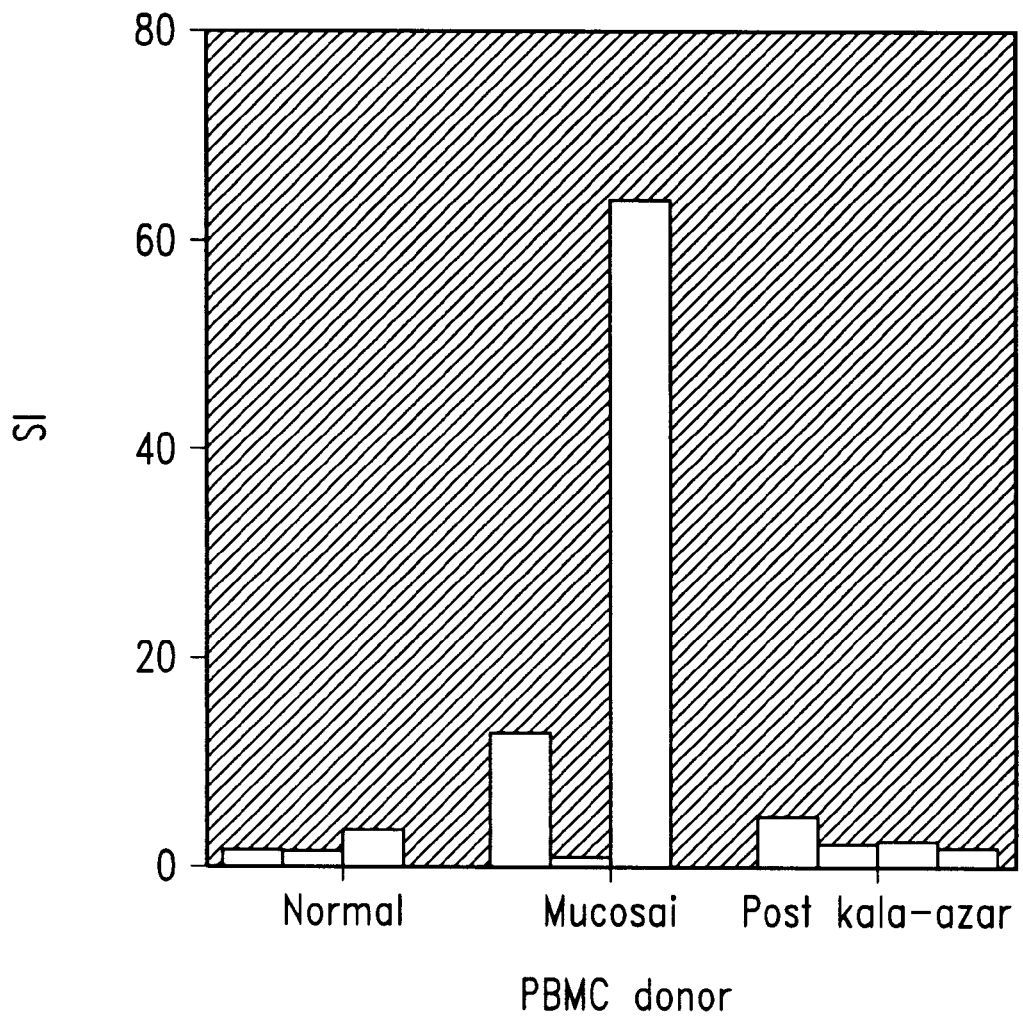

FIG. 24 illustrates the proliferation of PBMC isolated from uninfected-individuals, patients with active mucosal leishmaniasis and patients post kala-azar infection, stimulated by MAPS-1A.

Figure 25:
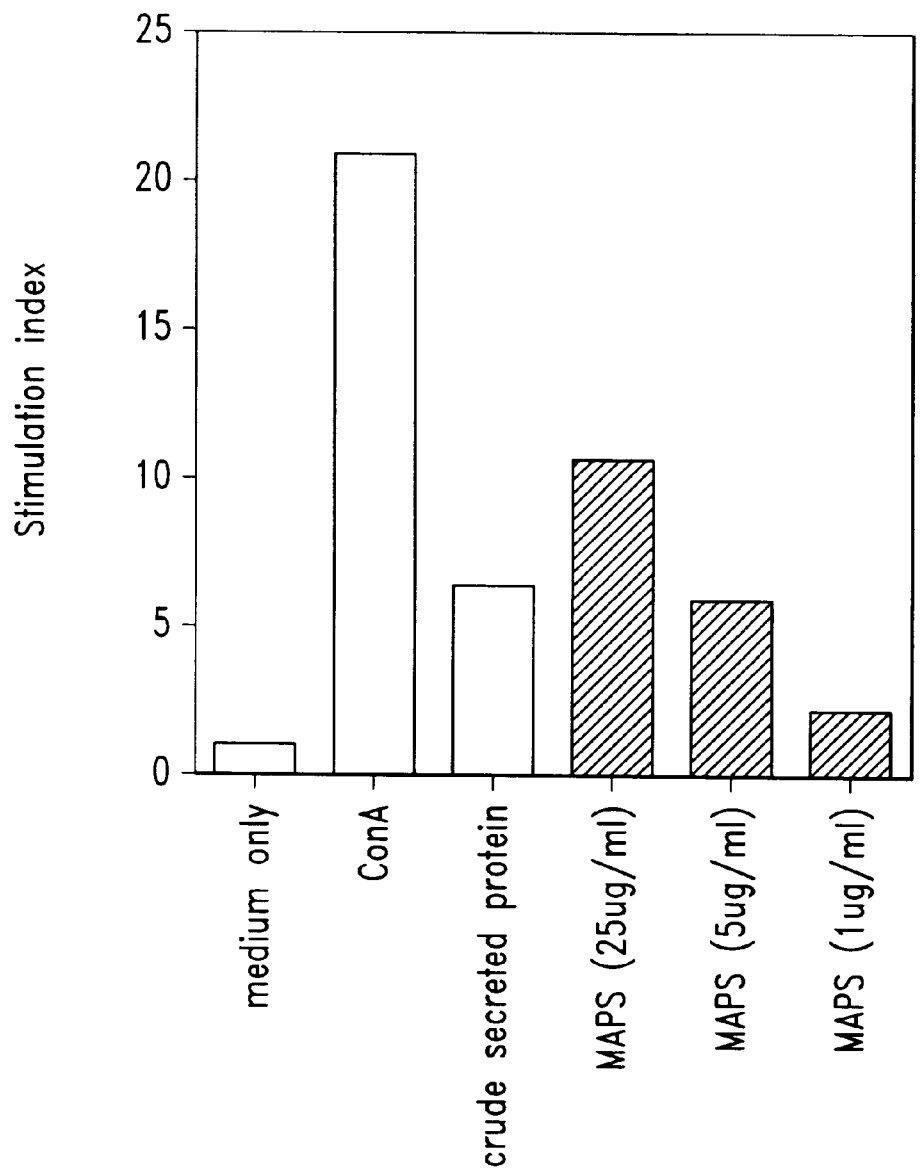

FIG. 25 illustrates the proliferation of murine lymph node cultures stimulated by MAPS-1A.

Figure 26:
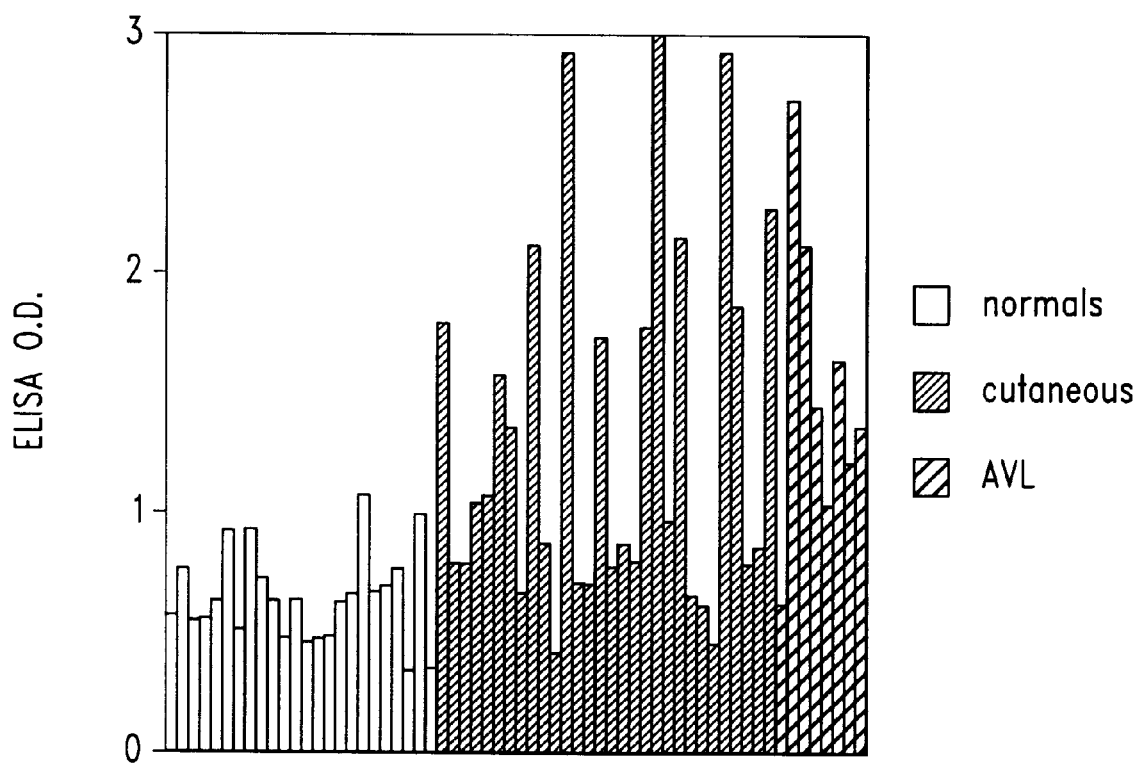

FIG. 26 illustrates the reactivity of MAPS-1A with sera from human leishmaniasis patients.

Figure 27:
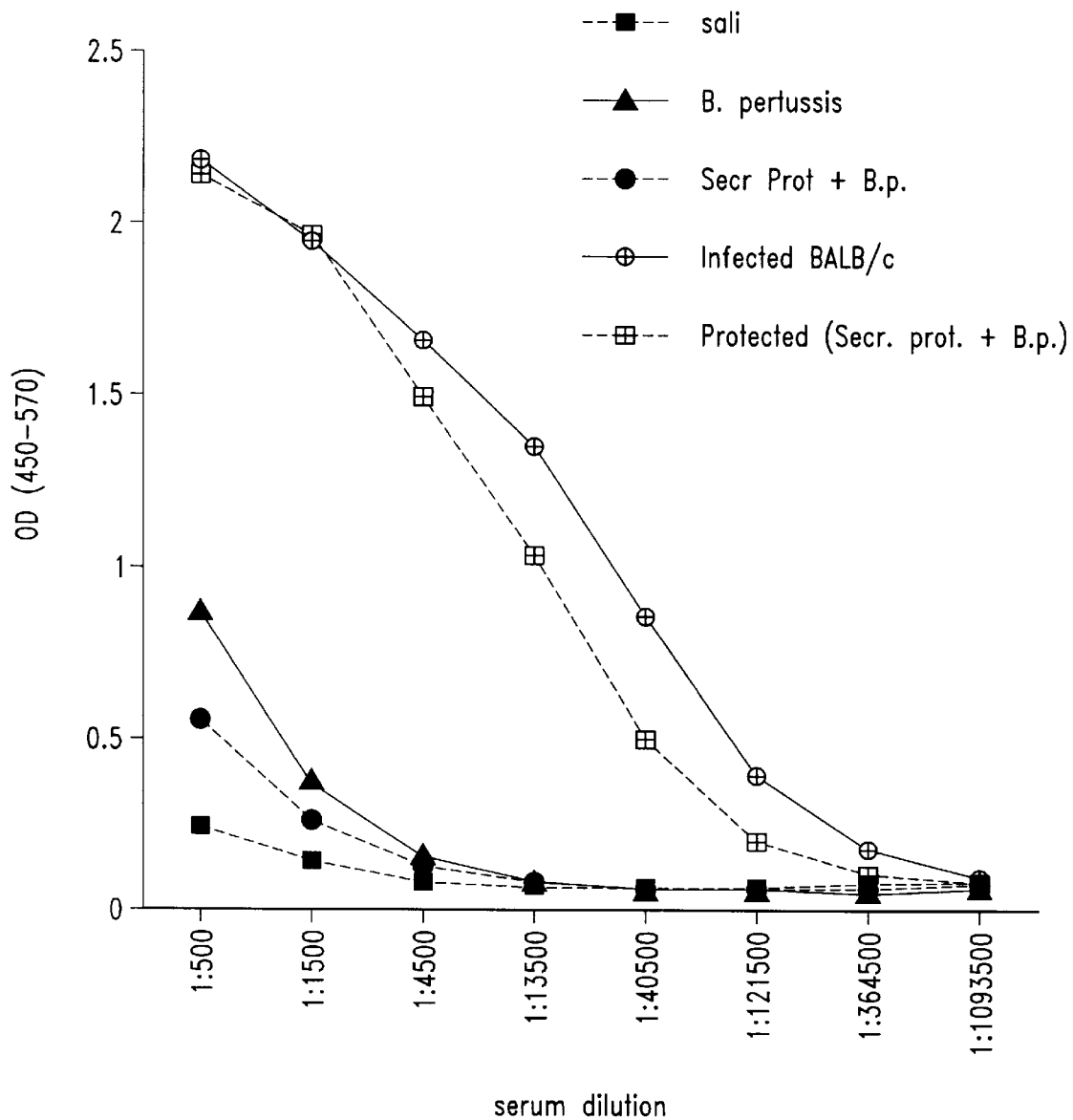

FIG. 27 illustrates the reactivity of MAPS-1A with sera from mice immunized against and/or infected with leishmaniasis.

Figure 28:
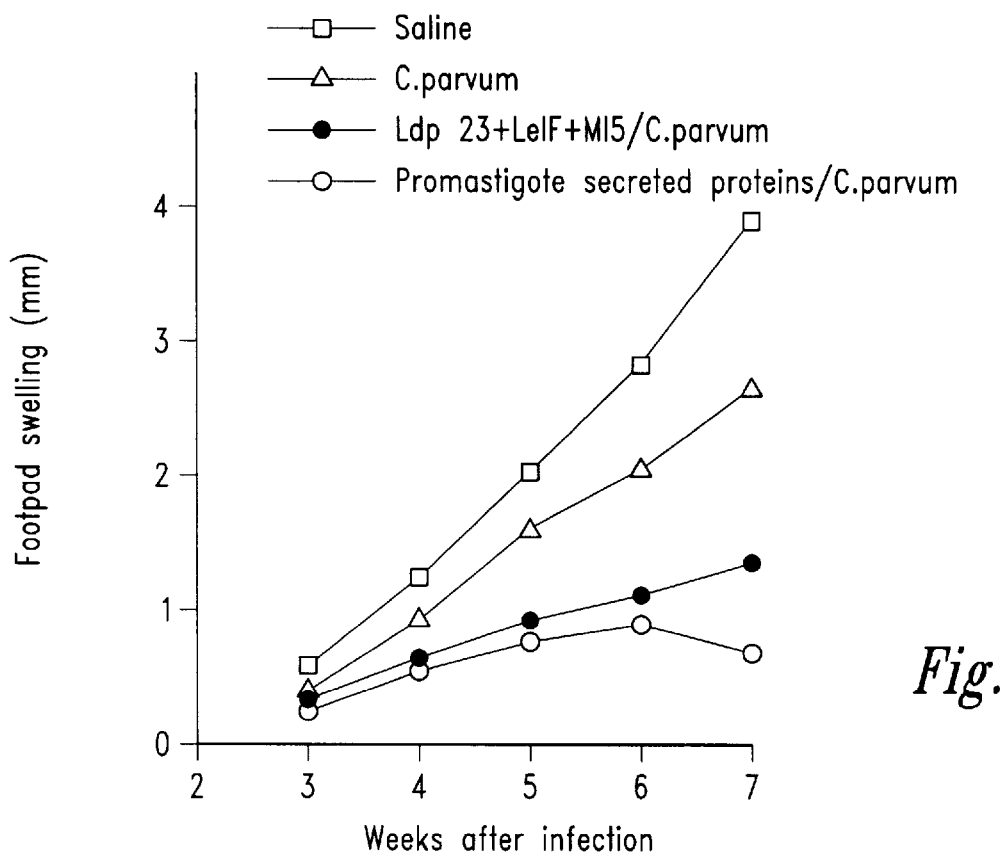

FIG. 28 illustrates the effectiveness of immunization with either soluble Leishmania antigens or a mixture of Ldp23, LbeiF4A and M15 plus adjuvant in conferring protection against infection (as measured by footpad swelling) in a murine leishmaniasis model system, as compared to the administration of adjuvant alone.

Figure 29:
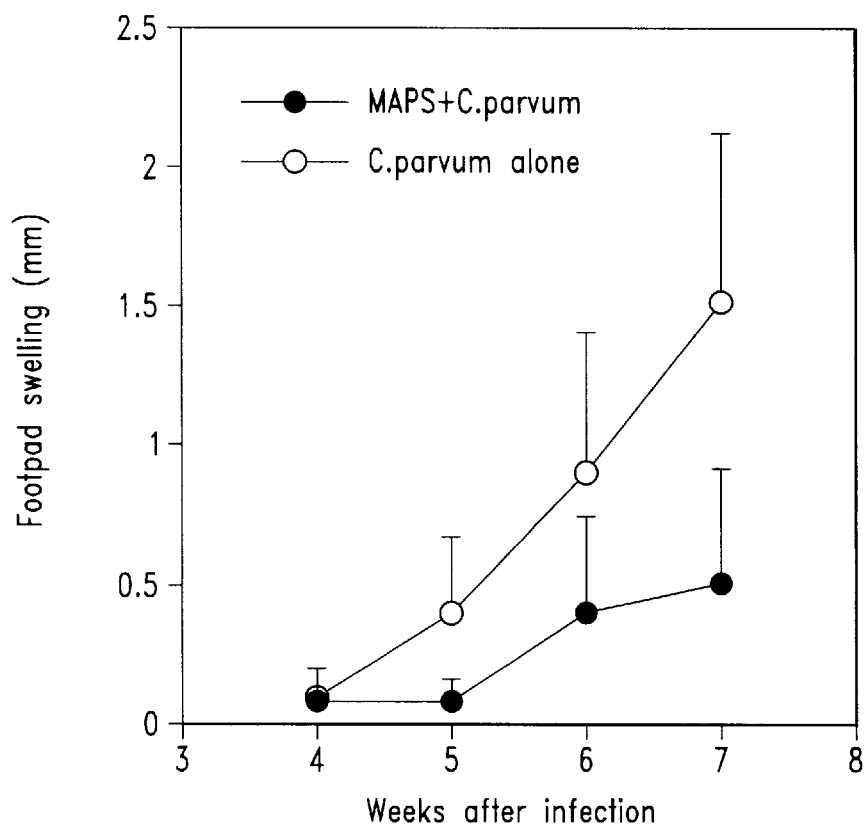

FIG. 29 illustrates the effectiveness of immunization with MAPS-1A plus adjuvant in conferring protection against infection (as measured by footpad swelling) in a murine leishmaniasis model system, as compared to the administration of adjuvant alone.

Figure 30A:
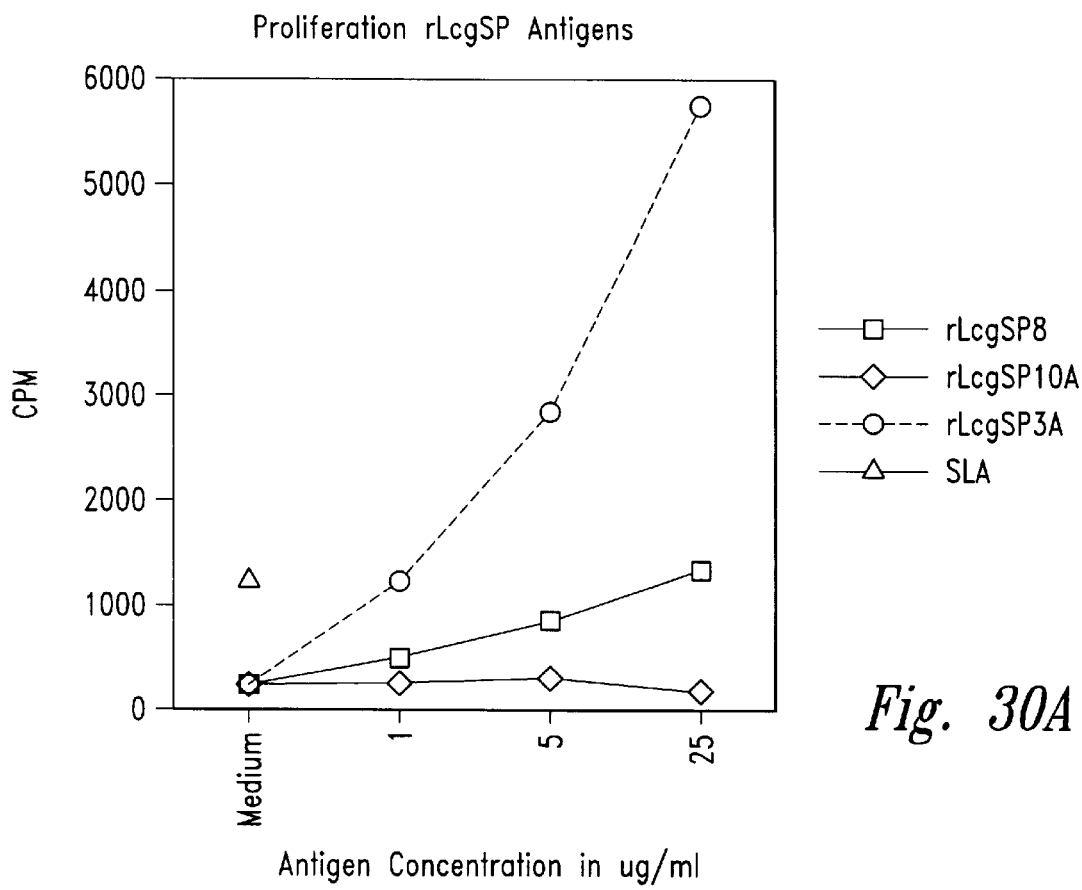

FIGS. 30A and B illustrate the proliferation of murine lymph node cultures stimulated with either LcgSP8, LcgSP10 or LcgSP3.

Figure 31:
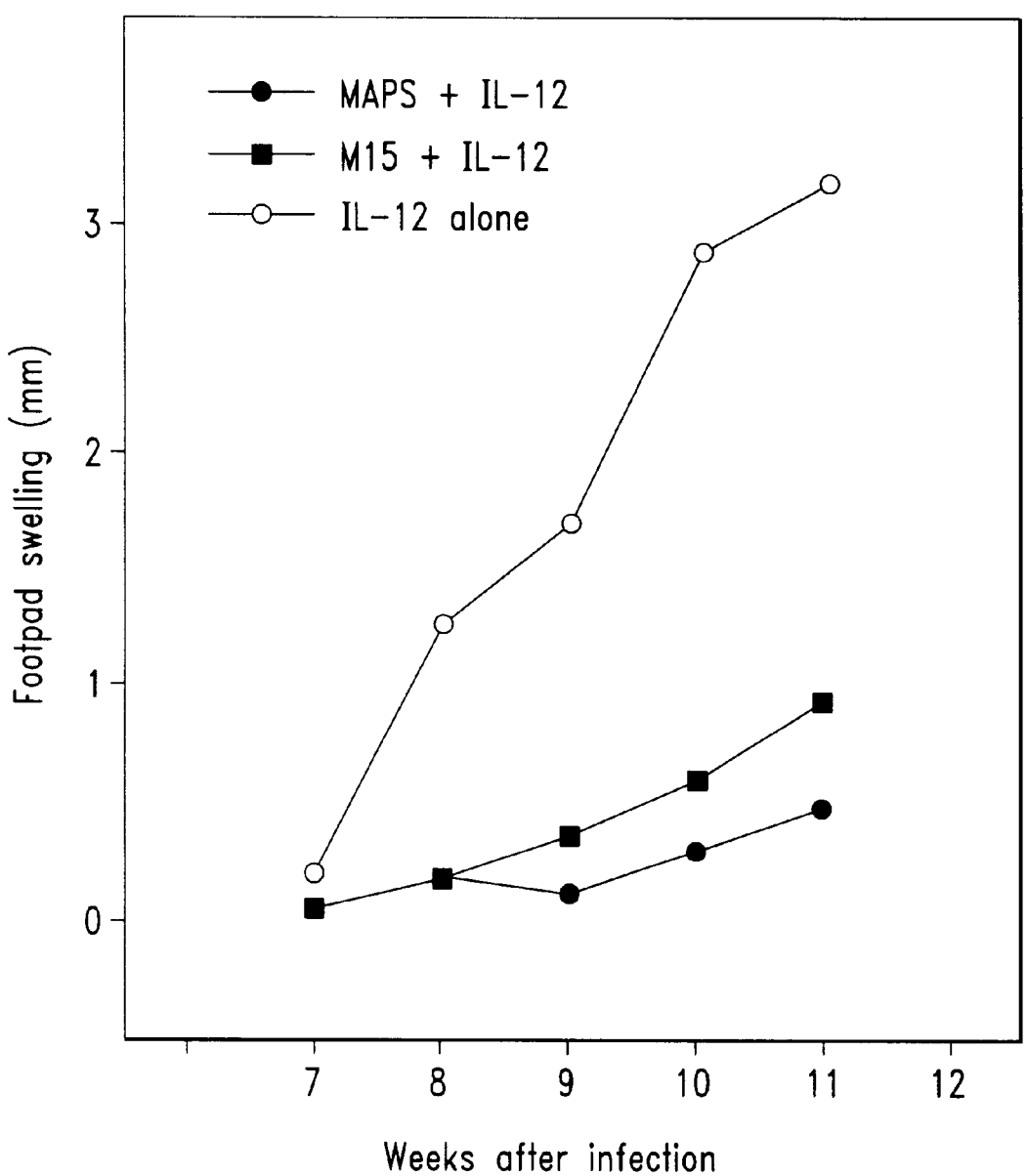

FIG. 31 illustrates the effectiveness of immunization with soluble Leishmania antigens, MAPS-1A and M15 plus adjuvant, IL-12, in conferring protection against infection (as measured by footpad swelling) in a murine leishmaniasis model system, as compared to the administration of adjuvant IL-12 alone.

Figure 32:
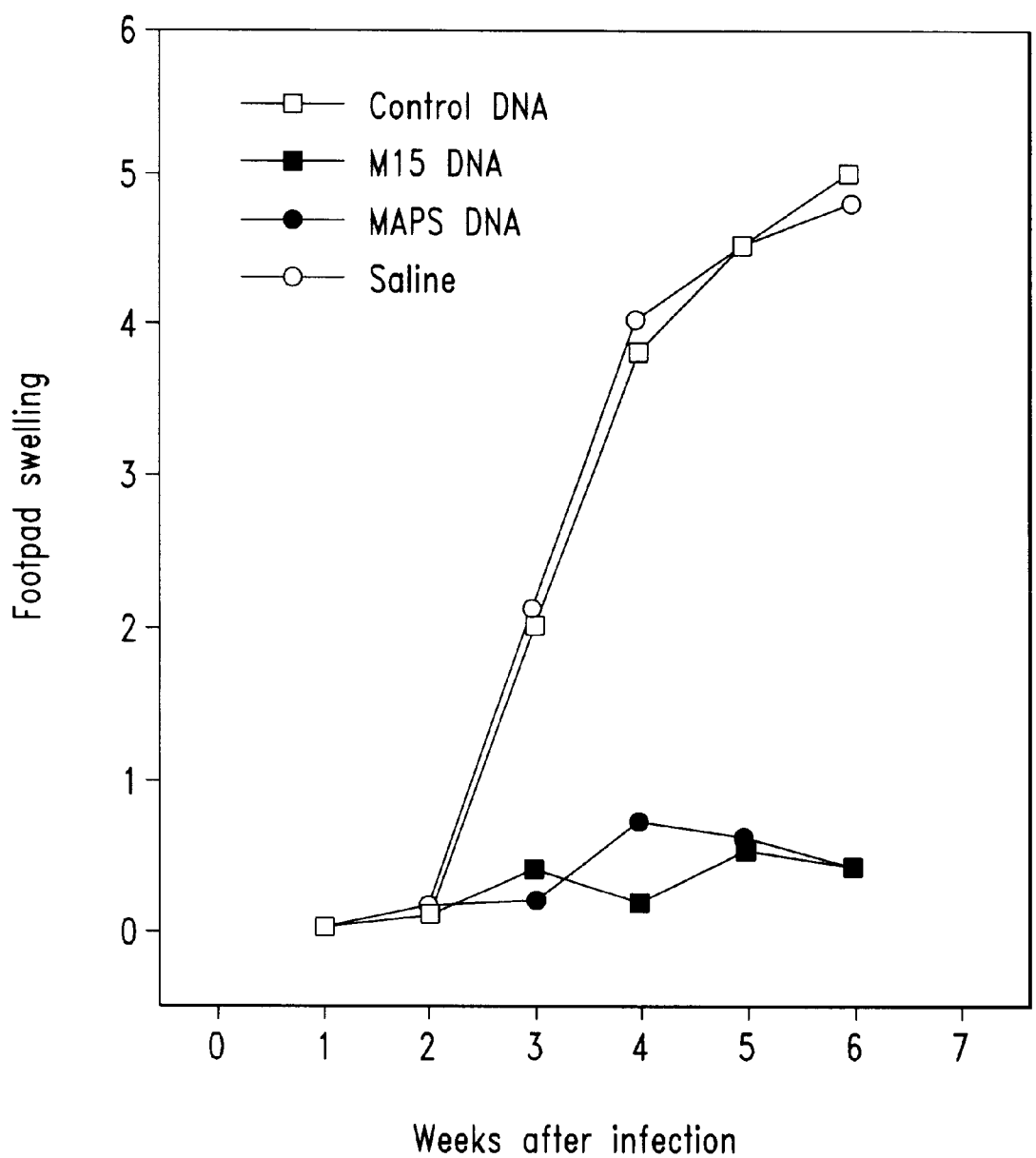

FIG. 32 illustrates the effectiveness of immunization with M15 DNA and MAPS-1A DNA in conferring protection against infection (as measured by footpad swelling) in a murine leishmaniasis model system, as compared to control DNA and saline.

Figure 33:
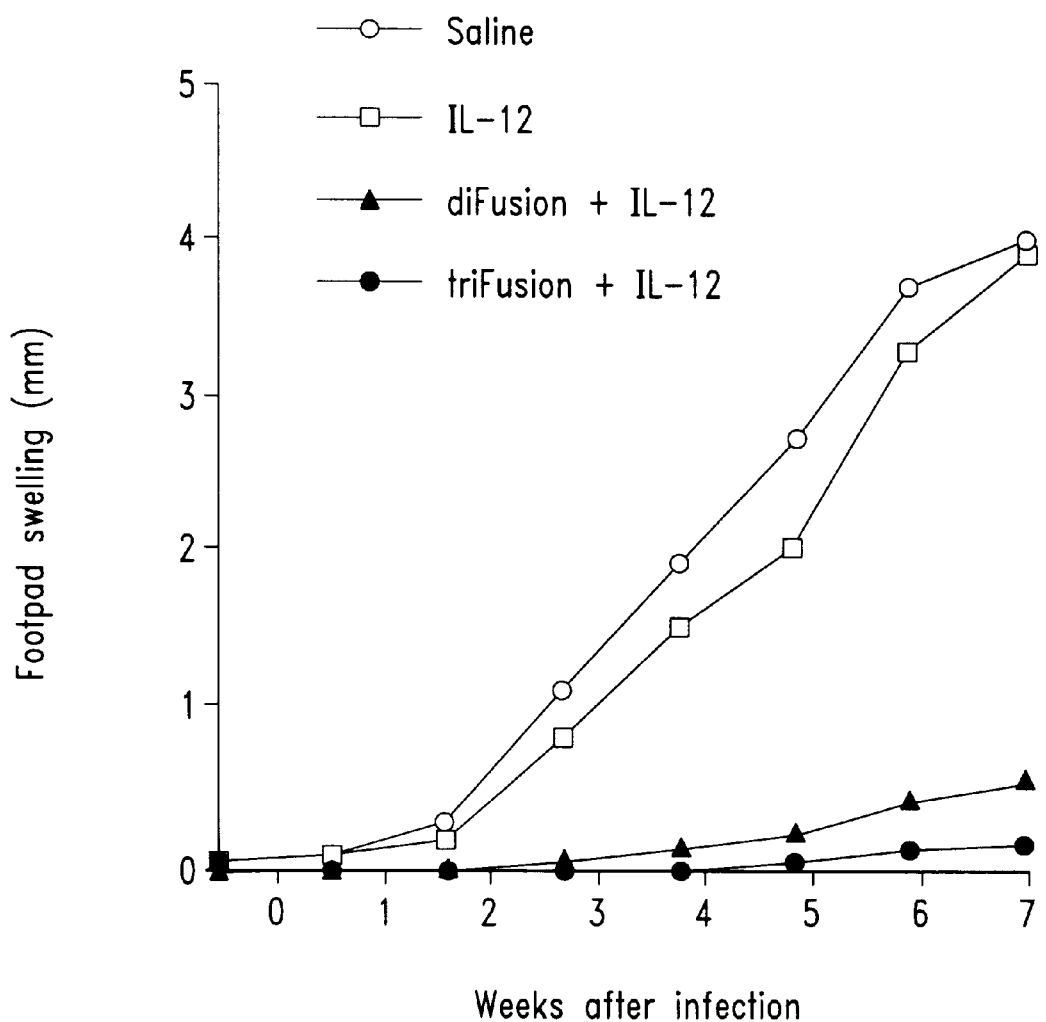

FIG. 33 illustrates the effectiveness of immunization with Leishmania fusion proteins plus IL-12 as adjuvant, in conferring protection against infection in a murine leishmaniasis model system.

Figure 34:
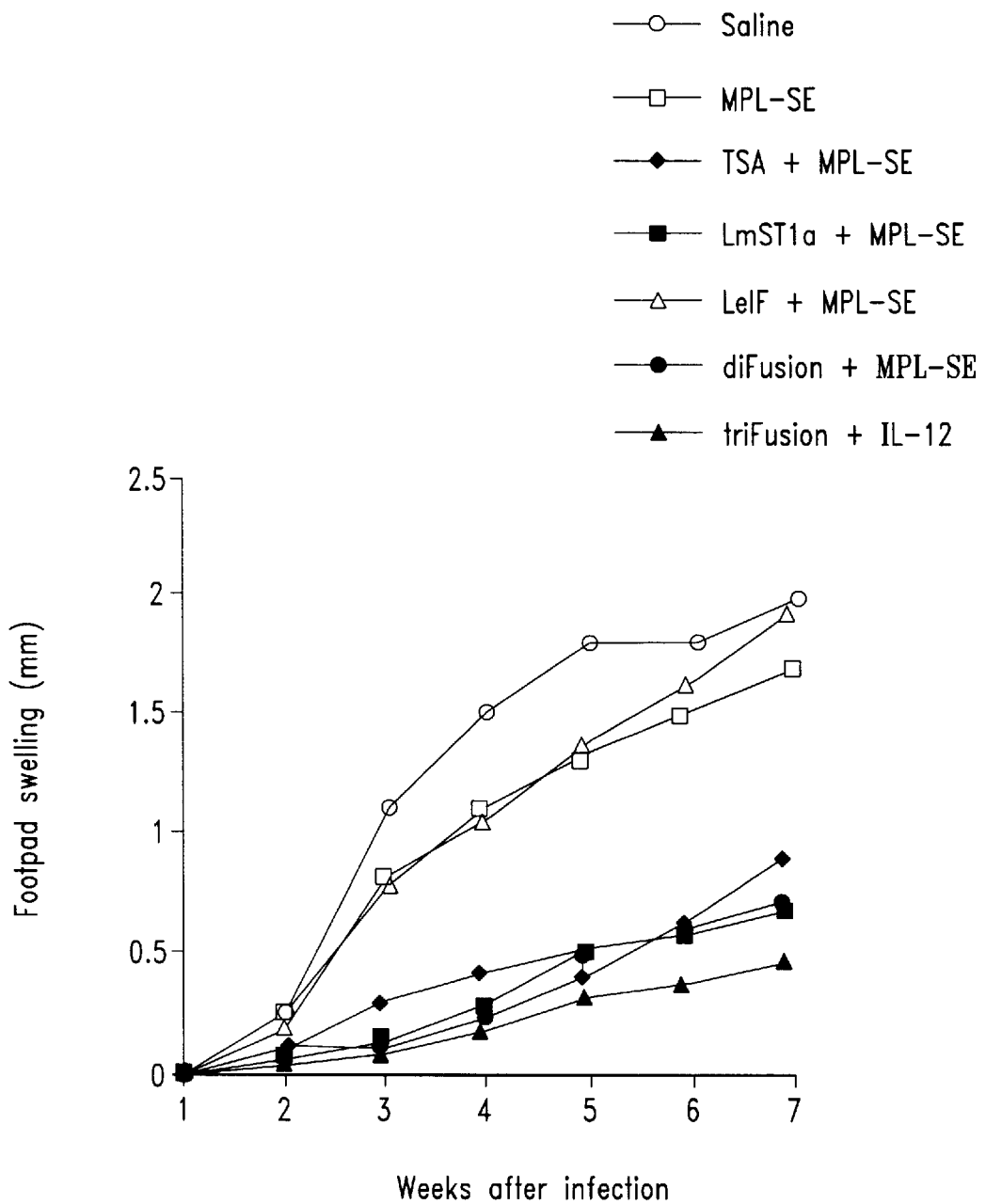

FIG. 34 illustrates the effectiveness of immunization with Leishmania fusion proteins plus the adjuvant MPL-SE, in conferring protection against infection in a murine leishmaniasis model system.

DETAILED DESCRIPTION OF THE INVENTION

As noted above, the present invention is generally directed to compositions and methods for preventing, treating and detecting leishmaniasis, as well as for stimulating immune responses in patients. The compositions of the subject invention include polypeptides that comprise at least an immunogenic portion of a Leishmania antigen, or a variant of such an antigen that differs only in conservative substitutions and/or modifications. In one preferred embodiment, compositions of the present invention include multiple polypeptides selected so as to provide enhanced protection against a variety of Leishmania species.

Polypeptides within the scope of the present invention include, but are not limited to, polypeptides comprising immunogenic portions of Leishmania antigens comprising the sequences recited in SEQ ID NO:2 (referred to herein as M15), SEQ ID NO:4 (referred to herein as Ldp23), SEQ ID NO:6 (referred to herein as Lbhsp83), SEQ ID NO:8 (referred to herein as Lt-210), SEQ ID NO:10 (referred to herein as LbeIF4A), SEQ ID NO: 20 (referred to herein as Lmsp1a), SEQ ID NO: 22 (referred to herein as Lmsp9a), SEQ ID NOs: 24 and 26 (referred to herein as MAPS-1A), and SEQ ID NO: 36–42, 49–53 and 55. As used herein, the term "polypeptide" encompasses amino acid chains of any length, including full length proteins (i.e., antigens), wherein the amino acid residues are linked by covalent bonds. Thus, a polypeptide comprising an immunogenic portion of one of the above antigens may consist entirely of the immunogenic portion, or may contain additional sequences. The additional sequences may be derived from the native Leishmania antigen or may be heterologous, and such sequences may (but need not) be immunogenic. An antigen "having" a particular sequence is an antigen that contains, within its full length sequence, the recited sequence. The native antigen may, or may not, contain additional amino acid sequence.

An immunogenic portion of a Leishmania antigen is a portion that is capable of eliciting an immune response (i.e., cellular and/or humoral) in a presently or previously Leishmania-infected patient (such as a human or a dog) and/or in cultures of lymph node cells or peripheral blood mononuclear cells (PBMC) isolated from presently or previously Leishmania-infected individuals. The cells in which a response is elicited may comprise a mixture of cell types or may contain isolated component cells (including, but not limited to, T-cells, NK cells, macrophages, monocytes and/or B cells). In particular, immunogenic portions are capable of inducing T-cell proliferation and/or a dominantly Th1-type cytokine response (e.g., IL-2, IFN-γ, and/or TNF-α production by T-cells and/or NK cells; and/or IL-12 production by monocytes, macrophages and/or B cells). Immunogenic portions of the antigens described herein may generally be identified using techniques known to those of ordinary skill in the art, including the representative methods provided herein.

The compositions and methods of the present invention also encompass variants of the above polypeptides. A polypeptide "variant," as used herein, is a polypeptide that differs from the native antigen only in conservative substitutions and/or modifications, such that the ability of the polypeptide to include an immune response is retained. Polypeptide variants preferably exhibit at least about 70%, more preferably at least about 90% and most preferably at least about 95% identity to the identified polypeptides. Alternatively, such variants may be identified by modifying one of the above polypeptide sequences and evaluating the immunogenic properties of the modified polypeptide using, for example, the representative procedures described herein.

A "conservative substitution" is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

Variants may also (or alternatively) be modified by, for example, the deletion or addition of amino acids that have minimal influence on the immunogenic properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

A nucleotide "variant" is a sequence that differs from the recited nucleotide sequence in having one or more nucleotide deletions, substitutions or additions. Such modifications may be readily introduced using standard mutagenesis techniques, such as oligonucleotide-directed site-specific mutagenesis as taught, for example, by Adelman et al. (*DNA*, 2:183, 1983). Nucleotide variants may be naturally occurring allelic variants, or non-naturally occurring variants. Variant nucleotide sequences preferably exhibit at least about 70%, more preferably at least about 80% and most preferably at least about 90% identity to the recited sequence. Such variant nucleotide sequences will generally hybridize to the recited nucleotide sequence under stringent conditions. As used herein, "stringent conditions" refers to prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

"Polypeptides" as described herein also include combination polypeptides, also referred to as fusion proteins. A "combination polypeptide" is a polypeptide comprising at least one of the above immunogenic portions and one or more additional immunogenic Leishmania sequences, which are joined via a peptide linkage into a single amino acid chain. The sequences may be joined directly (ie., with no intervening amino acids) or may be joined by way of a linker sequence (e.g., Gly-Cys-Gly) that does not significantly diminish the immunogenic properties of the component polypeptides.

Fusion proteins may generally be prepared using standard techniques, including chemical conjugation. Preferably, a fusion protein is expressed as a recombinant protein, allowing the production of increased levels, relative to a non-fused protein, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in frame. This permits translation into a single fusion protein that retains the biological activity of both component polypeptides.

A peptide linker sequence may be employed to separate the first and the second polypeptide components by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad. Sci. USA* 83:8258–8262, 1986; U.S. Pat. Nos. 4,935,233 and 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide. The preparation of fusion proteins of Leishmania antigens is described below in Example 19.

In general, Leishmania antigens having immunogenic properties, and DNA sequences encoding such antigens, may be prepared using any of a variety of procedures from one or more Leishmania species including, but not limited to, *L. donovani, L. chagasi, L. infantum, L. major, L. amazonensis, L. braziliensis, L. panamensis, L. mexicana, L. tropica,* and *L. guyanensis.* Such species are available, for example, from the American Type Culture Collection (ATCC), Rockville, Md. For example, peptides isolated from MHC class II molecules of macrophages infected with a Leishmania species may be used to rescue the corresponding Leishmania donor antigens. MHC class II molecules are expressed mainly by cells of the immune system, including macrophages. These molecules present peptides, which are usually 13–17 amino acids long, derived from foreign antigens that are degraded in cellular vesicles. The bound peptide antigens are then recognized by CD4 T-cells. Accordingly, foreign peptides isolated from MHC class II molecules of, for example, Leishmania-infected murine macrophages may be used to identify immunogenic Leishmania proteins.

Briefly, peptides derived from Leishmania antigens may be isolated by comparing the reverse phase HPLC profile of peptides extracted from infected macrophages with the profile of peptides extracted from uninfected cells. Peptides giving rise to distinct HPLC peaks unique to infected macrophages may then be sequenced using, for example, Edman chemistry as described in Edman and Berg, *Eur J.*

Biochem, 80:116–132 (1967). A DNA fragment corresponding to a portion of a Leishmania gene encoding the peptide may then be amplified from a Leishmania cDNA library using an oligonucleotide sense primer derived from the peptide sequence and an oligo dT antisense primer. The resulting DNA fragment may then be used as a probe to screen a Leishmania library for a full length cDNA or genomic clone that encodes the Leishmania antigen. Such screens may generally be performed using techniques well known to those of ordinary skill in the art, such as those described in Sambrook et al., *Molecular Cloning: A Laboratory Manual,* Cold Spring Harbor Laboratories, Cold Spring Harbor, N.Y. (1989).

This approach may be used to identify a 23 kD *Leishmania donovani* antigen (referred to herein as Ldp23). The sequence of a polynucleotide encoding Ldp23 is provided in SEQ ID NO:3 and the amino acid sequence of Ldp23 is provided in SEQ ID NO:4. Using the methods described herein, Ldp23 has been shown to induce a Th1 immune response in T-cells prepared from Leishmania-infected mice.

Alternatively, a Leishmania cDNA or genomic expression library may be screened with serum from a Leishmania-infected individual, using techniques well known to those of ordinary skill in the art. Polynucleotides encoding reactive antigens may then be used to express the recombinant antigen for purification. The immunogenic properties of the purified Leishmania antigens may then be evaluated using, for example the representative methods described herein.

For example, sera from Leishmania-infected mice may be used to screen a cDNA library prepared from Leishmania amastigotes. Reactive clones may then be expressed and recombinant proteins assayed for the ability to stimulate T-cells or NK cells derived from Leishmania-immune individuals (i.e., individuals having evidence of infection, as documented by positive serological reactivity with Leishmania-specific antibodies and/or a Leishmania-specific DTH response, without clinical symptoms of leishmaniasis). This procedure may be used to obtain a recombinant polynucleotide encoding the Leishmania antigen designated M15. The sequence of such a polynucleotide is provided in SEQ ID NO:1, and the amino acid sequence of the encoded protein is provided in SEQ ID NO:2.

A similar approach may be used to isolate a genomic polynucleotide encoding an immunogenic *Leishmania braziliensis* antigen, referred to herein as Lbhsp83. More specifically, a genomic clone encoding Lbhsp83 may be isolated by screening a *L. braziliensis* expression library with sera from a Leishmania-infected individual. The DNA encoding Lbhsp83 is homologous to the gene encoding the eukaryotic 83 kD heat shock protein. The sequence of a polynucleotide encoding nearly all of Lbhsp83 is presented in SEQ ID NO:5, and the encoded amino acid sequence is provided in SEQ ID NO:6. Using the methods described below, Lbhsp83 has been found to stimulate proliferation, and a mixed Th1 and Th2 cytokine profile, in PBMC isolated from *L. braziliensis*-infected patients. Accordingly, Lbhsp83 is an immunogenic Leishmania antigen. Regions of Lbhsp83 that are not conserved with the mammalian gene have been found to be particularly potent for T-cell stimulation and antibody binding. Such regions may be identified, for example, by visual inspection of the sequence comparison provided in FIG. 19.

This approach may also be used to isolate a polynucleotide encoding a 210 kD immunogenic *L. tropica* antigen, referred to herein as Lt-210. The preparation and characterization of Lt-210, and immunogenic portions thereof (such as Lt-1 and immunogenic repeat and non-repeat sequences), is described in detail in U.S. patent application Ser. No. 08/511,872, filed Aug. 4, 1995. The sequence of a polynucleotide encoding Lt-1 is provided in SEQ ID NO:7 and the encoded amino acid sequence is presented in SEQ ID NO:8.

The above approach may further be used to isolate a polynucleotide encoding a *L. braziliensis* antigen referred to herein as LbeIF4A. Briefly, such a clone may be isolated by screening a *L. braziliensis* expression library with sera obtained from a patient afflicted with mucosal leishmaniasis, and analyzing the reactive antigens for the ability to stimulate proliferative responses and preferential Th1 cytokine production in PBMC isolated from Leishmania-infected patients, as described below. The preparation and characterization of LbeIF4A is described in detail in U.S. patent application Ser. Nos. 08/454,036 and 08/488,386, which are continuations-in-part of U.S. patent application Ser. No. 08/232,534, filed Apr. 22, 1994. The sequence of a polynucleotide encoding LbeIF4A is provided in SEQ ID NO:9 and the encoded amino acid sequence is presented in SEQ ID NO:10. Homologs of LbeIF4A, such as that found in *L. major*, may also be isolated using this approach, and are within the scope of the present invention.

Compositions of the present invention may also, or alternatively, contain soluble Leishmania antigens. As used herein, "soluble Leishmania antigens" refers to a mixture of at least 8 different Leishmania antigens that may be isolated from the supernatant of Leishmania promastigotes of any species grown for 8–12 hours in protein-free medium. Briefly, the organisms are grown to late log phase in complex medium with serum until they reach a density of $2-3 \times 10^7$ viable organisms per mL of medium. The organisms are thoroughly washed to remove medium components and resuspended at $2-3 \times 10^7$ viable organisms per mL of defined serum-free medium consisting of equal parts RPMI 1640 and medium 199, both from Gibco BRL, Gaithersburg, Md. After 8–12 hours. the supernatant containing soluble Leishmania antigens is removed, concentrated 10 fold and dialyzed against phosphate-buffered saline for 24 hours. The presence of at least eight different antigens within the mixture of Leishmania antigens may be confirmed using SDS-PAGE (i.e., through the observation of at least 8 different bands). The immunogenic properties of the soluble Leishmania antigens may be confirmed by evaluating the ability of the preparation to elicit an immune response in cultures of lymph node cells and/or peripheral blood mononuclear cells (PBMC) isolated from presently or previously Leishmania-infected individuals. Such an evaluation may be performed as described below.

Individual antigens present within the mixture of soluble Leishmania antigens may be isolated by immunizing mice or rabbits with Leishmania culture supernatant, containing soluble antigens, and employing the resultant sera to screen a Leishmania cDNA expression library as described in detail below. This procedure may be used to isolate recombinant polynucleotides encoding the *L. major* antigens referred to herein as Lmsp1a, Lmsp9a and MAPS-1A. DNA sequences encoding Lmsp1a, Lmsp9a and MAPS-1A are provided in SEQ ID NO: 19, 21 and 23, respectively, with the corresponding predicted amino acid sequences being presented in SEQ ID NO: 20, 22 and 24, respectively. Similarly, sera from mice or rabbits immunized with *L. major* culture supernatant may be used to screen an *L. major* genomic DNA library. As detailed below, this procedure may be used to isolate polynucleotides encoding the *L. major* antigens referred to herein as LmgSP1, LmgSP3, LmgSP5, LmgSP8, LmgSP9, LmgSP13, LmgSP19, and polynucleotides encoding the *L. chagasi* antigens LcgSP1, LcgSP3, LcgSP4, LcgSP8, and LcgSP10. The DNA sequences encoding these antigens are provided in SEQ ID NO:29–35 and 44–48, respectively, with the corresponding amino acid sequences being provided in SEQ ID NO: 36–42 and 49–53. The *L. major* antigens referred to herein as 1G6-34, 1E6-44, 4A5-63, 1B11-39, 2A10-37, 4G2-83, 4H6-41 and 8G3-100 may be isolated by means of CD4+ T cell expression cloning as described below. DNA sequences encoding these antigens are provided in SEQ ID NO: 72–79, respectively, with the corresponding predicted amino acid sequences being provided in SEQ ID NO: 80–87. The immunogenic properties of the isolated Leishmania antigens may be evaluated using, for example, the representative methods described herein.

Regardless of the method of preparation, the antigens described herein are immunogenic. In other words, the antigens (and immunogenic portions thereof) are capable of eliciting an immune response in cultures of lymph node cells and/or peripheral blood mononuclear cells (PBMC) isolated from presently or previously Leishmania-infected individuals. More specifically, the antigens, and immunogenic portions thereof, have the ability to induce T-cell proliferation and/or to elicit a dominantly Th1-type cytokine response (e.g., IL-2, IFN-γ, and/or TNF-α production by T-cells and/or NK cells; and/or IL-12 production by monocytes, macrophages and/or B cells) in cells isolated from presently or previously Leishmania-infected individuals. A Leishmania-infected individual may be afflicted with a form of leishmaniasis (such as subclinical, cutaneous, mucosal or active visceral) or may be asymptomatic. Such individuals may be identified using methods known to those of ordinary skill in the art. Individuals with leishmaniasis may be identified based on clinical findings associated with at least one of the following: isolation of parasite from lesions, a positive skin test with Leishmania lysate or a positive serological test. Asymptomatic individuals are infected individuals who have no signs or symptoms of the disease. Such individuals can be identified based on a positive serological test and/or skin test with Leishmania lysate.

The term "PBMC," which refers to a preparation of nucleated cells consisting primarily of lymphocytes and monocytes that are present in peripheral blood, encompasses both mixtures of cells and preparations of one or more purified cell types. PBMC may be isolated by methods known to those in the art. For example, PBMC may be isolated by density centrifugation through, for example, Ficoll™ (Winthrop Laboratories, New York). Lymph node cultures may generally be prepared by immunizing BALB/c mice (e.g., in the rear foot pad) with Leishmania promastigotes emulsified in complete Freünd's adjuvant. The draining lymph nodes may be excised following immunization and T-cells may be purified in an anti-mouse Ig column to remove the B cells, followed by a passage through a Sephadex G10 column to remove the macrophages. Similarly, lymph node cells may be isolated from a human following biopsy or surgical removal of a lymph node.

The ability of a polypeptide (e.g., a Leishmania antigen or a portion or other variant thereof) to induce a response in PBMC or lymph node cell cultures may be evaluated by contacting the cells with the polypeptide and measuring a suitable response. In general, the amount of polypeptide that is sufficient for the evaluation of about $2\times10^5$ cells ranges from about 10 ng to about 100 μg, and preferably is about 1–10 μg. The incubation of polypeptide with cells is typically performed at 37° C. for about 1–3 days. Following incubation with polypeptide, the cells are assayed for an appropriate response. If the response is a proliferative response, any of a variety of techniques well known to those of ordinary skill in the art may be employed. For example, the cells may be exposed to a pulse of radioactive thymidine and the incorporation of label into cellular DNA measured. In general, a polypeptide that results in at least a three fold increase in proliferation above background (i.e., the proliferation observed for cells cultured without polypeptide) is considered to be able to induce proliferation.

Alternatively, the response to be measured may be the secretion of one or more cytokines (such as interferon-γ (IFN-γ), interleukin-4 (IL-4), interleukin-12 (p70 and/or p40), interleukin-2 (IL-2) and/or tumor necrosis factor-α (TNF-α)) or the change in the level of mRNA encoding one or more specific cytokines. In particular, the secretion of interferon-γ, interleukin-2, tumor necrosis factor-α and/or interleukin-12 is indicative of a Th1 response, which is responsible for the protective effect against Leishmania. Assays for any of the above cytokines may generally be performed using methods known to those of ordinary skill in the art, such as an enzyme-linked immunosorbent assay (ELISA). Suitable antibodies for use in such assays may be obtained from a variety of sources such as Chemicon, Temucula, Calif. and PharMingen, San Diego, Calif., and may generally be used according to the manufacturer's instructions. The level of mRNA encoding one or more specific cytokines may be evaluated by, for example, amplification by polymerase chain reaction (PCR). In general, a polypeptide that is able to induce, in a preparation of about $1–3\times10^5$ cells, the production of 30 pg/mL of IL-12, IL-4, IFN-γ, TNF-α or IL-12 p40, or 10 pg/mL of IL-12 p70, is considered able to stimulate production of a cytokine.

Immunogenic portions of the antigens described herein may be prepared and identified using well known techniques, such as those summarized in Paul, Fundamental Immunology, 3rd ed., 243–247 (Raven Press, 1993) and references cited therein. Such techniques include screening polypeptides derived from the native antigen for immunogenic properties using, for example, the representative techniques described herein. An immunogenic portion of a polypeptide is a portion that, within such representative assays, generates an immune response (e.g., proliferation and/or cytokine production) that is substantially similar to that generated by the full length antigen. In other words, an immunogenic portion of an antigen may generate at least about 25%, and preferably at least about 50%, of the response generated by the full length antigen in the model assays described herein.

Portions and other variants of immunogenic Leishmania antigens may be generated by synthetic or recombinant means. Synthetic polypeptides having fewer than about 100 amino acids, and generally fewer than about 50 amino acids, may be generated using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is commercially available from suppliers such as Perkin Elmer/Applied BioSystemsDivision, Foster City, Calif., and may be operated according to the manufacturer's instructions.

Recombinant polypeptides containing portions and/or variants of a native antigen may be readily prepared from a DNA sequence encoding the antigen. For example, supernatants from suitable host/vector systems which secrete recombinant protein into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant protein.

In general, any of a variety of expression vectors known to those of ordinary skill in the art may be employed to express recombinant polypeptides of this invention. Expression may be achieved in any appropriate host cell that has been transformed or transfected with an expression vector containing a polynucleotide that encodes a recombinant polypeptide. Suitable host cells include prokaryotes, yeast and higher eukaryotic cells. Preferably, the host cells employed are *E. coli*, yeast or a mammalian cell line such as COS or CHO. The DNA sequences expressed in this manner may encode naturally occurring antigens, portions of naturally occurring antigens, or other variants thereof. For example, variants of a native antigen may generally be prepared using standard mutagenesis techniques, such as oligonucleotide-directed site-specific mutagenesis, and sections of the DNA sequence may be removed to permit preparation of truncated polypeptides.

In another aspect, the present invention provides epitope repeat sequences, or antigenic epitopes, of a Leishmania antigen, together with polypeptides comprising at least two such contiguous antigenic epitopes. As used herein an "epitope" is a portion of an antigen that reacts with sera from Leishmania-infected individuals (i.e. an epitope is specifically bound by one or more antibodies present in such sera). As discussed above, epitopes of the antigens described in the present application may be generally identified using techniques well known to those of skill in the art.

In one embodiment, antigenic epitopes of the present invention comprise an amino acid sequence provided in SEQ ID NO:43, 56, 57 or 58. As discussed in more detail below, antigenic epitopes provided herein may be employed in the diagnosis and treatment of Leishmania infection, either alone or in combination with other Leishmania antigens or antigenic epitopes. Antigenic epitopes and polypeptides comprising such epitopes may be prepared by synthetic means, as described generally above and in detail in Example 15.

In certain aspects of the present invention, described in detail below, the polypeptides, antigenic epitopes and/or soluble Leishmania antigens may be incorporated into pharmaceutical compositions or vaccines. For clarity, the term "polypeptide" will be used when describing specific embodiments of the inventive therapeutic compositions and diagnostic methods. However, it will be clear to one of skill in the art that the antigenic epitopes of the present invention may also be employed in such compositions and methods. Pharmaceutical compositions comprise one or more polypeptides, each of which may contain one or more of the above sequences (or variants thereof), and a physiologically acceptable carrier. Vaccines comprise one or more of the above polypeptides and an immunostimulant, such as an adjuvant (e.g., LbeIF4A, interleukin-12 or other cytokines) or a liposome (into which the polypeptide is incorporated). In certain embodiments, the inventive vaccines include an adjuvant capable of eliciting a predominantly Th-1 type response. Preferred adjuvants for use in eliciting a predominantly Th1-type response include, for example, a combination of monophosphoryl lipid A, preferably 3-de-O-acylated monophosphoryl lipid A (3D-MPL), together with an aluminum salt. MPL adjuvants are available from Ribi ImmunoChem Research Inc. (Hamilton, Mont.; see U.S. Pat. Nos. 4,436,727; 4,877,611; 4,866,034 and 4,912,094). CpG-containing oligonucleotides (in which the CpG dinucleotide is unmethylated) also induce a predominantly Th1 response. Such oligonucleotides are well known and are described, for example, in WO 96/02555 and WP 99/33488. Immunostimulatory DNA sequences are also described, for example, by Sato et al., *Science* 273:352, 1996. Another preferred adjuvant is a saponin, preferably QS21 (Aquila, United States), which may be used alone or in combination with other adjuvants. For example, an enhanced system involves the combination of a monophosphoryl lipid A and saponin derivative, such as the combination of QS21 and 3D-MPL as described in WO 94/00153, or a less reactogenic composition where the QS21 is quenched with cholesterol, as described in WO 96/33739. Other preferred formulations comprise an oil-in-water emulsion and tocopherol. A particularly potent adjuvant formulation involving QS21, 3D-MPL and tocopherol in an oil-in-water emulsion is described in WO 95/17210.

Vaccines may additionally contain a delivery vehicle, such as a biodegradable microsphere (disclosed, for example, in U.S. Pat. Nos. 4,897,268 and 5,075,109). Pharmaceutical compositions and vaccines within the scope of the present invention may also contain other Leishmania antigens, either incorporated into a combination polypeptide or present within one or more separate polypeptides.

Alternatively, a pharmaceutical composition or vaccine may contain an immunostimulant such as, an adjuvant (e.g., LbeIF4A, interleukin-12 or other cytokines) or DNA coding for such enhancers, and DNA encoding one or more of the polypeptides as described above, such that the polypeptide is generated in situ. In such pharmaceutical compositions and vaccines, the DNA may be present within any of a variety of delivery systems known to those of ordinary skill in the art, including nucleic acid expression systems, bacteria and viral expression systems. Appropriate nucleic acid expression systems contain the necessary DNA sequences for expression in the patient (such as a suitable promoter and terminating signal). Bacterial delivery systems involve the administration of a bacterium (such as Bacillus-Calmette-Guerrin) that expresses an immunogenic portion of the polypeptide on its cell surface. In a preferred embodiment, the DNA may be introduced using a viral expression system (e.g., vaccinia or other pox virus, retrovirus, or adenovirus), which may involve the use of a non-pathogenic (defective), replication competent virus. Techniques for incorporating DNA into such expression systems are well known to those of ordinary skill in the art. The DNA may also be "naked," as described, for example, in Ulmer et al., *Science* 259:1745–1749 (1993) and reviewed by Cohen, *Science* 259:1691–1692 (1993). The uptake of naked DNA may be increased by coating the DNA onto biodegradable beads, which are efficiently transported into the cells.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention. Suitable biodegradable microspheres are disclosed, for example, in U.S. Pat. Nos. 4,897,268 and 5,075,109.

Any of a variety of adjuvants may be employed in the vaccines of this invention to nonspecifically enhance the immune response. Most adjuvants contain a substance designed to protect the antigen from rapid catabolism, such as aluminum hydroxide or mineral oil, and a nonspecific stimulator of immune responses, such as lipid A, *Bordella pertussis* or *Mycobacterium tuberculosis*. Suitable adjuvants are commercially available as, for example, Freund's Incomplete Adjuvant and Complete Adjuvant (Difco Laboratories, Detroit, Mich.), Merck Adjuvant 65 (Merck and Company, Inc., Rahway, N.J.), alum, biodegradable microspheres, monophosphoryl lipid A and quil A. Preferred adjuvants include LbeIF4A, IL-12 and other cytokines such as IFN-γ or granulocyte-macrophage colony stimulating factor (GM-CSF). By virtue of its ability to induce an exclusive Th1 immune response, the use of LbeIF4A, and variants thereof, as an adjuvant in the vaccines of the present invention is particularly preferred.

In one preferred embodiment, compositions of the present invention include multiple polypeptides selected so as to provide enhanced protection against a variety of Leishmania species. Such polypeptides may be selected based on the species of origin of the native antigen or based on a high degree of conservation of amino acid sequence among different species of Leishmania. A combination of individual polypeptides may be particularly effective as a prophylactic and/or therapeutic vaccine because (1) stimulation of proliferation and/or cytokine production by a combination of individual polypeptides may be additive, (2) stimulation of proliferation and/or cytokine production by a combination of individual polypeptides may be synergistic, (3) a combination of individual polypeptides may stimulate cytokine profiles in such a way as to be complementary to each other and/or (4) individual polypeptides may be complementary to one another when certain of them are expressed more abundantly on the individual species or strain of Leishmania responsible for infection. A preferred combination contains polypeptides that comprise immunogenic portions of M15, Ldp23, Lbhsp83, Lt-1 and LbeIF4A. Alternatively, or in addition, the combination may include one or more polypeptides comprising immunogenic portions of other Leishmania antigens disclosed herein, and/or soluble Leishmania antigens.

In another preferred embodiment, compositions of the present invention include single polypeptides selected so as to provide enhanced protection against a variety of Leishmania species. A single individual polypeptide may be particularly effective as a prophylactic and/or therapeutic vaccine for those reasons stated above for combinations of individual polypeptides.

In another embodiment, compositions of the present invention include individual polypeptides and combinations of the above described polypeptides employed with a variety of adjuvants, such as IL-12 (protein or DNA) to confer a protective response against a variety of Leishmania species.

In yet another embodiment, compositions of the present invention include DNA constructs of the various Leishmania species employed alone or in combination with variety of adjuvants, such as IL-12 (protein or DNA) to confer a protective response against a variety of Leishmania species.

The above pharmaceutical compositions and vaccines may be used, for example, to induce protective immunity against Leishmania in a patient, such as a human or a dog, to prevent leishmaniasis. Appropriate doses and methods of administration for this purposes are described in detail below.

The pharmaceutical compositions and vaccines described herein may also be used to stimulate an immune response, which may be cellular and/or humoral, in a patient. For Leishmania-infected patients, the immune responses that may be generated include a preferential Th1 immune response (i.e., a response characterized by the production of the cytokines interleukin-1, interleukin-2, interleukin-12 and/or interferon-γ, as well as tumor necrosis factor-α). For uninfected patients, the immune response may be the production of interleukin-12 and/or interleukin-2, or the stimulation of gamma delta T-cells. In either category of patient, the response stimulated may include IL-12 production. Such responses may also be elicited in biological samples of PBMC or components thereof derived from Leishmania-infected or uninfected individuals. As noted above, assays for any of the above cytokines may generally be performed using methods known to those of ordinary skill in the art, such as an enzyme-linked immunosorbent assay (ELISA).

Suitable pharmaceutical compositions and vaccines for use in this aspect of the present invention are those that contain at least one polypeptide comprising an immunogenic portion of a Leishmania antigen disclosed herein (or a variant thereof). Preferably, the polypeptides employed in the pharmaceutical compositions and vaccines are complementary, as described above. Soluble Leishmania antigens, with or without additional polypeptides, may also be employed.

The pharmaceutical compositions and vaccines described herein may also be used to treat a patient afflicted with a disease responsive to IL-12 stimulation. The patient may be any warm-blooded animal, such as a human or a dog. Such diseases include infections (which may be, for example, bacterial, viral or protozoan) or diseases such as cancer. In one embodiment, the disease is leishmaniasis, and the patient may display clinical symptoms or may be asymptomatic. In general, the responsiveness of a particular disease to IL-12 stimulation may be determined by evaluating the effect of treatment with a pharmaceutical composition or vaccine of the present invention on clinical correlates of immunity. For example, if treatment results in a heightened Th1 response or the conversion of a Th2 to a Th1 profile, with accompanying clinical improvement in the treated patient, the disease is responsive to IL-12 stimulation. Polypeptide administration may be as described below, or may extend for a longer period of time, depending on the indication. Preferably, the polypeptides employed in the pharmaceutical compositions and vaccines are complementary, as described above. A particularly preferred combination contains polypeptides that comprise immunogenic portions of M15, Ldp23, Lbhsp83, Lt-1 and LbeIF4A, Lmsp1a, Lmsp9a, and MAPS-1A. Soluble Leishmania antigens, with or without additional polypeptides, may also be employed.

Routes and frequency of administration, as well as dosage, for the above aspects of the present invention will vary from individual to individual and may parallel those currently being used in immunization against other infections, including protozoan, viral and bacterial infections. In general, the pharmaceutical compositions and vaccines may be administered by injection (e.g., intracutaneous, intramuscular, intravenous or subcutaneous), intranasally (e.g., by aspiration) or orally. Between 1 and 12 doses may be administered over a 1 year period. For therapeutic vaccination (i.e., treatment of an infected individual), 12 doses are preferably administered, at one month intervals. For prophylactic use, 3 doses are preferably administered, at 3 month intervals. In either case, booster vaccinations may be given periodically thereafter. Alternate protocols may be appropriate for individual patients. A suitable dose is an amount of polypeptide or DNA that, when administered as described above, is capable of raising an immune response in an immunized patient sufficient to protect the patient from leishmaniasis for at least 1–2 years. In general, the amount of polypeptide present in a dose (or produced in situ by the DNA in a dose) ranges from about 100 ng to about 1 mg per kg of host, typically from about 10 µg to about 100 µg. Suitable dose sizes will vary with the size of the patient, but will typically range from about 0.1 mL to about 5 mL.

In another aspect, this invention provides methods for using one or more of the polypeptides described above to diagnose Leishmania infection in a patient using a skin test. As used herein, a "skin test" is any assay performed directly on a patient in which a delayed-type hypersensitivity (DTH) reaction (such as induration and accompanying redness) is measured following intradermal injection of one or more polypeptides as described above. Such injection may be achieved using any suitable device sufficient to contact the polypeptide or polypeptides with dermal cells of the patient, such as a tuberculin syringe or 1 mL syringe. Preferably, the reaction is measured at least 48 hours after injection, more preferably 72 hours after injection.

The DTH reaction is a cell-mediated immune response, which is greater in patients that have been exposed previously to a test antigen (i.e., an immunogenic portion of a polypeptide employed, or a variant thereof). The response may measured visually, using a ruler. In general, induration that is greater than about 0.5 cm in diameter, preferably greater than about 1.0 cm in diameter, is a positive response, indicative of Leishmania infection, which may or may not be manifested as an active disease.

The polypeptides of this invention are preferably formulated, for use in a skin test, as pharmaceutical compositions containing at least one polypeptide and a physiologically acceptable carrier, as described above. Such compositions typically contain one or more of the above polypeptides in an amount ranging from about 1 µg to 100 µg, preferably from about 10 µg to 50 µg in a volume of 0.1 mL. Preferably, the carrier employed in such pharmaceutical compositions is a saline solution with appropriate preservatives, such as phenol and/or Tween 80™.

The inventive polypeptides may also be employed in combination with one or more known Leishmania antigens in the diagnosis of leishmaniasis, using, for example, the skin test described above. Preferably, individual polypeptides are chosen in such a way as to be complementary to each other. Examples of known Leishmania antigens which may be usefully employed in conjunction with the inventive polypeptides include K39 (Bums et al., *Proc. Natl. Acad. Sci. USA*, 1993 90:775–779).

The following Examples are offered by way of illustration and not by way of limitation.

EXAMPLES

Example 1

Preparation of M15

This Example illustrates the preparation of a Leishmania antigen M15, having the sequence provided in SEQ ID NO:2.

An *L. major* (Friedlan strain) amastigote cDNA expression library prepared in the λZAP II vector (Stratagene, La Jolla, Calif.) was screened according to manufacturer's instructions using sera obtained from *L. major* infected BALB/c mice (8 weeks post inoculation). Approximately 40,000 plaques were screened and four clones expressing reactive antigens were purified to homogeneity by two subsequent rounds of low density screening. Bluescript phagemid inserts were excised from positive clones for further analysis. An EcoRI/SstII restriction fragment from the 5' end of one partial cDNA insert isolated during first round screening (pLmal-1) was subsequently used as a probe to rescreen for clones containing full length cDNA inserts. The probe was labeled to high specific activity (~$10^9$ cpm/µg) with [$\alpha$-$^{32}$P]dCTP using the random primer method and was used to screen ~10,000 plaques of the *L. major* expression library described above. Positive clones were compared by restriction enzyme digestion and the clone with the largest insert (pfl1-1) was chosen for subsequent analysis.

DNA sequence analyses were performed on an Applied Biosystems automated sequencer using Taq polymerase and dye coupled ddNTP terminators or dye-labeled sequencing primers. The complete sequence of the 2685 bp insert was determined using a combination of primer-directed sequencing and by sequencing a series of overlapping Exonuclease III deletion subclones generated using the Erase-a-base system (Promega, Madison, Wis.). The sequence of this insert is provided in SEQ ID NO:1, and the deduced amino acid sequence is provided in SEQ ID NO:2.

The complete insert of clone pf1-1 was excised by digestion with BamHI/KpnI and was subcloned in frame into BamHI/KpnI digested pQE31 (QUIAGEN) to generate the construct pM151A. *E. coli* containing this construct inducibly expressed high levels of the *L. major* antigen encoded by pfl1-1 (designated as M15) with the addition of a 6-histidine tag at the amino terminus. Large volume cultures (500 ml) of *E. coil* host cells containing the pM151A construct were induced to express recombinant protein by the addition of 2 mM IPTG at mid-log phase of growth. Growth was continued for 4 to 5 hours and bacteria were then pelleted and washed once with cold PBS. Bacteria ere resuspended in 20 ml of lysis buffer (50 mM Na$_2$HPO$_4$, pH 8.0, 300 mM NaCl, 10 mM β-mercaptoethanol) containing 20 mg of lysozyme and were lysed by a 1 hour incubation at 4° C. followed by brief sonication. Insoluble material was removed by centrifugation at 10,000×g for 10 minutes and although the recombinant protein was found to be evenly distributed between the soluble and insoluble fractions the insoluble material was discarded at this point. Recombinant protein containing the amino terminal histidine tag was affinity purified using Ni-NTA resin (QIAGEN) according to the manufacturer's recommendations. Briefly, 8 ml of Ni-NTA resin resuspended in lysis buffer was added to the soluble lysate fraction and binding was conducted with constant mixing for 1 hour at 4° C. The mixture was then loaded into a gravity flow column and the non-binding material was allowed to flow through. The Ni-NTA matrix was washed 3 times with 25 ml of wash buffer (50 mM Na$_2$HPO$_4$, pH 6.0, 300 mM NaCl, 10 mM β-mercaptoethanol) and bound material was eluted in 25 ml of elution buffer (50 mM Na$_2$HPO$_4$, pH 5.0, 300 mM NaCl, 10 mM β-mercaptoethanol). The eluted material was then dialyzed against 3 changes of PBS, sterile filtered and stored at −20° C. The purified recombinant protein was shown by SDS-PAGE analysis to be free of any significant amount of *E. coli* protein. A small number of bands of lower molecular weight were assumed to be proteolytic products of the *L. major* antigen based on their reactivity by western blot analysis. A high titre polyclonal antisera against M15 was generated in rabbits by repeated subcutaneous injection of recombinant protein. Western blot analysis of lysates from *L. major* promastigotes and amastigotes using this antisera indicated that the protein is constitutively expressed throughout the parasite lifecycle.

Example 2

Preparation of Ldp23

This Example illustrates the preparation of a Leishmania antigen Ldp23, having the sequence provided in SEQ ID NO:4.

A. Purification of MHC Class II-associated Peptides from P388D1 Macrophages Infected with *L. donovani*

To ascertain that in vitro infection of macrophages would load their MHC class II molecules with parasite peptides, initial experiments were carried out to test the ability of *L. donovani*-infected macrophage cell line P388D1 to present parasite antigens to *L. donovani* specific T-cells. This macrophage cell line was chosen because it has the same H-2 haplotype as the BALB/c mouse, which is a strain of mouse moderately susceptible to *L. donovani* infection and selected to conduct the in vivo experiments. Using a proportion of 3–5 parasites per cell and an initial incubation at room temperature for 4–6 hours follows by 37° C. for 24–48 hours, close to 90% of the macrophages were infected. The level of MHC class II molecule expression, as determined by FACS analysis, indicated that infection did not cause an effect on the levels of MHC class II expression when compared to non-infected control cells.

To test the ability of the *L. donovani*-infected P388D1 cells to present parasite antigens, macrophages were infected as indicated above and incubated at 26° C. for 6 hours, and then as 37° C. for either 24, 48 or 72 hours. At each of these time points the non-adherent cells and free parasites were washed out and the adherent cells were mechanically dislodged, washed and fixed with paraformaldehyde. These cells were then used as antigen presenting cells (APCs) for purified lymph node T-cells from BALB/c mice immunized with *L. donovani* promastigotes. To generate these anti-*L. donovani* specific T-cells, BALB/c mice (H-$2^d$) of both sexes (The Jackson Laboratory, Bar Harbor, Me.) were immunized at 8 to 14 weeks of age in the rear foot pad with 5–10×$10^6$ *L. donovani* promastigotes emulsified in complete Freünd's adjuvant (CFA) (Difco Laboratories, Madison, Mich.) as described in Rodrigues et al., *Parasite Immunol.* 14:49 (1992). The draining lymph nodes were excised 8 days after the immunization and T-cells were purified in an anti-mouse Ig column to remove the B cells, as described in Bunn-Moreno and Campos-Neto, *J. Immunol.* 127:427 (1981), followed by a passage through a Sephadex G10 column to remove the macrophages.

Figure 1:
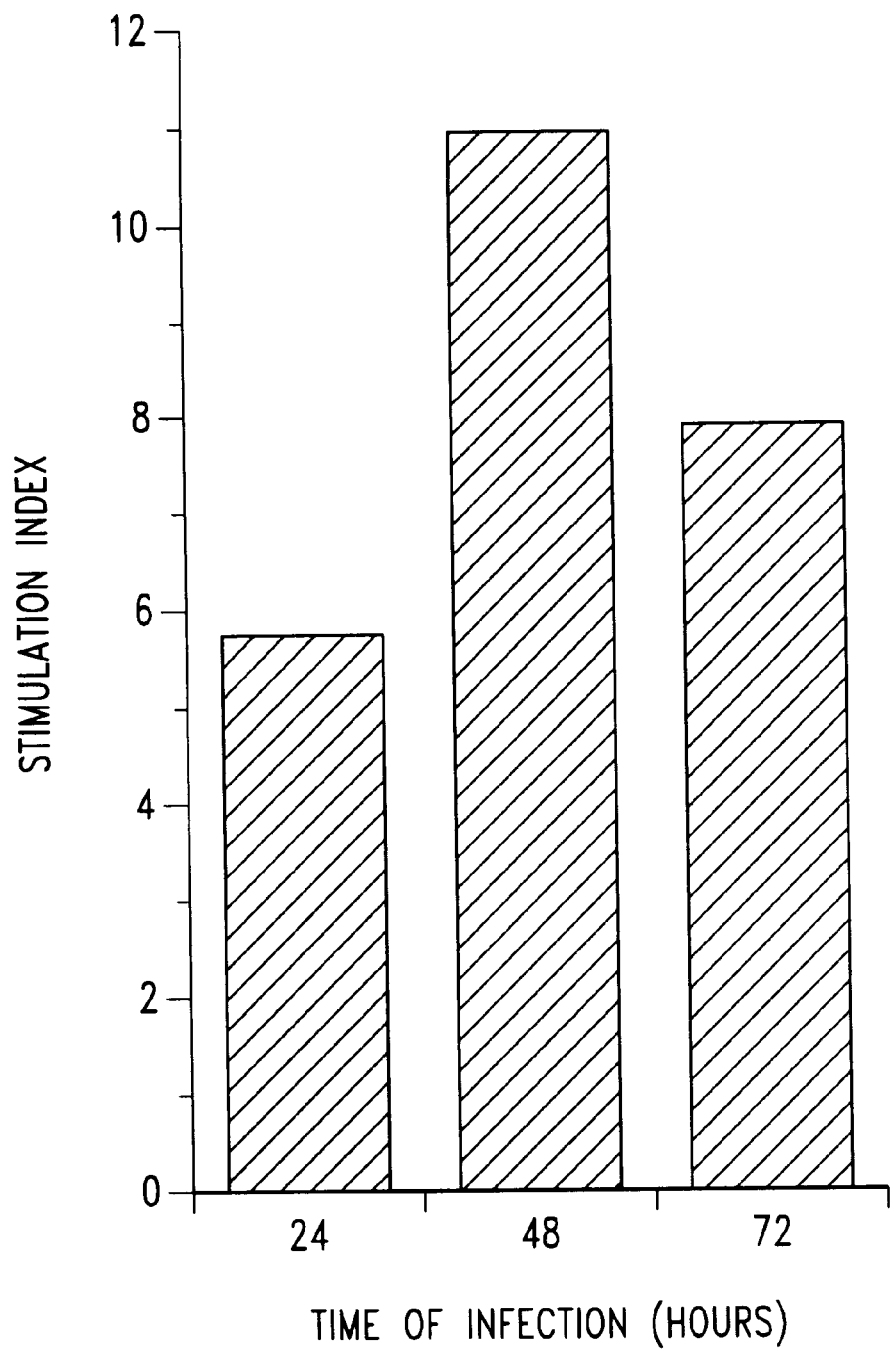
FIG. 1 shows the stimulation of proliferation of T-cells obtained from L. donovani-immunized BALB/c mice (represented by stimulation index) by L. donovani-infected macrophages after incubation for 24, 48 and 72 hours.

Stimulation index was calculated by dividing the cpm obtained for the cells cultured in the presence of infected P388D1 macrophages by the cpm obtained for the cells cultured in the presence of non-infected macrophages, but subjected to the same conditions as the infected macrophages. The results shown FIG. 1 indicate that *L. donovani*-infected P388D1 macrophage process parasite antigens and that optimal presentation occurs after 48 hours of infection. No stimulation of the T-cells by the non-infected macrophages was observed.

To isolate the MHC class II associated *L. donovani* peptides, P388D1 macrophages were infected with *L. donovani* promastigotes for an initial incubation of 6 hours at room temperature. The cultures were then transferred to 37° C. for the remainder of the 48 hour incubation period. At a ratio of 3–5 parasites per macrophage nearly 90% of the macrophages were infected after 24 hours of incubation at 37° C.

The MHC class II molecules were then affinity-purified. Approximately 1.5×$10^{10}$ *L. donovani*-infected or an equal number of non-infected P388D1 macrophages were used for each purification. The cells were harvested, washed with PBS and incubated for 30 minutes in cold lysis buffer (PBS, 1% Nonidet P40, 25 mM iodoacetamide, 0.04% sodium azide, 1 mM aprotinin and 1 mM PMSF). The insoluble material was removed by centrifugation at 40,000 g for 1 hour and the supernatant was recycled overnight at 4° C. over a 5 ml anti-MHC class II molecules (H-$2^d$) Sepharose column (Protein G Sepharose column to which the monoclonal antibody MK-D6 has been bound). Culture supernatants of MK-D6 hybridoma cells (American Type Culture Collection, Rockville, Md.) were employed as the source for anti-MHC class II (H-$2^d$) monoclonal antibody. The column was washed with 50 ml of lysis buffer and then with 50 ml of PBS containing 0.5% octyl glucopyranoside detergent. Bound molecules were eluted from the column with 1M acetic acid in 0.2% NaCl. The MHC/peptide molecules were separated from the IgG (MK-D6 monoclonal antibody) using a Centricon 100 filter unit (Amicon Division, W.R. Grace & Co., Beverly, Mass.). The peptides were then dissociated from the class II molecules by the addition of acetic acid to 2.5M, followed by separation using a Centricon 10 filter unit. The resulting peptide preparation, present in the low molecular weight sample, was then dried using a speed vac concentrator (Savant Instrument Inc., Farmingdale, N.Y.).

The peptides were redissolved in 200 μl of 0.05% TFA and separated by reverse-phase high performance liquid chromatography (RP-HPLC) using a 2.1 mm×25 cm Vydac C-18 column at a flow rate of 0.15 ml/min employing a 1 to 30% acetonitrile gradient (60 min) followed by a 30 to 60% gradient (30 min) and then a 60 to 80% gradient (90–110 min). Non-infected P388D1 cells were similarly processed to serve as background control for endogenous MHC class II associated peptides. FIG. 2 shows a representative experiment; four distinct peaks which are present only in the material isolated from infected macrophages (panel B), and not in the material isolated from uninfected macrophages (panel A) are indicated.

Out of three independent peptide extractions, twenty five distinct HPLC peptide peaks were isolated from *L. donovani*-infected macrophages and were subjected to protein sequence analysis using automated Edman degradation on an Applied Biosystems 477 gas-phase protein sequencer. Protein sequence and amino acid analysis were performed by the W.M. Keck Foundation, Biotechnology Resource Laboratory, Yale University. New Haven, Conn. In practically all determinations, no assignment could be made for the first position. Also, in most cases the definition of the amino acid residues of the 10–15 positions was based on the quantitative dominance of one residue over others. Using this approach, the sequences obtained for several peptides showed the presence of 3–6 different residues in many of the 10–15 sequence cycles analyzed for each determination, reflecting a mixture of peptides. In addition, sequences could not be obtained for some peaks because the peptides were blocked. Notwithstanding, three peptides sequences were determined. Amino-acid sequences were searched for identity with proteins in the GenBank database using the GENPETP, PIR and SWISSPROT programs. The sequence data base analysis revealed that one of the peptides was highly homologous to glyceraldehyde-3-phosphate dehydrogenase of various species. Another peptide had homology with elongation factor of several species, including Leishmania. The third sequence was not clearly related to any known proteins, and is shown below:

XQXPQ(L/K)VFDEXX (SEQ ID NO:11).

B. Cloning and Sequencing of the Ldp23 Gene

In order to retrieve the *L. donovani* protein that was processed into a peptide associated with the MHC class II molecules of infected macrophages, the peptide sequence of uncertain origin was chosen to guide the strategy for cloning the corresponding parasite gene. A DNA fragment was initially amplified from *L. donovani* promastigote cDNA by PCR. The sense primer was a peptide derived oligonucleotide (5'>GGAATTCCCCInCAGCTInGTInTTCGAC<3') (SEQ ID NO:12) containing an EcoRI restriction endonuclease site (underlined). The bases were selected following the preferential codon usage of *L. donovani*, as described in Langford et al., *Exp. Parasitol.* 74:360 (1992). Inosine was used for the residues of positions 4, 6 and 7 because of the low codon usage assurance for the corresponding amino acids. In addition, the carboxyl-terminal L-glutamic acid was not included for the design of the primer. The antisense primer was a poly-thymidine oligonucleotide (oligo dT, downstream primer) containing a XhoI restriction endonuclease site.

The gene fragment was amplified from a *L. donovani* promastigote cDNA preparation using the following reaction conditions: one cycle of 3 min at 94° C. immediately followed by 35 cycles of 1 min at 94° C., 1 min at 45° C. and 1 min at 72° C. The *L. donovani* cDNA was prepared from $5\times10^7$ washed promastigote forms harvested at the log growth phase (3 days culture). The cDNA was obtained using an Invitrogen cDNA cycle™ kit (Invitrogen Co., San Diego, Calif.). Oligonucleotide primers were synthesized by the DNA Synthesis Laboratory, Department of Pathology, Yale University School of Medicine.

The PCR products were analyzed by gel electrophoresis. Only one band of approximately 300 bp was obtained. This fragment was cloned and its sequence confirmed the sequence of the peptide-based primer including the glutamic acid codon, deliberately not included in the primer sequence.

The PCR amplified gene fragment was ligated into the pCR™ vector using the TA cloning system (Invitrogen Co., San Diego, Calif.). Transformants were selected in LB medium containing 100 µg/ml ampicillin and the plasmid DNA was isolated using the Wizard™ Minipreps DNA purification kit (Promega Co., Madison, Wis.). Insert DNA was released with the restriction enzymes EcoRI and XhoI (New England Biolabs, Beverly, Mass.), purified from an agarose gel electrophoresis and labeled with $^{32}P$ using a random priming method (Megaprime Labeling Kit, Amersham Life Science, Buckinghamshire, England).

This DNA fragment was used as probe to screen a *L. donovani* promastigote cDNA library as described in Skeiky et al., *Infect. Immun.* 62:1643 (1994). An approximately 650 bp cDNA (Ldp23) was excised from the phagemid by in vivo excision using the Stratagene protocol. DNA sequencing was performed using the Sequenase version 2 system (DNA sequencing kit) in the presence or absence of 7-deaza-GTP (United States Biochemical, Cleveland, Ohio). The sequence is provided as SEQ ID NO:3, and shows complete homology with the original 300 bp PCR fragment. A 525 bp open reading frame containing an ATG codon that follows the last 4 bases of the spliced leader sequence and 3 stop codons adjacent to the poly A tail was identified. This frame also codes the carboxyl terminal sequence (KVFDE) (SEQ ID NO:13) of the purified MHC class II associated peptide.

The sequence analysis of the deduced protein sequence revealed one potential glycosylation site (Asn-Cys-Ser) at positions 68–70.

Sequence analysis was performed using the University of Wisconsin Genetics Computer Group Programs and the GenBank and EMBL data bases of protein and DNA sequences. The search for homology of the Ldp23 gene with known sequences revealed no significant homology.

C. Bacterial Expression and Purification of Recombinant Protein

The recombinant *L. donovani* peptide donor protein was produced in *E. coli* transformed with the pGEX 2T expression vector in which the Ldp23 gene was subcloned in frame. PCR was used to subclone the cloned gene in frame into the expression vector pGEX 2T. Primers containing the appropriate restriction site enzymes, initiation and termination codons were: 5'>GGATCCATGGTCAAGTCCCAC-TACATCTGC<3' (SEQ ID NO:14) for the upstream primer and 5'>GAATTCAGACCGGATAGAAATAAGC-CAATGAAA<3' (SEQ ID NO:15) for the downstream primer (restriction sites of BamHI and EcoRI are underlined respectively). PCR conditions were as indicated above for the amplification of the original peptide related DNA fragment. The template used was pBluescript plasmid containing the cloned gene from the cDNA library.

Overexpression of the recombinant fusion protein was accomplished by growing the transformed *E. coli* (DH5α) and inducing the tac promoter with 1 mM isopropyl-β-thiogalactopyranoside (IPTG) (Stratagene, La Jolla, Calif.). Cells were collected, centrifuged, and analyzed for the presence of the fusion protein by SDS-PAGE. A glutathione-S-transferase fusion protein of 43–44 kD was produced, indicating a leishmanial protein of approximately 18 kD, as glutathione-S-transferase (GST) has a MW of 26 kD. However, the fusion protein was very insoluble and therefore could not be purified by affinity chromatography using a glutathione column. The use of low concentrations of detergents like SDS, sarcosyl, deoxycolate, and octyl-glucopyranoside during the extraction steps was efficient to solubilize the protein but unfortunately prevented its binding to the glutathione column. Other maneuvers, such as the growth of the *E. coli* and incubation and induction of the tac promoter with IPTG at 33° C., did not improve the protein solubility. However, the purification was achieved by preparative SDS-PAGE. The band was visualized with 0.1M KCl, cut and electroeluted from the gel followed by extensive dialysis against PBS and concentration on Centricon 10 filters.

Figure 3A:
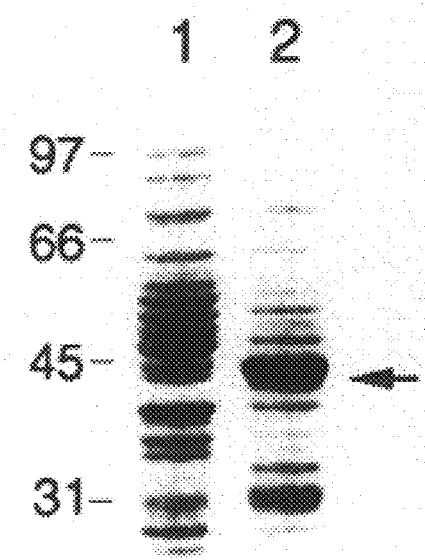
FIG. 3 illustrates the expression and purification of the Leishmania antigen Ldp23 as a recombinant fusion protein. Panel A shows a Coomassie blue-stained SDS-PAGE gel of lysed E. coli without (lane 1) and with (lane 2) IPTG induction of Ldp23 expression. Arrow indicates the recombinant fusion protein. Panel B shows the fusion protein following excision from a preparative SDS-PAGE gel, electroelution, dialysis against PBS and analytical SDS-PAGE.
Figure 3B:
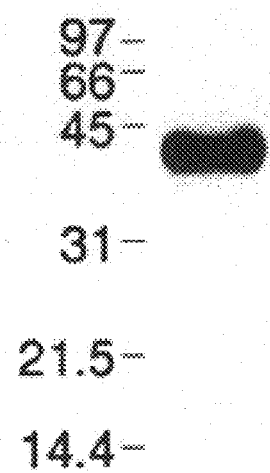

Approximately 500 µg of purified protein was obtained. The purified protein is shown in FIG. 3. In panel A, *E. coli* (DH5α) transformed with the expression vector pGEX 2T containing the Ldp23 gene was grown in LB medium and the tac promoter was induced with IPTG for 3 hours. The cells were pelleted, resuspended in loading buffer and submitted to SDS-PAGE (10%) under reducing condition. The gel was stained with Coomassie blue. Lane 1 shows the uninduced *E. coli* and land 2 shows the induced *E. coli*. The arrow indicates the recombinant protein. Panel B shows the protein prepared as in panel A and submitted to a preparative SDS-PAGE. The band corresponding to the overexpressed recombinant fusion protein was identified by KCl, cut out, electroeluted from the gel strip, dialyzed against PBS and submitted to analytical SDS-PAGE (12%). Numbers on the left side indicate the molecular weights of the markers. Attempts to further purify the leishmanial protein by cleaving it out from the fusion protein GST with thrombin were unsuccessful.

D. Expression of Ldp23

To ascertain that the Ldp23 peptide is expressed in Leishmania organisms, a Northern blot analysis was performed using RNA prepared from different promastigote growth phases (logarithmic and stationary) and from the amastigote form of these parasites.

The RNA was prepared from $2 \times 10^7$ parasite cells using the Micro RNA isolation kit (Stratagene, La Jolla, Calif.) according to the company's recommended instructions. RNA was prepared from *L. donovani* promastigotes (logarithmic growth phase); from *L. major* promastigotes (logarithmic and stationary growth phases); from *L. amazonensis*, both promastigotes (logarithmic and stationary growth phases) and amastigotes purified from CBA/J infected mice; and from *L. pifanoi*, both promastigotes (logarithmic and stationary growth phases) and amastigotes (from axenic culture medium). *L. donovani* (1S strain), *L. amazonensis* (MHOM/BR/77/LTB0016), *L. major* (MHOM/IR/79/LRC-L251) and *L. pifanoi (MHOM/VE/60/Ltrod)* promastigotes were grown and maintained at 26° C. in Schneider's medium containing 20% FCS and 50 μg/ml gentamicin. The amastigote forms of *L. amazonensis* were obtained by differential centrifugation of a "pus-like" foot pad lesion of a CBA/J mouse infected for 6 months with this parasite. *L. pifanoi* amastigotes were obtained from axenic culture as previously reported by Pan et al., *J. Euk. Microbiol.* 40:213 (1993).

The hybridization was carried out at 45° C. in the presence of 50% formamide, 5×Denhardt's solution, 0.1% SDS, 100 μg/ml single stranded salmon sperm DNA and 5×SSPE using 0.45 μm Nytran membrane filters (Schleicher & Schuell, Keene, NH). The probe was the $^{32}$P labeled Ldp23 gene.

Figure 4:
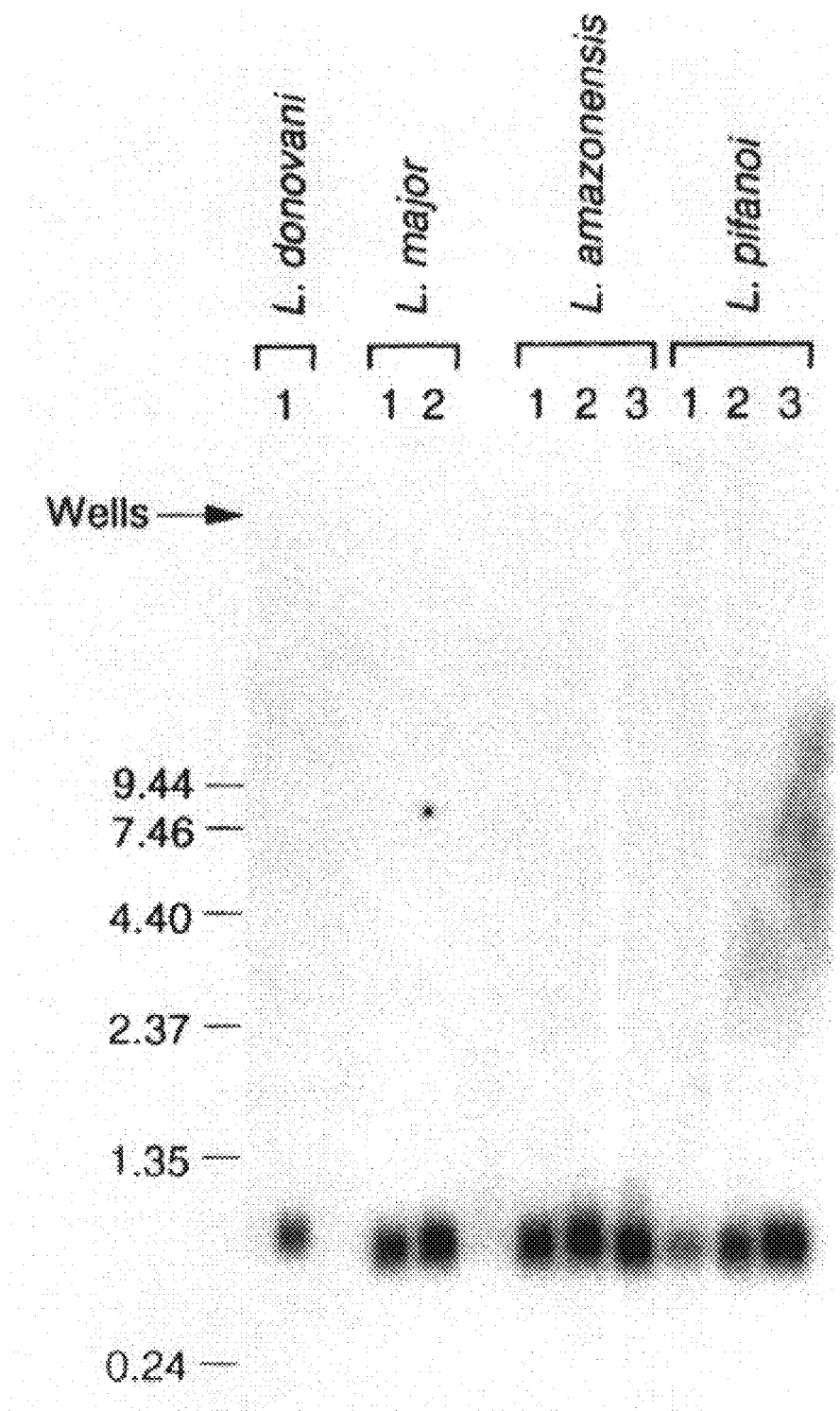
FIG. 4 presents a Northern blot analysis of total RNA prepared from L. donovani, L. major, L. amazonensis and L. pifanoi with a $^{32}P$ labeled Ldp23 gene. 1, 2 and 3 refer to RNA obtained from promastigotes at the logarithmic growth phase, promastigotes at the stationary growth phase and amastigote forms, respectively.

FIG. 4 shows that one single RNA band of 680 bp was observed for all growth phases and forms of all tested Leishmania. Within FIG. 4, the numbers 1, 2 and 3 refer to RNA obtained from promastigotes at the logarithmic growth phase, promastigotes at the stationary growth phase and amastigote forms, respectively, and the numbers on the left side indicate the molecular weights of the markers in base pairs. This result is consistent with the corresponding gene size (525 bp) and with the molecular weight of the expressed protein and points to the ubiquitous distribution and expression of this gene within the genus Leishmania.

E. Induction of Anti-*L. donovani* Antibody Response in Mice and Rabbits by Purified Recombinant Protein In order to evaluate the immunogenicity of the recombinant leishmanial protein, and to investigate its expression in the parasites, mice and rabbits were immunized with the GST-fusion protein in CFA. BALB/c mice were immunized in the rear foot pad with 5–10 μg of protein emulsified in CFA. Protein concentration was determined using the Bio-Rad Protein Assay reagent (Bio-Rad Laboratories, Richmond, Calif.). The mice were boosted 7 days later with 5–10 μg of protein emulsified in incomplete Freund's adjuvant (IFA) inoculated into the peritoneal cavity. The mice were bled 7 days after the second immunization. New Zealand white rabbits (Millbrook Farm, Amherst, Mass.) were immunized according to the following protocol: one intra-muscular (IM) injection of 25–30 μg of purified recombinant protein emulsified in CFA into each thigh on day one; one IM injection of 25–30 μg of purified protein emulsified in IFA into each shoulder on day 7; on day 15, 25–30 μg of the purified protein in PBS was injected into the subcutaneous tissue. The rabbit was bled 7 days after the last immunization.

Sera were prepared and the anti-Leishmania antibody response was measured by Western blot analysis and by FACScan. In both cases *L. donovani* promastigotes were used as antigen. Approximately $2 \times 10^6$ *L. donovani* promastigotes were grown in Schneider's medium for 3 days (log phase), were washed with PBS, lysed with SDS-PAGE loading buffer and submitted to electrophoresis under reducing conditions using a 15% polyacrylamide gel. The proteins were transferred onto 0.45μ Immobilon-P transfer membrane (Millipore Co., Bedford, Mass.) using a wet-type electroblotter (Mini Trans-Blot Electrophoretic Transfer Cell, Bio Rad Life Science Division, Richmond, Calif.) for 2 hours at 50 V. The membranes were blocked overnight at room temperature with PBS containing 3% normal goat serum (NGS), 0.2% Tween-20 and 0.05% sodium azide, followed by 3 washes with PBS. The blots were then incubated for 3–4 hours at 4° C. with a 1/200 dilution of pre-immune rabbit serum (lane A, FIG. 5) or with the same dilution of anti-fusion protein rabbit antiserum (lane B, FIG. 5). The sera was previously absorbed 2× with non-viable desiccated *Mycobacterium tuberculosis* H-37 RA (Difco Laboratories, Detroit, Mich.) and were diluted in PBS containing 1% NGS and 5% powdered non-fat bovine milk (Carnation, Nestlé Food Company, Glendale, Calif.). The membranes were then washed with PBS, incubated for 1 hour at room temperature with goat anti-rabbit IgG antibody conjugated with alkaline phosphatase (Promega, Madison, Wis.), washed once with PBS and 2× with veronal buffer pH 9.4. The reaction was visualized using the substrate mixture 5-bromo-4-chloro-3-indoyl-phosphate and nitroblue tetrazolium (Kirkegaard & Perry Laboratories Inc., Gaithersburg, Md.) according to the manufacturer's instructions.

Figure 5A:
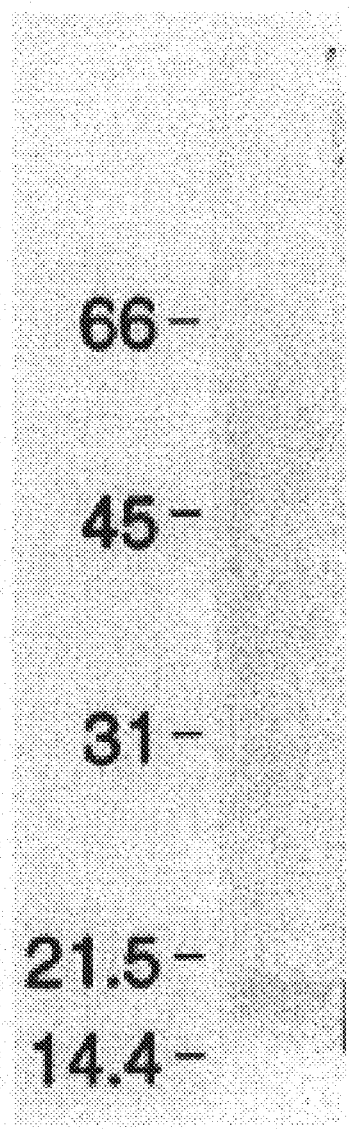
FIG. 5 shows a Western blot analysis of L. donovani promastigote antigens incubated with pre-immune rabbit serum (lane A) or with anti-Ldp23 rabbit antiserum (lane B).
Figure 5B:
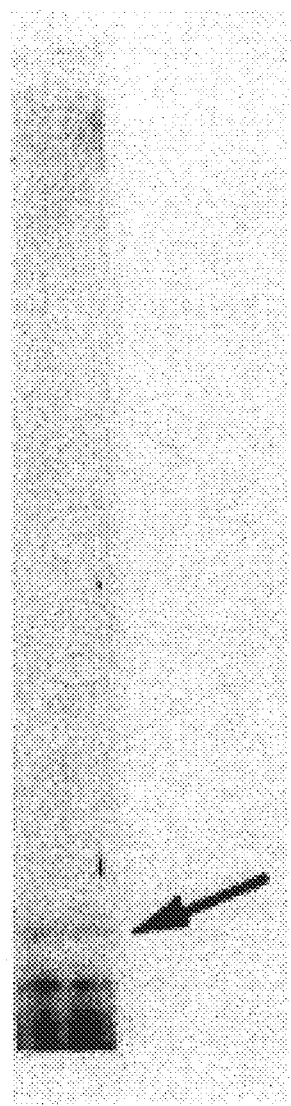
Figure 6:
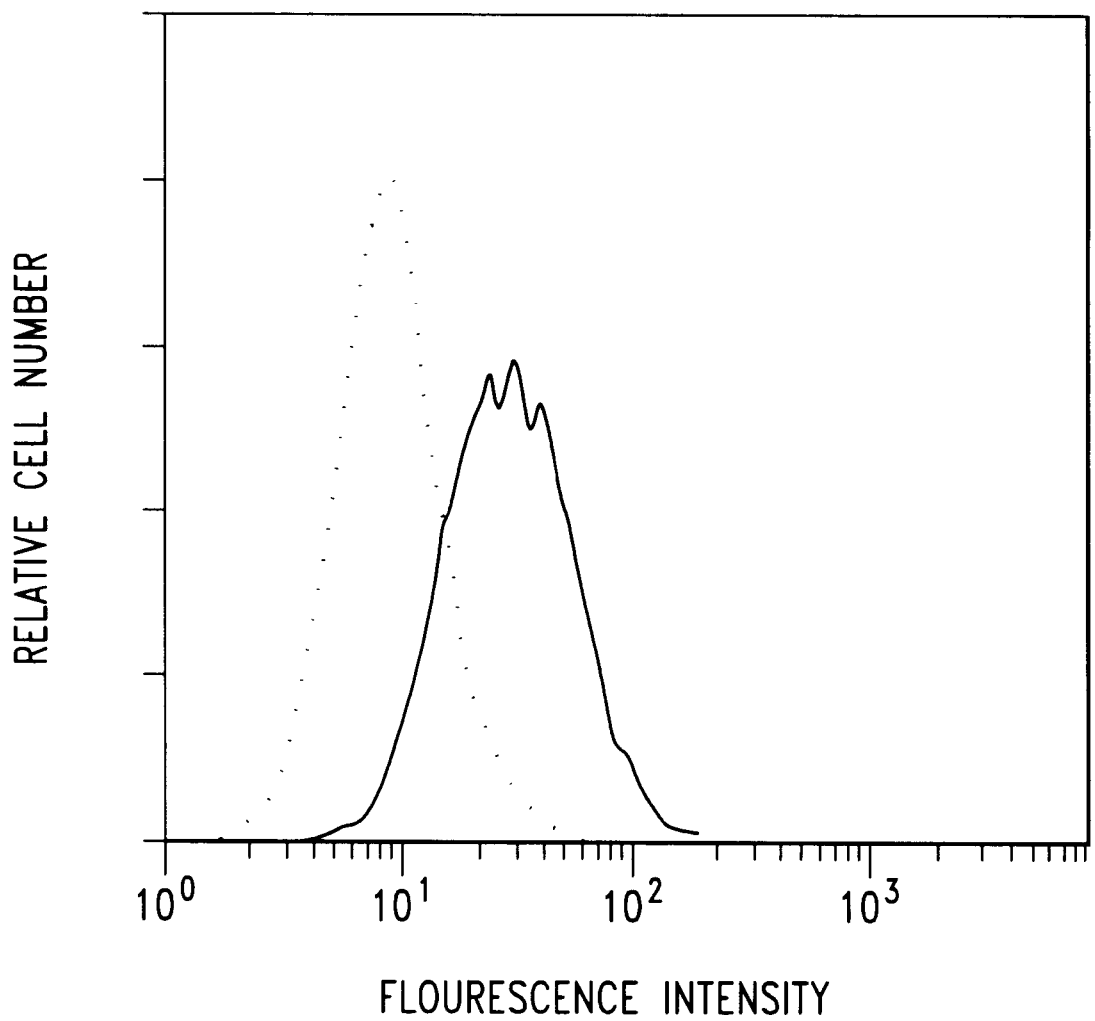
FIG. 6 illustrates the surface expression of Ldp23 on live L. donovani promastigotes. The dotted line shows the indirect immunofluorescence performed using pre-immune mouse serum and the solid line shows the result obtained with mouse anti-GST-Ldp23 antiserum. Fluorescence intensity was analyzed by FACScan.

FIG. 5 shows that the rabbit anti-recombinant protein antiserum detects a single protein of 23 kDa (Ldp23) in the Leishmania crude extract antigen preparation. No bands were observed when an anti-GST antiserum was used (not shown). Moreover, the FACScan analysis (FIG. 6) shows that the antibody induced by the recombinant Ldp23 reacts with intact live *L. donovani* promastigotes, thus pointing to a cell surface expression of this molecule on these organisms. The dotted line in FIG. 6 shows the indirect immunofluorescence performed using pre-immune mouse serum and the solid line in FIG. 6 shows the result obtained with mouse anti-GST-Ldp23 antiserun. Both sera were diluted at 1/100. Parasites were washed with staining buffer and incubated with FITC conjugated goat anti-mouse immunoglobulin antibody. Fluorescence intensity was analyzed by FACScan.

Figure 7:
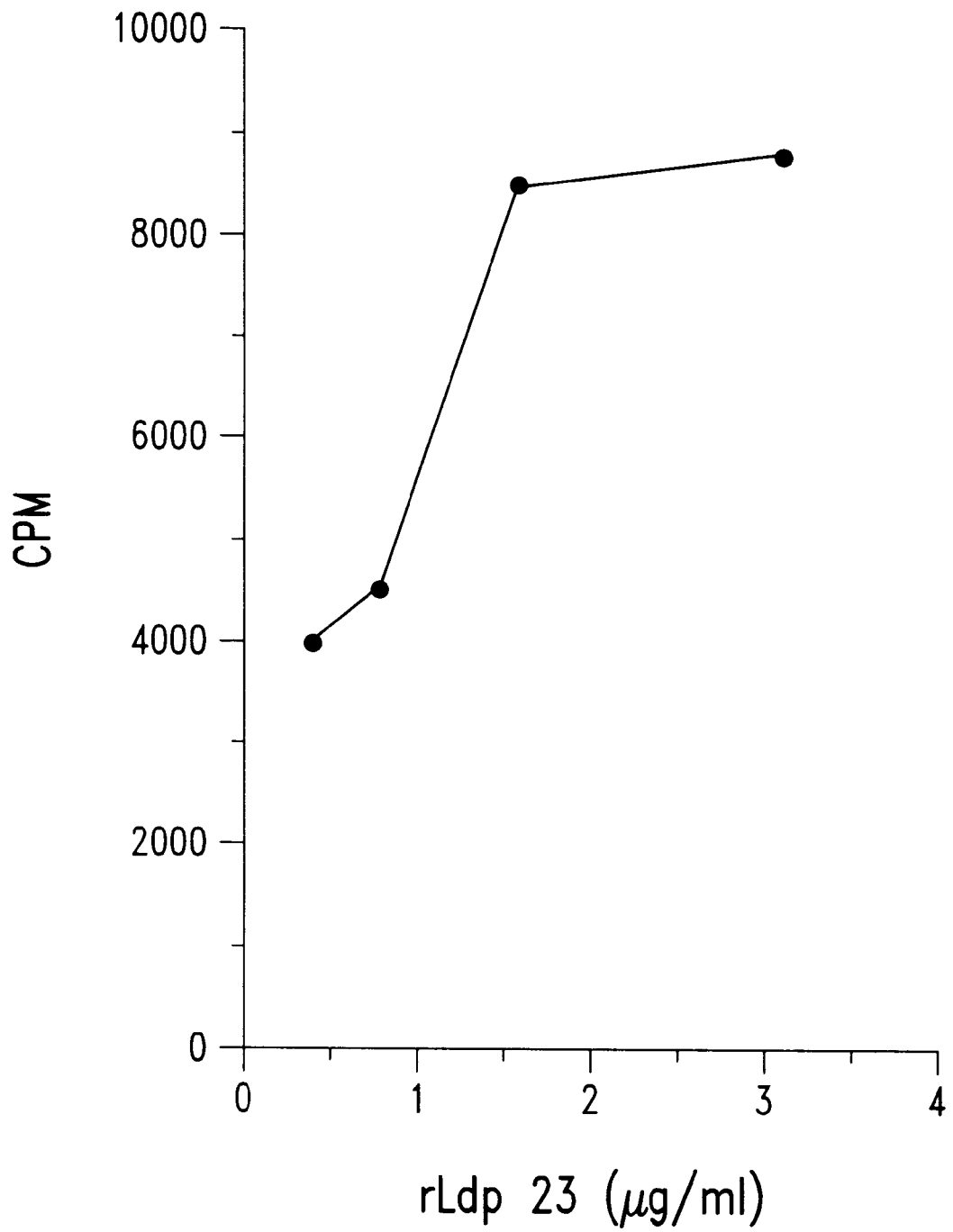
FIG. 7 shows the stimulation of Leishmania-specific T-cell proliferation by Ldp23. The results are presented as relative cell number as a function of fluorescence intensity.

F. Recognition of Recombinant Ldp23 by Leishmania-Specific Lymph Node T-cells To test the responsiveness of T-cells to the Ldp23 protein, two sets of experiments were performed. In the first experiment, lymph node T-cells ($10^5$/well) from BALB/c mice immunized with *L. donovani* promastigotes (as described above) were stimulated to proliferate with $2 \times 10^5$ Mitomycin C-treated normal mononuclear spleen cells (APC) and pulsed with the purified recombinant fusion protein. Proliferation of T-cells was measured at 72 hours of culture. Values are expressed in FIG. 7 as cpm and represent the mean of [$^3$H]TdR incorporation of triplicate cultures. Background cpm of cells (T cells+APC) cultured in the presence of medium alone was 1291. FIG. 7 shows that Leishmania specific T-cells proliferate well and in a dose response manner to recombinant Ldp23. No response was observed when purified GST was added instead of the recombinant fusion protein nor when lymph node T-cells from mice immunized with CFA alone were stimulated to proliferate in the presence of the Leishmanial fusion protein (not shown).

The recognition of the recombinant Ldp23 protein by Leishmania-specific T-cells was also tested using two murine models of leishmaniasis, the L. major highly susceptible BALB/c mice and the L. amazonensis susceptible CBA/J mice as described in Champsi and McMahon-Pratt, Infect. Immun. 56:3272 (1988). These models were selected to investigate the cytokine pattern induced by Ldp23. In the mouse model of leishmaniasis, resistance is associated with Th 1 cytokines while susceptibility is linked to Th 2 responses.

Lymph node cells were obtained 3 weeks after the initiation of infection of BALB/c mice with L. major and the ability of these cells to recognize the recombinant Ldp23 was measured by proliferation and by the production of the cytokines IFN-γ and IL-4. $2\times10^6$ cells obtained from the draining popliteal lymph node of infected mice were cultured for 72 hours in the presence of recombinant Ldp23 or Leishmania lysate. The levels of IFN-γ and IL-4 in culture supernatants were measured by ELISA as previously described (Chatelain et al., J. Immunol. 148:1172 (1992), Curry et al., J. Immunol. Meth. 104:137 (1987), and Mossman and Fong, J. Immunol. Meth. 116:151 (1989)) using specific anti IFN-γ and IL-4 monoclonal antibodies (PharMingen, San Diego, Calif.).

Ldp23 did stimulate these cells to proliferate (not shown) and induced a typical Th 1 type of cytokine response as indicated by the production of high levels of IFN-γ (panel A of FIG. 8) and no IL-4 (panel B of FIG. 8). Stimulation of these cells with a Leishmania crude lysate yielded a mixed Th cytokine profile. Exactly the same pattern of cytokine production was obtained from the CBA/J mice infected with L. amazonensis (not shown). These results clearly indicate that Ldp23 is a powerful and selective activator of the Th 1 cytokines by mouse cells.

Example 3

Preparation of Hsp83

This Example illustrates the preparation of a Leishmania antigen Hsp83, having the sequence provided in SEQ ID NO:6.

A genomic expression library was constructed with sheared DNA from L. braziliensis (MHOM/BR/75/M2903) in bacteriophage λZAP II (Stratagene, La Jolla, Calif.). The expression library was screened with Escherichia coli preadsorbed serum from an L. braziliensis-infected individual with ML. Immunoreactive plaques were purified, and the pBSK(-) phagemid was excised by protocols suggested by the manufacturer. Nested deletions were performed with exonuclease III to generate overlapping deletions for single-stranded template preparations and sequencing. Single-stranded templates were isolated following infection with VCSM13 helper phage as recommended by the manufacturer (Stratagene, La Jolla, Calif.) and sequenced by the dideoxy chain terminator method or by the Taq dye terminator system using the Applied Biosystems automated sequencer model 373A.

Recombinant antigens produced by these clones were purified from 500 ml of isopropyl-β-D-thiogalactopyranoside (IPTG)-induced cultures as described in Skeiky et al.,J. Exp. Med. 176:201–211 (1992). These antigens were then assayed for the ability to stimulate PBMC from Leishmania-infected individuals to proliferate and secrete cytokine. Peripheral blood was obtained from individuals living in an area (Corte de Pedra, Bahia, Brazil) where L. braziliensis is endemic and where epidemiological, clinical, and immunological studies have been performed for over a decade, and PBMC were isolated from whole blood by density centrifugation through Ficoll (Winthrop Laboratories, New York, N.Y.). For in vitro proliferation assays, $2\times10^5$ to $4\times10^5$ cells per well were cultured in complete medium (RPMI 1640 supplemented with gentamicin, 2-mercaptoethanol, L-glutamine, and 10% screened pooled A+ human serum; Trimar, Hollywood, Calif.) in 96-well flat-bottom plates with or without 10 μg of the indicated antigens per ml or 5 μg of phytohemagglutinin per ml (Sigma Immunochemicals, St. Louis, Mo.) for 5 days. The cells were then pulsed with 1 μCi of [$^3$H]thymidine for the final 18 h of culture. For determination of cytokine production 0.5 to 1 ml of PBMC was cultured at $1\times10^6$ to $2\times10^6$ cells per ml with or without the Leishmania antigens for 48 and 72 h.

The supernatants and cells were harvested and analyzed for secreted cytokine or cytokine mRNAs. Aliquots of the supernatants were assayed for gamma interferon (IFN-γ), tumor necrosis factor alpha (TNF-α), interleukin-4 (IL-4), and IL-10 as escribed in Skeiky et al., J. Exp. Med. 181:1527–1537 (1995). For cytokine mRNA PCR analysis, total RNA was isolated from PBMC and cDNA was synthesized by using poly(dT) (Pharmacia, Piscataway, N.J.) and avian mycloblastosis virus reverse transcriptase. Following normalization to β-actin, diluted cDNA was amplified by PCR using Taq polymerase (Perkin-Elmer Cetus, Foster City, Calif.) with 0.2 mM concentrations of the respective 5' and 3' external primers in a reaction volume of 50 μl. The nucleotide sequences of the primary pairs and the PCR conditions used were as described in Skeiky et al., J. Exp. Med. 181:1527–1537 (1995). We verified that our PCR conditions were within the semiquantitative range by initially performing serial dilutions of the cDNAs and varying the number of cycles used for PCR. Plasmids containing the human sequences for IL-2, IFN-γ, IL-4, IL-10, and β-actin were digested, and the DNA inserts were purified after separation on 1% agarose gels. Radiolabeled $^{32}$P probes were prepared by the random priming method. PCR products were analyzed by electrophoresis on 1.5% agarose gels, transferred to nylon membranes, and probed with the appropriate $^{32}$P-labeled DNA insert.

A recombinant clone was identified in the above assays which, following sequence comparison of its predicted amino acid sequence with sequences of other proteins, was identified as a Leishmania braziliensis homolog of the eukaryotic 83 kD heat shock protein (Lbhsp83). The sequence of the clone is provided in SEQ ID NO:5 and the deduced protein sequence is provided in SEQ ID NO:6. On the basis of the homology, this clone, designated Lbhsp83a, appears to lack the first 47 residues of the full length 703 amino acid residues. Lbhsp83 has an overall homology of 94% (91% identity and 3% conservative substitution), 91% (84% identity and 7% conservative substitution) and 77% (61% identity and 16% conservative substitution) with L. amazonensis hsp83, T. cruzi hsp83 and human hsp89, respectively. A second clone (designated Lbhsp83b), which contained the 43 kD C-terminal portion of hsp83 (residues 331 to 703) was also isolated. FIG. 19 presents a comparison of the Lbhsp83 sequence with L. amazonensis hsp83 (Lahsp83), T. cruzi hsp83 (Tchsp83) and human hsp89 (Huhsp89).

The results of proliferation assays using Lbhsp83a are shown in Table 1. Cells from all mucosal leishmaniasis (ML) patients proliferated strongly in response to Lbhsp83a, with stimulation indices (SIs) ranging from 19 to 558 (as compared to 20 to 1,634 for parasite lysate). Proliferation of PBMC from cutaneous leishmaniasis (CL) patients was variable and except for levels in two patients (IV and VII), levels were significantly lower than those of ML patients. By comparison, the proliferative responses of individuals with self-healing CL to Lbhsp83a were similar to those of individuals with ML. However, the responses of all six self-healing individuals to Lbhsp83 were consistently higher than those to Lbhsp83b. This suggests that PBMC from self-healing CL patients preferentially recognize one or more T-cell epitopes located within the amino portion of Lbhsp83.

TABLE 1

In vitro Proliferation of PMBC from *L. braziliensis*-infected Individuals in Response to Lbhsp83

| Group and Patient | Mean [³H] thymidine incorporation [10³ cpm (SD)], SI with: | | |
|---|---|---|---|
| | Lysate | Lbhsp83a | Lbhsp83b |
| ML | | | |
| I | 41.3, (1.3), 294 | 32.5, (6.6), 221 | 46.7, (1.4), 318 |
| II | 44.2, (0.5), 104 | 20, (3.7), 47 | 36.7, (0.76), 86 |
| III | 27.4, (1.5), 150 | 8.1, (1.7), 44 | 9.9, (0.32), 54 |
| IV | 52.7, (3.3), 138 | 54.1, (6.2), 142 | 32.0, (1.3), 84 |
| V | 140.6, (7.6), 308 | 151.8, (57), 333 | 150.4, (7.9), 331 |
| VI | 15.8, (1.8), 20 | 21.3, (4.4), 28 | 14.4, (1.3), 19 |
| VII | 300.1, (9.4), 1634 | 102.1, (7.6), 558 | 41.7, (4.9), 228 |
| CL | | | |
| I | 0.26, (0.0), 1.5 | 0.57, (0.3), 3.3 | 0.43, (0.17), 3.3 |
| II | 55.63, (8.6), 218 | 0.42, (0.0), 1.6 | 0.8, (0.14), 3.2 |
| III | 0.39, (0.5), 4.0 | 3.4, (0.5), 9 | 2.6, (0.9), 6.6 |
| IV | 19.14, (1.3), 87 | 7.17, (0.6), 32 | 5.9, (0.9), 27 |
| V | 0.32, (0.2), 3.0 | 1.47, (0.5), 14 | 0.3, (0.1), 3.0 |
| VI | 0.77, (0.1), 4.7 | 1.44, (0.2), 9 | 1.3, (0.6), 8.0 |
| VII | 4.01, (1.0), 2.0 | 60.3, (8.5), 15 | 66.7, (3.9), 16.6 |
| Self-healing CL | | | |
| I | 19.7, (4.4), 94 | 61.3, (4.6), 293 | 5.0, (2.0), 24 |
| II | 0.6, (0.1), 6.5 | 7.0, (2.0), 79 | 1.2, (0.8), 13 |
| III | 59.6, (7.1), 519 | 49.4, (3.1), 429 | 21.4, (3.7), 186 |
| IV | 0.2, (0.1), 1.6 | 13.1, (1.7), 108 | 0.6, (0.1), 5 |
| V | 27.1, (2.0), 225 | 6.3, (2.6), 52 | 3.0, (1.5), 25 |
| VI | 130.3, (14), 340 | 28.2, (2.9), 74 | 7.7, (3.8), 20 |
| Control (uninfected) | | | |
| I | 0.19, (0.0), 1.4 | 0.18, (0.0), 1.3 | 0.40, (0.16), 2.8 |
| II | 0.31, (0.1), 1.7 | 0.19, (0.0), 1.0 | 0.27, (0.0), 1.5 |
| III | 0.44, (0.2), 4.1 | 0.48, (0.1), 5.0 | 0.51, (0.2), 5.2 |
| IV | 0.4, (0.1), 3.2 | 0.52, (0.2), 5.1 | 0.50, (0.1), 5.0 |

A more detailed analysis of cytokine patterns of PBMC from ML patients was performed by reverse transcriptase PCR. Cytokine mRNAs were evaluated in cells prior to culturing (FIG. 9, lanes O) or following culturing in the absence (lanes-) or presence of the indicated antigen for 48 and 72 h. FIG. 4A shows the results for five of the six ML patients whose PBMC were analyzed. In about half of the ML patients, noncultured (resting) PBMC had detectable levels of mRNA for IFN-γ, IL-2, and IL-4 but not IL-10. CL patient PBMC, however, had IL-10 mRNA in the resting state in addition to mRNAs for the other cytokines tested (FIG. 4B). Following in vitro culture without antigen, the levels of mRNA for IFN-γ, IL-2, and IL-4 in resting cells from ML patients decreased to background levels while IL-10 mRNA levels increased. In contrast, PBMC of most CL patients had stable or increased IL-10 mRNA, while the mRNAs for IL-2, IFN-γ, and IL-4 were reduced to barely detectable levels in the absence of antigen stimulation.

In PBMC of three ML patients, stimulation with lysate resulted in increased expression of mRNA for IFN-γ, IL-2, and IL-4 but not IL-10. By comparison, both Lbhsp83 polypeptides elicited the production of mRNA for IFN-γ and IL-2 from all ML patient PBMC tested. In contrast, profiles of mRNA for IL-10 and IL-4 differed for the two hsp83 polypeptides. Lbhsp83a stimulated the production of IL-10 but not IL-4 mRNA (patients I, II, III, and IV), while Lbhsp83b stimulated the production of IL-4 but not IL-10 mRNA in all six patients.

All CL patients tested responded to both Lbhsp83 polypeptides as well as to the parasite lysate by upregulating the synthesis of mRNAs for IL-2 and IFN-γ, and in two of four patients (I and IV), the level of IL-4 mRNA also increased, indicating stimulation of both Th1 and Th2 cytokines. Interestingly and as in the case of ML patient uncultured PBMC which did not have detectable levels of IL-10 mRNA, Lbhsp83a and not Lbhsp83b stimulated PBMC from one CL patient (IV) to synthesize IL-10 mRNA. However, in the other three patients (I, II, and III) with resting levels of IL-10 mRNA, both rLbhsp83 polypeptides as well as the parasite lysate downregulated the expression of IL-10 mRNA.

Figure 10A:
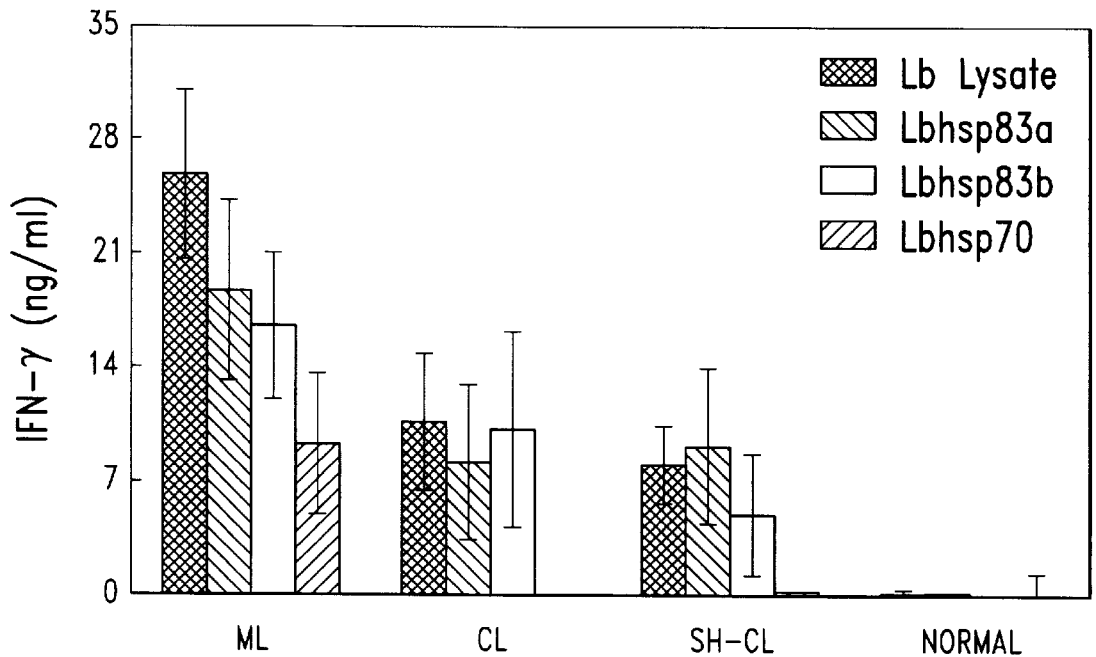

PBMC supernatants were also assayed for the presence of secreted IFN-γ, TNF-α, IL-4, and IL-10. Cells from all ML and self-healing CL patients (seven and six patients, respectively) and from four of seven CL patients were analyzed for secreted IFN-γ following stimulation with both rLbhsp83 polypeptides, parasite lysate and Lbhsp70, an *L. braziliensis* protein homologous to the eukaryotic 70 kD heat shock protein (FIG. 10A). In general, rLbhsp83a stimulated patient PBMC to secrete higher levels of IFN-γ than did rLbhsp83b (0.2 to 36 and 0.13 to 28 ng/ml, respectively). The presence of secreted IFN-γ correlated well with the corresponding mRNA detected by PCR.

Figure 10B:
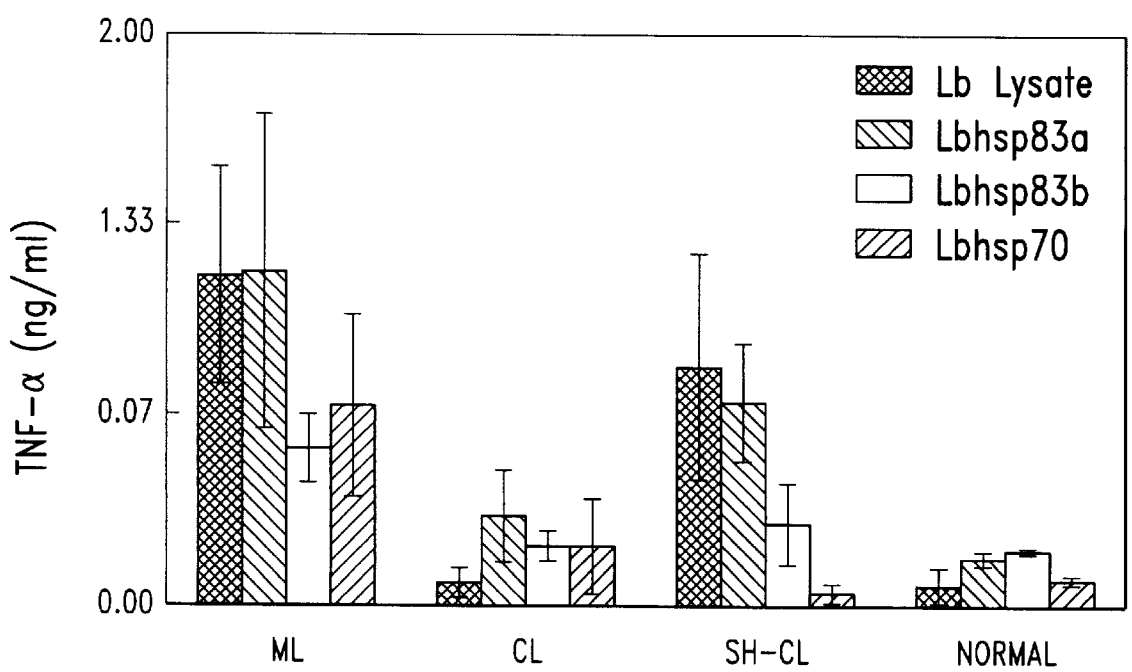

PBMC from four of five ML patients (I, II, V, and VII) had supernatant TNF-α levels (0.8 to 2.2 ng/ml) higher than those detected in cultures of PBMC from uninfected controls following stimulation with parasite lysate (FIG. 10B). Similarly, the same PBMC were stimulated by rLbhsp83 to produce levels of TNF-α in supernatant ranging from 0.61 to 2.9 ng/ml. Compared with those of uninfected controls, PBMC from three (I, V, and VI), five (I, II, IV, V, and VI), and two (II and V) of six individuals analyzed produced higher levels of TNF-α in response to parasite lysate, rLbhsp83a, and rLbhsp83b, respectively. The levels of TNF-α produced by PBMC from CL patients in response to parasite lysate were comparable to those produced by uninfected controls. However, rLbhsp83 stimulated TNF-α production in the PBMC of two of these patients. rLbhsp83a stimulated higher levels of TNF-α production than did rLbhsp83b. In the absence of antigen stimulation, only PBMC from ML patients (five of six) produced detectable levels of supernatant TNF-α (60 to 190 pg/ml).

In agreement with the IL-10 mRNA, IL-10 was detected by ELISA in the antigen-stimulated PMBC culture supernatants from ML and CL patients. The levels (49 to 190 pg) were significantly higher (up to 10-fold) following stimulation with rLbhsp83a compared with those after parallel stimulation of the same cells with rLbhsp83b (FIG. 11). Parasite lysate also stimulated PMBC from some of the patients to produce IL-10. Although rLbhsp83 stimulated PMBC from uninfected individuals to produce IL-10, with one exception, the levels were lower than those observed with patient PMBC. IL-4 was not detected in any of the supernatants analyzed. Therefore, the level of any secreted IL-4 is below the detection limit of the ELISA employed (50 pg/ml). Taken together, the results demonstrate that a predominant Th1-type cytokine profile is associated with PMBC from *L. braziliensis*-infected individuals following stimulation with rLbhsp83 polypeptides.

To determine the correlation between the observed T-cell responses and antibody production to Lbhsp83, we compared the antibody (immunoglobulin G) reactivities to Lbhsp83 in sera from the three patient groups (FIG. 12). The ELISA reactivities of ML patient sera with rLbhsp83a were comparable to those observed with parasite lysate, and in general, there was a direct correlation between ML patient anti-Lbhsp83 antibody titer and T-cell proliferation. Of 23 serum samples from ML patients analyzed, 22 were positive (~96%) with absorbance values of 0.20 to >3.0. Eleven of the ML patient serum samples had optical density values that were >1. In general, CL patients had significantly lower anti-Lbhsp83 antibody titers ($\bar{X}$=0.74; standard error of the mean [SEM]=0.1) compared to those of ML patients. Therefore, ML and CL patient anti-rhsp83 antibody titers correlated with their respective T-cell proliferative responses. Anti-rLbhsp83 antibody titers were significantly higher in patients with ML ($\bar{X}$=1.5; SEM=0.2) than in self-healing CL patients ($\bar{X}$=0.35; SEM=0.056), although their T-cell proliferative responses were similar. In fact, anti-Lbhsp83 antibody titers in serum from self-healing CL patients were comparable to those from uninfected controls ($\bar{X}$=0.24; SEM=0.028). By using 2 standard deviations greater than the mean absorbance value of uninfected control (0.484) as a criterion for positive reactivity to Lbhsp83, eight of nine of the self-healing patient serum samples tested were negative.

Example 4

Preparation of Clones Encoding Lt-210

This Example illustrates the preparation of clones encoding portions of the Leishmania antigen Lt-210, and which has the sequence provided in SEQ ID NO:8.

An expression library was constructed from *L. tropica* (MHOM/SA/91/WR1063C) genomic DNA. The DNA was isolated by solubilizing *L. tropica* promastigotes in 10 mM Tris-HCl, pH 8.3, 50 mM EDTA, 1% SDS and treating with 100 μg/ml RNaseA and 100 μg/ml proteinase K. The sample was then sequentially extracted with an equal volume of phenol, phenol: chloroform (1:1), and Chloroform. DNA was precipitated by adding 0.1 volume of 3M sodium acetate (pH 5.2) and 2.5 volume 95% ethanol. The precipitate was resuspended in 10 μM Tris, 1 mM EDTA. DNA was sheared by passage through a 30-gauge needle to a size range of 2–6 kilobase, and was repaired by incubation with DNA poll in the presence of 100 μM each dATP, dCTP, dGTP, and dTTP. EcoRI adapters were ligated to the DNA fragments. After removal of unligated adapters by passage over a G-25 Sephadex™ column, the fragments were inserted in EcoRI cut Lambda ZapII (Stratagene, La Jolla, Calif.).

Approximately 43,000 pfu were plated and screened with sera isolated from viscerotropic leishmaniasis (VTL) patients. Sera from VTL patients were received from Drs. M. Grogl and A. Magill. The VTL patient group included eight individuals from whom parasites were isolated and cultured, seven of which had confirmed infection with *L. tropica*. Four other patients were culture negative, but were still considered to be infected based on either PCR analysis or a positive monoclonal antibody smear (Dr. Max Grogl, personal communication). Serum samples from the 11 infected patients were pooled and anti-*E. Coli* reactivity removed by affinity chromatography (Sambrook et al., supra, p. 12.27–12.28). Lambda phage expressing reactive proteins were detected after antibody binding by protein A-horseradish peroxidase and ABTS substrate.

Three clones, Lt-1, Lt-2, and Lt-3, containing a portion of the Lt-210 gene were identified and purified. The clones ranged in size from 1.4 to 3.3 kb and encoded polypeptides of 75 kD, 70 kD, and 120 kD, respectively. These three clones contain partial sequences of the Lt-210 gene. Lt-1 and Lt-2 are overlapping clones and were chosen for further study.

The DNA sequences of Lt-1 and Lt-2 were determined. Exonuclease III digestion was used to create overlapping deletions of the clones (Heinikoff, *Gene* 28:351–359, 1984). Single strand template was prepared and the sequence determined with Applied Biosystems Automated Sequencer model 373A or by Sanger dideoxy sequencing. The sequence on both strands of the coding portion of Lt-1 clone was determined. The partial sequence of one strand of Lt-2 clone was determined.

SEQ ID NO:7 presents the DNA sequence of Lt-1, and SEQ ID NO:8 provides the predicted amino acid sequence of the open reading frame. The DNA sequence of the coding portion of the Lt-1 clone includes a repeated nucleotide sequence at the 5' portion of the clone containing eight copies of a 99 bp repeat, three copies of a 60 bp repeat unit, which is part of the larger 99 bp repeat, and 800 bp of non-repeat sequence. The deduced amino acid sequence of the 99 bp repeat contains limited degeneracies. The mass of the predicted recombinant protein is 67,060 Daltons. A database search of PIR with the predicted amino acid sequence of the open reading frame yielded no significant homology to previously submitted sequences. Predicted secondary structure of the repeat portion of the clone is entirely α-helical.

Sequence analysis of Lt-2 revealed that the 3' portion of the clone consisted of a mixture of 60 and 99 bp repeats that were identical, excepting occasional degeneracies, to the 60 and 99 bp repeats observed in Lt-1. Collectively, the sequencing data suggest that Lt-1 and Lt-2 are different portions of the same gene, Lt-2 being upstream of Lt-1, with possibly a small overlap.

Hybridization analysis confirmed that rLt-2 and rLt-1 contain overlapping sequences. Genomic DNAs of various Leishmania species were restricted with a variety of enzymes, separated by agarose gel electrophoresis, and blotted on Nytran membrane filter (Schleicher & Schuell, Keene, N.H.). Inserts from rLt-1 and rLt-2 were labeled with $^{32}$P-CTP by reverse transcriptase from random oligonucleotide primers and used as probes after separation from unincorporated nucleotides on a Sephadex G-50 column. Hybridizations using the rLt-1 or the rLt-2 probe are performed in 0.2M $NaH_2PO_4$/3.6 M NaCl at 65° C., whereas hybridization using the rLt-1r probe is performed in 0.2 M $NaH_2PO_4$/3.6 M NaCl/0.2 M EDTA at 60° C. overnight. Filters are washed in 0.075 M NaCl/0.0075 M sodium citrate pH 7.0 (0.15 M NaCl/0.0150 M sodium citrate for the Lt-1r probe), plus 0.5% SDS at the same temperature as hybridization.

Genomic DNA from a number of Leishmania species including *L. tropica* were analyzed by Southern blots as described above using the Lt-1, Lt-2, and Lt-1r inserts separately as probes. Collectively, various digests of *L. tropica* DNA indicate that this gene has a low copy nunber. A similar, overlapping pattern was observed using either the Lt-1 or Lt-2 insert as a probe, consistent with the premise that these two clones contain sequences near or overlapping one another. In addition, sequences hybridizing with these clones are present in other Leishmania species.

*L. tropica* isolates have limited heterogeneity. Southern analyses of digested genomic DNA from four *L. tropica* parasite strains isolated from VTL patients and three *L. tropica* parasite strains isolated from CL cases (two human, one canine) were performed. The Lt-1r insert described below was labeled and used as a probe. The seven different *L. tropica* isolates yielded similar intensities and restriction patterns, with only a single restriction fragment length polymorphism among the isolates. These data, along with Southern analyses with additional enzymes, indicate limited heterogeneity in this region among the *L. tropica* isolates.

The recombinant proteins of Lt-1 and Lt-2 were expressed and purified. The nested deletion set of Lt-1 formed for sequencing included a clone referred to as Lt-1r, which contains one and one-third repeats. This polypeptide was also expressed and purified. In vivo excision of the pBluescript $SK^-$ phagemid from Lambda Zap II was performed according to the manufacturer's protocol. Phagemid virus particles were used to infect *E. coli* XL-1 Blue. Production of protein was induced by the addition of IPTG. Protein was recovered by first lysing pellets of induced bacteria in buffer (LB, 50 mM Tris-HCl, pH 8.0, 100 mM NaCl, 10 mM EDTA) using a combination of lysozyme (750 μg/mL) and sonication. rLt-1, rLt-2, and rLt-1r, were recovered from the inclusion bodies after solubilization in 8M urea (rLt-1 and rLt-2) or 4M urea (rLt-1r). Proteins rLt-1 and rLt-2 were enriched and separated by precipitation with 25%–40% ammonium sulfate and rLt-1r was enriched by precipitation with 10%–25% ammonium sulfate. The proteins were further purified by preparative gel electrophoresis in 10% SDS-PAGE. Recombinant proteins were eluted from the gels and dialyzed in phosphate-buffered saline (PBS). Concentration was measured by the Pierce (Rockford, Ill.) BCA assay, and purity assessed by Coomassie blue staining after SDS-PAGE.

Example 5

Preparation of Lbeif4A

This example illustrates the molecular cloning of a DNA sequence encoding the *L. braziliensis* ribosomal antigen LbeIF4A.

A genomic expression library was constructed with sheared DNA from *L. braziliensis* (MHOM/BR/75/M2903) in bacteriophage λZAPII (Stratagene, La Jolla, Calif.). The expression library was screened with *E. coli*-preadsorbed patient sera from an *L. braziliensis*-infected individual with mucosal leishmaniasis. Plaques containing immunoreactive recombinant antigens were purified, and the pBSK(−) phagemid excised using the manufacturer's protocols. Nested deletions were performed with Exonuclease III to generate overlapping deletions for single stranded template preparations and sequencing. Single stranded templates were isolated following infection with VCSM13 helper phage as recommended by the manufacturer (Stratagene, La Jolla, Calif.) and sequenced by the dideoxy chain terminator method or by the Taq dye terminator system using the Applied Biosystems Automated Sequencer Model 373A.

The immunoreactive recombinant antigens were then analyzed in patient T-cell assays for their ability to stimulate a proliferative and cytokine production, as described in Examples 7 and 8 below.

A recombinant clone was identified in the above assays which, following sequence comparison of its predicted amino acid sequence with sequences of other proteins, was identified as a *Leishmania braziliensis* homolog of the eukaryotic initiation factor 4A (eIF4A). The isolated clone (pLeIF.1) lacked the first 48 amino acid residues (144 nucleotides) of the full length protein sequence. The pLeIF.1 insert was subsequently used to isolate the full length genomic sequence.

SEQ ID NO:9 shows the entire nucleotide sequence of the full-length LbeIF4A polypeptide. The open reading frame (nucleotides 115 to 1323) encodes a 403 amino acid protein with a predicted molecular weight of 45.3 kD. A comparison of the predicted protein sequence of LbeIF4A with the homologous proteins from tobacco (TeIF4A), mouse (MeIF4A), and yeast (YeIF4A) shows extensive sequence homology, with the first 20–30 amino acids being the most variable. The lengths (403, 413, 407, and 395 amino acids), molecular weights (45.3, 46.8, 46.4, and 44.7 kDa), and isoelectric points (5.9, 5.4, 5.5, and 4.9) of LbeIF4A, TeIF4A, MeIF4A and YeIF4A, respectively, are similar. LbeIF4A shows an overall homology of 75.5% (57% identity, 18.5% conservative substitution) with TeIF4A, 68.6% (50% identity, 18.6% conservative substitution) with MeIF4A and 67.2% (47.6% identity, 19.6% conservative substitution) with YeIF4A.

Example 6

Preparation of Soluble Leshmania Antigens

This Example illustrates the preparation of soluble Leishmania antigens from an *L. major* culture supernatant. *L. major* promastigotes were grown to late log phase in complex medium with serum until they reached a density of $2–3\times10^7$ viable organisms per mL of medium. The organisms were thoroughly washed to remove medium components and resuspended at $2–3\times10^7$ viable organisms per mL of defined serum-free medium consisting of equal parts RPMI 1640 and medium 199, both from Gibco BRL, Gaithersburg, Md. After 8–12 hours, the supernatant was removed, concentrated 10 fold and dialyzed against phosphate-buffered saline for 24 hours. Protein concentration was then determined and the presence of at least eight different antigens confirmed by SDS-PAGE. This mixture is referred to herein as "soluble Leishmania antigens."

Example 7

Comparison of Interleukin-4 and Interferon-γ Production Stimulated by Leishmania Antigens This Example illustrates the immunogenic properties of the antigens prepared according to Examples 1, 2, 5 and 6, as determined by their ability to stimulate IL-4 and IFN-γ in lymph node cultures from infected mice and in human PBMC preparations. Lymph node cultures for use in these studies were prepared from *L. major*-infected BALB/c mice 10 days after infection, as described in Example 2. PBMC were prepared using peripheral blood obtained from individuals with cured *L. donovani* infections who were immunologically responsive to Leishmania. Diagnosis of the patients was made by clinical findings associated with at least one of the following: isolation of parasite from lesions, a positive skin test with Leishmania lysate or a positive serological test. Uninfected individuals were identified based on a lack of clinical signs or symptoms, a lack of history of exposure or travel to endemic areas, and the absence of a serological or cellular response to Leishmania antigens. Peripheral blood was collected and PBMC isolated by density centrifugation through FiColl™ (Winthrop Laboratories, New York).

Culture supernatants were assayed for the levels of secreted IL-4 and IFN-γ. IFN-γ was quantitated by a double sandwich ELISA using mouse anti-human IFN-γ mAb (Chemicon, Temucula, Calif.) and polyclonal rabbit anti-human IFN-γ serum. Human rIFN-γ (Genentech Inc., San Francisco, Calif.) was used to generate a standard curve. IL-4 was quantitated in supernatants by a double sandwich ELISA using a mouse anti-human IL-4 mAb (M1) and a polyclonal rabbit anti-human IL-4 sera (P3). Human IL-4 (Immunex Corp., Seattle, Wash.) was used to generate a standard curve ranging from 50 pg/ml to 1 ng/ml.

FIGS. 13A and 13B, illustrate the mean level of secreted IL-4 and IFN-γ, respectively, 72 hours after addition of 10 μg/mL of each of the following antigens to a lymph node culture prepared as described above: soluble Leishmania antigen (i.e., an extract prepared from ruptured promastigotes which contains membrane and internal antigens (SLA)), Ldp23, LbeIF4A (LeIF), Lbhsp83, M15 and LmeIF (the *L. major* homolog of LbeIF4A). The levels of secreted IL-4 and IFN-γ in medium alone (i.e., unstimulated) are also shown. While SLA elicits a predominantly Th2 response from lymph node cells of Leishmania-infected mice, Ldp23, LbeIF4A, Lbhsp83 and M15 elicited relatively little IL-4 and large amounts of IFN-γ, consistent with a Th1 response profile.

FIG. 14 shows the level of secreted IFN-γ in culture filtrate from infected and uninfected human PBMC preparations 72 hours after addition of 10 μg/mL *L. major* lysate, M15 or L-Rack, an immunodominant leishmanial antigen in murine leishmaniasis. Similarly, FIG. 15 illustrates the level of secreted IFN-γ in culture filtrate from infected and uninfected human PBMC preparations 72 hours after addition of 10 μg/mL *L. major* lysate, soluble Leishmania antigens (prepared as described in Example 6) or L-Rack. These results indicate that M15 and soluble Leishmania antigens, but not L-Rack, are potent stimulators of IFN-γ production in patient PBMC, but not in PBMC obtained from uninfected individuals. Thus, M15 and soluble Leishmania antigens elicit a dominant Th1 cytokine profile in both mice and humans infected with Leishmania.

Example 8

Comparison of Proliferation Stimulated by Leishmania Antigens

This Example illustrates the immunogenic properties of the antigens prepared according to Examples 1, 2, 5 and 6, as determined by their ability to stimulate proliferation in lymph node cultures from infected mice and in human PBMC preparations.

For in vitro proliferation assays, 2–4×10$^5$ cells/well were cultured in complete medium (RPMI 1640 supplemented with gentamycin, 2-ME, L-glutamine, and 10% screened pooled A+ human serum; Trimar, Hollywood, Calif.) in 96-well flat bottom plates with or without 10 μg/ml of the indicated antigens or 5 μg/ml PHA (Sigma Immunochemicals, St. Louis, Mo.) for five days. The cells were then pulsed with 1 μCi of [$^3$H] thymidine for the final 18 hours of culture.

FIG. 16 illustrates the proliferation observed after addition of 10 μg/mL or 20 μg/mL of each of the following antigens to a lymph node culture prepared as described in Example 7: SLA, Ldp23, LbeIF4A, Lbhsp83, and M15. The level of proliferation without the addition of antigen is also shown. Data are represented as mean cpm. These results demonstrate that a variety of leishmanial antigens are capable of stimulatory lymph node cell proliferation from Leishmania-infected mice.

FIGS. 17 and 18 illustrate the proliferation observed in human PBMC preparations from Leishmania-immune and uninfected individuals following the addition of 10 μg/mL M15 and soluble Leishmania antigens, respectively. These values are compared to the proliferation observed following the addition of culture medium, *L. major* lysate or L-Rack. The results show that M15 and soluble Leishmania antigens stimulate proliferation in Leishmania-immune PBMC, but not in PBMC obtained from uninfected individuals, demonstrating that M15 and soluble antigens (but not L-Rack) are recognized by PBMC from individuals immune to Leishmania due to a previous infection.

Example 9

Preparation of Lmsp1a and Lmsp9a

This Example illustrates the preparation of two soluble Leishmania antigens, Lmsp1a and Lmsp9a.

A. Purification of Lmsp1a and Lmsp9a from a Mixture of Soluble *L. major* Antigens A high titer rabbit sera was raised against *L. major* soluble antigens, prepared as described above in Example 6. Specifically, a New Zealand white rabbit was immunized subcutaneously at multiple sites with 180 μg of *L. major* soluble antigens in a suspension containing 100 μg muramyl dipeptide and 50% incomplete Freund's adjuvant. Six weeks later the rabbit was given a subcutaneous boost of 100 μg of the same soluble antigen preparation in incomplete Freund's adjuvant. This was followed by two intravenous boosts spaced two weeks apart, each with 100 μg of the soluble antigen preparation. Sera was collected from the rabbit 11 days after the final boost.

Anti *E. coli* antibody reactivities were removed from the rabbit sera by pre-adsorbing on nitrocellulose filters containing lysed *E. coli*. Adsorbed sera were evaluated by Western blot analysis using 10 μg Leishmania promastigote lysate (lane 1) and 1 μg soluble *L. major* antigen mixture (lane 2). As shown in FIG. 20, the rabbit sera was found to be reactive with seven dominant antigens of the soluble *L. major* antigen mixture with molecular weights ranging from 18 to >200 kDa. A four times longer exposure of the same blot revealed three additional immunoreactive species with molecular weights less than 18 kDa. The same sera reacted with approximately 10 antigens of the promastigote lysate, but with a pattern significantly different from that observed with the soluble *L. major* antigens (FIG. 20). This is suggestive of potential post-translational modification of the same antigen before (intracellular localization) and after secretion/shedding. Such modifications may include cleavage of a leader sequence and/or the addition of carbohydrate molecules to the secreted/shed antigens.

The rabbit sera described above was subsequently used to screen an *L. major* cDNA expression library prepared from *L. major* promastigote RNA using the unidirectional Lambda ZAP (uni-ZAP) kit (Stratagene) according to the manufacturer's protocol. A total of 70,000 pfu of the amplified cDNA library was screened with the rabbit sera at a 1:250 dilution. Nineteen positive clones were confirmed in the tertiary screening. The phagemid were excised and DNA from each of the 19 clones was sequenced using a Perkin Elmer/Applied Biosystems Division automated sequencer Model 373A. All 19 clones were found to represent two distinct sequences, referred to as Lmsp1a and Lmsp9a. The determined cDNA sequences for Lmsp1a and Lmsp9a are provided in SEQ ID NO: 19 and 21, respectively, with the corresponding amino acid sequences being provided in SEQ ID NO: 20 and 22, respectively.

B. Characterization of Lmsp1a and Lmsp9a

FIG. 21 shows the full-length cDNA (SEQ ID NO: 19) and predicted amino acid sequence (SEQ ID NO: 20) for the antigen Lmsp1a. The EcoRI/XhoI insert is 1019 bp long and contains the following features: a) the last 17 nt of the spliced leader sequence characteristic of all trypanosoma nuclearly encoded mRNA; b) 39 nt of 5' untranslated sequence; c) an open reading frame of 453 nt long coding for a 151 deduced amino acid sequence with a predicted molecular mass of 16.641 kDa; and d) 471 nt of 3' untranslated sequence terminating with a poly A tail. The predicted amino acid sequence contains three potential phosphorylation sites at amino acid residues 3, 85 and 102. In addition, Lmsp1a contains an RGD sequence at residue 104, a sequence that may play a role in parasite invasion of the macrophage. RGD sequences have been shown to mediate the binding of various adhesion proteins to their cell surface receptors. There is no obvious leader sequence (secretory signal) at the amino terminal portion suggesting that the protein might be shed or excreted. Lmsp1a appears to be one of the most abundant antigens found in the culture supernatant of live promastigote, since 17 of the 19 clones contain sequences of variable lengths identical to Lmsp1a.

Comparison of the amino acid sequence of Lmps1a with known sequences using the DNA STAR system (Version 87) revealed that Lmsp1a shares between 65% to 70% homology with the eukaryotic nucleoside diphosphate kinase protein, also referred to in the mouse and human as a tumor metastasis inhibitor gene.

Southern blot analysis of genomic DNA from *L. major* (Friedlander strain) digested with a panel of restriction enzymes (lanes 1 to 7) and six other Leishmania species of different geographic locations digested with PstI (lanes 8 to 13) using the full-length cDNA insert of Lmps1a, demonstrated that Lmsp1a is present in all the species characterized with a high degree of conservation (FIG. 22). This suggests evolutionary significance for the maintenance of Lmsp1a and the existence of homologous species among all the Leishmania species.

The remaining two cDNA clones isolated from the soluble *L. major* antigen mixture represent identical sequences (referred to as Lmsp9a; SEQ ID NO: 21), suggesting that the two copies resulted from amplification of the primary library. Sequencing of the Lmsp9a cDNA revealed that the clone does not contain the full length 5' sequence since it is lacking both the spliced leader and 5' untranslated sequences. The 3' end of the cDNA contains a poly A stretch, as would be expected for a Leishmania mRNA. Of the predicted translated sequence (SEQ ID NO: 22), 34 of the 201 amino acids (17%) represent cysteine residues. Comparison of the predicted protein sequence with those of known proteins as described above, revealed some homology with other cysteine rich proteins such as the major surface trophozoite antigen of *Giardia lamblia* and furin proteases.

Example 10

Preparation and Characterization of MAPS-1A

This Example illustrates the preparation and characterization of the Leishmania antigen MAPS-1A (SEQ ID NO: 24).

A pool of sera was obtained from 5 BALB/c mice that had been given a primary immunization and two boosts with crude *L. major* promastigote culture supernatant as described below in Example 12. These mice were subsequently shown to be protected when challenged with a dose of live *L. major* promastigotes generally found to be lethal. The mouse sera thus obtained were used to screen an *L. major* amastigote cDNA expression library prepared as described in Example 1. Several seroreactive clones were isolated and sequenced using a Perkin Elmer/Applied Biosystems Division automated sequencer Model 373A (Foster City, Calif.).

One of these clones, referred to herein as MAPS-1A, was found to be full-length. Comparison of the cDNA and deduced amino acid sequences for MAPS-1A (SEQ ID Nos: 23 and 24, respectively) with known sequences in the gene bank using the DNA STAR system revealed no significant homologies to known Leishmania sequences, although some sequence similarity was found to a group of proteins, known as thiol-specific antioxidants, found in other organisms.

Recombinant MAPS-1A protein having an amino-terminal HIS-Tag was prepared using a high level *E. coli* expression system and recombinant protein was purified by affinity chromatography as described in Example 1. Southern blot analysis of genomic DNA from *L. major* digested with a panel of restriction enzymes, seven other Leishmania species digested with PstI, and two other infectious-disease pathogens (*T. cruzi* and *T. brucei*), using the full length insert of MAPS-1A, demonstrated that MAPS-1A is present in all eight Leishmania species tested (FIG. 23). Northern blot analysis of *L. major* promastigote aid amastigote RNAs indicated that MAPS-1A is constitutively expressed.

Using oligonucleotide primers (SEQ ID NOs:27 and 28) based on the MAPS-1A cDNA sequence provided in SEQ ID NO: 23, the corresponding gene was isolated from *L. tropica* by means of PCR (using 30 cycles of the following temperature step sequence: 94° C., 1 minute; 50° C., 1 minute; 72° C., 1 minute). The determined cDNA sequence for the *L. tropica* MAPS-1A protein is provided in SEQ ID NO: 25, with the corresponding amino acid sequence being provided in SEQ ID NO: 26.

The ability of recombinant MAPS-1A to stimulate cell proliferation was investigated as follows. PBMC from 3 *L. braziliensis*-infected patients having active mucosal leishmaniasis, from 4 patients post kala-azar infection (previously infected with *L. chagasi* and/or *L. donovani*) and from 3 uninfected-individuals were prepared as described above in Example 7. The ability of MAPS-1A to stimulate proliferation of these PBMC was determined as described in Example 8 above. As shown in FIG. 24, significant levels of MAPS-1A specific PBMC proliferation were seen in 2 of the 7 Leishmania patients.

The ability of MAPS-1A to stimulate proliferation in mice lymph node cultures was determined as described in Example 8. FIG. 25 shows the amount of proliferation stimulated by MAPS-1A (at 25 μg/ml, 5 μg/ml and 1 μg/ml) as compared to that stimulated by the positive control ConA and by crude *L. major* promastigote supernatant proteins, 20 days post-infection with *L. major*. Cells isolated 20 days post-infection were highly responsive to MAPS-1A, whereas cells isolated 10 days post-infection were unresponsive.

Example 11

Immunoreactivity of Soluble Leishmania Antigens with Sera from Leishmania-Infected Patents The reactivity of MAPS-1A with sera from uninfected individuals, from human leishmaniasis patients with cutaneous infection, from human patients with acute visceral leishmaniasis, and from *L. major*-infected BALB/c mice was determined as follows.

Assays were performed in 96-well plates coated with 200 ng antigen diluted to 50 μL in carbonate coating buffer, pH 9.6. The wells were coated overnight at 4° C. (or 2 hours at 37° C.). The plate contents were then removed and the wells were blocked for 2 hours with 200 μL of PBS/1% BSA. After the blocking step, the wells were washed five times with PBS/0.1% Tween 20™. 50 μL sera, diluted 1:100 in PBS/0.1% Tween 20™/0.1% BSA, was then added to each well and incubated for 30 minutes at room temperature. The plates were then washed again five times with PBS/0.1% Tween 20™.

The enyzme conjugate (horseradish peroxidase—Protein A, Zymed, San Francisco, Calif.) was then diluted 1:10,000 in PBS/0.1% Tween 20™/0.1% BSA, and 50 μL, of the diluted conjugate was added to each well and incubated for 30 minutes at room temperature. Following incubation, the wells were washed five times with PBS/0.1% ween 20™. 100 μL of tetramethylbenzidine peroxidase (TMB) substrate (Kirkegaard and Perry Laboratories, Gaithersburg, Md.) was added, undiluted, and incubated for about 15 minutes. The reaction was stopped with the addition of 100 μL of 1 N $H_2SO_4$ to each well, and the plates were read at 450 nm.

As shown in FIG. 26, approximately 50% of the samples from human leishmaniasis patients showed reactivities with recombinant MAPS-1A substantially above background. FIG. 27 shows the reactivity of MAPS-1A with increasing dilutions of sera from BALB/c mice previously administered either (i) saline solution; (ii) the adjuvant *B. pertussis*; (iii) soluble Leishmania antigens plus *B. pertussis*; (iv) live *L. major* promastigotes; or (v) soluble Leishmania antigens plus *B. pertussis* followed by live *L. major* promastigotes (as described below in Example 12). Considerably higher absorbances were seen with sera from mice infected with live *L. major* promastigotes and with mice infected with live *L. major* promastigotes following immunization with soluble Leishmania antigens plus *B. pertussis*, than with sera from the other three groups of mice, indicating that anti-MAPS-1A antibody titers increase following Leishmania infection.

Example 12

Use of Leishmania Antigens for Vaccination Against Leishmania Infection

This example illustrates the effectiveness of Leishmania antigens in conferring protection against disease in the experimental murine leishmaniasis model system. For a discussion of the murine leishmaniasis model system see, for example, Reiner et al. *Annu. Rev. Immunol.*, 13:151–77, 1995.

The effectiveness of (i) crude soluble Leishmania antigens, (ii) MAPS-1A, and (iii) a mixture of Ldp23, LbeIF4A and M15, as vaccines against Leishmania infection was determined as follows. BALB/c mice (5 per group) were immunized intra-peritoneally three times at biweekly intervals with either (i) 30 μg crude soluble Leishmania antigens, (ii)20 μg MAPS-1A or (iii) a mixture containing 10 μg each of LeIF, Ldp23 and M15, together with 100 μg of the adjuvant *C. parvum*. Two control groups were immunized with either saline or *C. parvum* alone. Two weeks after the last immunization, the mice were challenged with $2 \times 15^5$ late-log phase promastigotes of *L. major*. Infection was monitored weekly by measurement of footpad swelling. The amount of footpad swelling seen in mice immunized with either crude soluble Leishmania antigens, a mixture of Ldp23, LbeiF4A and M15 (FIG. 28), or MAPS-1A (FIG. 29) was significantly less than that seen in mice immunized with *C. parvum* alone. These results demonstrate that the Leishmania antigens of the present invention are effective in conferring protection against Leishmania infection.

Example 13

Isolation of DNA Encoding for Soluble Antigens from an *L. Major* Fenomic DNA Library This example illustrates the isolation of seven soluble Leishmania antigen genes from an *L. major* genomic DNA library.

An *L. major* genomic DNA expression library was prepared from *L. major* promastigotes using the unidirectional Lambda ZAP (uni-ZAP) kit (Stratagene) according to the manufacturer's protocol. This library was screened with a high titer rabbit sera raised against *L. major* soluble antigens, as described above in Example 9. Seven positive clones were identified. The phagemid were excised and DNA from each of the seven clones was sequenced using a Perkin Elmer/Applied Biosystems Division automated sequencer Model 373A. The DNA sequences for these antigens, referred to as LmgSP1, LmgSP3, LmgSP5, LmgSP8, LmgSP9, LmgSP13, LmgSP19, are provided in SEQ ID NO:29–35, respectively, with the corresponding amino acid sequences being provided in SEQ ID NO: 36–42, respectively. LmgSP13 was found to contain a 39 amino acid repeat sequence shown in SEQ ID NO:43.

Subsequent studies resulted in the isolation of a full-length sequence for LmgSP9. The full-length DNA sequence is provided in SEQ ID NO: 54, with the corresponding predicted amino acid sequence being provided in SEQ ID NO: 55. The amino acid sequence was found to contain six 14 amino acid repeat units (SEQ ID NO: 56), with each unit being further divided into two 7 amino acid units, provided in SEQ ID NO: 57 and 58.

Comparison of the DNA and amino acid sequences for the isolated antigens as described above, revealed no significant homologies to LmgSP1, LmgSP3, and LmgSP13. LmgSP5 was found to be related to the known PSA2 family. LmgSP8 was found to bear some homology to a sequence previously identified in *E. coli* (2-succinyl-6-hydroxy-2.4-cyclohexadiene-1-carboxylic acid synthase). LmgSP9 and LmgSP19 were found to be homologous to a *L. major* hydrophilic surface protein referred to as Gene B (Flinn, H. M. et al. *Mol. Biochem. Parasii.* 65:259–270. 1994), and to ubiquitin, respectively. To the best of the inventors' knowledge, none of these antigens have been previously shown to elicit T or B cell responses.

The reactivity of recombinant LmgSP9 with sera from patients with visceral leishnianiasis, (from both Sudan and Brazil) and from normal donors was evaluated by ELISA as described above. The absorbance values were compared with those obtained using the known Leishmania antigen K39 described above, with *L. chagasi* lysate being employed as a positive control. Representative results of these assays are provided below in Table 2, wherein all the patients from Brazil and those from the Sudan designated as "VL" were inflicted with visceral leishmaniasis. The results demonstrated that LmgSP9 specifically detects antibody in most individuals with visceral leishmaniasis, regardless of geographical location. In several cases, the absorbance values of the antibody reactivity to LmgSP9 were comparable to that observed with K39. In addition, LmgSP9 detected several cases of leishmaniasis that were not detected using K39. These results indicate that LmgSP9 can be used to complement the reactivity of K39.

TABLE 2

REACTIVITY OF LMGSP9 WITH SERA FROM LEISHMANIA PATIENTS

| Patient No. | L. chagasi lysate | K39 | LmgSP9 |
|---|---|---|---|
| Sudanese samples: | | | |
| B19 | 1.067 | 0.306 | 0.554 |
| B25 | 1.884 | 3.435 | 0.974 |
| B43 | 1.19 | 3.225 | 0.86 |
| B47 | 2.405 | 2.892 | 0.375 |
| B50 | 0.834 | 0.748 | 0.432 |
| B58 | 0.921 | 0.235 | 0.92 |
| B63 | 1.291 | 0.303 | 0.764 |
| B70 | 0.317 | 0.089 | 3.056 |
| VL4 | 1.384 | 3.035 | 2.965 |
| VL11 | 0.382 | 0.144 | 0.142 |
| VL12 | 0.277 | 0.068 | 0.098 |
| VL13 | 0.284 | 0.12 | 0.194 |
| Brazilian samples: | | | |
| 105 | 3.508 | 3.53 | 0.374 |
| 106 | 2.979 | 3.373 | 2.292 |
| 107 | 2.535 | 3.444 | 0.46 |
| 109 | 1.661 | 3.415 | 3.319 |
| 111 | 3.595 | 3.537 | 0.781 |
| 112 | 2.052 | 3.469 | 0.63 |
| 113 | 3.352 | 3.429 | 0.963 |
| 114 | 2.316 | 3.437 | 1.058 |
| 115 | 2.073 | 3.502 | 1.186 |
| 116 | 3.331 | 3.461 | 0.96 |
| Normal Donors: | | | |
| 129 | 0.157 | 0.104 | 0.08 |
| 130 | 0.195 | 0.076 | 0.095 |
| 131 | 0.254 | 0.134 | 0.086 |
| 132 | 0.102 | 0.035 | 0.043 |

In order to obtain a higher specificity for the detection of antibodies in sera from visceral leishmaniasis patients, a homologue of LmgSP9 was isolated from L. chagasi, one of the causative agents of visceral leishmaniasis. A total of 80,000 pfu of an amplified L. chagasi genomic library were screened with the entire coding region of LmgSP9 (amplified from L. major genomic DNA). Seven hybridizing clones were purified to homogeneity. The determined DNA sequences for two of these clones, referred to as Lc Gene A and LcGene B, are provided in SEQ ID NO: 59 and 60, respectively, with the corresponding predicted amino acid sequences being provided in SEQ ID NO: 61 and 62, respectively. The open reading frame for Lc Gene A was found to show some homology to Gene A/C, previously isolated from L. major (McKlean et al., Mol. Bio. Parasitol., 85:221–231, 1997). The open reading frame for Lc Gene B showed some homology to Gene B of L. major, discussed above, and was found to contain eleven repeats of a 14 amino acid repeat unit (SEQ ID NO: 63), with each repeat being further divided into two 7 amino acid units, provided in SEQ ID NO: 64 and 65.

The diagnostic potentials of lc Gene A and Lc Gene B were evaluated by ELISA as described above using sera from visceral leishmaniasis patients from Sudan and Brazil, and from uninfected controls. Absorbance vahles were compared to those obtained using LmgSP9. Much higher absorbance values were obtained with Lc Gene A and Lc Gene B than with LmgSP9, with Lc Gene B appearing to be more effective that Lc Gene A in detecting antibodies in certain cases. These results indicate that Lc Gene B is highly effective in the diagnosis of visceral leishmaniasis.

In order to assess the diagnostic potential of the repeats found within Lc Gene B, a series of 6 peptides were synthesized (SEQ ID NO: 66–71; referred to as Pep 1–6), differing in an R or H residue. An ELISA was carried out using the full-length LcGene B protein and the six peptides. The absorbance values obtained with Pep 3 were higher than those obtained with the other 5 peptides, however they were not as high as those obtained with the full length protein.

Example 14

Isolation and Characterization of DNA Encoding for Soluble Antigens from an L. Chagasi Genomic DNA Library This example illustrates the preparation of five soluble Leishmania antigen genes from an L. chagasi genomic DNA library.

An L. chagasi genomic DNA expression library was prepared from L. chagasi promastigotes using the unidirectional Lambda ZAP (uni-ZAP) kit (Stratagene) according to the manufacturer's protocol. This library was screened with a high titer rabbit sera raised against L. major soluble antigens, as described above in Example 9. Five positive clones were identified. The phagemid were excised and DNA from each of the Five clones was sequenced using a Perkin Elmer/Applied Biosystems Division automated sequencer Model 373A. The DNA sequences for these antigens, referred to as LcgSP1, LcgSP3, LcgSP4, LcgSP8, and LcgSP10 are provided in SEQ ID NO:44–48, respectively, with the corresponding amino acid sequences being provided in SEQ ID NO:49–53, respectively.

Comparison of these sequences with known sequences in the gene bank as described above, revealed no known homologies to LcgSP3, LcgSP4, LcgSP8 and LcgSP10. LcgSP1 was found to be homologous to the known antigen HSP70.

Figure 30B:
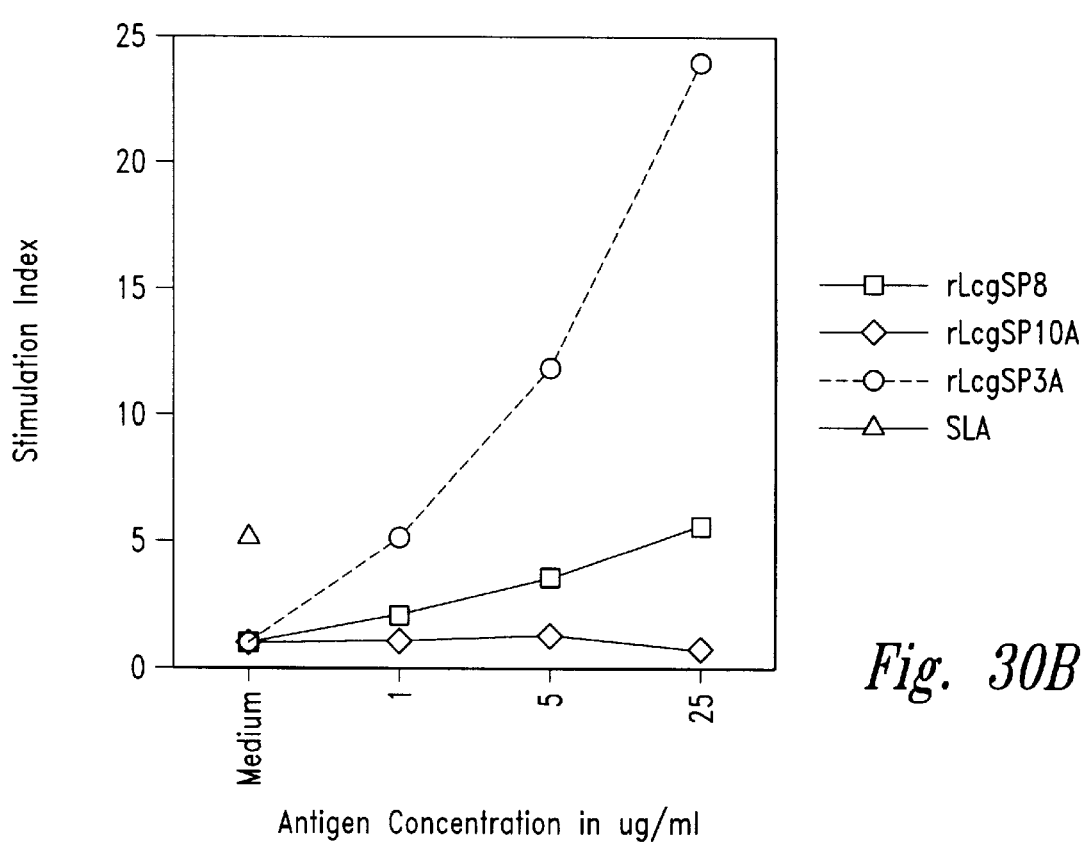

FIGS. 30A and B illustrate the proliferative response of murine lymph nodes to recombinant LcgSP8, LcgSP10 and LcgSP3. Lymph nodes were taken BALB/c mice 17 days after infection with L. major. Infection occurred by footpad injection of $2 \times 10^6$ parasites/footpad. The cells were stimulated with recombinant antigen and proliferation was measured at 72 hours using $^3$H-thymidine. FIG. 30A shows the CPM, a direct measurement of mitotic activity in response to the antigens, and FIG. 30B shows the stimulation index, which measures the proliferative response relative to the negative control.

Example 15

Isolation of DNA Encoding for L. Major Antigens by CD4+ T Cell Expression Cloning This example illustrates the isolation of T cell antigens of L. major using a direct T cell screening approach.

Leishmania-specific CD4+ T cell lines were derived from the PBMC of an individual who tested positive in a leishmania skin test but had no clinical history of disease. These T cell lines were used to screen a L. major amastigote cDNA expression library prepared as described in Example 1. Immunoreactive clones were isolated and sequenced as described above. The determined cDNA sequences for the 8 isolated clones referred to as 1G6-34, 1E6-44, 4A5-63, 1B11-39, 2A10-37, 4G2-83, 4H6-41, 8G3-100 are provided in SEQ ID NO: 72–79. respectively, with the corresponding predicted amino acid sequences being provided in SEQ ID NO: 80–87, respectively. The cDNA sequences provided for 1E6-44, 2A10-37. 4G2-83, 4H6-41 and 8G3-100 are believe to represent partial clones. All of these clones were shown to stimulate T cell proliferation.

Comparison of these sequences with those in the gene bank as described above revealed no known homologies to the antigen 4A5-63. 1G6-34 was found to have some homology to histone H2B previously identified in *L. enrietti*. Antigens 1E6-44, 1B11-39 and 8G3-100 showed some homology to sequences previously identified in other eukaryotes, in particular *Saccharomyces cerevisae*. 2A10-37 and 4H6-41 were found to be homologous to the two previously identified proteins alpha tubulin from *L. donovani* and beta tubulin from *L. major*, respectively, and 4G2-83 was found to be homologous to elongation initiation factor 2 previously identified in *T. cruzi*.

Example 16

Synthesis of Polypeptides

Polypeptides may be synthesized on a Perkin Elmer/Applied Biosystems Division 430A peptide synthesizer using FMOC chemistry with HPTU (O-Benzotriazole-N,N,N',N'-tetramethyluronium hexafluorophosphate) activation. A Gly-Cys-Gly sequence may be attached to the amino terminus of the peptide to provide a method of conjugation, binding to an immobilized surface, or labeling of the peptide. Cleavage of the peptides from the solid support may be carried out using the following cleavage mixture: trifluoroacetic acid:ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0%–60% acetonitrile (containing 0.1% TFA) in water (containing 0.1% TFA) may be used to elute the peptides. Following lyophilization of the pure fractions, the peptides may be characterized using electrospray or other types of mass spectrometry and by amino acid analysis.

Example 17

Use of Leishmania Antigens Plus Adjuvant for Vaccination Against Leishmania Infection This example illustrates the effectiveness of recombinant Leishmania antigens, M15 and MAPS, plus an adjuvant, IL-12, in conferring protection against disease in the experimental murine leishmaniasis model system. For discussion of the murine leishmaniasis model system see, for example, Reiner et al., *Annu. Rev. Immunol.*, 13:151–77, 1995. The effectiveness of M15 and MAPS in combination with IL-12, as vaccine against Leishmania infection was determined as follows: BALB/c mice (5 per group) were immunized subcutaneously in the left footpad, twice (3 weeks apart) with the 10 μg of the individual antigens mixed with 1 μg of IL-12. As controls, three separate groups of mice were immunized with soluble leishmania lysate antigens (SLA) plus IL-12, with IL-12 alone or with PBS. Three weeks after the last immunization the mice were infected in the right footpad with $2 \times 10^5$ promastigote forms of *L. major* (stationary phase). Footpad swelling was then measured weekly. Results are expressed in FIG. 31 and clearly indicate that the mice immunized with either M15 or MAPS and IL-12 were greatly protected against the infection; whereas mice immunized with IL-12 alone did not show protection from infection. The protection induced by these antigens was as efficient or better than that induced by SLA+IL-12, a regimen known to induce good protection against leishmaniasis in this animal model (Afonso, L. C. C., T. M. Scharton, L. Q. Vieira, M. Wysocka, G. Trinchieri, and P. Scott. 1994. *The adjuvant effect of interieukin-12 in a vaccine against Leishniania major. Science* 263:235–237). The same pattern of protection described above, was obtained i.e., M15, MAPS, and SLA, induced protection against *L. major* infection when *C. parvum* instead of IL-12 was used as adjtivant (Example 12). These results demonstrate that both M15 and MAPS recombinant antigens induce excellent protection against *L. major* infection in the BALB/c model of human leishmaniasis. In addition, both antigens induced protection when tested in two different adjuvant formulations, (e.g., IL-12 and *C. parvim*.) This finding is of high significance because it demonstrates that immunity to leishmaniasis can be induced by the specific antigens delivered in adjuvants that are suitable for human use.

Example 18

Use of Leishmania DNA for Vaccination Against Leishmania Infection

This example illustrates the effectiveness of Leishmania DNA in conferring protection against disease in the experimental murine leishmaniasis model system. For discussion of the murine leishmaniasis model system see, for example, Reiner et al., *Annu. Rev. Immunol.*, 13:151–77, 1995. The protection properties of the recombinant antigens was tested by immunizing mice with naked DNA containing the corresponding M15 and MAPS genes. The DNA construct used was the pcDNA3.1 vector (Invitrogen) containing a CMV promotor. BALB/c mice (5 per group) were injected in the left footpad three times (3 weeks apart) with 100 μg of the indicated naked DNA preparations. Mice were bled before and after the immunizations to monitor the development of specific immune response. The antibody response was evaluated by ELISA. Specific anti-M15 and anti-MAPS IgG2a antibodies were detected after the second immunization in the sera of the mice immunized with the respective naked DNA. The presence of specific antibodies indicates that the DNA immunization resulted in the production of specific protein antigen. Three weeks after the last immunization, the mice were then challenged in the right footpad with $2 \times 10^5$ promastigote forms of *L. major* (stationary phase). Footpad swelling was then measured weekly thereafter. Results are expressed in FIG. 32 and clearly indicated that, again, mice immunized with naked DNA containing either the M15 or MAPS genes were greatly protected against the infection with *L. major*. These results demonstrate that both M15 and MAPS genes induce excellent protection against *L. major* infection in the BALB/c model of human leishmaniasis.

Example 19

Preparation and Characterization of Leishmania Fusion Proteins

Fusion proteins comprising the Leishmania antigens MAPS-1A (SEQ ID NO: 24), M15 (SEQ ID NO: 2), Lbhsp83 (SEQ ID NO: 6) and LbeIF4A (SEQ ID NO: 10) were prepared as follows.

A fusion construct of MAPS-1A and M15 was prepared by first PCR amplifying the full-length coding sequence of MAPS-1A using the primers of SEQ ID NO: 88 and 89. The resulting products were digested with NdeI and BamHI follows by sub-cloning into the pET17b expression vector, also digested with NdeI and BamHI. The ligated products were transformed into *E. coli* and transformants containing the correct insert were identified by restriction digest and verified by DNA sequencing. The MAPS-1A-pET plasmid was digested with BamHI and EcoRI. The latter cuts within the poly-linker sequence of the pET vector which is located downstream of the BamHI site.

The primers of SEQ ID NO: 90 and 91 were employed to PCR amplify the full-length coding sequence of M15 and the resulting product was digested with BamHI and EcoRI followed by sub-cloning into the predigested MAPS1A-pET plasmid above. The ligated products were then transformed into *E. coli* and transformants with the correct insert were identified by restriction digest and verified by DNA sequencing. The MAPS1A-M15 pET construct was transformed into the bacterial host (BL21; pLysE). Expression of the protein resulted in a single recombinant molecule with a predicted molecular weight of 85.7 kDa. The recombinant MAPS1A-M15 fusion protein also contained 33 amino acid residues of run-through vector as a result of the removal of the stop codon of M15 and was subsequently digested with EcoRI. The DNA sequence of the MAPS1A-M15 construct is provided in SEQ ID NO: 101.

The primers of SEQ ID NO: 92 and 93 were used to PCR amplify the first 226 amino acid residues of LbeIF4A. The resulting PCR product was digested with EcoRI and sub-cloned into the MAPS1A-M15-pET plasmid. The ligated products were then transformed into *E. coli* and transformants with the correct insert and orientation were identified by restriction digest and verified by DNA sequencing. The expressed recombinant protein was purified by affinity chromatography over a Ni column. The DNA and amino acid sequences of the fusion protein MAPS1A-M15-LbeIF4A are provided in SEQ ID NO: 94 and 95, respectively.

Additional fusion proteins were prepared using the methodology described above. The amino acid sequences for the fusion proteins MAPS1A-M15-Lbhsp83 and MAPS1A-M15-Lbhsp83-LeIF4A are provided in SEQ ID NO: 97 and 96, respectively. The DNA sequence that encodes the amino acid sequence of SEQ ID NO: 96 is provided in SEQ ID NO: 98. The DNA sequences of MAPS1A-M15-Lbhsp83 and MAPS1A-M15-Lbhsp83-LeIF4A vectors employed in DNA vaccines are provided in SEQ ID NO: 99 and 100, respectively.

Example 20

Use of Leishmania Fusion Proteins Plus Adjuvant for Vaccination Against Leishmania Infection The ability of the Leishmania fusion proteins MAPS1A-M15 (referred to as the diFusion) and MAPS1A-M15-LbeIF4A (referred to as the triFusion), plus adjuvant, to confer protection against disease in the experimental murine leishmaniasis model system was examined as follows.

The diFusion and triFusion were prepared as described above. In a first series of experiments, groups of BALB/c mice were immunized with either the individual recombinant antigens, (MAPS1A, M15 or LbeIF4A), the diFusion or the triFusion, with IL-12 as an adjuvant, as described above in Example 17. Control mice were immunized with IL-12 alone or saline. Before challenge, some mice (three per group) were sacrificed and the immune responses to the fusion proteins and to the individual antigens were investigated. Both T cell (cytokine production by spleen cells) and B cell responses (antibody response) were evaluated. The results indicated that immunization of mice with the fusion proteins did not interfere with the immunogenicity of the individual antigens. More specifically, Th1 responses (namely induction of IFN-γ production and specific IgG2a production) were observed to both MAPS1A and M15, when mice were immunized with both the diFusion and triFusion recombinant proteins. In addition, immunization with the triFusion resulted in good immune response to LeIF.

To evaluate the protection conferred by these fusion proteins, the immunized and control mice were infected in the right footpad with 2×10³ amastigote forms of *L. major* and footpad swelling was measured weekly thereafter. The results, shown in FIG. 33, clearly indicated that both fusion proteins induced protection comparable to MAPS1A and M15.

A second series of experiments was performed in which MPLL-SE (Ribi ImmunoChem Research Inc. (Hamilton, Mont.) was employed as the adjuvant. BALB/c mice were immunized three times (three weeks interval) with 2 μg of the individual antigens (MAPS1A, M15 or LbeIF4A), diFusion or triFusion proteins plus MPL-SE, and tested for immunogenicity of the antigens and for protection as described above. As with the experiments performed with IL-12 as adjuvant, the mice immunized with the individual antigens as well as with the fusion proteins showed both specific T and B cell responses to the immunizing antigens. Moreover, no antigen competition between the individual antigens was observed when the fusion proteins were used as immunogens.

As with the protection studies in which IL-12 was used as adjuvant, protection was achieved with the individual antigens MAS1A and M15, as well as with the two fusion proteins (FIG. 34). Slightly better protection was observed in the group of mice immunized with the triFusion than in mice immunized with the diFusion.

From the foregoing, it will be appreciated that, although specific embodiments of the invention have been described herein for the purpose of illustration, various modifications may be made without deviating from the spirit and scope of the invention.

We claim:

1. A fusion protein comprising the amino acid sequence of SEQ ID NO: 95.

2. An immunogenic composition comprising the fusion protein according to claim 1 and an immunostimulant.

3. The immunogenic composition of claim 2, wherein the immunostimulant is a monophosphoryl lipid A.

4. A fusion protein comprising the amino acid sequence selected from the group consisting of SEQ ID NOs: 96 and 97.

5. An immunogenic composition comprising the fusion protein according to claim 4 and an immunostimulant.

6. A fusion protein comprising the amino acid sequence encoded by the polynucleotide sequence selected from the group consisting of SEQ ID NOs: 94 and 98.

7. An immunogenic composition comprising the fusion protein according to claim 6 and an immunostimulant.

* * * * *